(12) United States Patent
Mackenzie et al.

(10) Patent No.: US 10,058,044 B2
(45) Date of Patent: *Aug. 28, 2018

(54) METHODS AND COMPOSITIONS FOR OBTAINING USEFUL PLANT TRAITS

(71) Applicant: NUTECH VENTURES, Lincoln, NE (US)

(72) Inventors: Sally Ann Mackenzie, Lincoln, NE (US); Ying-Zhi Xu, Lincoln, NE (US)

(73) Assignee: NUTECH VENTURES, Lincoln, NE (US)

( * ) Notice: Subject to any disclaimer, the term of this patent is extended or adjusted under 35 U.S.C. 154(b) by 143 days.

This patent is subject to a terminal disclaimer.

(21) Appl. No.: 14/536,135

(22) Filed: Nov. 7, 2014

(65) Prior Publication Data

US 2015/0189842 A1 Jul. 9, 2015

Related U.S. Application Data

(60) Provisional application No. 61/901,349, filed on Nov. 7, 2013.

(51) Int. Cl.
| | |
|---|---|
| *A01H 1/04* | (2006.01) |
| *A01H 1/02* | (2006.01) |
| *A01H 1/06* | (2006.01) |
| *C12N 15/82* | (2006.01) |

(52) U.S. Cl.
CPC ............... *A01H 1/04* (2013.01); *A01H 1/02* (2013.01); *A01H 1/06* (2013.01); *C12N 15/8218* (2013.01); *C12N 15/8261* (2013.01); *Y02A 40/146* (2018.01)

(58) Field of Classification Search
CPC .................................. A01H 1/04; C12N 15/82
See application file for complete search history.

(56) References Cited

U.S. PATENT DOCUMENTS

| | | | | |
|---|---|---|---|---|
| 9,476,040 | B2 * | 10/2016 | Mackenzie | ............... A01H 1/04 |
| 9,708,672 | B2 * | 7/2017 | Mackenzie | ........... C12Q 1/6895 |
| 2002/0010953 | A1 | 1/2002 | Vliet | |
| 2004/0210962 | A1 | 10/2004 | Mackenzie et al. | |
| 2006/0248613 | A1 | 11/2006 | Mackenzie et al. | |
| 2012/0284814 | A1 | 11/2012 | Mackenzie et al. | |
| 2014/0157452 | A1 | 6/2014 | Mackenzie et al. | |
| 2015/0052630 | A1 | 2/2015 | Mackenzie et al. | |
| 2015/0113679 | A1 | 4/2015 | Mackenzie et al. | |
| 2017/0009308 | A1 | 1/2017 | Mackenzie et al. | |

FOREIGN PATENT DOCUMENTS

| | | |
|---|---|---|
| WO | 2005/118805 A1 | 12/2005 |
| WO | 2007/033436 A1 | 3/2007 |
| WO | 2012/151254 A1 | 11/2012 |

OTHER PUBLICATIONS

Xu, Y.Z. et al. (Jun. 2012) Plant Physiology; vol. 159, pp. 710-720.*
Xu, Y. et al. The Plant Cell, Sep. 2011; vol. 23, pp. 3428-3441.*
Galloway and Etterson, Science (Nov. 16, 2007;) vol. 318, pp. 1134-1136.*
Kimura, M. et al. Photochemistry and Photobiology, 2003, 77(2): 226-233.*
No art cited.*
Machczynska et al., "DNA Methylation Changes in Triticale Due to In Vitro Culture Plant Regeneration and Consecutive Reproduction", Plant Cell Tiss Organ Cult, Jun. 2014, pp. 289-299, vol. 119.
Palauqui et al., "Systemic Acquired Silencing: Transgene-Specific Post-Transcriptional Silencing is Transmitted by Grafting from Silenced Stocks to Non-Silenced Scions," The EMBO Journal, 1997, pp. 4738-4745, vol. 16 No. 15.
Galloway et al., "Transgenerational Plasticity is Adaptive in the Wild", Science, Nov. 16, 2007, pp. 1134-1136, vol. 318, No. 5853.
Kimura et al., "Identification of *Arabidopsis* Genes Regulated by High Light-Stress Using cDNA Microarray", Photochemistry and Photobiology, Feb. 2003, pp. 226-233, vol. 77, No. 2.
Abdelnoor et al., "Mitochondrial Genome Dynamics in Plants and Animals: Convergent Gene Fusions of a MutS-Homologue" J Mol. Evol, Mar. 1, 2006, pp. 165-173, vol. 63.
Accession No. NP__565131 dated Jan. 22, 2014.
Arrieta-Montiel et al., "Diversity of the *Arabidopsis* Mitochondrial Genome Occurs via Nuclear-Controlled Recombination Activitiy", Genetics, 2009, pp. 1261-1268, vol. 183.
Becker et al., "Spontaneous epigenetic variation in the *Arabidopsis thaliana* methylome" Nature, 2011, vol. 480, pp. 245-249.
Boyko et al., "Transgenerational Adaptation of *Arabidopsis* to Stress Requires DNA Methylation and the Function of Dicer-Like Proteins", Public Library in Science One, Mar. 2010, pp. 1-12, vol. 5, Issue 3, e9514.
Dahlgren et al., "Analysis of siRNA Specificity on Targets with Double-Nucleotide Mismatches", Nucleic Acids Research, 2008, pp. 1-7, vol. 36 No. 9.
Davila et al., "Double-Strand Break Repair Processes Drive Evolution of the Mitochondrial Genome in *Arabidopsis*", BMC Biology: Journal of Biology, 2011, pp. 1-14, vol. 9, No. 64.
Du et al., "A Systematic Analysis of the Silencing Effects of an Active siRNA at all Single-Nucleotide Mismatched Target Sites", Nucleic Acids Research, 2005, pp. 1671-1677, vol. 33, No. 5.
European Search Report and Written Opinion dated Feb. 11, 2015 issued in EP Patent Application No. EP 14 18 6459.
Gao et al., "Analysis of the Leaf Methylomes of Parents and Their Hybrids Provides New Insight Into Hybrid Vigor in Populus Deltoides", BMC Genetics, 2014, 17 pages, vol. 15, Suppl. 1, No. S8.

(Continued)

*Primary Examiner* — Russell Kallis
(74) *Attorney, Agent, or Firm* — Thompson Coburn LLP; Charles P. Romano

(57) ABSTRACT

The present disclosure provides methods for obtaining plants that exhibit useful traits by perturbation of organellar function in plants. Methods for identifying genetic loci that provide for useful traits in plants and plants produced with those loci are also provided. In addition, plants and grafted plants that exhibit, contain, or harbor the useful traits, parts of the plants including seeds, and products of the plants are provided as well as methods of using the plants. Recombinant DNA vectors and transgenic plants comprising those vectors that provide for organellar perturbation are also provided.

7 Claims, 20 Drawing Sheets

Specification includes a Sequence Listing.

(56) References Cited

OTHER PUBLICATIONS

Giannelos et al., "Tobacco Seed Oil as an Alternative Diesel Fuel: Physical and Chemical Properties", Industrial Crops and Products, Jul. 2002, pp. 1-9, vol. 16 Issue 1.
Greaves et al., "Inheritance of Trans Chromosomal Methylation Patterns from *Arabidopsis* F1 Hybrids", Proceedings of the National Academy of Sciences, Feb. 4, 2014, pp. 2017-2022, vol. 111, No. 5.
Groszmann et al. "Epigenetics in plants-vernalisation and hybrid vigour", Biochimica et Biophysica Acta, 2011, 1809, pp. 427-437.
Groszmann et al., "Intraspecific *Arabidopsis* Hybrids Show Different Patterns of Heterosis Despite the Close Relatedness of the Parental Genomes", Plant Physiology, Sep. 2014, pp. 265-280, vol. 166.
Groszmann et al., "The Role of Epigenetics in Hybrid Vigour", Trends in Genetics, Dec. 2013, pp. 684-690, vol. 29 No. 12.
Grouneva et al., "Phylogenetic viewpoints on regulation of light harvesting and electron transport in eukaryotic photosynthetic organisms", Planta, 2013, vol. 237, pp. 399-412.
Hauben et al. "Energy use efficiency is characterized by an epigenetic component that can be directed through artificial selection to increase yield", PNAS, 2009, vol. 106, No. 47, pp. 20109-20114.
Ifuku et al., "Molecular Functions of Oxygen-Evolving Complex Family Proteins in Photosynthetic Electron Flow", Journal of Integrative Plant Biology, Aug. 2010, pp. 723-734, vol. 52 No. 8.
Johannes et al., "Assessing the Impact of Transgenerational Epigenetic Variation on Complex Traits", Plos Genetics, 2009, vol. 5, Issue 6, e1000530.
Molinier et al., "Transgeneration Memory of Stress in Plants", Nature, Aug. 31, 2006, pp. 1046-1049, vol. 442, Nature Publishing Group, 2006.
Nisar et al., "Inflorescence Stem Grafting Made Easy in *Arabidopsis*", Plant Methods, Dec. 19, 2012, pp. 50, vol. 8 No. 1.
Reinders et al., "Compromised Stability of DNA methylation and transposon immobilization in mosaic *Arabidopsis* epigenomes", Genes & Development, 2009, vol. 23, pp. 939-950.
Roux et al., "Genome-Wide Epigenetic Perturbation Jump-Starts Patterns of Heritable Variation Found in Nature", Genetics, 2011, vol. 188, pp. 1015-1017.
Sandhu et al., "Trangenic Induction of Mitochondrial Rearrangements for Cytoplasmic Male Sterility in Crop Plants", Proceedings of the National Academy of Sciences, 2007, pp. 1766-1770, vol. 104, No. 6.
Santamaria et al., "MSH1-Induced Non-Genetic Variation Provides a Source of Phenotypic Diversity in Sorghum Bicolor", PLOS One, Oct. 2014, 8 pages, vol. 9, Issue 10, e108407.
Schmitz et al., "Transgenerational Epigenetic Instability is a Source of Novel Methylation Variants" Science, 2011, 334(6054): 369-373, 10 pages.
Shao et al., "Ws-2 Introgression in a Proportion of *Arabidopsis thaliana* Col-0 Stock Seed Produces Specific Phenotypes and Highlights the Importance of Routine Genetic Verification", Department of Agronomy and Horticulture, University of Nebraska, pp. 1-47, manuscript received for publication in The Plant Cell Jan. 26, 2016.
Shedge et al., "Extensive Rearrangement of the *Arabidopsis* Mitochondrial Genome Elicits Cellular Conditions for Thermotolerance", Plant Physiology, Apr. 2010, pp. 1960-1970, vol. 152, No. 4.
Shen et al., "Genome-Wide Analysis of DNA Methylation and Gene Expression Changes in Two *Arabidopsis* Ecotypes and Their Reciprocal Hybrids", The Plant Cell, Mar. 2012, pp. 875-892, vol. 24.
Stroud et al., "Plants regenerated from tissue culture contain stable epigenome changes in rice", eLife, 2013, No. 2: e00354, 14 pages.
Virdi et al., "*Arabidopsis* MSH1 Mutation Alters the Epigenome and Produces Heritable Changes in Plant Growth", Nature Communications, Feb. 27, 2015, 9 pages.
Virdi et al., "*Arabidopsis* MSH1 Mutation Alters the Epigenome and Produces Heritable Changes in Plant Growth", Nature Communications, Feb. 27, 2015, 23 pages including Supplemental Figures_2015b.
Virdi et al., "MSH1 is a Plant Organellar DNA Binding and Thylakoid Protein under Precise Spatial Regulation to Alter Development", Molecular Plant, 2015, pp. 1-16.
Wesley et al., "Construct Design for Efficient, Effective and High-Throughput Gene Silencing in Plants", The Plant Journal, Sep. 2001, pp. 581-590, vol. 27 Issue 6.
Xu et al., "MutS HOMOLOG1 is a Nucleoid Protein that Alters Mitochondrial and Plastid Properties and Plant Response to High Light", The Plant Cell, 2011, pp. 3428-3441, vol. 23.
Xu et al., "The Chloroplast Triggers Developmental Reprogramming When MUTS HOMOLOG1 is Supressed in Plants", Plant Physiology, 2012, pp. 710-720, vol. 159.
Yang et al., "MSH1-Derived Epigenetic Breeding Potential in Tomato", Plant Physiology Preview, Mar. 3, 2015, 34 pages.

* cited by examiner

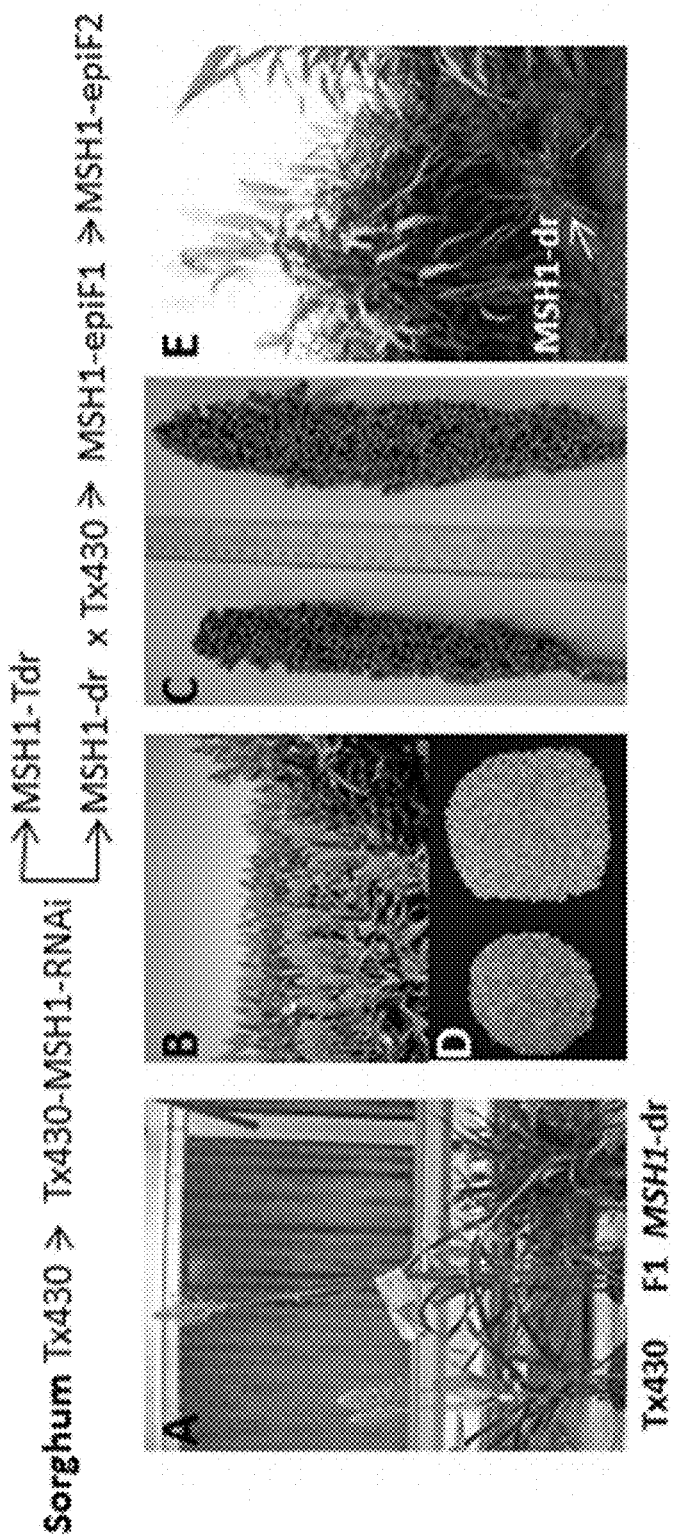
FIGURE 1A, B, C, D, E

| Fixed Effect | df | Denom | F-statistic | p-value |
|---|---|---|---|---|
| Line | 3 | 87.831 | 3.5988 | <0.05 |
| Location | 1 | 14.136 | 175.5053 | <0.001 |
| Line x Location | 3 | 87.831 | 16.2472 | <0.001 |

FIGURE 9A

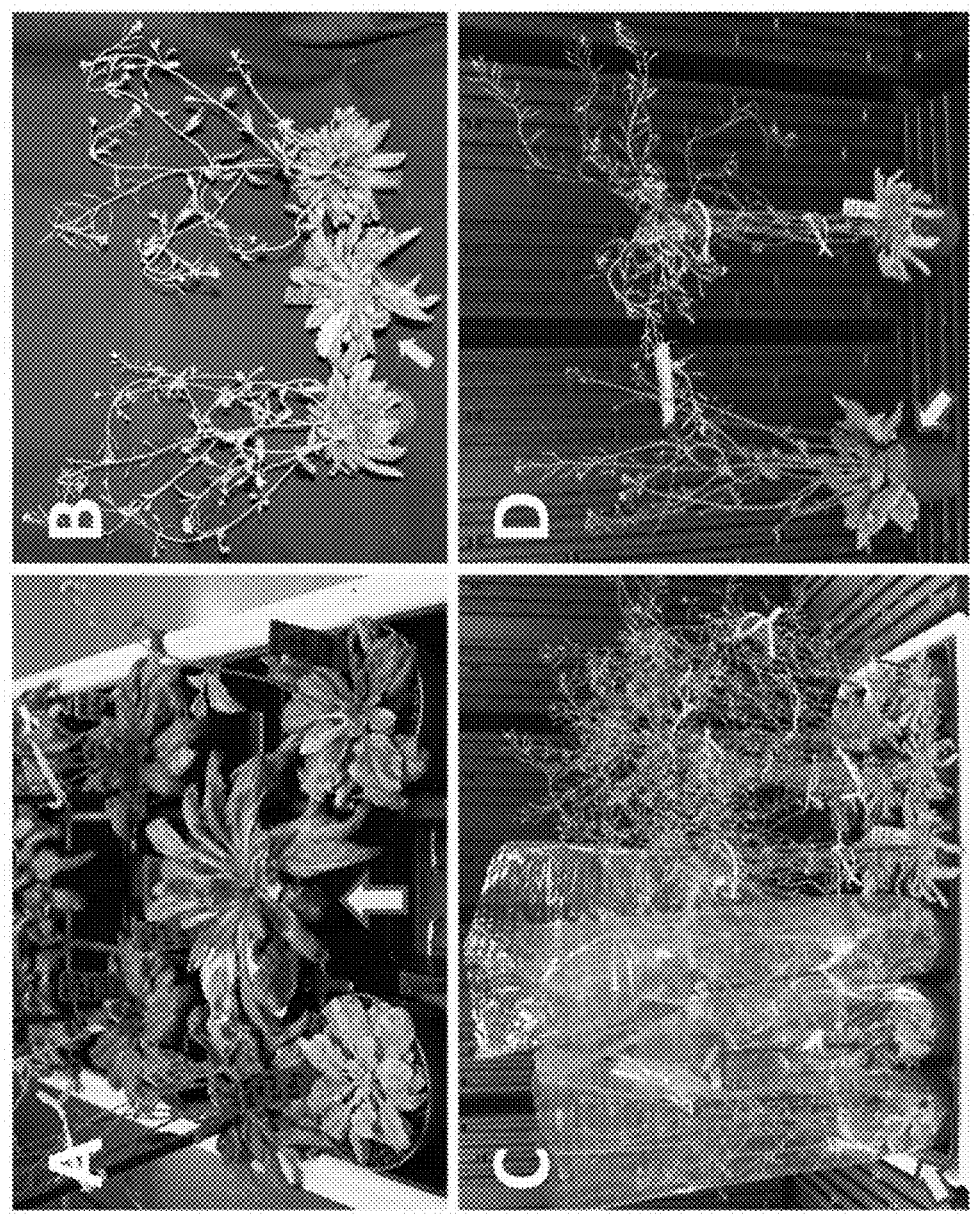
FIGURE 11A, B, C, D

SEQUENCE LISTING

<160> NUMBER OF SEQ ID NOS: 56

<210> SEQ ID NO 1
<211> LENGTH: 3730
<212> TYPE: DNA
<213> ORGANISM: Arabidopsis thaliana

<400> SEQUENCE: 1

```
agaggactgt gagattgtga attgcatagt cgtcgtcttc tggcgggaaa agaagcccta      60
gaaaaagggt gaaggtgaa  aactctactt cttcttcttc ttcttcttca gagtgtgaga     120
gagatgcatt ggattgctac cagaaacgcc gtcgtttcat tcccaaaatg gcggttcttc     180
ttccgctcct catatcgcac ttactcttcc ctcaaaccct cctcccaat  tctacttaat     240 agaaggtact ctgaggggat atcttgtctc agagatggaa agtctttgaa aagaatcaca     300
acggcttcta agaaagtgaa gacgtcaagt gatgttctca ctgacaaaga tctctctcat     360
ttggtttggt ggaaggagag attgcagaca tgtaagaaac catctactct tcagcttatt     420
gaaaggctta tgtacaccaa tttacttggt ttggaccctc gcttgaggaa tggaagttta     480
aaagatggaa acctcaactg ggagatgttg cagtttaagt caaggtttcc acgcgaagtt     540
ttgctctgca gagtaggaga attttatgag gctattggaa tagatgcttg tatacttgtt     600
gaatatgctg gtctcaatcc ttttggtggt cttcgatcag atagtattcc aaaggctggc     660
tgcccaatta tgaatcttcg acagactttg gatgacctga cacgcaatgg ttattcagtg     720
tgtattgtgg aggaagttca ggggccaaca ccagcacgct cccgtaaagg tcgatttatt     780
tcagggcatg cacatccagg aagtccttat gtatatgggc ttgtcggtgt tgaccatgat     840
cttgactttc ctgatcctat gcctgttgtt gggatatctc gttcagcaag ggggtattgt     900
atgatatcta ttttcgagac tatgaaagca tattcgctag atgatggtct aacagaagaa     960
gccttagtta ccaagctccg cactcgtcgc tgtcatcatc ttttcttaca tgcatcgttg    1020
aggcacaatg catcagggac gtgccgctgg ggagagtttg gggaaggggg tctactctgg    1080
ggagaatgca gtagcaggaa ttttgaatgg tttgaaggag atactctttc cgagctctta    1140
tcaagggtca aagatgttta tggtcttgat gatgaagttt cctttagaaa tgtcaatgta    1200
ccttcaaaaa atcggccacg tccgttgcat cttggaacgg ctacacaaat tggtgcctta    1260
cctactgaag gaataccttg tttgttgaag gtgttacttc catctacgtg cagtggtctg    1320
ccttctttgt atgttaggga tcttcttctg aaccctcctg cttacgatat tgctctgaaa    1380
attcaagaaa cgtgcaagct catgagcaca gtaacatgtt caattccaga gtttacctgc    1440
gtctcttctg ctaagcttgt gaagcttctt gagcaacggg aagccaacta cattgagttc    1500
tgtcgaataa aaaatgtgct tgatgatgta ttacatatgc atagacatgc tgagcttgtg    1560
gaaatcctga aattattgat ggatcctacc tgggtggcta ctggtttgaa aattgacttt    1620 gacactttg  tcaacgaatg tcattgggcg tctgatacaa ttggtgaaat gatctcttta    1680
```

```
gatgagaatg aaagtcatca gaatgtaagt aaatgtgaca atgtcccgaa cgaattcttt    1740
tatgatatgg agtcttcatg gcgaggtcgc gttaagggaa ttcatataga ggaagaaatc    1800
actcaagtag aaaaatcagc tgaggcttta tctttagcag tagctgagga ttttcaccct    1860
attatatcaa gaattaaggc caccactgct tcacttggtg gcccgaaagg cgaaatcgca    1920
tatgcaagag agcatgagtc tgtttggttc aaggggaaac ggtttacgcc atctatctgg    1980
gctggtactg caggggaaga ccaaataaaa cagctgaaac ctgccttaga ctcgaaagga    2040
aaaaaggttg gagaagaatg gtttacgacc ccaaggtgg aaattgcttt agtcagatac      2100
catgaagcta gtgagaatgc aaaagctcgg gtgttgaac tgttgcgcga gttatccgtt      2160
aaattgcaaa caaaaataaa tgttcttgtc tttgcatcta tgcttctggt catttcaaaa    2220
gcattatttt cccatgcttg tgaagggaga aggcgaaagt gggttttttcc aacgcttgtc   2280 ggattcagtt tagatgaggg cgcaaaacca ttagatggtg ccagtcgaat gaagctgaca    2340
ggcctgtcac cttattggtt tgatgtatct tctggaaccg ctgttcacaa taccgttgac    2400
atgcaatcac tgtttcttct aactggacct aacggtggtg gtaaatcgag tttgctcaga    2460
tcaatatgcg cagctgctct acttggaatt tccggtttaa tggttccagc tgaatcagct    2520
tgtattcctc actttgattc catcatgctt cacatgaaat catatgacag ccctgtagac    2580
ggaaaaagtt ctttccaggt agaaatgtcg gaaatacgat ctattgtaag ccaggctact    2640
tcgagaagcc tagtgcttat agatgagata tgccgaggga cagagacagc aaaaggcacc    2700
tgtatcgctg gtagtgtggt agagagtctt gacacaagtg gttgtttggg tattgtatct    2760
actcatctcc atggaatctt cagtttacct cttacagcga aaacatcac atataaagca     2820 atgggagccg aaaatgtcga agggcaaacc aagccaactt ggaaattgac agatggagtc    2880
tgcagagaga gtcttgcgtt tgaaacagct aagagggaag gtgttcccga gtcagttatc    2940
caaagagctg aagctctttta cctctcggtc tatgcaaaag acgcatcagc tgaagttgtc    3000
aaacccgacc aaatcataac ttcatccaac aatgaccagc agatccaaaa accagtcagc    3060
tctgagagaa gtttggagaa ggacttagca aaagctatcg tcaaaatctg tgggaaaaag    3120
atgattgagc ctgaagcaat agaatgtctt tcaattggtg ctcgtgagct tccacctcca    3180
tctacagttg gttcttcatg cgtgtatgtg atgcggagac ccgataagag attgtacatt    3240
ggacagaccg atgatcttga aggacgaata cgtgcgcatc gagcaaagga aggactgcaa    3300
gggtcaagtt ttctataccct tatggttcaa ggtaagagca tggcttgtca gttagagact   3360
ctattgatta atcaactcca tgaacaaggc tactctctgg ctaacctagc cgatggaaag    3420
caccgtaatt tcggaacgtc ctcaagcttg agtacatcag acgtagtcag catcttatag    3480
tttgaaacat tagctgtgtt tgtagttgat catctctatg tgcaattgaa caagtcagtt    3540
tgctagaact agagtagatt actaagaaac catgccgttt tcattttga gattttgcaa     3600 aacggcatgc agttcgggta agtcggatgc cgcaattacc aattttgggt cagtctgtgt    3660
aattgtcgtt tcataaatcc gattaacgtg tactttgaac aaaactcagc agtaaacttc    3720
tttattcatc                                                          3730
```

<210> SEQ ID NO 2
<211> LENGTH: 1118
<212> TYPE: PRT
<213> ORGANISM: Arabidopsis thaliana

<400> SEQUENCE: 2

```
Met His Trp Ile Ala Thr Arg Asn Ala Val Ser Phe Pro Lys Trp
 1               5                  10                  15

Arg Phe Phe Arg Ser Ser Tyr Arg Thr Tyr Ser Ser Leu Lys Pro
             20                  25                  30

Ser Ser Pro Ile Leu Leu Asn Arg Arg Tyr Ser Glu Gly Ile Ser Cys
             35                  40                  45

Leu Arg Asp Gly Lys Ser Leu Lys Arg Ile Thr Thr Ala Ser Lys Lys
 50                  55                  60

Val Lys Thr Ser Ser Asp Val Leu Thr Asp Lys Asp Leu Ser His Leu
 65                  70                  75                  80

Val Trp Trp Lys Glu Arg Leu Gln Thr Cys Lys Lys Pro Ser Thr Leu
                 85                  90                  95

Gln Leu Ile Glu Arg Leu Met Tyr Thr Asn Leu Leu Gly Leu Asp Pro
             100                 105                 110

Ser Leu Arg Asn Gly Ser Leu Lys Asp Gly Asn Leu Asn Trp Glu Met
             115                 120                 125

Leu Gln Phe Lys Ser Arg Phe Pro Arg Glu Val Leu Leu Cys Arg Val
         130                 135                 140

Gly Glu Phe Tyr Glu Ala Ile Gly Ile Asp Ala Cys Ile Leu Val Glu
145                 150                 155                 160

Tyr Ala Gly Leu Asn Pro Phe Gly Leu Arg Ser Asp Ser Ile Pro
                 165                 170                 175

Lys Ala Gly Cys Pro Ile Met Asn Leu Arg Gln Thr Leu Asp Asp Leu
                 180                 185                 190

Thr Arg Asn Gly Tyr Ser Val Cys Ile Val Glu Glu Val Gln Gly Pro
             195                 200                 205

Thr Pro Ala Arg Ser Arg Lys Gly Arg Phe Ile Ser Gly His Ala His
210                 215                 220

Pro Gly Ser Pro Tyr Val Tyr Gly Leu Val Gly Val Asp His Asp Leu
225                 230                 235                 240

Asp Phe Pro Asp Pro Met Pro Val Val Gly Ile Ser Arg Ser Ala Arg
                 245                 250                 255

Gly Tyr Cys Met Ile Ser Ile Phe Glu Thr Met Lys Ala Tyr Ser Leu
                 260                 265                 270

Asp Asp Gly Leu Thr Glu Glu Ala Leu Val Thr Lys Leu Arg Thr Arg
             275                 280                 285

Arg Cys His His Leu Phe Leu His Ala Ser Leu Arg His Asn Ala Ser
             290                 295                 300

Gly Thr Cys Arg Trp Gly Glu Phe Gly Glu Gly Gly Leu Leu Trp Gly
305                 310                 315                 320

Glu Cys Ser Ser Arg Asn Phe Glu Trp Phe Glu Gly Asp Thr Leu Ser
                 325                 330                 335

Glu Leu Leu Ser Arg Val Lys Asp Val Tyr Gly Leu Asp Asp Glu Val
             340                 345                 350

Ser Phe Arg Asn Val Asn Val Pro Ser Lys Asn Arg Pro Arg Pro Leu
             355                 360                 365

His Leu Gly Thr Ala Thr Gln Ile Gly Ala Leu Pro Thr Glu Gly Ile
             370                 375                 380

Pro Cys Leu Leu Lys Val Leu Leu Pro Ser Thr Cys Ser Gly Leu Pro
385                 390                 395                 400

Ser Leu Tyr Val Arg Asp Leu Leu Asn Pro Pro Ala Tyr Asp Ile
                 405                 410                 415

Ala Leu Lys Ile Gln Glu Thr Cys Lys Leu Met Ser Thr Val Thr Cys
```

-continued

```
            420                 425                 430
Ser Ile Pro Glu Phe Thr Cys Val Ser Ala Lys Leu Val Lys Leu
            435                 440                 445

Leu Glu Gln Arg Glu Ala Asn Tyr Ile Glu Phe Cys Arg Ile Lys Asn
450                 455                 460

Val Leu Asp Asp Val Leu His Met His Arg His Ala Glu Leu Val Glu
465                 470                 475                 480

Ile Leu Lys Leu Leu Met Asp Pro Thr Trp Val Ala Thr Gly Leu Lys
                485                 490                 495

Ile Asp Phe Asp Thr Phe Val Asn Glu Cys His Trp Ala Ser Asp Thr
                500                 505                 510

Ile Gly Glu Met Ile Ser Leu Asp Glu Asn Glu Ser His Gln Asn Val
            515                 520                 525

Ser Lys Cys Asp Asn Val Pro Asn Glu Phe Phe Tyr Asp Met Glu Ser
            530                 535                 540

Ser Trp Arg Gly Arg Val Lys Gly Ile His Ile Glu Glu Ile Thr
545                 550                 555                 560

Gln Val Glu Lys Ser Ala Glu Ala Leu Ser Leu Ala Val Ala Glu Asp
                565                 570                 575

Phe His Pro Ile Ile Ser Arg Ile Lys Ala Thr Thr Ala Ser Leu Gly
                580                 585                 590

Gly Pro Lys Gly Glu Ile Ala Tyr Ala Arg Glu His Glu Ser Val Trp
            595                 600                 605

Phe Lys Gly Lys Arg Phe Thr Pro Ser Ile Trp Ala Gly Thr Ala Gly
            610                 615                 620

Glu Asp Gln Ile Lys Gln Leu Lys Pro Ala Leu Asp Ser Lys Gly Lys
625                 630                 635                 640

Lys Val Gly Glu Glu Trp Phe Thr Thr Pro Lys Val Glu Ile Ala Leu
                645                 650                 655

Val Arg Tyr His Glu Ala Ser Glu Asn Ala Lys Ala Arg Val Leu Glu
                660                 665                 670

Leu Leu Arg Glu Leu Ser Val Lys Leu Gln Thr Lys Ile Asn Val Leu
            675                 680                 685

Val Phe Ala Ser Met Leu Leu Val Ile Ser Lys Ala Leu Phe Ser His
            690                 695                 700

Ala Cys Glu Gly Arg Arg Arg Lys Trp Val Phe Pro Thr Leu Val Gly
705                 710                 715                 720

Phe Ser Leu Asp Glu Gly Ala Lys Pro Leu Asp Gly Ala Ser Arg Met
                725                 730                 735

Lys Leu Thr Gly Leu Ser Pro Tyr Trp Phe Asp Val Ser Ser Gly Thr
                740                 745                 750

Ala Val His Asn Thr Val Asp Met Gln Ser Leu Phe Leu Leu Thr Gly
            755                 760                 765

Pro Asn Gly Gly Gly Lys Ser Ser Leu Leu Arg Ser Ile Cys Ala Ala
            770                 775                 780

Ala Leu Leu Gly Ile Ser Gly Leu Met Val Pro Ala Glu Ser Ala Cys
785                 790                 795                 800

Ile Pro His Phe Asp Ser Ile Met Leu His Met Lys Ser Tyr Asp Ser
                805                 810                 815

Pro Val Asp Gly Lys Ser Ser Phe Gln Val Glu Met Ser Glu Ile Arg
                820                 825                 830

Ser Ile Val Ser Gln Ala Thr Ser Arg Ser Leu Val Leu Ile Asp Glu
            835                 840                 845
```

Ile Cys Arg Gly Thr Glu Thr Ala Lys Gly Thr Cys Ile Ala Gly Ser
    850                 855                 860

Val Val Glu Ser Leu Asp Thr Ser Gly Cys Leu Gly Ile Val Ser Thr
865                 870                 875                 880

His Leu His Gly Ile Phe Ser Leu Pro Leu Thr Ala Lys Asn Ile Thr
                885                 890                 895

Tyr Lys Ala Met Gly Ala Glu Asn Val Glu Gly Gln Thr Lys Pro Thr
            900                 905                 910

Trp Lys Leu Thr Asp Gly Val Cys Arg Glu Ser Leu Ala Phe Glu Thr
        915                 920                 925

Ala Lys Arg Glu Gly Val Pro Glu Ser Val Ile Gln Arg Ala Glu Ala
    930                 935                 940

Leu Tyr Leu Ser Val Tyr Ala Lys Asp Ala Ser Ala Glu Val Val Lys
945                 950                 955                 960

Pro Asp Gln Ile Ile Thr Ser Ser Asn Asn Asp Gln Gln Ile Gln Lys
                965                 970                 975

Pro Val Ser Ser Glu Arg Ser Leu Glu Lys Asp Leu Ala Lys Ala Ile
            980                 985                 990

Val Lys Ile Cys Gly Lys Lys Met  Ile Glu Pro Glu Ala  Ile Glu Cys
        995                 1000                1005

Leu Ser  Ile Gly Ala Arg Glu  Leu Pro Pro Ser  Thr Val Gly
    1010                1015                1020

Ser Ser  Cys Val Tyr Val Met  Arg Arg Pro Asp  Lys  Arg Leu Tyr
    1025                1030                1035

Ile Gly  Gln Thr Asp Asp Leu  Glu Gly Arg Ile Arg  Ala His Arg
    1040                1045                1050

Ala Lys  Glu Gly Leu Gln Gly  Ser Ser Phe Leu Tyr  Leu Met Val
    1055                1060                1065

Gln Gly  Lys Ser Met Ala Cys  Gln Leu Glu Thr Leu  Leu Ile Asn
    1070                1075                1080

Gln Leu  His Glu Gln Gly Tyr  Ser Leu Ala Asn Leu  Ala Asp Gly
    1085                1090                1095

Lys His  Arg Asn Phe Gly Thr  Ser Ser Ser Leu Ser  Thr Ser Asp
    1100                1105                1110

Val Val  Ser Ile Leu
    1115

<210> SEQ ID NO 3
<211> LENGTH: 3765
<212> TYPE: DNA
<213> ORGANISM: Glycine max

<400> SEQUENCE: 3
gtcagataca gagtccttcc ctcctcgtgt gtggactgtg gcgggaactc attttgctag      60
tttgcttcct ctctctctct cgttcccatt caacgcaatg tacagggtag ccacaagaaa     120
cgtcgccgtt ttcttccctc gttgctgttc cctcgcgcac tacactcctt ctctatttcc     180
cattttcact tcattcgctc cctctcgttt ccttagaata aatggatgtg taaagaatgt     240
gtcgagttat acgataaga aggtttcaag ggggagtagt agggccacca agaagcccaa     300
aataccaaat aacgttttag atgataaaga ccttcctcac atactgtggt ggaaggagag     360
gttgcaaatg tgcagaaagt ttcaactgt ccagttaatt gaaagacttg aattttctaa     420
tttgcttggc ctgaattcca acttgaaaaa tggaagtctg aaggaaggaa cactcaactg     480

```
ggaaatgttg caattcaagt caaaatttcc acgtcaagta ttgctttgca gagttgggga    540
attctatgaa gcttgggGaa tagatgcttg tattcttgtt gaatatgtgg gtttaaatcc    600
cattggtggt ctgcgatcag atagtatccc aagagctagt tgtcctgtcg tgaatcttcg    660
gcagacttta tgatgatctga caacaaatgg ttattcagtg tgcattgtgg aggaggctca    720
gggcccaagt caagctcgat ccaggaaacg tcgctttata tctgggcatg ctcatcctgg    780
aaatccctat gtatatggac ttgctacagt tgatcatgat cttaactttc cagaaccaat    840
gcctgtagta ggaatatctc attctgcgag gggttattgc attaatatgg tactagagac    900
catgaagaca tattcttctg aagattgctt gacagaagaa gcagttgtta cgaagcttcg    960
tacttgccaa tatcattact tattttttgca tacatccttg aggcggaatt cttgtggaac   1020
ctgcaactgg ggagaatttg tgagggagg gctattatgg ggagaatgta gttctagaca   1080
ttttgattgg tttgatggca accctgtctc cgatcttttg gccaaggtaa aggaacttta   1140
tagtattgat gatgaggtta cctttcggaa cacaactgtg tcttcaggac atagggctcg   1200
accattaact cttggaacat ctactcaaat tggtgccatt ccaacagaag gaataccttc   1260
tttgttgaag gttttacttc catcaaattg caatggatta ccagtattgt acataaggga   1320
acttcttttg aatcctcctt catatgagat tgcatccaaa attcaagcaa catgcaaact   1380
tatgagcagt gtaacgtgtt caattccaga atttacatgt gtttcgtcag caaagcttgt   1440
aaagctactt gaatggaggg aggtcaatca tatggaattt tgtagaataa agaatgtact   1500
ggatgaaatt ttgcagatgt atagtacctc tgagctcaat gaaatattga acatttaat   1560 cgagcccaca tgggtggcaa ctgggttaga aattgacttt gaaaccttgg ttgcaggatg   1620
tgagatcgca tctagtaaga ttggtgaaat agtatctctg gatgatgaga atgatcagaa   1680
aatcaactcg ttctctttta ttcctcacga atttttttgag gatatggagt ctaaatggaa   1740
aggtcgaata aaaagaatcc acatagatga tgtattcact gcagtggaaa aagcagctga   1800
ggccttacat atagcagtca ctgaagattt tgttcctgtt gtttctagaa taaaggctat   1860
tgtagcccct ctcggaggtc ctaagggaga aatatcttat gctcgggagc aagaagcagt   1920
ttggttcaaa ggcaaacgct ttacaccgaa tttgtgggct ggtagccctg agaggaaca   1980 aattaaacag cttaggcatg cttagattc taaaggtaga aaggtagggg aggaatggtt   2040
taccacacca aaggtcgagg ctgcattaac aaggtaccat gaagcaaatg ccaaggcaaa   2100
agaaagagtt ttggaaattt taaggggact cgctgctgag ttgcaataca gtataaacat   2160
tcttgtcttt tcttccatgt tgcttgttat tgccaaagct ttatttgctc atgcaagtga   2220
agggagaaga aggagatggg tctttcccac gcttgtagaa tcccatgggt ttgaggatgt   2280
gaagtcattg gacaaaaccc atgggatgaa gataagtggt ttattgccat attggttcca   2340
catagcagaa ggtgttgtgc gtaatgatgt tgatatgcaa tcattatttc tgttgacagg   2400
accgaatggt ggtgggaaat caagttttct taggtcaatt tgtgctgctg cactacttgg   2460
gatatgtgga ctcatggttc ctgcagaatc agccctaatt ccttattttg actccatcac   2520
gcttcatatg aagtcatatg atagtccagc tgataaaaag agttcctttc aggttgaaat   2580
gtcagaactt cgatccatca ttggcggaac aaccaacagg agccttgtac ttgttgatga   2640
aatatgccga ggaacagaaa ctgcaaaagg gacttgcatt gctggtagca tcattgaaac   2700
ccttgatgga attgggtgtc tgggtattgt atccactcac ttgcatggaa tatttacttt   2760 gccctaaac aaaaaaaaca ctgtgcacaa agcaatgggc acaacatcca ttgatggaca   2820
aataatgcct acatggaagt tgacagatgg agtttgtaaa gaaagtcttg cttttgaaac   2880
```

-continued

| | |
|---|---|
| ggctaagagg gaaggaattc ctgagcatat tgttagaaga gctgaatatc tttatcagtt | 2940 |
| ggtttatgct aaggaaatgc tttttgcaga aaatttccca aatgaagaaa agttttctac | 3000 |
| ctgcatcaat gttaataatt tgaatggaac acatcttcat tcaaaaaggt tcctatcagg | 3060 |
| agctaatcaa atggaagttt tacgcgagga agttgagaga gctgtcactg tgatttgcca | 3120 |
| ggatcatata aaggacctaa aatgcaaaaa gattgcattg gagcttactg agataaaatg | 3180 |
| tctcataatt ggtacaaggg agctaccacc tccatcggtt gtaggttctt caagcgtcta | 3240 |
| tgtgatgttc agaccagata agaaactcta tgtaggagag actgatgatc tcgagggacg | 3300 |
| ggtccgaaga catcgattaa aggaaggaat gcatgatgca tcattccttt attttcttgt | 3360 |
| cccaggtaaa agcttggcat gccaatttga atctctgctc atcaaccaac tttctggtca | 3420 |
| aggcttccaa ctgagcaata tagctgatgg taaacatagg aattttggca cttccaacct | 3480 |
| gtatacataa ctagtctata gacattgata ttatctacct caatcgcgta ttttttgcctc | 3540 |
| ttttaaatgg ctcaaagact tcaatcatcg atgttaagtt taggaaacaa tgtctgcagc | 3600 |
| attttttgtta gaattagttg ctgcagctgc atttatgtcc acatcttcaa gtgtggaaat | 3660 |
| tcttgttcat tagcttgtaa gtacaaaagt gtttgtgtac gtttggagtc ccgagagaat | 3720 |
| atacaagtac aaatgaacaa atatattagt aatgaatgca ctaga | 3765 |

<210> SEQ ID NO 4
<211> LENGTH: 3642
<212> TYPE: DNA
<213> ORGANISM: Zea mays

<400> SEQUENCE: 4

| | |
|---|---|
| gcgcactacc ccgagaaacg tgcgacggga acctccgcgg ttccccaagt tcgcctcctt | 60 |
| cactactctc gcgccccggc acgcctgaaa accccaccc ctcctgccgc tccgcctctc | 120 |
| ccatcacttc ccacgcccct cgccgcctcc cattccagcg tggacacgac gccactcgcc | 180 |
| agcacggaga cgcgcgcctc gaagcactac tgcactagcc agccgtcgtt cttccgcgcc | 240 |
| ggcgccatgc accgggtgct cgtgagctcg cttgtggccg ccacgccgcg atggctgccc | 300 |
| ctcgccgact ccatcctccg gcgccgccgg ccgcgctgct cccctcttcc cgtgctgatg | 360 |
| ttcgatcgga gggcttggtc caagccaagg aaggtctcac gaggcatttc agtggcgtcc | 420 |
| aggaaagcta acaaacaggg agaatactgt gatgaaagta tgctgtcgca tatcatgtgg | 480 |
| tggaaagaga aaatggagag gtgcagaaaa ccatcatcca tacaattgac tcagaggctt | 540 |
| gtgtattcaa atatattagg gttggatccg aatttaagaa acggaagctt gaaagatgga | 600 |
| accctgaaca tggagatttt ggtatttaaa tcaaaatttc ctcgtgaggt tctactttgc | 660 |
| agagtaggag atttctatga agctatcggt tttgatgcct gtattctcgt agagcatgca | 720 |
| ggcttaaatc cttttggagg tttgcgttcc gacagtattc ctaaagctgg gtgtccagtc | 780 |
| gtgaatttac ggcagacatt ggatgatttg actcgatgtg gttattccgt gtgcatagtc | 840 |
| gaggaaattc aaggcccaac tcaagcccgt gctcggaaaa gtcgatttat ttctgggcat | 900 |
| gcccatcctg gtagtcctta tgtatttggt cttgctgaag tagaccatga tgtagagttc | 960 |
| cctgatccga tgcctgttgt tgggatttca cattctgcaa aaggttattg cttgatatct | 1020 |
| gtgctagaga caatgaaaac ttattcagct gaggagggct taacagagga ggctattgtt | 1080 |
| actaagctcc gcatatgtcg ttatcaccat ctataccttc acaattcttt gaagaataat | 1140 |
| tcttcaggga catcacgctg gggtgaattc ggtgaaggtg ggctcttgtg gggagagtgc | 1200 |

```
agtgggaagt cctttgagtg gtttgacggt tcacctattc aagaactttt atgcaaggta    1260
cgggaaatat atggccttga tgagaaaacg gtttttcgcg atgtcaccgt ctcattggaa    1320
ggcaggcccc aacctcttca tcttgggact gctactcaaa ttggagtcat accaactgag    1380
ggaataccga gtttgttaag aatggtgctt ccttcaaatt gtggcgggct tccatcaatg    1440
tatattagag atcttcttct taatcctcca tcatttgagg ttgcagcagc gatccaagag    1500
gcttgcaggc ttatgggcaa cataacctgc tccattcctg aatttacatg catatcagca    1560
gcaaagcttg tgaaactact tgagtcgaaa ggggtcaatc acattgaatt ttgtagaata    1620
aaaaatgtcc ttgatgagat tatgctcatg aacagggatg ctgagctttc tgcaatcctg    1680
catgaattac tggtacctgc ttctgtggct actggtttca aagttgaagc tgatatgcta    1740
atgaacggat gtagcattat ttcacaacga atagctgaag tgatttcttt aggtgttgaa    1800
agtgatcagg caataacttc attggaatat attccaaagg agttcttcaa tgatatggag    1860
tcatcttgga aggggcgcgt gaaaaggatc catgctgaag aagagtttgc aaatgttgat    1920
agggctgctg aggcattatc aattgcggtc attgaagatt ttatgccaat tatttcgagg    1980
gtgaaatctg tagtgtcctc gaatggaggt ttgaaaggag aaatcggtta tgcaaaagaa    2040
catgaagctg tttggtttaa aggaaagaga ttcataccaa atgtatgggc taacacacct    2100
ggtgagcagc aaataaaaca actgaagcct gcaattgatt caaaaggcag aaaggttggg    2160
gaggaatggt ttacaacaag caaagttgag aatgctttag ccaggtacca tgaagcttgt    2220
gataatgcaa gaaataaagt tcttgagctg ttgagaggcc tttctagtga attgcaggac    2280
aaaattaaca tacttgtctt ttgctcaaca ctgctcatca ttgcaaaagc acttttttggt   2340
catgttagtg aggctcgaag aagaggttgg atgcttccta ctatatctcc cttatcaaag    2400
gactgtgttg tggaggaaag ttcaagtgca atggatttag taggactatt tccttactgg    2460
cttgatgtta atcaaggaaa tgcaatattg aatgatgtcc acatgcactc tttatttgtt    2520
cttactggcc caaatggtgg tggtaaatct agcatgttgc gatcagtctg tgcagctgtg    2580
cttcttggaa tatgtggcct gatggtacct tcaacttcag ctgtaatccc acattttgat    2640
tccattatgc tgcatatgaa agcctatgat agcccagcag atgggaaaag ttcatttcag    2700
attgaaatgt cggagatacg tgctttagtc agccgagcta ctgctaggag tcttgttctg    2760
attgatgaaa tatgtagagg cacagaaact gcaaaaggaa catgtatagc tggtagcatc    2820
attgaaagac ttgataatgt tggctgccta ggcatcatat caactcacct gcatgggatt    2880
ttcgacctgc ctctctcact tagcaacact gatttcaaag ctatgggaac tgaagtggtc    2940
gatggatgca ttcatccaac atggaaactg attgatggca tatgtagaga aagccttgct    3000
tttcaaacag caaggaggga aggcatgcct gacttgataa tcaccagggc tgaggagcta    3060
tatttgagta tgagtacaaa taacaagcag ggagcatcag tggcgcacaa tgagcctcct    3120
aatggcagcc ccagtgtaaa tggcttggtt gaggagcctg aatctctgaa gaacagacta    3180
gaaatgctgc ctggtacctt tgagccgctg cggaaggaag ttgagagtgc tgttactacg    3240
atgtgtaaga aaatactgtc ggacctttac aacaaaagta gcatcccaga actggtcgag    3300
gtggtctgcg ttgctgtagg tgctagagag caaccaccgc cttccactgt ggcagatct    3360
agcatctacg tgattatcag aagcgacaac aggctctatg ttggacagac ggacgatctt    3420
ctggggcgct tgaacgccca cagatcgaag gaaggcatgc gggacgctac ggtattatac    3480
gtcttggtcc ctggcaagag cgttgcctgc cagctgaaaa cccttctcat aaaccagctc    3540
ccttcgaggg gcttcaagct catcaacaag gcagacggga agcacaggaa cttcggtata    3600
```

```
tctcgaatct ctggcgaggc agttgctact ggacggaact ag              3642
```

<210> SEQ ID NO 5
<211> LENGTH: 3373
<212> TYPE: DNA
<213> ORGANISM: Lycopersicon esculentum

<400> SEQUENCE: 5

```
atgtattggg ttacggcaaa aaacgtcgtc gtttcagttc ccgttggcg ttcactgtcc     60
cttttcctcc gtccaccact tcgccggcgt ttcttatctt tctctccaca tactctgtgc   120
cgagagcaga tacgttgcgt gaaggagcgg aagttttttg ccacaacggc aaaaaaactc   180
aaacaaccaa aaagtattcc agaggaaaaa gactatgtta atattatgtg gtggaaagag   240
agaatggaat tcttgagaaa gccttcttcc gctcttctgg ctaagaggct tacatattgt   300
aacttgctgg gtgtggatcc gagtttgaga atggaagtc ttaaagaggg aacacttaac   360
tcggagatgt tgcagttcaa gtcaaaattt ccacgtgaag ttttgctctg tagagtaggt   420
gatttttatg aagctattgg attcgatgct tgtattcttg tggaatatgc tggtttaaat   480
ccatttggtg gcctgcactc agatagtata ccaaaagctg gttgtccagt tgtgaatcta   540
agacagacgc ttgatgatct cacacgtaat ggtttctctg tgtgcgtcgt ggaggaagtt   600
cagggtccaa ctcaagctcg tgctcgtaag agtcgattta tatcagggca tgcacatcca   660
ggcagtccct atgttttgg ccttgttgga gatgatcaag atcttgattt tccagaacca   720
atgcctgttg ttggaatatc ccgttcagcg aaggggtatt gcattatctc tgtttacgag   780
actatgaaga cttactctgt ggaagatggc ctaactgaag aagccgtagt caccaaactt   840
cgtacttgtc gatgccatca ttttttttg cataattcat tgaagaacaa ttcctcagga   900
acatcgcgtt ggggagagtt tggtgaaggt ggactttgt ggggagaatg taatgctaga   960
cagcaggaat ggttggatgg caatcctatc gatgagcttt tgttcaaggt aaaagagctt  1020
tatggtctca atgatgacat tccattcaga aatgtcactg ttgtttcaga aaataggccc  1080
cgtcctttac accttggaac tgccacacaa attggtgcta ttccaaccga agggattcca  1140
tgtttgttaa aggtgttgct tcctcctcat tgcagtggtc taccagtcct gtatattagg  1200
gatcttcttt taaatccacc agcctatgag atttcttcag acattcaaga ggcatgcaga  1260
cttatgatga gtgtcacatg ttcaattcct gattttacct gtatttcatc tgcaaagctg  1320
gtcaagctgc ttgagttgag ggaggcaaat cacgttgagt tctgcaaaat aaagagcatg  1380
gtcgaagaga tactgcagtt gtatagaaat tcagagcttc gtgctattgt agagttactg  1440
atggatccta cttgggtggc aactgggttg aaagttgatt ttgatacact agtaaatgaa  1500
tgtgaaaga tttcttgtag aatcagtgaa ataatatccg tacatggtga aaatgatcaa  1560
aagattagtt cctatcctat catcccaaat gatttctttg aagatatgga gttgttgtgg  1620
aaaggccgtg tcaagaggat ccatttggag gaagcatatg cagaagtaga aaaggctgcg  1680
gatgctttat ctttagccat aacagaagat ttcctaccta ttatttcaag aataagggcc  1740
acgatggccc cacttggagg aactaaaggg gagattttgt atgcccgtga gcatggagct  1800
gtatggttta agggaaagag atttgtacca actgtttggg ctggaaccgc tggagaagaa  1860
caaattaagc aactcagacc tgctctagat tcaaagggga agaaggttgg agaagaatgg  1920
ttcactacaa tgagggtgga agatgcaata gctaggtatc acgaggcaag tgctaaggca  1980
aagtcaaggg tcttggaatt gctaagggga ctttcttctg aattactatc taagatcaat  2040
```

| | |
|---|---|
| atccttatct tttgcatctgt cttgaatgtg atagcaaaat cattattttc tcatgtgagt | 2100 |
| gaaggaagaa gaagaaattg gattttccca acaatcacac aatttaacaa atgtcaggac | 2160 |
| acagaggcac ttaatggaac tgatggaatg aagataattg gtctatctcc ttattggttt | 2220 |
| gatgcagcac gagggactgg tgtacagaat acagtagata tgcagtccat gtttcttta | 2280 |
| acaggtccaa atggtggggg caaatcaagc ttgctgcgtt cgttgtgtgc agctgcattg | 2340 |
| ctaggaatgt gtgggttcat ggttccagct gaatcagctg tcattcctca ttttgactca | 2400 |
| attatgctgc atatgaaatc atatgatagt cctgttgatg gaaaaagttc atttcagatt | 2460 |
| gaaatgtctg aaattcggtc tctgattact ggtgccactt caagaagtct tgtacttata | 2520 |
| gatgaaatat gtcgaggaac agaaacagca aagggacat gtattgctgg aagtgtcata | 2580 |
| gaaaccctgg acgaaattgg ctgtttggga attgtatcaa cccacttgca tggaatattt | 2640 |
| gatttacccc tgaaaatcaa gaagaccgtg tataaagcaa tgggagctga atatgttgac | 2700 |
| ggtcaaccaa taccaacttg gaaactcatt gatgggatct gtaaagagag tctagcattt | 2760 |
| gaaacagctc agagagaagg aattccagaa atattaatcc aaagagcaga agaattgtat | 2820 |
| aattcagctt acgggaatca gataccaagg aagatagacc aaataagacc tctttgttca | 2880 |
| gatattgacc tcaatagcac agataacagt tctgaccaat taaatggtac aagacaaata | 2940 |
| gctttggatt ctagcacaaa gttaatgcat cgaatgggaa tttcaagcaa gaaacttgaa | 3000 |
| gatgctatct gtcttatctg tgagaagaag ttaattgagc tgtataaaat gaaaaatccg | 3060 |
| tcagaaatgc caatggtgaa ttgcgttctt attgctgcca gggaacagcc ggctccatca | 3120 |
| acaattggtg cttcaagtgt ctatataatg ctaagacctg acaaaaagtt gtatgttgga | 3180 |
| cagactgatg atcttgaggg cagagtacgt gctcatcgct tgaaggaggg aatggaaaac | 3240 |
| gcgtcattcc tatatttctt agtctctggc aagagcatcg cctgccaatt ggaaactctt | 3300 |
| ctaataaatc aacttcctaa tcatggtttt cagctaacaa acgttgctga tggtaagcat | 3360 |
| cgtaattttg gca | 3373 |

<210> SEQ ID NO 6
<211> LENGTH: 3180
<212> TYPE: DNA
<213> ORGANISM: Sorghum bicolor

<400> SEQUENCE: 6

| | |
|---|---|
| atgcaccggg tgctcgtgag ctcgctcgtg ccgccacgc cgcggtggct ccccctcgcc | 60 |
| gactccatcc tccggcgccg ccgcccgcgc tgctctcctc ttcccatgct gctattcgac | 120 |
| cggagggctt ggtccaagcc aaggaaggtc tcacgaggca tctcagtggc gtctaggaaa | 180 |
| gctaacaaac agggagaata ttgtgatgaa agcatgctat cgcatatcat gtggtggaaa | 240 |
| gagaaaatgg agaagtgcag aaaaccatca tccgtacaat tgactcagag gcttgtgtat | 300 |
| tcaaatatat tagggttgga tccaaatcta gaaatggaa gcttgaaaga tggaaccctg | 360 |
| aacatggaga ttttgctatt taaatcaaaa tttcctcgtg aggttctact ttgcagagta | 420 |
| ggagacttct atgaagctat tggttttgat gcctgtattc tcgtagagca tgcaggctta | 480 |
| aatccttttg gaggtttgcg ttctgacagt atccctaaag ctgggtgtcc agtcgtgaat | 540 |
| ttacggcaga cattggatga tttgactcga tgtggttatt ctgtgtgcat agttgaggaa | 600 |
| attcaaggcc caacacaagc ccgttcccgg aaaagtcgat ttatttctgg gcatgcccat | 660 |
| cctggtagtc cttatgtatt tggtcttgct gaagtagacc atgatgtaga gttccctgat | 720 |
| ccgatgcctg ttgttgggat ttcacattct gcaaaaggtt attgcttgat atctgtgcta | 780 |

```
gagacaatga aaacttattc agctgaggag ggcttaacag aagaggctat tgttactaag    840
ctccgcatat gtcgttatca tcatctatac cttcacaatt ctttgaagaa taattcttca    900
gggacatcac gctggggtga attcggtgaa ggagggctct tgtggggaga gtgcagtggg    960
aagtcctttg agtggtttga tggtttacct attgaagaac ttttatgcaa ggtacgggaa   1020
atatatggcc ttgatgagaa aactgttttt cgcaatgtca ccgtctcatt ggaaggcagg   1080
ccccaacctc tttatcttgg aactgctact caaattggag tcataccaac tgagggaata   1140
ccgagtttgc taaaaatggc actcccttca agttgtggcg ggcttccatc aatgtatatt   1200
agagatcttc ttcttaatcc tccatcattt gatgttgcgg cagcggtcca agaggcttgc   1260
aggcttatgg ggagcataac ttgttctgtt cctgaattta cttgcatatc acttgtgaag   1320
ctacttgagt ctaaagaggt caatcacatt gaattttgta gaataaaaaa tgtccttgat   1380
gagattatgc tcatgaacag gaatgctgag cttctgcaa tcctgaacaa attgctggta    1440
cctggttctg tggctactgg tttgaaagtt gaagctgata tgctagtcat tgaagatttt   1500
atgccaatta tttcaagggt gaaatctgta gtgtcctcaa atggaggttc gaaaggagaa   1560
atctgttatg caaagaaca tgaagctgtt tggtttaaag aaagcgatt cacaccaact      1620 gtatgggcta acacacctgg tgagcagcaa ataaaacaac tgaagcctgc aattgattcg   1680
aaaggcagaa aggttgggga ggaatggttt acaacaagca agttgagaa tgctttagcc    1740 aggtaccatg aagcttgtga taatgcaaga ataaagttg ttgagctgtt gagagggctt    1800
tcaagtgaat tgcaggacaa aattaacata cttgtctttt gctcaacact gctcatcatt   1860
gcaaaagcac ttttggtca tgttagtgag gctcggagaa gaggctggat gcttcctact     1920
atatttccct tgtcaaagga ctgtgttgca gaggaaagtt caaatgcaat ggatttagta   1980
ggactctttc cttactggct tgatgttaat caaggaaatg caatattgaa tgatgtccac   2040
atgcactctt tatttgttct tactggtcca aatggtggtg gtaaatctag tatgttgcga   2100
tcagtctgtg cagctgcgct gcttggaata tgtggcctga tggtaccttc aacttcagct   2160
gtaatcccgc attttgattc cattatgctg catatgaaag cctacgatag cccagccgat   2220
gggaaaagtt catttcagat tgaaatgtcg gagatacgtg ctttagtcag ccgagctact   2280
gctaggagtc ttgtcctgat tgatgaaata tgtaggggca cagaaactgc aaaaggaacc   2340
tgtattgctg gtagcatcat cgaaaggctg ataatgttg ctgcctagg catcatatca     2400 actcacctgc atgggatttt tgacttgcct ctctcactca gcactactga tttcaaagct   2460
atgggaactg aagtggtcga cgggtgcatt catccaacat ggaaactgat ggatggcatc   2520
tgtagagaaa gccttgcttt tcaaacagcc aggagggaag gcatgcctga gttcataatc    2580
agaagggctg aggagctata tttgactatg agtacaaata caagcagac cgcatcaatg    2640 gtccacaatg agcctcgtaa tgacagcccc agtgtaaatg gcttggttga aagcctgaa    2700 tatctgaaat acagactaga aattctgcct ggtacctttg agccgttgcg gagggaagtt   2760
gagagtgctg ttactatgat atgcaagaaa aaactgttgg atctttacaa taaaagtagc   2820
atcccagaac tggttgaggt ggtctgtgtt gctgtaggtg ctagagagca accaccacct   2880
tccactgttg gcaggtctag catctatgtg attatcagaa gcgacaacaa gctttatgtt   2940
ggacagacgg atgatcttct ggggcgcctt cacgcccaca gatcgaagga aggcatgcag   3000
gatgctacga tattatacat cttggttcct ggcaagagcg ttgcctgcca gctgaaaccc   3060
cttctcataa atcagcttcc ttcgagggc ttcaagctca tcaacaaggc agacggaaag    3120
```
cataggaact tcggtatatc tcgaatctct ggagaggcaa tcgccaccca gctaaactaa    3180

<210> SEQ ID NO 7
<211> LENGTH: 3399
<212> TYPE: DNA
<213> ORGANISM: Oryza sativa

<400> SEQUENCE: 7

```
atggccattc agcggctgct cgcgagctcg ctcgtggccg ccacgccgcg gtggcttccc      60
gtcgccgccg actcgtttct ccggcgccgc caccgccctc gctgctcccc gctcccgcg     120
ctgctattta acaggaggtc ctggtctaaa ccaaggaaag tctcacgaag catttccatt     180
gtgtctagga agatgaacaa acaaggagat ctctgtaatg aaggcatgct gccacatatt     240
ctgtggtgga agagaaaat ggagaggtgc aggaaaccat catcaatgca attgactcag     300
agacttgtgt attcaaatat tttaggattg gatccaactt taagaaatgg aagcttgaag     360
gatggaagcc tgaacacgga aatgttgcaa ttcaaatcga gtttcctcg tgaagttcta     420
cttttgcagag tgggagattt ctacgaggct gttgggtttg atgcatgtat ccttgtggag     480
catgcaggct taaatccttt tggaggcttg cgttctgata gtattccaaa agctggatgt     540
ccagtcatga atttgcggca gacattggat gatttgactc gatgtggtta ctctgtgtgc     600
atagttgaag aaattcaagg cccaacccaa gctcgtgcta ggaaaggccg atttatttct     660
ggccatgcac atcctggtag tccttatgta tttggtcttg ctgaagtaga ccatgatgtt     720
gagttccctg atccaatgcc tgtagttggg atttcacgat ctgcaaaagg ctattgcctg     780
atttctgtgc tagagacaat gaaaacatat tcagctgagg agggcttaac agaggaagca     840
gttgttacta agcttcgcat atgccgttat catcatctat accttcatag ttctttgagg     900
aacaattctt caggcacatc acgctgggga gaatttggcg aaggtgggct attgtgggga     960
gagtgcagtg gaaaatcttt tgagtggttt gatggtaatc ctattgaaga actgttatgc    1020
aaggtaaggg aaatatatgg gcttgaagag aagactgttt tccgtaatgt cagtgtctca    1080
ttggaaggga ggcctcaacc cttgtatctt ggaacagcta ctcaaattgg ggtgatacca    1140
actgagggaa tacccagttt gctaaaaatt gttctccctc caaactttgg tggccttcca    1200
tcattgtata ttagagatct tcttcttaac cctccatctt tgatgttgc atcatcagtt    1260
caagaggctt gcaggcttat gggtagcata acttgctcga ttcctgaatt tacatgcata    1320
ccggcagcaa agcttgtgaa attactcgag tcaaagagg ttaatcacat cgaattttgt    1380
agaataaaga atgtcctcga tgaggtgttg ttcatgggta gcaatgctga gctttctgct    1440
atcctgaata aattgcttga tcctgccgcc atagttactg ggttcaaagt tgaagccgat    1500
atactagtga atgaatgtag ctttatttca caacgtatag ctgaagtaat ctctttaggt    1560
ggtgaaagtg accaggcaat aacttcatct gaatatattc cgaaagagtt cttcaatgat    1620
atggagtcat cttggaaggg acgtgtaaaa agggtgcatg ctgaagagga gttctcaaat    1680
gttgatatag ctgctgaggc actgtcaaca gcggtcattg aagattttct gccaattatt    1740
tcaagagtaa aatctgtgat gtcctcaaat ggaagttcga agggagaaat cagttatgca    1800
aaagagcatg aatctgtttg gtttaaaggg aggcgattca caccaaatgt gtgggccaac    1860
actcctggtg aactacagat aaagcaattg aagcctgcaa ttgactcaaa aggtagaaag    1920
gtcggagaag aatggttcac cactatcaaa gttgagaatg cttaaccag gtaccatgaa    1980
gcttgtgata atgcaaaacg taagttctt gagttgttga gaggactttc aagtgaattg    2040
caggacaaga ttaatgtcct tgtctttgc tcaacgatgc tcatcataac aaaagcactt    2100
```

```
tttggtcatg ttagtgaagg acgaagaagg ggttgggtgc ttcctactat atctcccttg    2160
tgtaaggata atgttacaga ggaaatctca agtgaaatgg aattgtcagg aacttttcct    2220
tactggcttg atactaacca agggaatgca atactgaatg atgtccatat gcactctttg    2280
tttattctta ctggtccaaa cggtggtggt aaatccagta tgctgagatc agtctgtgct    2340
gctgcattac ttggaatatg tggcctgatg gtgccagctg cttcagctgt catcccacat    2400
ttcgattcca tcatgctgca tatgaaagca tatgatagcc cagctgatgg taaaagttcg    2460
tttcagattg aaatgtcaga gatacgatct ttagtctgcc gagctacagc taggagtctt    2520
gttctaattg atgaaatatg taggggcaca gaaacagcaa aggaacatg tatagctggt    2580 agcatcattg aaagactcga taatgttggc tgcataggca tcatatcaac tcatttgcat    2640
ggcatttttg accttccact gtcactccac aatactgatt tcaaagctat gggaaccgaa    2700
atcatcgata ggtgcattca gccaacatgg aaattaatgg atggcatctg tagagagagt    2760
cttgcttttc aaacagccag gaaagaaggt atgcctgact tgataattag agagctgag    2820 gaactatatt tggctatgag cacaaacagc aagcagacat catcagctgt ccaccatgaa    2880 atatcccatag ccaactctac tgtaaatagc ttggttgaga agcctaatta cctgagaaat    2940
ggactagagc ttcaatctgg ttccttcgga ttactaagaa aagaaattga gagtgttgtt    3000
accacaatat gcaagaagaa actgttggat ctctacaaca aaaggagcat ctcagaactg    3060
attgaggtgg tctgtgttgc tgtgggtgct agggagcaac ccccaccttc aactgttggc    3120
aggtccagca tttatgtaat tatcagacgt gacagcaagc tctatattgg acagacggat    3180
gatcttgtgg gtcgacttag tgctcacaga tcgaaggaag gtatgcagga tgccacgata    3240
ttatatattt tggtacctgg gaagagcatt gcatgccaac tggaaactct tctcataaat    3300
cagctacctt tgaaaggttt caagctcatc aacaaggcag atggcaagca tcgaaatttc    3360
ggtatatctc ttgtcccagg agaggcaatt gccgcatag                           3399

<210> SEQ ID NO 8
<211> LENGTH: 3381
<212> TYPE: DNA
<213> ORGANISM: Brachypodium distachyon

<400> SEQUENCE: 8
atgcagcggc ttctggcgag cacgatcgtg gccgccacgc cgcgttggct ccccctcgcc     60
gactctatcg tccggcgccg ccgcccgcgc cgttccccgc tccccgtcct gctattccac    120
agatcattgt acaaaccaag gaaggtttca cgaggcatta caatggtgtc taataaggtg    180
aacaaacagg gagatctctg caatgaaggc atgctgtcac atattatgtg gtggaaagag    240
aaaatggaga gctgcaggaa accatcatct gtgcagttga ctcagagact tgtgtactct    300
aatatattag ggttggatcc aactttaagg aatggaagct taaaagatgg aaccctgaac    360
atggagatgt tacaatttaa atcaaagttt ccacgtgagg tcctactttg cagagtagga    420
gatttctatg aagccattgg gtttgatgcc tgcattcttg tagagcatgc aggcctaaat    480
ccttttgggg gcttgcgttc tgacagtatt ccaaaagctg gatgtccaat catgaatttg    540
cggcaaacat tggatgattt gactcggtct ggttattctg tgtgcatagt tgaggaaatt    600
caaggcccaa ctcaagcccg tgctcggaaa ggtcgattta tctctggcca tgcgcatcct    660
ggcagtcctt atgtatttgg tcttgctgaa gtagatcatg atcttgagtt tcctgaccca    720
atgcctgtag ttgggatttc acgctctgca aaaggctatt gcttgatttc tgtgctagag    780
```

```
acgatgaaaa cttattcagc tgaggagggc ctaacagaag aagctgtagt gactaagctg      840
cgcatatgcc gttatcatca tctataccttt cacagttctt tgaggaataa ttcttcaggg     900
acatcacgct gggggaatt cggagaggga ggactcttgt gggagagtg cagtggaaag       960 tgttttgaat ggtttgatgg ttctcctatt gaggaacttt tatgcaaggt aagggagata    1020
tatgggctgg atgagaaaac taatttccgc aatgtcactg tctcattgga agggaggcct    1080
caacctttat atcttggaac tgctactcaa attggagtga tacaaacgga gggaattccc    1140
agtttactaa aaatgctact ccctccaaac tatggcgggc ttccatcaat gtatatcaga    1200
gatcttcttc ttaatcctcc atcttttgat gtcgcgtctg caattcagga ggcttgcagg    1260
cttatgggca gcataacttg ttcgattcct gaatttactt gcataccatc agcgaagctt    1320
gtgaaattac tcgagtcaaa agaggttaat cacattgaat tttgtagaat aaagaatgtc    1380
cttgatgaca ttatattaat gaatggaaac actgagcttt ctgctatcat ggacaaattg    1440
ctcgaacctg cttcggtggt tactggtttg aaagttgatg ctgatatact aattagagaa    1500
tgtagcctta tctcacaacg tataggtgaa gtcatctctt taggtgggga aagcgatcag    1560
gcaataactt catcggaata tattcccaag gagttcttta atgatatgga gtcatcttgg    1620
aaggggcgtg tgaaaagggt tcatgctgaa gaagagttca caaatgtcga tgtagctgct    1680
gaagcattat caaccgcggt aactgaagat tttctgccaa ttattgtaag agttaaatct    1740
gtgatatctt cacatggagg ttctaaaggg gaaatctctt atgcaaaaga acacgaagct    1800
gtttggttta agggaagcg attcacacca aatgtctggg cgaacacacc tggtgaacaa    1860
cagataaaac aactaaagcc tgcgattgat tcaaaaggta gaaagttgg ggaggaatgg    1920 tttacaacaa tcaaagttga gaatgcttta gccaggtatc atgaagcttg tgatagtgca    1980
aaaggcaaag ttcttgagct gttgagaggt ctttcaagtg aattgcagga caagattaat    2040
atacttgtct tctgctcgac gctgctcatc atagcaaaag cacttttgg tcatgttagc    2100 gagggtctta aagggggttg ggtgcttcct gccatatctc ccctatctaa ggactatagt    2160
actgaagaag gctcaagtga aatggattta ttgagactct ttccttactg gcttgacagt    2220
aatcaaggga atgcaatact gaatgatgtc aatatgcact cttttgtttat tctgactggc    2280 ccaaatggtg gaggtaaatc cagtatgttg cgatcagtct gtgcagctgc attgcttgga    2340
atatgtggtc tgatggtgcc agctgcttca gctgtcatcc cacactttga ttccatcatg    2400
ctgcatatga aggcctatga tagcccagct gatgggaaaa gttcgtttca gattgaaatg    2460
tcagagatcc gatctttagt cagccgtgct actggtagga gtcttgttct cattgatgaa    2520
atatgtaggg gcacagaaac tgcaaaagga acttgtatag ctggtagcat catcgaaagg    2580
ctcgacgatg ttggctgcct aggcatcata tcaaccccatt tgcatggcat tttttgacttg    2640 cctctgtcac tcggcaatac tgatttcaaa gctatgggaa cagaagttgt caatgggtgc    2700
attcagccaa catggagatt aatggatggt atctgtagag aaagccttgc ttttcaaaca    2760
gcaaggaagg aaggtatgcc tgacttgata attaaaagag cagaggagct atacagtact    2820
atgggcagaa gcaagacgtc atcaacagtc caccatggtc catccgttgc taagtctaaa    2880
gcaagtggat tggttgatat gcctgatggt ctgggaaatg gattagaact tccatctggt    2940
gcttttgcac tgctgcgaaa ggatgtcgaa ataattgtga ccgcaatatg caaggataaa    3000
ttgttggatc tctacaacaa aagaagcatc tcagagctgg ttgaggtggt ttgtgttact    3060
gtaggtgcta gggagcaacc gccaccttca actgttggca ggtccagcat ctacatagtt    3120
atcaggcgtg acaacaagct ctatgttgga cagacggatg atcttgttgg ccgtcttgct    3180
```

| | |
|---|---|
| gttcatagat ccaaggaagg tatgcagggt gccacaatat tatatatcgt ggttcctggc | 3240 |
| aagagcgttg cgtgccagct ggagacactt ctcataaacc agcttccctc gaaaggtttt | 3300 |
| aagctcacga acaaggcaga tggcaagcat cggaacttcg gcatgtctgt tatctctgga | 3360 |
| gaagccattg ctgcacactg a | 3381 |

<210> SEQ ID NO 9
<211> LENGTH: 3520
<212> TYPE: DNA
<213> ORGANISM: Vitis vinifera

<400> SEQUENCE: 9

| | |
|---|---|
| atgtactggc tgtcaaccaa aaacgtcgtc gtttcattcc ctcgattcta ctctctcgct | 60 |
| cttcttctcc gttccctgc ctgcaaatac acttcatttc gttcttctac acttctactc | 120 |
| caacagtttg agaagagccg atgtctcaac gaaaggaggg ttttgaaagg agctggaaga | 180 |
| atgacaaaaa atgttatagg attgcaaaat gagctagatg aaaaggatct ttctcacata | 240 |
| atgtggtgga aggagaggat gcaaatgtgt aaaaagccgt ccactgtcca ccttgttaaa | 300 |
| aggcttatat attccaattt gctaggagtg atcctaact tgaaaaatgg gaatctaaaa | 360 |
| gaaggaacgc tgaactggga gatgttgcag ttcaagtcaa agtttcctcg tgaagtttta | 420 |
| ctctgcagag tagggatttt ttatgaagcc atcggaattg atgcttgtat tcttgttgaa | 480 |
| tatgctggtt tgaatccttt tggtggttg cgctcagaca gtataccaag agctggctgc | 540 |
| ccagtcatga atctacgaca aactttggat gacctgacac gtagcgggta ttcagtttgc | 600 |
| atagtggagg aagttcaggg tccaactcaa gctcgttctc gtaaaggtcg ttttatctct | 660 |
| gggcatgcgc atccgggtag tccttatgta tttggacttg ttggggttga tcatgatctt | 720 |
| gattttccag aaccaatgcc tgtagttgga atttctcgtt ctgcgaaggg ttattctata | 780 |
| attttagtcc ttgagactat gaagacgttt tcagtagagg atggtctgac agaagaggct | 840 |
| ttagttacca agcttcgcac ttgtcactac catcatttat tgctgcatac atctctgaga | 900 |
| cgcaactcct caggtacttg tcgttgggga gaatttggtg agggaggact attatgggga | 960 |
| gaatgtagtg ctagacactt tgaatggttt gaaggggatc ctgtatctca acttttgttt | 1020 |
| aaggtgaagg agctctatgg ttttgatgat caagttacat ttagaaatgt cactgtgtct | 1080 |
| tcagagaaaa gaccccgttc tttacacctt ggcacagcta cacaaattgg tgccatacca | 1140 |
| acagagggca taccgtgttt gttaaaggtg ttgcttccat caaattgcac tggtctacct | 1200 |
| cttttgtatg ttagagatct tcttctcaac cctcctgctt atgagattgc atccataatt | 1260 |
| caagcaacat gcagactcat gaacaatgta acgtgctcga ttcctgagtt tacttgtgtt | 1320 |
| tcccctgcaa agcttgtgaa gctacttgag cttagggagg ctaatcatat tgagttctgc | 1380 |
| agaataaaaa gtgtacttga tgaaatattg cagatgcata gaaactctga tcttaacaaa | 1440 |
| atccttaaat tattgatgga tcctacctgg tggcaactg gattgaagat tgactttgac | 1500 |
| acattggtga acgaatgtga atggatttca gctagaattg gtaaaatgat ctttcttgat | 1560 |
| ggtgaaaatg atcaaaagat aagttaccat cctatcattc caaatgactt ttttgaggac | 1620 |
| atggaatctc cttggaaggg tcgtgtgaag aggatccatg tagaagaagc atttgctgaa | 1680 |
| gtggaaagag cagctgaggc attatcttta gctatctccg aagattttct acctattatt | 1740 |
| tcaagaataa aagctaccac agccccactt ggaggtccaa aggagaagt tgtatatgct | 1800 |
| cgagagcatg aagctgtttg gttcaaggga aaacgttttg caccagttgc atgggcaggt | 1860 |

| | |
|---|---|
| actccagggg aagaacaaat taagcagctt agacctgcta tagattcaaa aggtagaaag | 1920 |
| gttggattgg aatggtttac cacagtgaag gtggaggatg cactaacaag gtaccatgag | 1980 |
| gctggggaca aggcaaaagc aagggtcttg gaattgttga ggggactttc tgcggagtta | 2040 |
| caaactaaaa ttaacatcct tatctttgct tccatgttgc ttgtcattgc aaaggcatta | 2100 |
| tttgctcatg tgagtgaagg gagaagaagg aaatgggttt tcccctctct tgtagagttg | 2160 |
| cataggtcta aggacatgga acctctggat ggagctaatt ggatgaagat aactggttta | 2220 |
| tcaccatatt ggttggacgt ggcacaaggc agtgctgtgc ataatacagt tgatatgaaa | 2280 |
| tcattgtttc ttttgacagg acctaatggg ggtggtaaat caagtttgct tcgatcaatt | 2340 |
| tgtgcagccg cattacttgg aatatgtgga tttatggtgc ctgcagaatc ggccttgatt | 2400 |
| cctcattttg attctattat gcttcacatg aaatcttatg atagcccagc tgatggaaaa | 2460 |
| agttcatttc agattgaaat gtcagagatg cgatccataa tcactggagc cacttcaaga | 2520 |
| agcctggtgc tgatagatga aatctgccga ggaacagaaa cagcaaaggg gacatgtatt | 2580 |
| gctggtagca tagttgaaac tcttgataag attggttgtc tgggtattgt atccactcac | 2640 |
| ttgcatggta tatttacctt gggactgaat actaagaatg ctatttgtaa agcaatggga | 2700 |
| actgaatatg ttgatggcaa aacaaaaccg acctggaagt tgatagatgg aatctgtaga | 2760 |
| gaaagccttg cctttgaaac agctcagaag gagggaattc ctgaaacaat tatccgaaga | 2820 |
| gcagaagagc tgtatctttc aatccattca aaagacttaa ttacaggggg aactatttgt | 2880 |
| cctaaaattg agtcaacaaa tgaaatggaa gtcttacata gaaagttga gagtgcagtc | 2940 |
| accattgttt gccaaagaa gctgaaggag ctctataagc agaaaaacac gtcaaaactt | 3000 |
| ccagagataa actgtgtggc cattttgcca ggggaacagc cgccgccatc aacaattggt | 3060 |
| gcttcaagtg tgtatgtgtt gtttagcact gataagaaac tttatgttgg agagacagat | 3120 |
| gatcttgaag gcagagtccg tgcgcatcga tcaaaggaag gaatgcagaa ggcctcattc | 3180 |
| ctttattttg tggtcccagg gaagagcttg gcatgccaac tcgaaacgct tctcatcaac | 3240 |
| cagctccctg tccaggggtt ccaactggtc aatagagctg atggtaaaca tcgaaatttt | 3300 |
| ggcacattgg atcactccgt ggaagttgtg accttgcatc aatgagcctg cgctccttgc | 3360 |
| cacccatttt gtagaatggt tccatctttg aaatatgtac ttgaatgaca aaaccagat | 3420 |
| gaaagtggct gcagcaattt tggttttttg atgtacgttg ctccacttgc attagtatta | 3480 |
| tctacctgat gaaatatgca ttgatattgc ttgctctaca | 3520 |

<210> SEQ ID NO 10
<211> LENGTH: 3615
<212> TYPE: DNA
<213> ORGANISM: Cucumis sativus

<400> SEQUENCE: 10

| | |
|---|---|
| atggaaatat ccatctatgt cgatgtggca ttgtggcggg aagtatcgga aaccaagggt | 60 |
| tttctgttcc ggcgacgacg agttacaaac accctcctca tttcaaacca aaacgcttta | 120 |
| aaacttccaa tcacaacaag attgaagctc acaaaccatc cattttatc caccgccatg | 180 |
| tactgggcgg caacacgaac cgttgtttct gcttcccgt ggcgttttct ggctcttttg | 240 |
| attcgcttcc ctccgcgtaa cttcacctca gttactcatt cgccggcatt tatagaaagg | 300 |
| caacagcttg aaaagttgca ctgttggaaa agcagaaaag gttcaagagg aagcatcaaa | 360 |
| gctgctaaga agtttaagga taataatatt ctccaagaca ataagtttct ttctcacatt | 420 |
| ttatggtgga aagagacggt ggaatcatgc aagaagccgt catctgtcca gctggttaag | 480 |

```
aggcttgact tttccaactt gctaggttta gatacaaacc tgaaaaatgg gagtcttaaa      540
gaaggaactc ttaactgtga gattctacag ttcaaggcaa agtttcctcg agaagttttg      600
ctctgtagag ttggagattt ttatgaagca attggaatag atgcttgcat acttgtggaa      660
tatgctggtt taaatccttt tggaggtcag cgtatggata gtattccaaa agctggttgc      720
cccgttgtga atcttcgtca aactttggat gatctgacac gcaatgggtt ctcagtgtgc      780
atagtggaag aagttcaggg cccaattcaa gctcgttctc gcaaaggacg ttttatatct      840
gggcatgcac acccaggcag tccctatgtt tttgggcttg tcggggttga tcacgatctt      900
gactttccag aaccgatgcc tgtgattgga atatctcgat ccgcaagggg ctattgcatg      960
agccttgtca tagagaccat gaagacatat tcatcagagg atggtttgac agaagaggcc     1020
ttagttacta aactgcgcac ttgtcaatac catcatttat ttcttcacac gtcattaagg     1080
aacaactcct caggcacttg ccgctggggt gaatttggtg agggtggccg gctatggggg     1140
gaatgtaatc ccagacattt tgagtggttc gatggaaagc ctcttgataa tcttatttct     1200
aaggttaaag agctttatgg tcttgatgat gaagttacat ttagaaatgt tacaatatcg     1260
tcagaaaata ggccacatcc gttaactcta ggaactgcaa cacagattgg tgccatacca     1320
acagagggaa taccttgttt gctgaaggtt ttgcttccat ccaattgtgc tggccttcct     1380
gcattgtata tgagggatct tcttctcaat cctcctgctt atgagactgc atcgactatt     1440
caagctatat gcaggcttat gagcaatgtc acatgtgcaa ttccagactt cacttgctttt    1500 cccccagcca agcttgtgaa gttattggaa acgaggaggg cgaatcatat tgaattctgt     1560
agaatgaaga atgtacttga cgaaatatta caaatgcaca aaaattgcaa gctaaacaat     1620
atcctgaaat tgctgatgga tcctgcatct gtggcaactg ggttgaaaat tgactatgat     1680
acatttgtca acgaatgtga atgggcttcc agtagagttg atgaaatgat ttttcttggt     1740
agtgaaagtg aaagtgatca gaaaatcagt tcttatccta ttattcctaa tggttttttc     1800
gaggacatgg aattttcttg gaaaggtcgt gtgaagagga ttcacattga agaatcttgt     1860
acagaagttg aacgggcagc tgaagcactc tcccttgcag ttactgaaga ttttgtccca     1920
atcatttcta gaatcagggc tactaatgca ccactaggag gtccaaaggg agaaatatta     1980
tatgctcggg accatcaatc tgtctggttc aaaggaaaac ggtttgcacc atctgtatgg     2040
gctggaagcc ctggagaagc agaaattaaa caactgaaac ctgctcttga ttcaaaggga     2100 aaaaagttg gggaggagtg gtttaccacg aagaaggtgg aggattcttt aacaaggtac     2160
caagaggcca ataccaaagc aaaagcaaaa gtagtagatc tgctgaggga actttcttct     2220
gaattgttag ctaaaattaa cgtcctaata tttgcttcca tgctactcat aattgccaag     2280
gcgttatttg ctcatgtgag tgaagggagg aggaggaaat gggttttttcc cacccttgct     2340 gcacccagtg ataggtccaa ggggaaagtt gcgatgaagc tggttggtct atctccctat     2400
tggtttgatg ttgtcgaagg caatgctgtg cagaatacta ttgagatgga atcattattt     2460
cttttgactg gtccaaatgg gggtggaaaa tctagtttgc ttcgatcgat ttgtgctgct     2520
actttgcttg ggatatgtgg atttatggta ccggcagagt ccgccctgat tccccacttc     2580
gactcaatta tgcttcatat gaatcttttt gatagtcctg ctgatggaaa agttctcttt     2640
caggtggaaa tgtcagagat gagatccatt gtcaatagag taacggagag aagtcttgta     2700
cttatcgatg aaatctgtcg tggaacagaa acagcaaaag gaacttgtat tgccgggagc     2760
attattgaag ctcttgataa agcaggttgt cttggcattg tctccactca cttgcatgga     2820
```

| | |
|---|---|
| atatttgatt tgcctttaga tacccaaaac attgtgtaca aagcaatggg aactgtttct | 2880 |
| gcggaaggac gcacggttcc cacttggaag ttgattagtg gaatatgtcg agagagcctt | 2940 |
| gcctttgaaa cagcaaagaa tgaaggaatc tctgaagcta taattcaaag ggctgaagat | 3000 |
| ttgtatctct caaattatgc taaagaaggg atttcaggaa aagagacgac agatctgaac | 3060 |
| ttttttgttt cttctcatcc aagccttaat ggtaatggca ctggaaaatc caatctcaag | 3120 |
| tcaaacggtg tgattgtaaa ggctgatcag ccaaaaacag agacaactag caaaacaggt | 3180 |
| gtcttgtgga agaaacttga gagggctatc acaaagatat gccaaaagaa gttgatagag | 3240 |
| tttcatagag ataaaaacac attgacacct gctgaaattc aatgtgttct aattgatgca | 3300 |
| agagagaagc cacctccatc aacaataggt gcttcgagcg tatatgtgat tcttagaccg | 3360 |
| gatggcaaat tctatgttgg acagactgat gatctggatg gtagggtcca atcacatcgt | 3420 |
| ttaaaggaag gaatgcggga tgctgcattc ctttatctta tggtgcctgg gaagagctta | 3480 |
| gcttgccaac ttgaaactct tctcatcaat cgacttcctg atcacgggtt ccagctaact | 3540 |
| aacgttgctg atggaaagca tcggaatttt ggcacagcca atctcttatc cgacaatgtg | 3600 |
| actgtttgct catga | 3615 |

<210> SEQ ID NO 11
<211> LENGTH: 660
<212> TYPE: DNA
<213> ORGANISM: Gossypium hirsutum

<400> SEQUENCE: 11

| | |
|---|---|
| ggcacgaggt tgctattgct gcaagggaac agccacctcc atcaactatc ggtgcttctt | 60 |
| gcgtatatgt catgttcaga cctgataaga aactatacat tggagagacg gatgatcttg | 120 |
| atggtcgaat tcgttcgcat cgttcaaagg acgggatgga aaatgcttct ttcctatatt | 180 |
| tcacagttcc agggaagagt attgctcgcc aactcgaaac tcttctaatc aaccaactct | 240 |
| taagtcaagg cttcccgatc gccaacttgg ctgacggtaa gcatcagaat tttggcacat | 300 |
| ccagtctctc atttgacggc ataaccgtag cctaacgagt taaaatgtat atcaatacgt | 360 |
| aatttatatc gaaattgaca tagaagtggc ggcagcaatt ttgccttga tctcggttgc | 420 |
| tccacttgct ttgtacatgc atcaccctt taaccaaggg taaagttttc tagtcataat | 480 |
| ttaatagcat gtatctatta agtccatttt gaggtttata tgaatcaggt tttcatcatt | 540 |
| aattggttaa attctgttat tagctcctct actttactaa agttgtagat ttagttctta | 600 |
| tactttaatt agattatttt tactctatac ttttcgaatg ataaaatttt agtcttcatt | 660 |

<210> SEQ ID NO 12
<211> LENGTH: 2225
<212> TYPE: DNA
<213> ORGANISM: Oryza sativa

<400> SEQUENCE: 12

| | |
|---|---|
| agaaaagcta aaatggatga aaaaaacaga gaaaagaaa tcctacccctc catagcgagc | 60 |
| agtggtggtc tgcactctgc aggcaggcag gcacccaggc ctgcagctcg atggcgccgc | 120 |
| cgccgccgtc gccgccgcga tctctcacct ccgtctccct ccggactcct ctgagccctc | 180 |
| tcctcttcct acggccagct tcttgcaatc catcggcggt ctccggctcc tgcagcagcg | 240 |
| gagcatgccg cggcgtgcgc tgctcggcgg cgaacaagcc ttctccttcc accgctccgg | 300 |
| gcaccgaggt aaggtagccg gctagccgcc ccccatattc ttgtttctgt gttgatcgga | 360 |
| gctcgatggc tggggtgctc tgggctcgtc gtcgtcggtc gatcgtcatg gcttgcttcg | 420 |

```
tttcttgcag ctcgacctcc atggcaaaga taaggagtga ggtgctgtcc ccgttccgct    480
ccgtgcggat gttcttctac ctcgcgttca tggccagcgc cgggctcggg gccctcatcg    540
cgctcacgca gctcatcccg cgctgtcca gcccggcgag gcggccgcc gcggggaga      600 cgctcaaggg cctgggcatc gacgtcgcgg cggtctccgt cttcgcgttc ctctactggc    660
gcgagagcaa ggccaaggac gcgcaggtgg cgaagctcac gcgggaggag aacctgtcca    720
ggctcaggat ccgcgccggc gagggccgcc cgcccgtccc gctcggcgag ctgaggggca    780
ccgcgcggct cgtcatcgtc gccggccccg cggcgttcgt caccgagtcg ttccgccgga    840
gcaagccgtt cttgaaggac ctcatggagc gcggcgtgct tgtcgtgccc ttctcgacgg    900
acggcaacgc gccggacctg cagttcgacg aggccgacga ggaggaggag gaggcggcgg    960
cggcggctgg gaagatgaag cggaggctct ggcagctcac tccggtttac acttctgaat   1020
gggccaagta cgcgcaaagc cgggatccca tgaatttagc tgcttaaatt tcttcttcat   1080
gtcaatcgaa attcaaatgc aaattagtat ctcatttca aatcgattgc tgcttcttgc    1140
agatggctag atgagcagaa gaagctagcc aacgtgtcac ctgattcccc cgtgtgagta   1200
tcaaaaacta ctctgaattt gtctgaaaat ataactgaag tttctgcagc tgctgaactg   1260
aaaccgcatc actcttgcag gtatctctcg ctccggctgg acggccgcgt ccgtggcagc   1320
ggcgtcgggt accgccgtg gcaagcgttc gtggcgcagc tgccgccggt gaaggggatg    1380
tggtccggcc tccttgatgg gatggacggg agggtgcttt gaatatttga ctgatacaga   1440
ccgtgaaaac attagttgat tggagaaaaa aaaggacggc cgggttcgat ctatagctta   1500
tactagaaca agaacaggaa gagtttgatg attgctttaa cttctgtggg gttgattttg   1560
cttcctgcat cccagcgaca tcgcccaagt gaatgtgata tgccatgtgc ccatgtacat   1620
gttgttttgc agcctacgtg acttgattat taacgagaat cctgtgtcaa agatcgcttt   1680
ttccgtggta ggcttctcca tttattttta tttttgaata tatatacgaa ccgtgacaaa   1740
tctgatggaa cactggacca tgggggtaat gatactgtag tcgcctggtc tttttatcag   1800
gcgctaaatg caaacaatca gacagcttaa acaacctgag gttgttcagc cagcccagaa   1860
tacaaaaagc ccatggaccg tgagcccgtg aaaccatggc ccacccatca gtcacgtcac   1920
gtcgggacgt gtgcgcacta ccccgagaag cgcgcggccg taagccacaa ccacaacccc   1980
acaccgcctc ttggctgctc gcgccctgac acttcccaaa accccaaacc gcccatatct   2040
ctctcctctt ctccgctcct cgcttccccc aaaaccctcg cggtggcggt gggccgccgg   2100
tctcattccg ccggcgtcca cggaggcggc cggagccagg cgctccgcgg gccggggagc   2160
caccggaagg ctggaaccct agcggcggcg ggtctcctcc ccctccccgc gcgccgggcg   2220
gcgcc                                                              2225
```

<210> SEQ ID NO 13
<211> LENGTH: 2000
<212> TYPE: DNA
<213> ORGANISM: Solanum lycopersicum

<400> SEQUENCE: 13

```
cacgcatcaa catgtactag ctaactttgt ccaccaagga atatctatta ccttcaacca     60
gcaacaagta tcagctaact ttgtccattt aggttaaaac cttgactaaa tccattgaaa    120
acctattacc tcccaccagc aacttatgcc aactaacatt gtctaccaag ggatatccgt    180
tgcctcaaca ttgtccatcg agggatatcc attgcctccc agcagcaaca agtaccagct    240
```

| | |
|---|---:|
| aacattgtcc aatcgaggga catccatacc aaataatttt tgagaaagta attatttagg | 300 |
| gtgatgttta tttgtgcttg gaaaacaaat agccattgaa ttagtaaaat ttgcaattaa | 360 |
| atcacattac aaaaatgtct aaggtaattt atcctaaata caatagtgat atcaataata | 420 |
| atatatttga gtgtaatgtc ataatcaaga atttataaaa ataatatgtc agtaggttta | 480 |
| attactgata tattaaaatt gtttcgataa attcttgatt taaagagtac aatcaacaaa | 540 |
| taaaagaaca aatagtaaaa tataagatac gtatatttt aaatagtagt gtacagtagg | 600 |
| actagatgac aaaataaaat tgtaagaaga agaggatagt ctttaccatt ctcacacaaa | 660 |
| atcatatctc gtcacaaatg aatttacagt tactcataaa tatatttaat aaaatgatag | 720 |
| tattagcaaa acataattga tgtgttagtt catcagttat tatgcactta aagttattta | 780 |
| taaaaaaaaa aggtcaaatg ccccccctaa tctgttgtcc gatttctaag tacgtacgta | 840 |
| aactttagag gggtcatatc accccctgaac tgtttaaaat tgaaattttt gtactcctaa | 900 |
| aaagccataa ccatatttat gttgatgagt gaaactcacg cgttttgaca catgaaaaat | 960 |
| ccattagaaa aagttttcct tcaattttt cattattctt tattctttc ttctattttt | 1020 |
| tcaccatctc tccaacacaa aaatattttc actatttct ccattatcat aaacaccaaa | 1080 |
| ggttcactaa tcactacaat cttcaaaacg aaaaggtcgg cagtgatttt gattcttatt | 1140 |
| tgtcatttcg cccactactt agttggtgct aagatcattt tcatgaatac atgtgtcaaa | 1200 |
| tttctcaaat tagagtaaat gaataacaat ggaggaaagt cgaatgtggg ttttattaaa | 1260 |
| aatttaaaat tcttcgtttg tttgaattaa aattacaaat ttggagcttt gaagaaccaa | 1320 |
| aaaaagaatt tgccgaccta attgacctta atttgtcgtt tgaccatgta caaggatgat | 1380 |
| taacaactcc aataatatcg ataaagagtt gatttttcaaa aactcttaat tccatacaca | 1440 |
| aattaaaatc aagaaaaatg cgaaaatttt atgaacaaat ctaataacaa agaacgaaaa | 1500 |
| aatttctacg aagaacaaag aaaagaataa ggaagaagat aaaatatttg ttttggtgct | 1560 |
| cactctatca gggagtgaaa tacattcact atggagatga taatttcaat tttaaacagt | 1620 |
| tcaggaaggt gatatgcgta aagtttaagt taatagataa tcaaagatat ctgttgacgt | 1680 |
| attgattcaa tgttaaatat acagttgagt tacttataac ttataaatac aataagtaat | 1740 |
| tttttttcctt ctaccatttg aaaaaaaata acgcgtacgt cattgtcttc aatcatcaac | 1800 |
| gatttattat tttcaatgtg attatattat taagtaatta attcgtccca aataccaata | 1860 |
| tctactaaca ttctttgcct aatgtttaat tgtaattcct acagatttta tttttttgaa | 1920 |
| aataatataa agtacaccat ttctctgccg ggaagaacaa atacacagag agagagtgta | 1980 |
| ttgtgcactg atatcgagca | 2000 |

<210> SEQ ID NO 14
<211> LENGTH: 2000
<212> TYPE: DNA
<213> ORGANISM: Sorghum bicolor

<400> SEQUENCE: 14

| | |
|---|---:|
| tggcacataa gtaaaattgc tgacttggta gggtcattta atgaaggaat ttcatgagat | 60 |
| gagagagaag tttcatcccc atgaaactca tatggctcgg ttacttggta actgtgtcat | 120 |
| caaactatgc attgagactg gcctgcatgt ttcatgagag tgtcatgcac attaaataag | 180 |
| atatcacata agcaaaattg ctgacttagc tgggtcatta aatgaaggag tttcatcaga | 240 |
| tgagagagga gtttcatctt cataaaactc ttgtggctcg gttacctagt ttttagtctc | 300 |
| ggtaactgtg tcatgaaact ataatacatg ttttatggaa gtgtcacgca tattatagggg | 360 |

```
tgccacataa gtaaaattgt taacttgaca gagtcattaa atgaagaagt tcatcagat      420 gagagaggag tttcatcccc ataaaattca tgtggctcag ttacctagtt tatagtcttg     480
gtaactgtgc catgaaacta tgcattgaga ctagcctaac aaggtgataa ggccagtctc     540
aatgcatgtt tcataagagt gtcatgcaca ttaaataaga tgccacataa gcaaaattgc    600
tgacttgaca gggtcattaa atgaaggagt tcgttagat gagagaggag tttcatcccc     660
atgaaactct tatggctcga ttacctagtt tatagtcttg ataactgtgt catgaaacta    720
tgtattaaga ctggagactc aaatacaaat tgtatatagc ctatggctct atttgtttcc    780
gcgaccggcc aacccgtgac cacgattaag caaacacgac tcgagatcgt gtatgtataa    840
atttggatct tcggtggttt aattttagtt tttttagcta agagaattta tatacatttt    900
ccattattaa accatgtttc aaggtttcta attccatgct ctaaataat atattatttt     960 atggaaaata gatattttg aaattaaatg tatgtataaa ttttcaagac tatataaaat    1020
aataaaagct ctaatctatt gatgtagttc aattttatc tccctagagc tgatgtggca    1080
ccacatacgg tgccacctag gttaaaacta acctcaaaac ccggctaggt tgtgatttg    1140 cctcgtattt gatagtttag ggtgtactcc gtataagatt atctgtatat tcagagatta   1200
gaaaatcaaa cacatctact aaattttaga acaagcatca ccctgtttgg cggctagtcg   1260
taaaagtaac tgatgttaat ttattgtgag agtaaaatac tgttgtttga taataaaact   1320
tttacttata atttcaagct aatagagccc ataaagacaa acctgtctca caagttagaa   1380
ttcttacaac ttttcgtcta atcacatcga atatttgaac acatgtatat agtattaaat   1440
ataataaaaa tatttaattg tacagtttac ctatatttac aagacgaata ttttaaatat   1500
aattagttta ttattaaaca ctaattacta taattataaa tatactacaa tataaaaaaa   1560
aaactttcgt ttttgcgagc taaacaccgg gacacaaaac gctcctgtct cctgggcggc   1620
ttgggcctgc cagagcccgg gaaccgtgag cccgtgaccc cagcgggccc aaccagtcag   1680
acgagagtcg aaaggcgtgc gcactacccc gagaaacgtg cgacaggaac ctccccttc    1740 ccggcctggg agcggcctgg cgagtggcga ctggcgtctt ccgcggttcc ccccagttcg   1800
cctccttcac tgccgcccgc gcgccccgac acgcctgaaa aaccccacct ctcccctccg   1860
ctccgcctct ctcgccctcc acttcccacg ccccacgccg cctgccattc cagttccagc   1920
gtggactcga cgccagcgcg gagacgcgcg tctcgaagca ctagccccc gttgttctgc    1980 cgcgccggcg cgccggcgcc                                               2000

<210> SEQ ID NO 15
<211> LENGTH: 2049
<212> TYPE: DNA
<213> ORGANISM: Arabidopsis thaliana

<400> SEQUENCE: 15
catatgaaac atttcctgta gcagtgagat ggttacaaga ggatccatac ccgagtgctg     60
tgcaatcaga caaactacaa gcatagtcga tattatcagg caagtcatcg aggttatatg    120
cattagggtc aagaatacac caagttttgg gcagatactt cacatcttcc acaggaacca    180
aaggcttgtc atttccttta cctgacaagt caagctcata tttcggtctc ccatcaaact    240
caaagatccc ccagtgcctc tcaaaagtcc ccggtgctat actcttggcg tcctcatcaa    300
caaggctgaa aaggtaaaca tccataatca ctcctttcct cgcaggcgtt ccatttccag    360
acatagcatg ctttaccatt ccctgattga atctctttgc actctttaca ttagcgttct    420
```

| | |
|---|---|
| tgtctccatc cgtaggccac ccgacctctc ctacaatgat cttcatcccc aagaagctat | 480 |
| atctctccat agcacaaatc aaagtgtcga gattcgcatc aaacacattg gtgtagacca | 540 |
| aatttccatc tctcaaagac ttgttagtcc catcaaagaa ggcaaaatcc aaaggaaagt | 600 |
| aagcatttcc atagagacta agaaaagggt atatgttaac cgtgaaaggc gaatcatgtg | 660 |
| aatacaagaa attgattatc tcaatcgttg catcccttag ctcaggtcta aagtctccag | 720 |
| ctgatggaac agggttcgct tcaggggaaa aatagatgtc tgcgttgaaa ggaacagtga | 780 |
| cttcacatt tttcagatca gcttcctcta gtgctcgttg gatgttgata agagctggta | 840 |
| atgtgaactc aacgtaagtt ccattatatg tctgaaggaa aggctcgttt ccaacagcta | 900 |
| tgtacttgat gttgactcca ccgttgtaag aataagcagt aacgttttct tcaacccatg | 960 |
| aagctgctac agatgtatct tgagccattt cttt aagaaa ccggtttggt attcctatca | 1020 |
| tgacttcaat gtctgagcca attagagcgt ctaagatgtt ttggtcggct tcaaatagtt | 1080 |
| tcagcttagt gaaactattg tccattagca tcttcacaac ctttt ctggt ggaagctggt | 1140 |
| gactcgccat tattccccag ttaactccta cattactcgt gttgcttgag gcaatggaaa | 1200 |
| cttgtgagat gataagaaag taacaaagaa taatctgatg attataaaag tggtttgttg | 1260 |
| ttaactttga tctctctcct gccattttt tctctgttta tgagtctttt cttctctttt | 1320 |
| ctttatggag tctttgttaa gggagaagat gaaatgtgat tggatatttg tgatttgtac | 1380 |
| ttagttcagt taaagaagca gacacaacat gcaaaatagc cattggtgaa acactttgtg | 1440 |
| catgcctatc tgataaatcc attgactcac cacaaattct tatgtaattc tagatgtttc | 1500 |
| gtatttgttg tgccaaacaa acacacacac tcacacactg cactgagtct agacatttag | 1560 |
| tggttttgtt ttcttattat taatactcat tagagtatta agtttgtata gaattcagaa | 1620 |
| acaactgata gtcatttt aa gatttctaat tacaaaactt ttgatcctct ttgaaaagca | 1680 |
| gagaaattac aatctttaca acaaaactg agagattaga gatgtgttca tagagatggg | 1740 |
| ttctttgtta gacattccaa aaagatacaa aactagccga tgattaattt tggtaaatta | 1800 |
| atgaacaaga atgtaatttg aaacattata gggagcaaat gagaaattac tctttttaaa | 1860 |
| aggctaaaat cctaattacc tttaaactaa gaagacaaga agagaagaga aaacatgttt | 1920 |
| tccattagag gactgtgaga ttgtgaattg catagtcgtc gtcttctggc gggaaaagaa | 1980 |
| gccctagaaa aagggtgaaa ggtgaaaact ctacttcttc ttcttcttct tcttcagagt | 2040 |
| gtgagagag | 2049 |

<210> SEQ ID NO 16
<211> LENGTH: 946
<212> TYPE: DNA
<213> ORGANISM: Arabidopsis thaliana

<400> SEQUENCE: 16

| | |
|---|---|
| aaaagttgaa acagcaaagt agcgatagat ttcgtgaaaa cagagaagcg gacatatctt | 60 |
| gaaacacatg gcagcgattt ctccatggtt atcttctcct cagagctttt cgaatccccg | 120 |
| cgttaccatt acagattcca gaagatgttc atcaatttct gcggcaatct ctgttcttga | 180 |
| cagctccaac gaggaacaac atcgaatttc gtctagagat catgtgggga tgaagagaag | 240 |
| agacgtcatg ttacagatag cttcctctgt tttcttcctt ccattggcca tttcacctgc | 300 |
| atttgcagag acaaatgcat cagaagcttt ccgtgtgtac acagatgaaa cgaacaaatt | 360 |
| cgagatatca atcccacaag attggcaagt cgggcaagca gaacctaatg gattcaagtc | 420 |
| aatcacagct ttttacccac aagaaacttc aacttccaat gtgagtatag cgatcactgg | 480 |

```
actaggtcca gacttcacca ggatggaatc attcggaaag gtcgaagctt tcgccgaaac   540
attggtcagt ggattggata aagctggca aaaaccagta ggagtgactg caaagctaat   600
cgatagcaga gcttctaagg gattctatta catcgagtac accttacaaa accctggaga   660
agctcgcaag catttgtact ctgcaattgg aatggcaaca aacggatggt acaaccgttt   720
atacactgtc acaggacagt ttacagatga agaatctgct gaacaaagct ctaagatcca   780
gaagacagtc aagtctttca gattcatctg agaatgtcat tcatatctat cagcggaact   840
aaattataga attgatcaaa caatttgttt actgaacaat tacttttttg caatgaaatt   900
ctgagaaaag agcctactcc atactttgaa gtaagcttca gtaaac        946

<210> SEQ ID NO 17
<211> LENGTH: 807
<212> TYPE: DNA
<213> ORGANISM: Arabidopsis lyrata

<400> SEQUENCE: 17
tccagaagat gttcatcaat tcctgtagca atctcagctc tagacagctc caacgaggaa    60
caacatcgaa tttcgtctag agatcatgtg gggattaaaa aagagaaagc catgttacag   120
atagcttcct ctgttttctt ccttccattg gccgtttcac ctgcatttgc agagacaaat   180
gcatcagaag ctttccgtgt gtacacagat gaagcgaaca aattcgagat atcaatccca   240
caagaagatt ggcaagtcgg gcaagcagaa cctaatggat tcaagtcaat cacagccttt   300
taccctcagg aaacttcaac ttccaacgtg agcatagcga tcactggact aggtccggac   360
ttcaccagga tggaatcttt tggaaaggtc gaagctttcg ctgaaacact ggtcagtgga   420
ttggatagaa gttggcaaaa accagcagga gtgactgcaa agctaatcga tagcagatct   480
tccaagggat tctattacat cgagtacacc ttacaaaacc ctggagaagc tcgcaagcat   540
ctgtactctg caattggaat ggcaacaaac ggttggtaca accgcttata cactgtcaca   600
ggacagttta cagatgaaga atctgctgaa caaagctcca agatccaaaa gacagtcaag   660
tctttcagat tcatctgaga atgttattca tatctatcag cggaactata ttattgaatt   720
gatcaagcaa tttgttttact gaacaatcac ttttttcaat gaaattctga gaaaagagcc   780
aactccatac tttgaagtaa gcttcag                                        807

<210> SEQ ID NO 18
<211> LENGTH: 1054
<212> TYPE: DNA
<213> ORGANISM: Cucumis sativus

<400> SEQUENCE: 18
ggagcgcatt gtacaaagaa aatccatctc taatctttga gtggactaca agcatggcga    60
tggcgtccct tctttcaccc agcgctgtaa tcctacgccc tcactcattc cgcttctcac   120
aatcatcact ctccaatgga ttctccatta ttcctatccg ctcaacactt cgtgttttct   180
gctctgccaa tggcaacagc atccacactt ctaacaaaaa cccagttatt tggcgagcgg   240
ggtcaacaga cgagaaatta tgctagggat tggattcact gcattttcat ttcaagaagt   300
tgtttctaat gccctagctg agagtgttgt ggttgctgaa gattatcgga cgtatacaga   360
cgaagcgaat aagttcagct tggtgattcc tcaagattgg caagtgggta atggtgaacc   420
gaatggattc aagtcggtta cggcattttt tcctcaagaa acttcaactt ccaatgtcag   480
tgttgtaatc tcggggcttg gtcctgatta cacgaggatg gaatcctttg gcaaggttga   540
```

| | | |
|---|---|---|
| ggaatttgct gatacattgg tgagtggact ggacagaagc tggaaaaggc caccaggtgt | 600 | |
| ggcggcgaaa cttatcgact gtagatcatc taaagggata tattacatag agtacacact | 660 | |
| gcagaatcca ggtgaaagcc gcaaacattt atactcagca attgggatgt catccaatgg | 720 | |
| ctggtacaat agactttaca ccataacagg acagtatgca gatgaagaat cggagagcta | 780 | |
| tagctccaaa atcgagaagg ttgtcaattc cttcgctttc atttgatgat tgccacagaa | 840 | |
| ttggcctcca ccacactatc ataatggtta aatgttttcc acatctctct ctaattatag | 900 | |
| ttctcttttg ttattattat tattattatt ttttgtaatg agttctaaac ataatattga | 960 | |
| attgtctttg atgcatctat attttacat tttcacgagg aatgaattca catttctatt | 1020 | |
| aattcataaa agaatccaca aaacagaaaa aaaa | 1054 | |

<210> SEQ ID NO 19
<211> LENGTH: 795
<212> TYPE: DNA
<213> ORGANISM: Ricinus communis

<400> SEQUENCE: 19

| | | |
|---|---|---|
| atggcttcaa tttctttact ctgttgcaat tgctacttca catctttctc caacaagaca | 60 | |
| cctctccatc ttttgaaacc taacttaaac ttcctctctg cttcaccttc ttttcgattt | 120 | |
| aacagttgca gaaagcaaca tcttccatgt tgcaccaact ctttcccaga cgaagaccaa | 180 | |
| caccaaccat tattctgtcg ttttaggctt caagaaccat atggaagaag agaagctttg | 240 | |
| ttcagcgtgg catttaccac tgggtttact tttccagggc ttatttctaa tgcatttgca | 300 | |
| gagattgatg acttccgcct ttatactgat gatgccaaca agttccaaat atcgattccc | 360 | |
| caagactgga gagtaggtgc tggagaacct aatgggttca aatcagtgac cgctttctac | 420 | |
| ccagaagaag cttcaggctc tagtgtcagt gtagtgatca caggactcgg tccggatttt | 480 | |
| actagaatgg agtcttttgg caaagtggaa gccttcgccg aaactctggt tagtggattg | 540 | |
| gacagaagct ggcaaaggcc cccaggcgtt gcagcaaaac ttatcgactg taaagcgact | 600 | |
| aaagggattt actacattga gtacacatta caaaacccag gcgaaggtcg caaacatctg | 660 | |
| ttttctgctc ttgggatggc tttcaatggt tggtataaca gactgtatac agtgacaggg | 720 | |
| cagtttgtgg aagaggagtc agagaattat ggatcaaagg ttcagaaggt tgtttcatca | 780 | |
| ttcaagttca tctga | 795 | |

<210> SEQ ID NO 20
<211> LENGTH: 1028
<212> TYPE: DNA
<213> ORGANISM: Vitis vinifera

<400> SEQUENCE: 20

| | | |
|---|---|---|
| caatcaaaaa aagcatggct ctgtattttc cacttcctct ccgttctggg tcctgcgact | 60 | |
| tctcagctta ttcgagtaaa aaaggttatg ggtcaagaac cgggaaatgt ggaaaaaagc | 120 | |
| aacgtgttgt cttctgcaag aatgagaaca aggaagaaga aaaacaagt tttgggatta | 180 | |
| aagaacaaca tggaggtgga agaagggagg ttgtgctaca gatggtgttc agtacaattt | 240 | |
| cccttcaggc aattgttcct aacgcactgg ccgatactga ggtgccagag gatttcaagg | 300 | |
| tttactcaga tgaggtcaac aagttcaaaa tacagattcc ccaagattgg caggtgggtt | 360 | |
| caggagaacc aagtggattt aaatcagtga cagcattcta cccagaagaa gcttctggtt | 420 | |
| caaatgtcag cgtagttatc actgggcttg gcgcggattt taccgactc gagtcttttg | 480 | |
| gcaaagttga tgcttttgca gagaatctgg taaatggatt ggatagaagc tggcaaaggc | 540 | |

```
ccctggtat tgctgcaaaa ctcattgact gcagagctgc taatgggttt tattacattg    600
agtattggct tcagaatcct ggggaaagtc gtagacattt attttcagct gttgggatgg    660
caaacaacgg ttggtacaac aggctttata ctgtgaccgg acagtatttg gaagaagaat    720
cagaaaaatt cagttctaaa attgagaagg ttgttgcatc cttcaggttt atttgaagaa    780
aaatttgcat gttcaggata taaactgagg ctgaagatta ctggttcagc aactctgtgg    840
atttcacaat gcacacgaat tggcattgtg caaaaagatg agatgattta tatactcaga    900
ttgcatcagg tgtctttttgt tgtaaaattg taaggaaggg gaagggaaat tatctctatg    960
ctaccattga aaattttttc cacacctttg cagttgcttc acattcattt gcagaattga   1020
tggatgag                                                            1028
```

<210> SEQ ID NO 21
<211> LENGTH: 726
<212> TYPE: DNA
<213> ORGANISM: Medicago truncatula

<400> SEQUENCE: 21

```
atggcatcca tttcatggtt cagctgtcta cacatccgac caacagccac tgccggcgac     60
aaaggtttat catctcccat aaccgtggaa catcataaaa caagaccaca aaatttactc    120
tcatcctcgg aagaaggact tgcgattaat agaagacaac taattcttta cacatccact    180
gcagcaattg cagcttcatc tactgactca aatgcattgg cactcaatga tgtatctgag    240
gattttagta tctacactga tgatgagaac aagttcaaga tagatattcc acaagagtgg    300
caaattggaa caggagagtc tgcagggttc aaatcattaa ctgcttttcta cccaaaagag    360 caatctaatt ccaatgtgag cgttgtgatc acaggagtgg gtccagattt cactaagatg    420
gaatcattcg gcaaagttga agaatttgct gacactctgg ttagtgggtt ggatagaagc    480
tggaaaaaac cacctggtgt ggctgctaaa ctcatagatt gtaaatcatc taaaggattt    540
tatttcattg agtatacgct gcaaagtcct ggtgagggtc gcaaacatct atattcagct    600
attgggatgt taacaaatgg ctggtataac agactgtata cagtgacagg acagtatggg    660
gaagaggaaa cagacaagta tgcttccaaa attcagaagg cagttcgatc gtttaagttc    720
atataa                                                              726
```

<210> SEQ ID NO 22
<211> LENGTH: 579
<212> TYPE: DNA
<213> ORGANISM: Populus trichocarpa

<400> SEQUENCE: 22

```
ggaactaaaa gaagagaagc tttattcaat atggtattta ctgctttac tttccctgca     60 attgcctcta ctgcattggc agccacaggc gtggcagagg attcacgtgt ttataccgat    120
gatgcgaaca gtttaagat atctattccc caaggctggc aagtaggtgc aggagaacca    180
agtggataca atccgtcac tgctttctat ccagaagaag cttctaattc aagtgtcagc    240
gttgtgatca ccgggcttgg tccagatttt actagattgg aatcatttgg caaagttgat    300
gcctttgctg agactctggt gggtggattg acaggagct ggcagaggcc cccgggcgtg    360
gcagcaaaac ttatagactc taaagctgct aatgggcttt actacatcga gtatacgctg    420
caaaatccag gcgaaagtcg cagacatttg ctttcagcac ttggagttac attcaatggt    480
tggtacaaca gactatatac ggtgacaggg cagtttgtcg atgaagaatc agagaaattc    540
```

```
ggcaccgaga tcaggaaggt atatcagaac tcttcattt                             579
```

<210> SEQ ID NO 23
<211> LENGTH: 951
<212> TYPE: DNA
<213> ORGANISM: Lotus japonicus

<400> SEQUENCE: 23

```
ggaatggcgt ccatttcctg gtcttgttgt ctgcgttggc gaccaacaat atccgaccgc       60
acagcctctg cggccgacaa aggtttctca cctcccataa cattggagca tcataaaaaa      120
acaccatgtt tactatcagc acgcaattcc tccattgaag aaggacatgc ggttaacaga      180
agacaacttg ttttctacac gtcactagct gcatttgcag ctgccccatc tactgtcctg      240
aaggcattgg cactcaatga tgtggttgag gatgttcgta tctacattga tgatgagaac      300
aagttcaaga tagagattcc ccaagattgg gaagtaggaa caggagactc tagtgggttc      360
aaatcattaa ctgcattcta ccccaaagag gcatctagtt ccaatgtgag tgttgctatc      420
acagggttgg ggccggattt cactaagatg gagtcgtttg gcaaggttga tgagtttgct      480
gagactctgg ttagtgggct ggacagaagc tggagaaaac cgcctggtgt agctgctaaa      540
ctcataaata gtaaaccatc taaaggaatt tattatatcg agtactcgtt gcaaaatcct      600
ggtgagagtc gcagacatct atattcagct atagggatgg caacaaatgg ttggtataac      660
agactgtata ctgtgacagg acagtatgtg aagaggaaa cagacaagta tgcttccgaa       720
attcagaagg cggtcacatc atttaagttc atataaagaa atgctcatga tgaaggagaa      780
atttccccac agccatcttt cctatataaa tacagatttg tgccttccta cagtgtagga      840
ttcttatgag caagagagga ttcttatatt tgtctttatg agcaaaatgg aatacttcat      900
tatttcattc ctctcttatg tctcttgctc ctcagattat gtatattgta t               951
```

<210> SEQ ID NO 24
<211> LENGTH: 866
<212> TYPE: DNA
<213> ORGANISM: Fragaria vesca

<400> SEQUENCE: 24

```
atggcttctg ttgcgtcttg gcatcctctg ttccttcgac ctcgcacatc ccatttcacc       60
acgacctcct acaacacagg caccgccata tgtagaaaga gctatctgca atgttgcaac      120
aacaaagaac aagaaccaca accagaacaa gaagaaaaat cggtttttgg gatgcaatgc      180
caagccaaga gaagacaagt tttgcttggg actactttg ctgcattttc ttttccggaa       240
atttattcca acattgcatt ggccgagaat gacgattttc gtgttttcac cgatgatgtc      300
aacaagttcc agatatcaat tcccctagac tggcaagtag cgcaggggga accaagtggg      360
ttcaagtcag ttactgcttt ttacccggaa gagggatcta gctcaattag tgtcgtaatc      420
acggggcttg gtccggattt tacgaagatg gaatcctttg gcaaagttga cgaattcgct      480
gagactctgg tcagtggact agataggagc tggcaaagga cagcaggagt tgcagcaaaa      540
ctcatagatt gcaaatcatc taaagggatt tactacattg agtattcgct acagaaacct      600
ggtgaaagta tcaagcacct ctattcagct cttgggatgg caacaacgg ctggtacaac       660
agactatata ccgtcactgg ccagtttgga gaggaggaag cggataaata cagatccaaa      720
attgagaagg ctgtaaaatc cttcaagttc atatgataaa caacctccag aggggcagag      780
tttgaattgt gaactacggt ttaccaattt tgattgggtc agttgtacac aaatttttca      840
tcgtaatcta atgtaataca tttgaa                                          866
```

<210> SEQ ID NO 25
<211> LENGTH: 1015
<212> TYPE: DNA
<213> ORGANISM: Glycine max

<400> SEQUENCE: 25

```
gtgaataata atcagaacaa aaccaaccat ttaaaaaaaa aaaaaaaaga aatggtggca      60
gagaagctga tctgaaagga atggcgttca tttggcggtt ctgtggtgtg tctctatgca     120
acttcacagc tctaatgcc cagaaaggtc cttctccttc tctgcccata accttggact     180
tggagcatca tataacaacc ccatctttac tttcttccat cgaagaagaa gaaggacgcg     240
cggttaatag gagacaactt attcttcaca cgccagtagc tgcagcagct gcatttgcag     300
tcccaaatgc attggcactc aatgatgtgt ctgaggatgt tcgtgtctac actgacgatg     360
agaacaagtt caagattgag attcccgaag agtggcaagt gggaacagga gacggagaat     420
ctagtgggtt taaatccata actgcttct acccaacaca ggcatccaat tccaatgtga      480
gcgttgtgat cacagggctg ggaccggatt tcaccaggat ggaatccttt ggcaaagttg     540
acgagtttgc tcagactcta gttagtgggc ttgacagaag ctggcgaaaa ccccccgggtg    600
tggctgctaa actcatagat tgtaaatcat ctaatgggat ttattacatc gagtatttgc     660
tgcaaaatcc tggtgagagt cgcaggtatt tgtattcagc tattgggatg gcatcaaatg     720
gttggtataa cagactgtat accgtgacag gacagtatgt ggaagaggac acagacaagt     780
atgcttcaaa agttcagaag gtagttgcat catttaggtt catatgaaga aaatggtcat     840
gacgaggaag aatttttatc acagcacttc atctattcta tttcattatg gattttcctg     900
gcattgttct ttaagctaga tatggcattc tagatcggac tggtatgata aaaaccatga     960
catttccttc gagattgttg aatgaaagta atatacttag tggccataat tgaca         1015
```

<210> SEQ ID NO 26
<211> LENGTH: 1159
<212> TYPE: DNA
<213> ORGANISM: Solanum lycopersicum

<400> SEQUENCE: 26

```
ggctgtgaat tggatacacc aatatctctg cttcttcaaa gaaaacaaaa aaaataaaaa      60
cagaaatggc gactctttca tcttcatctt catcttcatc ttcatcttca tctccatgtt     120
tgaaccagta ccagtatcaa gctattcttc gcttgccacg tgtccctta atttcctctc      180
atcttcttaa agttcccaag aaaaatcgaa actcacttat tttctgctgc aacaacactg     240
tgcctgattc aagaacaggt gagcaagtta aggagaatg cttaaccaag agaagagagc      300
tcctgctaca gcaggctct gttgcatttt ctctgtccgc ctttacatcg attgcattgg      360
cagagaagga tgtcccggag gagtttcgtg tttattcaga tgatgtcaac aagtttaaga     420
tcatgatacc tagtgattgg caaataggcg cgggagaagg tgatggagta aggtcactct     480
tagctttcta tcctccagaa gcttctaact caaatgtcag catagtaatc acaagccttg     540
gtgctgattt caccaagttg gaatctttcg ggaaagttga tgcttttgct gagaatctgg     600
tcagcggatt tgatagaagc tggcaaaggc ctccggggag gaaagcaaaa ctcatagata     660
gcaaagcttc taagggggttg tattacatcg agtacactct ccaaaatccc ggtgaaagtc     720
tcagacatct atttttcagtg cttgggatag caaacaatgg gatttacaac agactgtata     780
ctctcactgg acagtttgta gacgaggagg cagagaaata tggtgccaaa atacagaagg     840
```

```
ctgtttcttc tttcagatta atatgatgac atgaacagag agcgcgatat cgcaaatttt    900
ggcttgagct tctggttttt ctcgtttggt gaatggtaaa cataattgag agcgcgatat    960
cacagattca agttctggtt aaggtatatt atgacgactc gagaaaaaac tggagttgta   1020
agtatgaact agcaacttga tcaatgttag agttagtatt tgcatatatc gttatatacc   1080
aaaactgtat cgattttttg ataaaaatat gaccttagtg caaataattt gatgctcaag   1140
ttttgattat atatttgta                                                 1159
```

<210> SEQ ID NO 27
<211> LENGTH: 1680
<212> TYPE: DNA
<213> ORGANISM: Cicer arietinum

<400> SEQUENCE: 27

```
tctcgtaaaa gaatgagatt cagttgaagt tatcgaagaa gaagaatgca gcagaggaaa     60
aggcaaagta tggatgggcc tagcatctat gcgtggttgt tttgtgtcat tggaatgaca    120 tcactttcg gtgctgcttt cctaccacca gatatagga ttgtgttttt tctcagacaa     180
atatgtctgt ttgtgtttcg atctatgtgg atgacaaggt tggtgttttt tctagctgca    240
gctgcacatg tcattgaggc tatctatgct tggtgcttgg ctagaagact ggatccttcc    300
aattcaaggg cttggttttg gcaaacattg gctctaggct tttttcatt gcgttttcta    360 ttgaaattga aagatcaaa ggaataactt tgaaataatc acttcttgta ccattgttat    420
tttcagaaat caattatctt tcccatcaat tgtatgcctt tttttatgt aaaattaata    480 ttttacaag ttgttattag ttatcactgt cgaataaatt taccatgaca gtacatatct    540
tttaattttg aaaattgtcc attttgtttt cttatctata atggttttct tctctattta    600
attttggatt taattaaatt agaaatagtg tcttctctgt ggaggataaa agtgtaatta    660
aatagataat aataataaag gaaatgaagg gtgagaaaga gaagctgatc taaaaaggaa    720
tggcatcaat ttcatggttc agctgtttac acattccacc aacatcctct gctgccgata    780
aaggtttatc atcatctccc ataaccgtgg aacatcataa acaacaaca cgtttaatct    840 cttcctttga aggacaacaa catgttgtta atagaagaca actgattctt tatacatcca    900
cagcagcaat tgcagcacta tctactgtcc caaatgcatt ggcactaaat gatgtgtctg    960
aggatgttag tatctacact gatgatgaga acaagttcaa gatagaaatt cctcaagagt   1020
ggcagatagg aacaggagag tctgcagggt ttaaatcctt aactgctttc tacccaaaag   1080
atgaatctaa ttccaacgtg agcgttgtga tcacaggggt cggaccggat ttcactaaga   1140
tggaatcatt cggcaaagtt gaagaatttg ctgacactct ggtaagtggg cttgacagaa   1200
gctggaaaag accccctggt gtggctgcta aactcataaa ttgtaaatca tctaaaggat   1260
tttattacat tgagtatacg ctgcaaaatc ccggcgagag tcgcaagcat ctatattcag   1320
ttattgggat gtcaacagtt ggctggtata acagactgta tactgtgaca ggacagtttg   1380
tggaagagga aacagaaaag tatgcttcca aaatttttgaa ggcggttgca tcgtttaagt   1440
tcatataaag aaatgcttgt gacgggagag aaatgttctc attggtttct ttcatgggct   1500 gccgttaat gttttcatga catttttgt aagctagaaa tggcgtctaa atgttataaa   1560
tatgatattt gctatggtac ttccttcaaa aactgataaa ccagagtagg ctaaatgaat   1620
ggcacaaatt gatgtaatgg ataagatatt ttgcagtgaa tatcagcacc ttcagttaaa   1680
```

<210> SEQ ID NO 28
<211> LENGTH: 1068

<212> TYPE: DNA
<213> ORGANISM: Triticum aestivum

<400> SEQUENCE: 28

```
gaagcacagc agcgtcgtcg accaccatcg agccgtactc catggctgcc gtgaccaccg      60
cctctctctg tcccggcctc ggcaagcccc gccgagacca cgcgaagcca ccgagaacca     120
cggtctgcca ttgcctccct gctcggagga cggaggaggg ggtgaagcgg cgggacgccc     180
tgctcggcgt cctcctctcc gctaccgccg cgtcgtcggc gccgctgctc gtccccgccg     240
aggctttcgc cgaggtcgcc gatgcgcagg aggggttcac cgcgtacgag gacgaggcca     300
acaagttcac cctcgtgatt ccacaaggct ggcaggtcgg cgcaggtgaa cgcagcggct     360
tcaagaacgt gacagcgttc ttccccgagc aaaaccccaa ctccagcgtc agcgtcgtga     420
tcaccgggat cgggccggac ttcaccagcc tcaagtcctt cggtaacgtc gacgagttcg     480
ccgaaaacct ggtgaccggc ctggacagga gctggcagag gccggcgggg ctcgcagcga     540
agctcatcga ctccaaggca tcaaacggct tgtactacat cgagtacacg ctgcagaacc     600
ccggcgagaa gcgccgccac atcgtctccg ccatcgggat ggcattcaac ggctggtaca     660
atcggctgta cacggtgaca gggcagtaca tcgacgacga cgaggagtca gccatataca     720
aacctgagat agagaagtct gtcaagtcgt tcaagttcac atgaaatgcc cccaaaaagg     780
aagttcaggt gagaacaagt atagagtgac agagaagaga gagtatacaa agctagtagc     840
tcctgatgtc aagttcaatt agtgagtatg catatgtttg tcgaatttac cggaaagaaa     900
agatgaacac cagatgttcg aagacttcga tggcgtagct tggctgagaa cagcattggc     960
agcatgagtg tgagatagag catgagtgtc gttggttcta agaaaattgc tagaactctg    1020
ttacaaggaa actaaaattg ctctgatgta aaaaaaaaaa aaaaacga                 1068
```

<210> SEQ ID NO 29
<211> LENGTH: 1037
<212> TYPE: DNA
<213> ORGANISM: Oryza sativa

<400> SEQUENCE: 29

```
gcaaggcagg cagcagcgac cagacgaagc agagagagcg cccgcgccgc gccggccatg      60
gctgccgccg tgaccaccac caccaccgcc acaaccaccc atctctgccg tggcctctcc     120
tcctcctccg ccgccgccgc caagccgcgg cgagcgacga cgctcagatg cggcgccgct     180
gctcgggtgg aagggctggg gcggagggag gcgttgctcg gcgtgctcct ctccacggcg     240
acggcggcgt ccgcgcccgt cgccgccgtg gccgcgaccg ccgagttgca ggaggggttc     300
cgcacgtacg aggatgaggc caacaagttc agcatcgcca ttccacaaga ctggctgatc     360
ggcgccggcg aggtcagcgg cttcaagtcc gtcacgcgcg tctaccctga ccaagtcgcc     420
gactccaatg tcagcgtagc catcaccgga atcggccccg atttcaccag cctcaagtcg     480
ttcggcgacg tcgacgcctt cgcagagacc ctggtgaacg gcctggacag gagctggaaa     540
cggccgccgg gggtcgccgc gaagctcatc aactccaggg cagccaacgg gttttactac     600
atcgagtaca cgctgcagaa ccccggcgag cagcgccggc acattgtctc ggccatcggg     660
atggcgttca acggctggta caaccggctc tacacggtga caggccagta catcgatgag     720
gacggggatg tagacaagta cagggctcag atagagaagt gtgttcagtc attcaggttc     780
acatgaaaga ggagcatcct acacaacatc caacaaggcg aggacgaaaa acattttgta     840
aaccaacgta tttcgttata attgtaaatc aatcagtata ttcatgtcat cagttcaacc     900
```

```
aactaaatgt acaccaattg ttccgagatt ttgacgatgc ggccttgccg aggccaacat      960
gagctaatta tgttgtggca agtcataagc attgttttct atgcattttt aagggagaaa     1020
aaacaggtgt atttgtt                                                    1037
```

<210> SEQ ID NO 30
<211> LENGTH: 1269
<212> TYPE: DNA
<213> ORGANISM: Brachypodium distachyon

<400> SEQUENCE: 30

```
atggcccggc tcggcccggc ccacgtgttt tacagccgtt gggctgggcc gtactgccaa       60
aacgtgtcca atggcccac  gtcgaagacg aactctcacg ggccgacgtc cttggcgcgc      120
ggccatggcc catgggtaag taagatacga ggggccgaa  gcaatgtgcg gcggaagttc      180
ccggacgacg acacgacggc cggccaccgt acaaagcttc tcagcaaaat atcctccccc      240
tcgaaagcca ccagcgcagc agcagcgcag agccattcgc tcgccatggc tgccgtgacc      300
accgcctcct ccgccatctg ccccggcttc agcagcaacc ccgccgagg  ccacgcgaag      360 ccgcggagat ccacggcctg gcctgccat  tgccgccgct ccctgccct  gcgcgagcaa      420 caacctacgg cggccgttgc cgggacggcg gaggagggggc tcaggcggag ggatgccctg     480
ctcggcgtcg tcttctcggc cggcacggcg acgctgctcg ctagtcccgc cggtgctctc      540
gccgaggccg ctgccgaggt gcaggagggg ttcagcgagt accaggacga ggccaacaag      600
ttcagcatcg tggttccgca aggatggcag atgggcgctg gtgagggcag cggcttcaag      660
aacgtcacgg cgttcttccc ggacaaggcc gccgactcga gcgttagcgt ggtcatcacc      720
gggatcgggc cggacttcac cagcctcaag tccttcggcg acgtcgacgc cttcgccgag      780
aacctggtga ccgggctgga caggagctgg cagcggcctg cggggggtcac cgcgaagctc     840 atcgactcca gggcgtccaa cggcatgtac tacatcgagt acacactgca gaaccccggc      900
gataagcgcc ggcacatcgt ctccgccatc ggcatggcgt tcaacggctg gtacaaccgg      960
ctctacacgg tgacagggca gtacatcgaa gatgacgagg agtccgtcaa gttcaagcct     1020
cagattgaga gtctgtcaa  atcattcaag ttcacatgaa atgccttcaa acaaaggtc      1080 acatgaaaat aagtactgct actactttg  aatgaagtac tatatctaag cagagaagag     1140
aaggtatata aaggcagctt ccggtaatgt gtgcagaacg aaatgaacta aacctttgtg     1200
aatgtaaggg ttgtgagctt tgagaatata tatgtttgtc aattttactg aatacatagc     1260
tctagactt                                                            1269
```

<210> SEQ ID NO 31
<211> LENGTH: 1024
<212> TYPE: DNA
<213> ORGANISM: Phyllostachys edulis

<400> SEQUENCE: 31

```
atagtgccat acgccatggc cgccgtaact accgcctccc tctttcctgg cctctcctcc       60
tgcagcccca agcccagaag ccacaggaag ctgcagagaa cgacggtctg ccaatgccgc      120
cctgctcgga tggaggggat gaaacggagg gaggccttgc ttagcatcct cctctccact      180
gccgcttcgg cgccgccgct tgctcctgcc gaagctttgg ccgagaccac cgagttgcag      240
gagggcttcc gtacgtacga ggacgaggct aacaagttta gcattgcggt tccacaagac      300
tggatggtcg gcgcaggcga gggcagcggc ttcagtcccg tcacggcgtt ctaccctgaa      360
ggcgccgact cgagcgtcag cgtcgtgatc accggaatcg gaccggattt caccagcctc      420
```

```
aagtccttcg gcgacgtcga cgccttcgcc gagagcctgg tgaacggcct ggacaggagc      480
tggcagaggc cgccggggct cgccgcgaag ctcatcgact ccagggcagc gaacggtctg      540
tactacgtcg agtacacgct gcagaacccc ggcgaaaagc ggcggcatat cgtctcggcc      600
gtcgggatgg cgttcaacgg ctggtacaac aggctctaca cggtgacagg cagtacatc      660 gatgacgacg acgagccagg caagtacaag cctcagatag agaagtctgt cctatcgttc      720
aggttcacat gaaagaacta aactacagtc tacccagagt gcaacaatat gcagagaaga      780
taaagtagat aaaagccctt ccgcagataa gttcagaacg aagatacgt tgtgatttt       840 gtcaatcagt gagcatatgt ttgtcgattt gaccaaataa aatatgtact ccacatgttc      900
gacgacttgc tgtgcccagc atgagttaat tgtaagagaa gttaccatgc gccggacctg      960
tcattctgaa actgtgatga gtgacattct gaaactgtaa catagtaaac gtatgttcag     1020
tttt                                                                  1024

<210> SEQ ID NO 32
<211> LENGTH: 1053
<212> TYPE: DNA
<213> ORGANISM: Hordeum vulgare

<400> SEQUENCE: 32
agagccgtac tccatggccg ccgtgaccac cgcctccctc tgcccgggcc tcggcaagac       60
ccaacgaggc cacgcgaagc cgccgagaac aacggtctgc cattgcctcc ctgctcggag      120
gacggaggag ggggtgaagc ggcgggacgc cctgctcggc gtcctcctct ccgctaccgc      180
cgcgtcgtcg gcgccactgc tcgtccccgc cgaggctttc gccgaggccg ccgaggcgca      240 ggagggttc accgcgtacg aggatgaggc caacaagttc accctcgcga ttccacaagg      300
ctggcaggtc ggcgcaggtg aacgcagcgg cttcaagaac gtgacggcgt tcttccccga      360
gcaaaacccc aactcgagtg tcagcgtcgt gatcaccgga atcgggccag acttcaccag      420
cctcaagtcc ttcggtaatg tcgacgagtt cgccgagaac ctggtgacag gcctggacag      480
gagctggcag cggccggcgg ggctcaccgc gaagctcatc gactccaagg cagcaaacgg      540
tctctactac atcgagtaca cgctgcagaa ccccggcgag aagcgccgcc acatcgtgtc      600
cgccatcggg atggcgttca acggctggta caaccggctc tacacggtga caggacagta      660
catcgatgac gacgaggatt cagccatata caagcctgag atagagaagt ctgtcaagtc      720
tttcaagttc acatgaaatg cctccaaaaa ggaagttcag gtgagaacaa gtatagagga      780
acagagaaga gaaagtatac aaaactggta gctcttcatg ttaagttcaa ttagtgagtg      840
tgtatatgtt tgtcgaattt accggaagaa aatatgaaca ccaaatgttc aaagacttcg      900
atggcgttgc ttggctgagg acagcaatgg cagcatgagg gtatgagata gagcatgaga      960
atgtcgtttg ttctgagaac attgctagaa ctccttataa gaaactaaaa ttgctccgat     1020
gtaaacttct tcctagcatc tattttggg ctc                                   1053

<210> SEQ ID NO 33
<211> LENGTH: 1138
<212> TYPE: DNA
<213> ORGANISM: Zea mays

<400> SEQUENCE: 33
cccgttgcca cacatacgga tccaacaaaa tctcccgcaa agacaacggc gagccaacca       60
ccaccagcgt cccgcgctag ctgcggcacc gcatggctgc cgtgaccagc accgcctcca      120
```

```
tctgcccggc cgcagccggc gccctctctt cgctgccgtc cttcatcacg cgcaagccca     180
ccagcggcag caggaggttg cagcaggcag cagcgacgac agtctgccac tgccgctctg     240
ctcgggtaga ggaggggctg ctgggccgga gggacgcctt attgctcggc atcgtcttct     300
ccgccgcgac gccgccgctg ctcgcccctg ccggcgctct ggcggacgag gccaccgccg     360
agtcgcagga gggcttcact acgtacgagg atgaggccaa caagttcagc attcaagttc     420
cgcaaggctg gctggtcggc gccgcgagg ccagcggcat caagtctgtc acggcgttct      480
accccgagca ggccgccacc gactccaatg tcagcgtcgc catcaccggg atcgggccgg     540
acttcaccag cctcaagtcc ttcggcgacg tcgatgcctt cgccgagggt ctggtgaacg     600
gcctggacag gagctggcag aggccgccgg ggctcgccgc caagctcatc gactccaggg     660
cggcaaacgg cctgtactac ctggagtaca cgctgcagaa ccccggcgag cgacggcgcc     720
acatcgtctc ggccatcggg atggccttca acggctggta caaccgcctc tacactgtga     780
cgggccagta catcgacgac gatgactcgg agaagtacag gcctcagata gagaaggctg     840
ttggatcgtt caggctgaca tgaaagatgc gatgtcatcc agcaccagca gcagcagccg     900
cccacggtac ataaaccctg aatatgtatg cggagaggtc cagcaacatg ttgtgcccga     960
aaattgacac cttgccattt cgatgagaca agacaaggca tgtgcctatt gccctattcc    1020
aattcttgag cactgtaaca ctgccaatat gcagagtata tgttttctgc ctgttgaggt    1080
ggatacaaat gcatgctttt tttttttatta ataactcatg tgtaacactg ctgcctttt    1138
```

<210> SEQ ID NO 34
<211> LENGTH: 1162
<212> TYPE: DNA
<213> ORGANISM: Sorghum bicolor

<400> SEQUENCE: 34

```
agcgcgagcc tgccagccaa ccaccgccac cggctttcat cccgcgcgtg cgtcctgcgc      60
tagctgcgcc catggctgcc gtgaccagca ccgcctccct ctgcccggcc gcagccggcg     120
gcctctctgc ctcgtcgtcg tcgccgttca cgcgcaagcc cagcagcagc aggaggctgc     180
aggcagcgtc cacggcctgc cactgccgcc ctgctcgggt agtagagggg ctggaccgga     240
gggacgcctt gctcggcatc gtcctctccg ccgcggtggc gccgctgctc gcccctgccg     300
gtgctctagc ggacgagccc accaccgagt cgcaggaggg cttcactacg tacgaagatg     360
aggccaacaa gttcagcatt caagttccac agggctggct ggtcggcgcc ggcgaggcca     420
gcggcatcaa gtcggtcacg gcgttctacc cggagcaggc agccgccgat tccaacgtca     480
gcgtcgccat caccgggatc gggccggact tcaccagcct caagtccttc ggcgacgtcg     540
actccttcgc cgagggccct gtgaacggcc tggacaggag ctggcagagg ccgccggggc     600
tcgccgccaa gctcatcgac tccagggcgg caaacggttt gtactacctg gagtacacgc     660
tgcagaaccc cggcgagcgg cggcggcaca tcgtctcggc catcgggatg gcgttcaacg     720
gctggtacaa ccgcctctac acggtgacag gccagtacat cgacgacgat gacgattccg     780
aaaagtacag gcctcagata gagaaggctg ttcgatcgtt caggctgaca tgaaagatgc     840
catgtcattc agcagaggtc ttgtgcctga aaattgacac cttgccattt ccatgagatg     900
agacaagaca agacatgtat gccaattctt gagcactgta acactgcaag tatgcgaata     960
tatttctcc tttttgaggt ggatataaat atgttttttg taactcttgt gtaacgttgc     1020
tgcggtgttt ttttggttgt gtatatgtaa tgtttagagg gtcgggctga aggagcaact    1080
atgtgacctt tattctcttt ttaaggcaaa gttcgtgtca cttctttca aaacaagcaa     1140
```

```
atggttttgt tcttgagct gg                                                  1162

<210> SEQ ID NO 35
<211> LENGTH: 1062
<212> TYPE: DNA
<213> ORGANISM: Setaria italica

<400> SEQUENCE: 35
cggtgcctac caaaacacac ggctggaaca aaatatcccc cacgaaaaca aacggcgagc          60
caaccgcaac caccactcgg caccggctgg cctgcggcgc gcgccatggc tgccgtgacc         120
agcaccgcct tcctctgccc ggccgccggc ggcctctccc cctcgccgcc cttcaggcgc         180
aatcccggca gcagcagcag ccgcaggagg ctgcagctgc aggtctgcca ctgccgccct         240
gctcgggtag aggggctgga ccggaggag gccttgctcg gcgtcgccct ctccgccgcc          300
gcgccggcgc tcttcgcccc cgcggctgct ctggcggccg aggccaccgg tactttgcag         360
gagggcttca ccacgtacga ggatgaggcc aacaagttca gcattgtggt tccacaaggc         420
tggctgatcg gcgccggcga gtccagcggc atcaagtccg tcacggcgtt ctaccccgag         480
caggccgccg actccaacgt cagcgtcgcg atcaccggca tcgggccgga cttcaccagc         540
ctcaagtcct tcggcgatgt cgacgccttc gccgagggcc tggtgaacgg cctggacagg         600
agctggcaga ggccgccggg gctcgccgcg aagctcatcg attccaaggc ggcaaacggt         660
ctgtactacg tggagtacac gctgcagaac cccggcgagc ggcggcggca tcctctct          720
gcaatcggga tggcgttcaa cggctggtac aaccgcctct acacggtgac aggccagtac         780
atcgacgacg aggagtcgga gaagttcagg cctcagattg agaaggcggt tcgatcgttc         840
aggctgacat gagagtgctt cgcactgtgt agcattcaga gatgcacggt atgcaggtgg         900
acgcctgtaa attgaccaac tcgtcttcca cattattaag tttttttta agcaagtctc         960
acggtatgtt ggaaagtaca ttgctacacc tcaacaatcc catagatcgt ctcatgtaat        1020
gccacatata atttttgctg gtgtggagga aggagggtga tg                          1062

<210> SEQ ID NO 36
<211> LENGTH: 1091
<212> TYPE: DNA
<213> ORGANISM: Picea glauca

<400> SEQUENCE: 36
acttcaaaat cccaaaccca tcagaggagg gagttccaac agatgactat cgtggtgaag          60
atgggcatgc ttggcctggt gtcatcacca tcaattccca ctactcacaa tctatgctct         120
ccagtccaac cattcagaag gaatttcaag aatttcaagc aggggaaaaa gcaagtcaca         180
ggctgtttcg aaatccagaa caatctgtcc tcccatgaat tgtcaagaaa tggaagaagg         240
caggccatat gtcagattgc tgctttgttc tcagcgattc cttgtactgt tcagcggca          300
agggcagcag aaactgagct tcaagaagat tacgagttgt ataaggacga cagacaaa          360
ttttcactac tagttcctcg agactggata aagggtgaag gaaaaacaga tggacagaga         420
gcagtgactg ccttctaccc tgaaagcggc atagttccta atgtgaatgt aataataaca         480
ggactttctg ctgactatac aaaaatgaat tcatttggca ctgttgatgc atttgctgag         540
acccctggtta attctctaga tagaagctgg aaaagaccgc cagggcaagc agcaaagctg         600
cttaatgcaa aatccaaaaa cggcttgtat tatatagagt attcattgca aaagcctggg         660
gagagtaaga tccatcttct ctctgcgatc ggaatggcaa tgaatggttg gtacaacagg         720
```

| | |
|---|---|
| ctttacactg taacggggca gtatctagaa gacgatgctg gcaaatatgg ctcaaagatt | 780 |
| gaaaagtcca tttcatcttt cagattagtt tgaaagatta attaccttcc atgtgaggca | 840 |
| tcaagtatgt tgggaaaaga cttataatat acaagagcat aaaggtgata aatattaaat | 900 |
| aattaaaaat cccccatttt attcatcttc aattatgtct ggaataaact tgatttacct | 960 |
| tgtaatatat aatgtatgac ctaatatctt atttggaact aagtgtgaaa ccactcatag | 1020 |
| ttattccaac taaattttag tttagacaag ggaataaaat acattcaatg tccttattgt | 1080 |
| ttactaaaaa a | 1091 |

<210> SEQ ID NO 37
<211> LENGTH: 355
<212> TYPE: DNA
<213> ORGANISM: Arachis diogoi

<400> SEQUENCE: 37

| | |
|---|---|
| ggggtgggtc cggatttttac taagatggaa tcgtttggta aagtggaaga atttgccgag | 60 |
| actctgattg gtggattgga cagaagctgg caaagaccac cgggtgtggc tgccaaactc | 120 |
| atagattgta aatcatccaa ggggttttat tacatagagt attcactgca aaatccgggt | 180 |
| gagagtcgca gaaccttata ttctgctatt ggaatggcat caaatggttg gtataacaga | 240 |
| ctctacacgg tgacaggaca gtttgtagaa gaggaaactg acaagtatgc ttccaaagtg | 300 |
| aaaaaggctg ttgcatcatt taggttcata tgaacaaaga gttcatgagg gagat | 355 |

<210> SEQ ID NO 38
<211> LENGTH: 1089
<212> TYPE: DNA
<213> ORGANISM: Physcomitrella patens

<400> SEQUENCE: 38

| | |
|---|---|
| gcaggagcaa tggacgctgt cgttggtcgc acctcatgcc ccttgtctct gtcttcctcg | 60 |
| tatcaatgga ttgctgggtc gccatctgct tctcgtgcta cagtcgttgt tagaggtaca | 120 |
| agccggcgtg acggtaaaca caaagcagtg cgttgcgagc aggttccaga atgcagcacc | 180 |
| agcaattgtc aaacaatgca gagacgagag gttatcggtc aagctctatt agccatgtcc | 240 |
| atgagctttg ctcctccagc tcgttcggcc acagacacag atgctgctac tgaatttacg | 300 |
| acttacgagg atgcagccga taaattcaca ttgctcgtgc cacaagcctg aacagaggc | 360 |
| gaagggaaaa cgtccgggca aggaaagtc acggctttct atcctgcgga tggcggtctt | 420 |
| accaatgtaa atatagtcat aacaggactc ggagcagatt tcacgagttt aggatccttt | 480 |
| ggcacggccg acaatttcgc ggagaatttg gtgaacagtt tggacaggag ttggcagaaa | 540 |
| ccccccgggcc agaaagcaag gcttgtggat tgtaaatcaa gagcagataa atactatgta | 600 |
| gaatacacta tacagagact cggagagcag cagcggcact tagtctcagt tgttgggatt | 660 |
| ggaaacaatg gatgggtcaa cagattatac accgtcacgg gccagtactt tgaggaagac | 720 |
| tcagccaaat ataaacaaga cattaacaag atcatctcct ctttcaaaat actgtagttc | 780 |
| atagatcgaa gactcggggc acagactgca gaccatggag tttatgactg accagcattg | 840 |
| tggtaaaacc tgggattttc gttcctcatg cttcgtgtca cagagaagct cattgagttg | 900 |
| ggagaactga agtggttgtg taaacacgct ggggttgttt tgcatgtggt gagagcagat | 960 |
| gtccttcgag cagccattca taaatctcaa gatgagttta ttctgttctg cagaaactgc | 1020 |
| cgaacctgga ttcttgtaat agaaccattc aataatttcc aaggtcacca ttgggcctga | 1080 |
| gatatcatc | 1089 |

<210> SEQ ID NO 39
<211> LENGTH: 2425
<212> TYPE: DNA
<213> ORGANISM: Selaginella moellendorffii

<400> SEQUENCE: 39

```
atgggggagg agaagcgcga gaatctcatg gagtcgctct tcggggagga gtcggatgac      60
gacgccgatg ccgctgcctc ctactctgag gaggagggcg aaggcgaagg cgaggcagag     120
ggcggtggtg ccgagagcgg tggcgacagg gaagagagcg agggcgagcg ggaagccagt     180
gagggcgaca aggaggagag cgagcatgag agagtgtcca ggaggagcag tgatgacgga     240
ggtggtgaag aagggagcgc cgccagcggc tctgagaacg atggacaagt ccaggaaagg     300
gaagcaactc gcagcgagga ggtggaggag cagcgtggtg ctagaattcg tgcagcattg     360
ggtgattctg atgacgacga tcaggaggaa ggaggagttg acggccctcg caagccatcg     420
agtccagagg gggagggctc ggacttggag gaagctacc acaaagatag taagcggggt      480
gcagaggatg acgaggagca gtattactct gatgaagagc gcgcagaaat caagaaaccc     540
aagggtgaac ctcttacagt agaagttcca ctcaggcaac ctccaactca ggctcacaac     600
gcaagtagtt tggcacttgt ttctttttca ttatctcgtg agcttacggg cctttgcttt     660
cagatgaatc tcgtcaggat ctccaacatt atggatatag agcaaaggcc ttttgatcca     720
aagacatacg tcgaagagga tggatttgtt gatgaaactg gccgacgccg tatacgtata     780
gaggagaacg tggtgcgctg gagatacgtc aggaatcggg atggctcgcg ctcggccgag     840
agcaacgccc ggtttgtgaa gtggtccgat ggtagcatgc aacttcttct cggcaatgaa     900
gttctggatc ttgctgttca agatgggcaa caagacgaat cacacttgtt tatccgtcag     960
cccaagggat tattacaagc ccaagggagg ctggcacgta gatgagatt catgccttcg     1020
tcgttgagat cgaagtcgca ccgtctctta actgctctcg tggattctac gcacaagaag    1080
gtgttcaaag tgaagaatgt gatcacggac ttcgatcccg agaaggacaa agaacaaaaa    1140
gagaaggcag cagaacagag gattaaaagc aaagaagatc tccaaaaaaa gcaggagaag    1200
acgatgcgta aatacccccc tacacgggag agagaacctc agctttctcc tggatacctt    1260
gaaggggcgc ttgaagagga ggatgaagat tatgacgacg aggggcgtag caaccgacgg    1320
taccaagacc agcttgatgc cgaaagcagg gcggagagac gaatcaacca ggttaagcgg    1380
caaccaccaa aggcaatgga gcgacgccct tcttcgcgga gcaggaggga tattttggaa    1440
gacgaggatt cagacgagag cgaccgcaat agaggtgcgc gaggtgatga aggtgaggaa    1500
gagcaggaag atgacgaggg ggaggaagaa gaggaggaag tggaggcaag ggatagccgc    1560
cgcaagagga aagacaggga cagggaacag ctgcagcagc agcaaaattc gcctcccaga    1620
aagcagcaaa cgcacaggcg gagagcagta gtttggtttc tcgccacagg ttgcaagagt    1680
agaatagata ggggcagcca gggaagtgtg gcgtcatggc aagtgtgcat acaaactgct    1740
atgttcgtcc agcagttcca gccagttcaa gtcgaccgcc attcaatgct cctgctactg    1800
ctgcctgtcc accgctgagc aagagaaatc tcttattgct ggtgcctctg ttggcgatgc    1860
cggcgacgcc tgtgtttgct gctggtattg tacttgtcaa tcgttcgtta aactttgatg    1920
caagacagga gcctcagatg aatatcaagt atacgaggaa caagacaagt tctccctcac    1980
tgtacccaaa gactggataa aaggcgaggg gaaagtcgga tccagaagag tggtggcatt    2040
ccatccatcc aaggctactt tcccaaacgt gaacgtgatc atcacgaacc tgggtgccga    2100
```

```
tttcaccggg atcggctcac tgggatccgt ggactcgttc gccgcgagcg tggttggcag    2160
catggataga agctacaagc ggccgcctgg aacagcggct cggctggtga atgctgtgtc    2220
gagaaacggc atgtattatc tcgactacac cgtccagacg cccggggaag cccagcgcca    2280
tttcttctcg gtggccggtg ttggcgagac acagttttac aagcagctct acacggcaac    2340
cggccagtac tgggaggctg atggagacag ggacaggaaa gcattgcaag aggcgataga    2400
gtcattccgg attgttcaca agtga                                         2425
```

<210> SEQ ID NO 40
<211> LENGTH: 832
<212> TYPE: DNA
<213> ORGANISM: Camellia sinensis
<220> FEATURE:
<221> NAME/KEY: misc_feature
<222> LOCATION: (90)..(90)
<223> OTHER INFORMATION: n is a, c, g, or t

<400> SEQUENCE: 40

```
atacccaaag ttgccaagtg gggccggggg aaataaagga gatcaagtca gtaacggagt     60
tgtacccgat gggacctctg atgaaagtcn cgtggtaatc gcggcctggt gcgggtttta    120
ccagaataga aatcttttgg taaagatgat gcttttgcag agaatctgct acgggctggg    180
acaagaagct ggcaaaggcc accgggggt aagagcaaaa ctcatagact ctaaaactgc    240
taatggtttg tattcattg aatatacact gcaaaatcct ggccaaagtt gcagacattt     300
atttcagtgc ttgggatccg aacaatggtt ggtatccaga ctatataccg tcactggaca    360
gtttgttgat gaggattcag aaaaatatgg ctccaaaatt gagaaggctg tttcatcgtt    420
cagattaaac tgagattttg aggatccttt ccattttgc tttcaacatc ggctctcatc    480
gctgcaacat gtccaattga agtcaagttt actaaaggaa gcaaagcatt gaatgatgtt    540
tgcatcctgg ccgaggattt ccatgcacct ggagccagct gtttggaaga caccaagagg    600
cggctagatt gtggcatatt tactctctgt tttacttttg ttattcctag cctttcttgc    660
aacttttctt gaagtatgct ggaacccttta ttattttatt gactaggaaa tttattctta    720
ataccaccag aaagagatag acaaaaacta ccttggtgat tgcattgaat taacataaag    780
tgcccaaaaa tattttgcta agaaaaaaaa aaaaaaaaaa aaaaaaaaaa aa            832
```

<210> SEQ ID NO 41
<211> LENGTH: 2246
<212> TYPE: DNA
<213> ORGANISM: Zea mays

<400> SEQUENCE: 41

```
tttggtgttt ctcgcagtgc gcagagggct tcagtcatta tcgtctcgtg ctctctattg     60
atggtagttt tttgcttggg aagtataggg gcacattgtt ggttgccatt tcatgtgacg    120
tggacaacgc attggttctt ttggcatttg ctttggtggt gagggagaac agagatagtt    180
cgttttggtt cttgcgactt gttcggatcc atgtcgtggg ccctggtcgg agattggtg    240 tcatatatga cagaaaccag ggtattctta atgtagtgca agagcagatt cctggctaca    300
cacccatgca ccacagatgg agcactcgac acctagtaga aaatcttttt cgaaagggtt    360
gtaccaagaa taattccccc cttttgagg aggtctgtcg acagttggag gtttcgttat    420
tcgaggataa gttgaaggaa ttaaaagata caacaaatga tgaaggtgaa aaatggattg    480
ctagatttcc taactgtatt tcctcgtctc ctacacaaaa aacagtaagt acgaatgcaa    540
cattacgact gatgctatca aaaagcaata tcaacctcat cgtaatctac cacatgtcca    600
```

```
aaaataaccc acaccaagat cagaaggaac taatccatac ttagcttcat taaaaccgcc    660
actcattttt tcttttcctt tgcctctggc tcaggccaat gggacctagg accatacaac    720
cactctatga aactcacctt acgcccaccg tatggccgta ggggaataaa ttagtaaatt    780
tgtgaaaaaa taacaaaatt ttggacattt gttatgcact cacataatta ctgttgggac    840
acacgaagta cttcacagtg tccttacata agacaacacg atctccgcaa tcacaccgag    900
gcggagactt cagtcgtctt tctgcgacta agttcttctt ctcatccgtc attggtgtcg    960
tgtcggggga ggaggcaccc aacgcttaaa acactgtata ttccttctgg acaaccaatt   1020
agcgaaaagg agatatcgat ggtcaaattt atgaggaccg tcgatccatt ggaaaacaca   1080
tcaagtgatc ctacagaaat ggaatgaagc attagtacac atgtagtaaa catcaataac   1140
acacaagtca taagctacat atgttaaaaa cgccacaagt gtagaagcag cgagcagccg   1200
tgtctagata tttgaattga catacccaag gcggtctgcc acagtcacaa ttaggtacag   1260
gaagatcagg aggaacatga gcatccttac tagatacatc cagatacaac tcccgaggac   1320
gatctctctt ctgccacaac gactcctaat acatgtcttt tcatctaaca aacgattata   1380
tattaacaca actatataga aataacagaa atgattttaa cttataaata catgtatttc   1440
ataaattatc taacaaactg tagtcattat atgaaccata tatcatagga ttcataacta   1500
atagcaatat gagcaacaat caaaactaat taatcgaaaa catacaacgc aatatacgta   1560
acaaatgaat cagtgagaca ctataccttg gtcttcaaag ttttccaact cgaatacgaa   1620
gattggagca cctctgggtg gtatggaaga agatacaaat ggttgggtgc agctctcggc   1680
taggaaacaa ccgatttata ggccttccta gctcggcgcc acagatccat ggcgccgagc   1740
tagtgccatg tcggtgctgc atcagccctc gacgctagcg gccttgtgtt accttggtgc   1800
tacaacttat gatattgagc aacgagtcca aatgcagaaa taagttatct aggggtctaa   1860
acattaaaca cgattttttt cttaaaaagg accaacataa aaaaaactcg ggctggcggc   1920
ctgccagcgc ccggggaccg tgagcccgtg accccagcgg gcccaaccag tcaaaaccgc   1980
aagagagagt cgtgaggcgt gcgcactacc ccgagaaacg tgcgacggga acctccgcgg   2040
ttccccaagt tcgcctcctt cactactctc gcgcccggc acgcctgaaa aaccccaccc    2100
ctcctgccgc tccgcctctc ccatcacttc ccacgcccct cgccgcctcc cattccagcg   2160
tggacacgac gccactcgcc agcacggaga cgcgcgcctc gaagcactac tgcactagcc   2220
agccgtcgtt cttccgcgcc ggcgcc                                        2246
```

<210> SEQ ID NO 42
<211> LENGTH: 27
<212> TYPE: DNA
<213> ORGANISM: Artificial
<220> FEATURE:
<223> OTHER INFORMATION: synthetic

<400> SEQUENCE: 42

```
tttttaggaa ttattgagta ttattga                                         27
```

<210> SEQ ID NO 43
<211> LENGTH: 24
<212> TYPE: DNA
<213> ORGANISM: Artificial
<220> FEATURE:
<223> OTHER INFORMATION: synthetic

<400> SEQUENCE: 43
aaataaaaat catacccaca tccc                                        24

<210> SEQ ID NO 44
<211> LENGTH: 26
<212> TYPE: DNA
<213> ORGANISM: Artificial
<220> FEATURE:
<223> OTHER INFORMATION: synthetic

<400> SEQUENCE: 44
tgttgaatta ttaagatatt taagat                                      26

<210> SEQ ID NO 45
<211> LENGTH: 25
<212> TYPE: DNA
<213> ORGANISM: Artificial
<220> FEATURE:
<223> OTHER INFORMATION: synthetic

<400> SEQUENCE: 45
tcaaccaata aaaattacca tctac                                       25

<210> SEQ ID NO 46
<211> LENGTH: 30
<212> TYPE: DNA
<213> ORGANISM: Artificial
<220> FEATURE:
<223> OTHER INFORMATION: synthetic

<400> SEQUENCE: 46 taagttttt ttaagagttt gtatttgtat                                   30

<210> SEQ ID NO 47
<211> LENGTH: 25
<212> TYPE: DNA
<213> ORGANISM: Artificial
<220> FEATURE:
<223> OTHER INFORMATION: synthetic

<400> SEQUENCE: 47
taaaaataat caaaacctaa cttac                                       25

<210> SEQ ID NO 48
<211> LENGTH: 25
<212> TYPE: DNA
<213> ORGANISM: Artificial
<220> FEATURE:
<223> OTHER INFORMATION: synthetic

<400> SEQUENCE: 48
attgtttatt aaatgttttt tagtt                                       25

<210> SEQ ID NO 49
<211> LENGTH: 24
<212> TYPE: DNA
<213> ORGANISM: Artificial
<220> FEATURE:
<223> OTHER INFORMATION: synthetic

<400> SEQUENCE: 49
ctaacaattc ccaaaaccct tatc                                        24

<210> SEQ ID NO 50
<211> LENGTH: 24
<212> TYPE: DNA
<213> ORGANISM: Artificial

```
<220> FEATURE:
<223> OTHER INFORMATION: synthetic

<400> SEQUENCE: 50
gtgtactcat ctggatctgt attg                                           24

<210> SEQ ID NO 51
<211> LENGTH: 25
<212> TYPE: DNA
<213> ORGANISM: Artificial
<220> FEATURE:
<223> OTHER INFORMATION: synthetic

<400> SEQUENCE: 51
ggttgaggag cctgaatctc tgaac                                          25

<210> SEQ ID NO 52
<211> LENGTH: 1000
<212> TYPE: DNA
<213> ORGANISM: Arabidopsis thaliana

<400> SEQUENCE: 52
acagaaaaaa aaaaactaat ttcgattcca caatgccgaa acccagaaaa attctcaaaa    60
cgaagtcact caagaagata atcaacaaag cgaaaacgga gaagggtttg ggtttaaggt   120
accgtaacga actccggtaa gttccgatga tggtgttgac agcgaagctt cgtggaacag   180
cgtgaccgtc gttactcact ggatttgccg gtgaatttga tgagtcaaaa atataactag   240
cagctggtca aagtaaccac tctgaataag acacgtgtca gaaactttgt tgaccattct   300
gactaaagaa accttgtaac caaaaacatc cacatttta catgctctgt catatttcaa    360
ctgtatacta aagttgaaat atgactatgg taacttatgt ttttttagtt gaaaactaag   420
gtaaactatt ctatgccagc aggtaaaaga tgtggatgac caactactgc tggcataatt   480
tattctatga ctaaggtaaa actaaaagtt aatatcactc gaaatattta caaaagtatt   540
agataaagta ctaaaaattt taagttagaa atgatgaaat taaagatat atgtggctta    600 tttaggaaaa tagatacttt taatatgatg gttgggtagt tttattattg tttgggattg   660
aaaaaaacta tgaaagtgtc tccaagtaca gtaatattta acaactaact aggaaggtgt   720
acattgttca gtattcatca ttctaattaa tacaaataat tttaaaaatt tggggtcgtc   780
aattgctcaa agatattcat tatttttataa ttttctacat tttatcaaaa acagaattgt   840
gtaaatgttg tgtcattatg tgtcgacttg gatgtatgca ttacataatt ttattttata   900 tatgtttta attgttagag catttattcg aaaattataa atattgaatt ttaatcctca    960
gtcacttaat aaaaacatta ttttaggact aaaaaataat                        1000

<210> SEQ ID NO 53
<211> LENGTH: 1000
<212> TYPE: DNA
<213> ORGANISM: Oryza sativa

<400> SEQUENCE: 53
caacgacggc ttgcaggaat ttttaaaaaa ctataaaaaa aatcatatca ataatacgga    60
tcttaccggt gtagtgagat gacaaagaag agaagcaatg ggcaggtgag cgtgcgcaaa   120
caaatgagat aggaggcagt tgccacagga gggcatgccg agggtggtaa agtaaataaa   180 aaataatta taagagttca agtagaatta caatttataa atgaaagaaa tatcacaata   240
agaaatattt attttttgaaa aaaatagtcc atacagacca caacatgaca aattataata   300
```

| | | |
|---|---|---|
| aaaaaacaag agaatagacc cataaaaaat tagagtggtg taggtagatg ggacatctaa | 360 | |
| aaactataaa caaaacctta aatagaatat caatgataat taagaggagg gacaacgagc | 420 | |
| cggtcgttaa gcagcacgat ctcgacgatt ggagggattt ctagaaagta aaaaaaaact | 480 | |
| ctcaattata atcatgttcg attttcaaat ctcaacgata ataaaaatgg gaagcaatgg | 540 | |
| acgggccaaa gaggagtata gtggcggcgt ttagcgagac ttataaaaat tataaaaatg | 600 | |
| aaacccaaca atacaatgaa ctctaaaacc acaaggtcaa atttgtagag gttccaggaa | 660 | |
| ggatgaatga aagcattggt agatcgagca agtaaataaa gcgatgataa agaaataatg | 720 | |
| cgtagtgatt agcatgacta ttaaaagcac cgggatgata aagtcggttt ctaacatata | 780 | |
| gttatttaac aaattttaag taaaatcata tgtaaaaaat agataatttt gtatgggtgc | 840 | |
| tagcccgcgc aattgcgcgg gccacctagc tagttttttt aaaaatgtaa atataaaaaa | 900 | |
| ttcgaccacc acgcatcgcc tgctctgccg cggcgacgcg agccacaaag ccgtcgacca | 960 | |
| ccgcaacaac aaaatatcct cctcccgacg caaaccggtt | 1000 | |

<210> SEQ ID NO 54
<211> LENGTH: 1000
<212> TYPE: DNA
<213> ORGANISM: Solanum lycopersicum

<400> SEQUENCE: 54

| | | |
|---|---|---|
| atgtttaatt tatgggtaat gtagaagtgt atttaaaaaa aaaaaattga taaatatgtt | 60 | |
| tatattatat gtgtaatgtg tgttaatatt tcggtgatg gaataatata tgataaatca | 120 | |
| tttagactca tgaagctctt cttaaatata atgaaaagac ttccaatgta aaaaattata | 180 | |
| atcggaagcg gagccaatat atatttaggg gttcatttga attctcttta gcgaaaaata | 240 | |
| tagtactatt tatatatgat cagttatttt ttttatgca tatgtagtag atattaaatc | 300 | |
| tccttcgatt atttcgtgtg tttacttctt gagattttaa attccctatt caaaaatcct | 360 | |
| agcctcgcca ttgtccgtaa caagagata ctaaatcgta tcttgtactc cctgtgtccc | 420 | |
| aatttatgcg acttacgttg cttttagtc agtccaaaaa taatgacaca attctatatt | 480 | |
| aagtaacaat ttaactataa aacgtcgatt ttatccttaa tgaaacgatt taccaccaca | 540 | |
| caaatttctc attttagact gcaagttttt taaaaatttt catttcttc ttaaaactct | 600 | |
| gtgccgaata aaactacttt acgtaaaata gaaaggagga aatatttatt tacacatcat | 660 | |
| aaaaagtctc gaggaaaatc aaaaaaacgt cacaacaaac ataatatttt cattgaaaaa | 720 | |
| atcgtttcat acctatttct tttgttgtct cttttcatc cagtgttcag tactcactat | 780 | |
| aaacactgac caatataaaa ctattcgcgc tccaaaatac cacattaaat aaaagcaact | 840 | |
| tcatacataa aactcgaact cataatctcc cgttataaaa ggataccaca acttttagt | 900 | |
| gctcttttc aataataact tttttttat aaaaaaaaac taactgccag agtggaattt | 960 | |
| ccaactgtat ctatttgatg aaaatagcag aaaactggtt | 1000 | |

<210> SEQ ID NO 55
<211> LENGTH: 24
<212> TYPE: DNA
<213> ORGANISM: Artificial sequence
<220> FEATURE:
<223> OTHER INFORMATION: synthetic

<400> SEQUENCE: 55

| | |
|---|---|
| gtgtactcat ctggatctgt attg | 24 |

```
<210> SEQ ID NO 56
<211> LENGTH: 25
<212> TYPE: DNA
<213> ORGANISM: Artificial sequence
<220> FEATURE:
<223> OTHER INFORMATION: synthetic

<400> SEQUENCE: 56
ggttgaggag cctgaatctc tgaac                                          25
```

US 10,058,044 B2

METHODS AND COMPOSITIONS FOR OBTAINING USEFUL PLANT TRAITS

CROSS-REFERENCE TO RELATED APPLICATIONS

This U.S. Non-Provisional Patent Application claims the benefit of U.S. Provisional Patent Application No. 61/901,349, filed Nov. 7, 2013 and incorporated herein by reference in its entirety.

STATEMENT REGARDING FEDERALLY SPONSORED RESEARCH OR DEVELOPMENT

This invention was made with Government Support under a grant from the National Science Foundation (IOS 1126935). The government has certain rights to this invention.

INCORPORATION OF SEQUENCE LISTING

The sequence listing contained in the file named "46589_136656_SEQ_LST.txt", which is 110,576 bytes in size (measured in operating system MS-Windows), contains 56 sequences, and which was created on Nov. 3, 2014, is contemporaneously filed with this specification by electronic submission (using the United States Patent Office EFS-Web filing system) and is incorporated herein by reference in its entirety.

BACKGROUND

Evidence exists in support of a link between environmental sensing and epigenetic changes in both plants and animals (Bonasio et al., *Science* 330, 612, 2010). Trans-generational heritability of these changes remains a subject of active investigation (Youngson et al. *Annu. Rev. Genom. Human Genet.* 9, 233, 2008). Previous studies have shown that altered methylation patterns are highly heritable over multiple generations and can be incorporated into a quantitative analysis of variation (Vaughn et al. 2007; Zhang et al. 2008; Johannes et al. 2009). Earlier studies of methylation changes in *Arabidopsis* suggest amenability of the epigenome to recurrent selection and also suggest that it is feasible to establish new and stable epigenetic states (F. Johannes et al. *PLoS Genet.* 5, e1000530 (2009); F. Roux et al. *Genetics* 188, 1015 (2011). Manipulation of the *Arabidopsis* met1 and ddmt mutants has allowed the creation of epi-RIL populations that show both heritability of novel methylation patterning and epiallelic segregation, underscoring the likely influence of epigenomic variation in plant adaptation (F. Roux et al. *Genetics* 188, 1015 (2011)). In natural populations, a large proportion of the epiallelic variation detected in *Arabidopsis* is found as CpG methylation within gene-rich regions of the genome (C. Becker et al. *Nature* 480, 245 (2011), R. J. Schmitz et al. *Science* 334, 369 (2011).

Induction of traits that exhibit cytoplasmic inheritance (Redei Mutat. Res. 18, 149-162, 1973; Sandhu et al. Proc Natl Acad Sci USA. 104:1766-70, 2007) or that exhibit nuclear inheritance by suppression of the MSH1 gene has also been reported (WO 2012/151254; Xu et al. Plant Physiol. Vol. 159:711-720, 2012).

SUMMARY

Methods for producing a plant having a useful trait that exhibits nuclear inheritance comprising the steps of: (a) selfing a first plant wherein said plant or a parent plant thereof is or had been subjected to perturbation of organellar function; (b) screening a population of progeny plants obtained from the selfed plant of step (a) for the useful trait; and, (c) selecting one or more progeny plants having the useful trait that exhibits nuclear inheritance and having recovered organellar function are provided herein. In certain embodiments of the methods, organellar function has been recovered in any of: (i) the selfed first plant in step (a); (ii) at least a portion of the progeny plants of step (b); or (iii) one or more of the selected progeny plants in step (c). In certain embodiments of the methods, the selfed first plant of step (a) exhibits a wild type phenotype or an improvement in a useful trait in comparison to a control plant. In certain embodiments, the selfed first plant of step (a) does not exhibit any MSH1-dr phenotypes. In certain embodiments, the selfed first plant of step (a) exhibits one or more MSH1-dr phenotypes. In certain embodiments, the selfed first plant of step (a) exhibits all MSH1-dr phenotypes. In certain embodiments of the methods, the perturbed organellar function is a plastid function selected from the group consisting of a sensor, photosystem I, photosystem II, NAD (P)H dehydrogenase (NDH) complex, cytochrome b6f complex, and plastocyanin function. In certain embodiments of the methods, the photosystem II function and/or sensor function is perturbed by suppressing expression of a gene selected from the group consisting of an MSH1, PPD3, a PsbO-1, a PsbO-2, PsbY, PsbW, PsbX, PsbR, PsbTn, PsbP1, PsbP2, PsbS, PsbQ-1, PsbQ-2, PPL1, PSAE-1, LPA2, PQL1, PQL2, and a PQL3 gene. In certain embodiments of the methods, selfed plant in step (a) is an inbred plant. In certain embodiments of the methods, about 1% to about 45% of the population of progeny plants in step (b) are selected for the useful trait in step (c). In certain embodiments of any of the aforementioned methods, the method further comprises making a first cross of the selected progeny plant(s) of step (c) to one or more second plant(s). In certain embodiments of the aforementioned method, the selected progeny plant(s) and the second plant(s) used in the first cross are in a single heterotic group. In certain embodiments of the aforementioned methods, the second plant is isogenic to the plant or parent plant of step (a). In certain embodiments of the aforementioned methods, the second plant and the selected plant are in distinct heterotic groups. In certain embodiments of the aforementioned methods, the method further comprises the step of selecting of one or more progeny of the first cross that exhibit an improvement in a useful trait in comparison to progeny of a control cross. In certain embodiments the aforementioned methods, the selected progeny of the first cross comprise about 1% to about 45% of the population of progeny plants obtained from the first cross. In certain embodiments of the aforementioned methods, the plants used in the control cross are of the same heterotic group as the selected progeny plant(s) and the second plant(s), but had not been subjected to organellar perturbation. In certain embodiments of the aforementioned methods, the plants used in the control cross are isogenic to the selected plant and the second plant, but had not been subjected to organellar perturbation. In certain embodiments of the aforementioned methods, the methods further comprise the step of making a second cross of the one or more of the selected progeny plant(s) of the first cross to one or more third plants. In certain embodiments of the aforementioned methods, the methods further comprise the step of selecting of one or more progeny of the second cross that exhibit an improvement in a useful trait in comparison to progeny of a control cross. In certain embodiments of any of the aforementioned methods, the methods further comprise the second plant or a parent plant thereof had been subjected to perturbation of organellar function. In certain embodiments of any of the aforementioned methods, the selfed plant in step (a) is a plant wherein a scion is grafted to rootstock that had been subjected to perturbation of organellar function. In certain embodiments of any of the aforementioned methods, the organellar function is a plastid function or a mitochondrial function. In certain embodiments of any of the aforementioned methods, the useful trait is transmitted by using selected progeny plant(s) or progeny thereof as pollen donors. Also provided are plants or progeny thereof that exhibit a useful trait that are made by the aforementioned methods. Plant parts obtained from the plant or progeny thereof made by the aforementioned methods are also provided. In certain embodiments, the part is selected from the group consisting of a seed, leaf, stem, fruit, and a root. Processed plant products obtained from the plant parts are also provided. Clonal propagates obtained from the plants, the progeny thereof, or from the plant parts are also provided.

Also provided herein are methods for producing a plant having a useful trait that exhibits nuclear inheritance comprising the steps of: (a) crossing one or more first plant(s) to one or more second plant(s), wherein at least said first plant(s) or a parent plant thereof is or had been subjected to perturbation of organellar function and wherein either: (i) the first plant or a parent plant thereof does not exhibit any MSH1-dr phenotypes; or (ii) wherein the first plant or a parent plant thereof exhibits one or more MSH1-dr phenotypes and the perturbation of does not comprise direct suppression of MSH 1 gene expression; (b) screening a population of progeny plants obtained from the cross of step (a) for the useful trait; and, (c) selecting one or more progeny plants having the useful trait that exhibits nuclear inheritance and having recovered organellar function, thereby producing a plant exhibiting a useful trait that exhibits nuclear inheritance. In certain embodiments of the methods, organellar function has been recovered in any of: (i) the first plant in step (a); (ii) at least a portion of the population of progeny plants of step (b); or (iii) one or more of the selected progeny plants in step (c). In certain embodiments of the methods, the first plant(s) of step (a) exhibit a wild type phenotype or an improvement in a useful trait in comparison to a control plant. In certain embodiments of the methods, about 1% to about 45% of the population of progeny plants in step (b) are selected for the useful trait in step (c). In certain embodiments of the methods, the perturbed organellar function is a plastid function selected from the group consisting of a sensor, photosystem I, photosystem II, NAD (P)H dehydrogenase (NDH) complex, cytochrome b6f complex, and plastocyanin function. In certain embodiments of the methods, the photosystem II function and/or sensor function is perturbed by suppressing expression of a gene selected from the group consisting of an MSH1, PPD3, a PsbO-1, a PsbO-2, PsbY, PsbW, PsbX, PsbR, PsbTn, PsbP1, PsbP2, PsbS, PsbQ-1, PsbQ-2, PPL1, PSAE-1, LPA2, PQL1, PQL2, and a PQL3 gene, with the proviso that the gene is not MSH1 when first plant or a parent plant thereof exhibits one or more MSH1-dr phenotype(s). In certain embodiments of the methods, the first plant in step (a) is an inbred plant. In certain embodiments of any of the aforementioned methods, the method further comprises making a second cross of the selected progeny plant(s) of step (c) to one or more third plant(s). In certain embodiments of the aforementioned methods, the selected progeny plant(s) and the third plant are in a single heterotic group. In certain embodiments of the aforementioned methods, the third plant is isogenic to the first plant or parent plant of step (a). In certain embodiments of the aforementioned methods, the methods further comprise the step of selecting of one or more progeny of the second cross that exhibit an improvement in a useful trait in comparison to progeny of a control cross. In certain embodiments of the aforementioned methods, the selected progeny of the second cross comprise about 1% to about 45% of the population of progeny plants obtained from the second cross. In certain embodiments of the aforementioned methods, the methods comprise the step of making a third cross of the one or more of the selected progeny plants of the second cross to one or more fourth plants. In certain embodiments of the aforementioned methods, the second plants or a parent plant thereof had been subjected to perturbation of organellar function. In certain embodiments of the aforementioned methods, the third plants or a parent plant thereof had been subjected to perturbation of organellar function. In certain embodiments of any of the aforementioned methods, the first plant(s) or a parent plant thereof in step (a) that is or had been subjected perturbation of organellar function is a plant wherein a scion is grafted to grafted to rootstock that had been subjected to perturbation of organellar function. In certain embodiments of any of the aforementioned methods, the organellar function is a plastid or a mitochondrial function. In certain embodiments of the aforementioned methods, the useful trait is transmitted by using selected progeny plant(s) or progeny thereof as pollen donors. Also provided are plants or progeny thereof that exhibit a useful trait that are made by the aforementioned methods. Plant parts obtained from the plant or progeny thereof made by the aforementioned methods are also provided. In certain embodiments, the part is selected from the group consisting of a seed, leaf, stem, fruit, and a root. Processed plant products obtained from the plant parts are also provided. Clonal propagates obtained from the plants, the progeny thereof, or from the plant parts are also provided.

Also provided herein are methods of identifying a plant harboring a useful trait comprising the steps of: (a) crossing a candidate plant to a second plant, wherein the candidate plant is progeny of: (i) a selfed plant wherein said plant or a parent plant thereof is or had been subjected to perturbation of organellar function; or of (ii) a cross wherein at least one crossed plant or a parent plant thereof is or had been subjected to perturbation of organellar function; and, (b) identifying one or more progeny plants from the cross in step (a) that exhibit a useful trait to a greater extent than the candidate plant, the second plant, or a control plant, thereby identifying the candidate plant as a plant that harbors a useful trait. In certain embodiments of the methods, the control plant is progeny of a cross between; (i) a plant that is not progeny of a selfed plant, a crossed plant, or parent thereof that is or had been subjected to organellar perturbation; and (ii) a plant that is isogenic to the second plant. In certain embodiments of the methods, the selfed plant or a parent plant thereof in (i) or the crossed plant or parent plant thereof in (ii) does not exhibit any MSH1-dr phenotypes. In certain embodiments of the methods, the selfed plant or a parent plant thereof in (i) or the crossed plant or parent plant thereof in (ii) exhibits one or more MSH1-dr phenotypes. In certain embodiments of the methods, the perturbation does not comprise direct suppression of MSH 1 gene expression. In certain embodiments of any of the aforementioned methods, the candidate plant is used as a pollen donor in the crossing step (a). In certain embodiments of any of the aforementioned methods, the selfed plant in (i) or at least one of the plants used in the cross of (ii) that is or had been subjected perturbation of organellar function is a plant wherein a scion is grafted to grafted to rootstock that had been subjected to perturbation of organellar function. In certain embodiments of any of the aforementioned methods, the organellar function is a plastid or a mitochondrial function. In certain embodiments of any of the aforementioned methods, the identifying further comprises showing that the harbored trait exhibits nuclear inheritance. Also provided is a plant, progeny thereof, or seed thereof that harbors a useful trait, wherein said plant, progeny thereof, or seed thereof is identified or identifiable by any of the aforementioned the methods.

Also provided herein are methods of identifying a organellar perturbation agent that comprises: (a) assaying one or more candidate agents for inhibition of an interaction of an MSH-1 protein or fragment thereof with at least one assistant protein selected from the group consisting of PPD3, PsbA (D1), a PsbO-1, a PsbO-2, PetC, CAD9, KAB1, GOS12, ELI3-1, STT3B, a fragment thereof, and combinations thereof; and, (b) selecting an agent that inhibits the interaction of MSH-1 or fragment thereof with the assistant protein, thereby identifying a organellar perturbation agent. In certain embodiments of the methods, the fragment of MSH-1 comprises a peptide of at least about 10 amino acids located within Domain 2, 3, or 6 of MSH-1. In certain embodiments of the methods, the agent is selected from the group consisting of a compound, a peptide, and a peptidomimetic compound. In certain embodiments of the methods, the peptide is comprises a peptide of a peptide of at least about 10 amino acids located within Domain 2, 3, or 6 of MSH-1.

Plants comprising a scion grafted to rootstock that had been subjected to perturbation of organellar function are provided herewith. Such grafted plants can be used in methods for producing a plant exhibiting useful traits, methods for identifying one or more altered chromosomal loci in a plant that can confer a useful trait, and in methods for obtaining plants comprising modified chromosomal loci that can confer a useful trait. Such grafted plants that exhibit useful traits, progeny of the grafted plants exhibiting the useful traits, parts of the grafted or progeny plants including cells, leafs, stems, flowers and seeds, methods of using the grafted or progeny plants and plant parts, and products of those plants and plant parts, including processed products such as a feed or a meal are also provided herein.

Plants comprising a scion to which a rootstock had been grafted, where the rootstock is obtained from a plant or a parent plant thereof had been subjected to perturbation of organellar function are provided herein. In certain embodiments, the rootstock confers to the grafted plant or to the progeny thereof an improvement in a useful trait in comparison to a control plant which lacks a graft to the rootstock or in comparison to progeny of the control plant. In certain embodiments, the rootstock that is grafted to the scion in step (a) is obtained from a plant that was selected for the useful trait and that was derived from a parent plant that had been subjected to organellar perturbation. In certain embodiments, the plant comprising rootstock obtained from a plant that was selected for the useful trait and that was derived from a parent plant that had been subjected to organellar perturbation exhibits the useful trait. In certain embodiments, the organellar function that is perturbed is a plastid function selected from the group consisting of a sensor, photosystem I, photosystem II, NAD(P)H dehydrogenase (NDH) complex, cytochrome b6f complex, and plastocyanin function. In certain embodiments, the perturbation comprises suppression of a sensor gene selected from the group consisting of MSH1 and PPD3. In certain embodiments, the photosystem II function is perturbed by suppressing expression of a gene selected from the group consisting of an PsbO-1, a PsbO-2, PsbY, PsbW, PsbX, PsbR, PsbTn, PsbP1, PsbP2, PsbS, PsbQ-1, PsbQ-2, PPL1, PSAE-1, LPA2, PQL1, PQL2, and a PQL3 gene. In certain embodiments, the control plant comprises either: (i) a scion grafted to rootstock that had not been subjected to organellar perturbation; or (ii) a whole plant that lacks any root graft and that had not been subjected to organellar perturbation.

Also provided are methods for producing a plant exhibiting a useful trait comprising the steps of: (a) obtaining a population of progeny plants from a grafted plant comprising a scion to which a rootstock had been grafted, wherein the rootstock is obtained from a plant or a parent plant thereof had been subjected to perturbation of organellar function; and, (b) selecting one or more progeny plants from the population, wherein the selected progeny plant exhibit an improvement in the useful trait in comparison to a control plant, thereby producing a plant that exhibits a useful trait. In certain embodiments, the population of progeny plants are obtained from seed of the grafted plant of step (a). In certain embodiments, the population of progeny plants are obtained from clonal propagates of the grafted plant of step (a). In certain embodiments, organellar function has been recovered in the rootstock that is grafted to the scion in step (a). In certain embodiments, the rootstock that is grafted to the scion in step (a) is obtained from a plant that was selected for the useful trait and that was derived from a parent plant that had been subjected to organellar perturbation. In certain embodiments, the grafted plant comprising rootstock obtained from a plant that was selected for the useful trait and that was derived from a parent plant that had been subjected to organellar perturbation exhibits the useful trait. In certain embodiments, the plant comprising rootstock obtained from a plant that was selected for the useful trait and that was derived from a parent plant that had been subjected to organellar perturbation. In certain embodiments, the organellar perturbation is a perturbation of a plastid function is selected from the group consisting of a sensor, photosystem I, photosystem II, NAD(P)H dehydrogenase (NDH) complex, cytochrome b6f complex, and plastocyanin function. In certain embodiments, the perturbation comprises suppression of a sensor gene selected from the group consisting of MSH1 and PPD3. In certain embodiments, the photosystem II function was perturbed by suppressing expression of a gene selected from the group consisting of an PsbO-1, a PsbO-2, PsbY, PsbW, PsbX, PsbR, PsbTn, PsbP1, PsbP2, PsbS, PsbQ-1, PsbQ-2, PPL1, PSAE-1, LPA2, PQL1, PQL2, and a PQL3 gene. In certain embodiments, the control plant comprises either: (i) a scion grafted to rootstock that had not been subjected to organellar perturbation; or (ii) a whole plant that lacks any root graft and that had not been subjected to organellar perturbation. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. In certain embodiments, the scion contain(s) one or more epigenetic changes in one or more nuclear chromosomes, wherein the epigenetic changes are absent from nuclear chromosomes of the control plant or are absent from nuclear chromosomes of a plant from which the scion was obtained. In certain embodiments, the epigenetic change(s) are also present in the rootstock that had been subjected to perturbation of organellar function. In certain embodiments, the epigenetic changes are associated with the improvement in the useful trait. In certain embodiments, the rootstock contain(s) one or more epigenetic changes in one or more nuclear chromosomes that are absent from nuclear chromosomes of rootstock obtained from a plant or are absent from nuclear chromosomes of a parent plant thereof had not been subjected to perturbation of organellar function. In certain embodiments, the scion and/or the rootstock exhibit CG hypermethylation of a region encompassing a MSH1 locus in comparison to a control plant that had not been subjected to the organellar perturbation. In certain embodiments, the scion and/or the rootstock exhibit pericentromeric CHG hyper-methylation in comparison to a control plant that had not been subjected to the organellar perturbation. In certain embodiments, the scion and/or the rootstock exhibit CG hypermethylation and/or CHG hyper-methylation at one or more nuclear chromosomal loci in comparison to corresponding nuclear chromosomal loci of a control plant that had not been subjected to the organellar perturbation. In certain embodiments, the plant is selected from the group consisting of a crop plant, a tree, a bush, and a vine. In certain embodiments, the crop plant is selected from the group consisting of corn, soybean, cotton, canola, wheat, rice, tomato, tobacco, millet, potato, sugarbeet, cassava, alfalfa, barley, oats, sugarcane, sunflower, strawberry, and *sorghum*. In certain embodiments, the tree is selected from the group consisting of an apple, apricot, grapefruit, orange, peach, pear, plum, lemon, coconut, poplar, eucalyptus, date palm, palm oil, pine, and an olive tree. In certain embodiments, the bush is selected from the group consisting of a blueberry, raspberry, and blackberry bush. Also provided are plants or progeny thereof obtained by any of the aforementioned methods. Also provided are plant parts obtained from the plant or progeny thereof that were made by any of the aforementioned methods. In certain embodiments, the plant part is selected from the group consisting of a seed, leaf, stem, fruit, and a root. Also provided are clonal propagates obtained from the plant or progeny thereof that were made by any of the aforementioned methods.

Plants comprising a scion that had been subjected to perturbation of organellar function grafted to rootstock that had not been subjected to plastid perturbation are also provided herewith. Such grafted plants can be used in methods for producing a plant exhibiting useful traits, methods for identifying one or more altered chromosomal loci in a plant that can confer a useful trait, and in methods for obtaining plants comprising modified chromosomal loci that can confer a useful trait. Such grafted plants that exhibit useful traits, progeny of the grafted plants exhibiting the useful traits, parts of the grafted or progeny plants including cells, leafs, stems, flowers and seeds, methods of using the grafted or progeny plants and plant parts, and products of those plants and plant parts, including processed products such as a feed or a meal are also provided herein. In certain embodiments, a tiller, shoot or other clonal propagate from the bottom rootstock of the grafted plant is used to regenerate a plant, progeny thereof, or seed therefrom that exhibit or contain the useful trait.

Plants comprising a scion to which a rootstock had been grafted, where the scion is obtained from a plant or a parent plant thereof had been subjected to perturbation of organellar function are provided herein. In certain embodiments, the scion confers to the grafted plant or to the progeny thereof an improvement in a useful trait in comparison to a control plant which lacks a graft to the rootstock or in comparison to progeny of the control plant. In certain embodiments, the scion that is grafted to the rootstock is obtained from a plant that was selected for the useful trait and that was derived from a parent plant that had been subjected to organellar perturbation. In certain embodiments, the grafted plant comprising the scion obtained from a plant that was selected for the useful trait and that was derived from a parent plant that had been subjected to organellar perturbation exhibits the useful trait. In certain embodiments, the organellar function that is perturbed is a plastid function selected from the group consisting of a sensor, photosystem I, photosystem II, NAD(P)H dehydrogenase (NDH) complex, cytochrome b6f complex, and plastocyanin function. In certain embodiments, the perturbation comprises suppression of a sensor gene selected from the group consisting of MSH1 and PPD3. In certain embodiments, the photosystem II function is perturbed by suppressing expression of a gene selected from the group consisting of an PsbO-1, a PsbO-2, PsbY, PsbW, PsbX, PsbR, PsbTn, PsbP1, PsbP2, PsbS, PsbQ-1, PsbQ-2, PPL1, PSAE-1, LPA2, PQL1, PQL2, and a PQL3 gene. In certain embodiments, the control plant comprises either: (i) a scion that had not been subjected to organellar perturbation grafted to rootstock; or (ii) a whole plant that lacks any scion graft and that had not been subjected to organellar perturbation.

Also provided are methods for producing a plant exhibiting a useful trait comprising the steps of: (a) obtaining a population of progeny plants from a grafted plant comprising a scion to which a rootstock had been grafted, wherein the scion is obtained from a plant or a parent plant thereof had been subjected to perturbation of organellar function; and, (b) selecting one or more progeny plants from the population, wherein the selected progeny plant exhibit an improvement in the useful trait in comparison to a control plant, thereby producing a plant that exhibits a useful trait. In certain embodiments, the population of progeny plants are obtained from seed of the grafted plant of step (a). In certain embodiments, the population of progeny plants are obtained from clonal propagates of the grafted plant of step (a). In certain embodiments, the clonal propagates comprise shoots or tillers from the grafted plant. In certain embodiments, organellar function has been recovered in the scion that is grafted to the rootstock in step (a). In certain embodiments, the scion that is grafted to the rootstock in step (a) is obtained from a plant that was selected for the useful trait and that was derived from a parent plant that had been subjected to organellar perturbation. In certain embodiments, the grafted plant comprising a scion obtained from a plant that was selected for the useful trait and that was derived from a parent plant that had been subjected to organellar perturbation exhibits the useful trait. In certain embodiments, the plant comprises a scion obtained from a plant that was selected for the useful trait and that was derived from a parent plant that had been subjected to organellar perturbation. In certain embodiments, the organellar perturbation is a perturbation of a plastid function is selected from the group consisting of a sensor, photosystem I, photosystem II, NAD(P)H dehydrogenase (NDH) complex, cytochrome b6f complex, and plastocyanin function. In certain embodiments, the perturbation comprises suppression of a sensor gene selected from the group consisting of MSH1 and PPD3. In certain embodiments, the photosystem II function was perturbed by suppressing expression of a gene selected from the group consisting of an PsbO-1, a PsbO-2, PsbY, PsbW, PsbX, PsbR, PsbTn, PsbP1, PsbP2, PsbS, PsbQ-1, PsbQ-2, PPL1, PSAE-1, LPA2, PQL1, PQL2, and a PQL3 gene. In certain embodiments, the control plant comprises either: (i) a scion that had not been subjected to organellar perturbation grafted to rootstock; or (ii) a whole plant that lacks any scion graft and that had not been subjected to organellar perturbation. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. In certain embodiments, the rootstock also contain(s) one or more epigenetic changes in one or more nuclear chromosomes, wherein the epigenetic changes are absent from nuclear chromosomes of the control plant or are absent from nuclear chromosomes of a plant from which the rootstock was obtained. In certain embodiments, the epigenetic change(s) are also present in the scion that had been subjected to perturbation of organellar function. In certain embodiments, the epigenetic changes are associated with the improvement in the useful trait. In certain embodiments, the scion contain(s) one or more epigenetic changes in one or more nuclear chromosomes that are absent from nuclear chromosomes of scion obtained from a plant or are absent from nuclear chromosomes of a parent plant thereof had not been subjected to perturbation of organellar function. In certain embodiments, the scion and/or the rootstock exhibit CG hypermethylation of a region encompassing a MSH1 locus in comparison to a control plant that had not been subjected to the organellar perturbation. In certain embodiments, the scion and/or the rootstock exhibit pericentromeric CHG hyper-methylation in comparison to a control plant that had not been subjected to the organellar perturbation. In certain embodiments, the scion and/or the rootstock exhibit CG hypermethylation and/or CHG hypermethylation at one or more nuclear chromosomal loci in comparison to corresponding nuclear chromosomal loci of a control plant that had not been subjected to the organellar perturbation. In certain embodiments, the plant is selected from the group consisting of a crop plant, a tree, a bush, and a vine. In certain embodiments, the crop plant is selected from the group consisting of corn, soybean, cotton, canola, wheat, rice, tomato, tobacco, millet, potato, sugarbeet, cassava, alfalfa, barley, oats, sugarcane, sunflower, strawberry, and *sorghum*. In certain embodiments, the tree is selected from the group consisting of an apple, apricot, grapefruit, orange, peach, pear, plum, lemon, coconut, poplar, eucalyptus, date palm, palm oil, pine, and an olive tree. In certain embodiments, the bush is selected from the group consisting of a blueberry, raspberry, and blackberry bush. Also provided are plants or progeny thereof obtained by any of the aforementioned methods. Also provided are plant parts obtained from the plant or progeny thereof that were made by any of the aforementioned methods. In certain embodiments, the plant part is selected from the group consisting of a seed, leaf, stem, fruit, and a root. Also provided are clonal propagates obtained from the plant or progeny thereof that were made by any of the aforementioned methods. In certain embodiments, the clonal propagates are shoots or tillers.

Also provided are methods for producing a plant exhibiting a useful trait comprising the steps of: (a) crossing a first plant to a second plant, wherein the first plant is any of the aforementioned plants comprising a scion to which a rootstock had been grafted; and, (b) selecting one or more progeny plants obtained from the cross for an improvement in the useful trait in comparison to a control plant, thereby producing a plant exhibiting a useful trait. In certain embodiments, the control plant is selected from the group consisting of progeny of a cross between a plant which lacks a graft to the rootstock and a plant that is isogenic to the second plant, progeny of a self of a plant that lacks a graft to the rootstock, and progeny of a self of the second plant. In certain embodiments, at least the scion of the first plant is from a different heterotic group than the second plant. In certain embodiments, the scion and the rootstock of the first plant are from a different heterotic group than the second plant. In certain embodiments, the scion and the rootstock of the first plant are both from the same heterotic group but are from a different heterotic group than the second plant. In certain embodiments, at least the scion of the first plant is from the same heterotic group as the second plant. In certain embodiments, the scion and the rootstock of the first plant are from the same heterotic group as the second plant. In certain embodiments the second plant and at least the scion of the first plant are isogenic. In certain embodiments, the second plant and the scion and the rootstock of the first plant are isogenic. In certain embodiments of any of the aforementioned methods, the second plant or a parent thereof had also been subjected to perturbation of organellar function. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. Also provided are plants obtained by any of the aforementioned methods. Also provided are plant parts obtained from plants made by any of the aforementioned methods. In certain embodiments, the plant part is selected from the group consisting of a seed, leaf, stem, fruit, and a root. Also provided are processed plant products obtained from plants made by any of the aforementioned methods or plant parts obtained from those plants.

Also provided are methods for producing a plant exhibiting a useful trait comprising the steps of: (a) selfing a plant, wherein the plant is any of the aforementioned plants comprising a scion to which a rootstock had been grafted or wherein the plant is a plant made by any of the aforementioned methods; and, (b) selecting one or more progeny plants obtained from the self for an improvement in the useful trait in comparison to a control plant, thereby producing a plant exhibiting a useful trait. In certain embodiments, the control plant is a progeny plant of a self of a plant which lacks a graft to the rootstock. In certain embodiments of any of the aforementioned methods, the useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. Also provided are plants obtained by any of the aforementioned methods. Also provided are plant parts obtained from plants made by any of the aforementioned methods. In certain embodiments, the plant part is selected from the group consisting of a seed, leaf, stem, fruit, and a root. Also provided are processed plant products obtained from plants made by any of the aforementioned methods or plant parts obtained from those plants.

Also provided are methods for producing a seed lot comprising: (i) growing a population of plants, wherein said population comprises two or more of any of the aforementioned plants comprising a scion to which a rootstock had been grafted and/or plants made by any of the aforementioned methods; (ii) selecting a first sub-population of plants exhibiting a useful trait; and, (ii) obtaining a seed lot from the first selected sub-population of step (i) or, optionally, repeating steps (i) and (ii) on a second population of plants grown from the seed obtained from the first selected sub-population of plants. Also provided are seed lots produced by the aforementioned methods, as well as plants, plant parts, and processed plant products obtained from the seed lots.

Also provided are methods for producing a seed lot comprising: (i) growing a population of plants, wherein said population comprises two or more of any of the aforementioned plants comprising a scion to which a rootstock had been grafted and/or plants made by any of the aforementioned methods; and (ii) obtaining a seed lot from the population. Also provided are seed lots produced by the aforementioned method as well as plants, plant parts, and processed plant products obtained from the seed lots.

Also provided are methods for identifying plants harboring a useful trait comprising the steps of: (a) crossing a candidate plant to a second plant, wherein the candidate plant is progeny of: (i) any of the aforementioned grafted plants comprising a scion to which a rootstock had been grafted, wherein the rootstock is obtained from a plant or a parent plant thereof had been subjected to perturbation of organellar function and/or plants made by any of the aforementioned methods; or (ii) a plant that had been subjected to perturbation of organellar function or progeny thereof; and, (b) identifying one or more progeny plants from the cross in step (a) that exhibit a useful trait to a greater extent than the candidate plant, the second plant, or a control plant, thereby identifying the candidate plant as a plant that harbors a useful trait. In certain embodiments of the methods, the control plant is progeny of a cross between a plant that is not progeny of a plant or a grafted plant that had been subjected to organellar perturbation and a plant that is isogenic to the second plant. Also provided are plants or progeny thereof that harbor a useful trait, wherein said plant or progeny thereof is identified or identifiable by any of the aforementioned methods.

Also provided are methods of identifying a plant harboring a useful trait comprising the steps of: (a) selfing a candidate plant, wherein the candidate plant is progeny of: (i) any of the aforementioned grafted plants comprising a scion to which a rootstock had been grafted, wherein the rootstock is obtained from a plant or a parent plant thereof that had been subjected to perturbation of organellar function; or (ii) a plant that had been subjected to perturbation of organellar function or progeny thereof; and, (b) identifying one or more progeny plants from the self in step (a) that exhibit a useful trait to a greater extent than the candidate plant or a control plant, thereby identifying the candidate plant as a plant that harbors a useful trait. In certain embodiments of the methods, the control plant is progeny of a self of plant that is not progeny of a plant or a grafted plant that had been subjected to organellar perturbation but is otherwise isogenic to the candidate plant. Plants or progeny thereof that harbor a useful trait, wherein the plant or progeny thereof is identified or identifiable by the aforementioned methods are also provided.

In certain embodiments, any of the aforementioned plants, parental plants or progeny thereof, plant parts, or processed products thereof produced by the methods provided herein exhibit a useful trait is selected from the group consisting of improved yield, delayed flowering, non-flowering, increased biotic stress resistance, increased abiotic stress resistance, enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to the control plant. In certain embodiments, organellar function has been recovered in the plant. In certain embodiments, the plants, parental plants, progeny thereof, plant parts, or processed products thereof contains one or more epigenetic changes in one or more nuclear chromosomes, wherein the epigenetic changes are absent from the nuclear chromosomes of a control plant, plant part, or processed product thereof. In certain embodiments, the epigenetic changes are associated with the improvement in the useful trait. In certain embodiments, the plants, parental plants, progeny thereof, plant parts, or processed products thereof exhibit CG hypermethylation of a region encompassing a MSH1 locus in comparison to a control plant that had not been subjected to the organellar perturbation. In certain embodiments, plants, parental plants, progeny thereof, plant parts, or processed products thereof exhibit pericentromeric CHG hyper-methylation in comparison to a control plant that had not been subjected to the organellar perturbation. In certain embodiments, plants, parental plants, progeny thereof, plant parts, or processed products thereof exhibit CG hypermethylation and/or CHG hypermethylation at one or more nuclear chromosomal loci in comparison to corresponding nuclear chromosomal loci of a control plant that had not been subjected to the organellar perturbation. In certain embodiments, the organellar perturbation comprises perturbation of plastid function or perturbation of mitochondrial function. In certain embodiments, the plant is selected from the group consisting of a crop plant, a tree, a bush, turf grass, pasture grass, and a vine. In certain embodiments, the crop plant is selected from the group consisting of corn, soybean, cotton, canola, wheat, rice, tomato, tobacco, millet, potato, sugarbeet, cassava, alfalfa, barley, oats, sugarcane, sunflower, strawberry, and *sorghum*. In certain embodiments, the tree is selected from the group consisting of an apple, apricot, grapefruit, orange, peach, pear, plum, lemon, coconut, poplar, eucalyptus, date palm, palm oil, pine, and an olive tree. In certain embodiments, the bush is selected from the group consisting of a blueberry, raspberry, and blackberry bush.

BRIEF DESCRIPTION OF THE DRAWINGS

The accompanying drawings, which are incorporated in and form a part of the specification, illustrate certain embodiments of the present disclosure. In the drawings:

FIG. 11A, B, C, D. Drought tolerant and robust 2nd generation msh1 mutants. A) Late flowering 2nd generation plants in flat. Note the large plant in the center (arrow). B) Large 2nd generation plant (arrow) compared to two normal flowering/normal phenotype siblings. C) Four days after drought conditions 2nd generation msh1 plants (left) remain green while Col-0 (yellow stake) and 1st generation msh1 plants (green flags) fail to recover. D) Comparison of the large 2nd generation msh1 plant (left) to Col-0 (right) four days after drought conditions.

DESCRIPTION

Figure 1F:
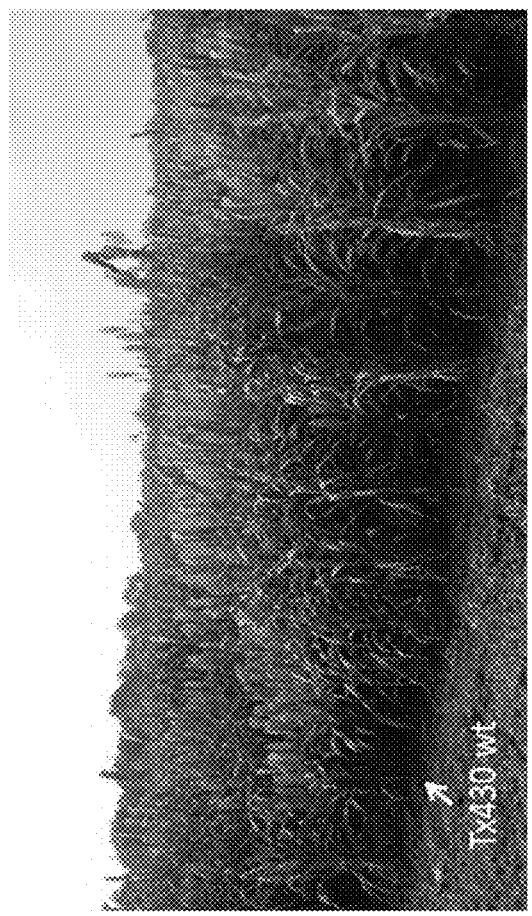
FIGS. 1A, B, C, D, E, and F illustrate the enhanced growth phenotype of MSH1-epi lines in *sorghum*. The transgene and crossing procedure used to derive *sorghum* epi-populations is indicated. A. The phenotype of the epi-F1 progeny derived from crossing Tx430×MSH1-dr. B. Field grown epi-F2, F3 and F4 *sorghum* lines show variation in plant architecture and height. C, Panicles from Tx430 (on left, 66 g, 8 mm stem) versus epi-F2 individual (on right, 112 g, 11 mm stem). D, Seed yield from the panicles shown in c. E, The MSH1-dr *sorghum* phenotype under field conditions. F. *Sorghum* MSH1-epiF2, epiF3 and epiF4 populations grown in progeny rows in the field in Summer, 2011. Wild-type inbred Tx430 is indicated. Dramatic variation visible in plant height, flowering time and plant architecture is apparently non-genetic; all plants shown are non-transgenic and Tx430 genotype.

As used herein, the phrase "chromosomal modification" refers to any of: a) an "altered chromosomal loci" and an "altered chromosomal locus"; b) "mutated chromosomal loci", a "mutated chromosomal locus", "chromosomal mutations" and a "chromosomal mutation"; or c) a transgene.

As used herein, the phrases "altered chromosomal loci" (plural) or "altered chromosomal locus (singular) refer to portions of a chromosome that have undergone a heritable and reversible epigenetic change relative to the corresponding parental chromosomal loci. Heritable and reversible genetic changes in altered chromosomal loci include, but are not limited to, methylation of chromosomal DNA, and in particular, methylation of cytosine residues to 5-methylcytosine residues, and/or post-translational modification of histone proteins, and in particular, histone modifications that include, but are not limited to, acetylation, methylation, ubiquitinylation, phosphorylation, and sumoylation (covalent attachment of small ubiquitin-like modifier proteins). As used herein, "chromosomal loci" refer to loci in chromosomes located in the nucleus of a cell.

As used herein, the phrase "clonal propagate" refers to a plant or progeny thereof obtained from a plant cell. Clonal propagates can be obtained by methods including but not limited to regenerating whole plants from plant cells, plant embryos, cuttings, and the like. Various techniques used for such clonal propagation include, but are not limited to, meristem culture, somatic embryogenesis, thin cell layer cultures, adventitious shoot culture, and callus culture.

As used herein, the term "comprising" means "including but not limited to".

As used herein, the phrase "crop plant" includes, but is not limited to, cereal, seed, grain, fruit, and vegetable crop plants.

As used herein, the phrases "mutated chromosomal loci" (plural) (plural), "mutated chromosomal locus" (singular), "chromosomal mutations" and "chromosomal mutation" refer to portions of a chromosome that have undergone a heritable genetic change in a nucleotide sequence relative to the nucleotide sequence in the corresponding parental chromosomal loci. Mutated chromosomal loci comprise mutations that include, but are not limited to, nucleotide sequence inversions, insertions, deletions, substitutions, or combinations thereof. In certain embodiments, the mutated chromosomal loci can comprise mutations that are reversible. In this context, reversible mutations in the chromosome can include, but are not limited to, insertions of transposable elements, defective transposable elements, and certain inversions. In certain embodiments, the chromosomal loci comprise mutations are irreversible. In this context, irreversible mutations in the chromosome can include, but are not limited to, deletions.

As used herein, the term "discrete variation" or "$V_D$" refers to distinct, heritable phenotypic variation, that includes one or more but not all MSH1-dr traits of male sterility, dwarfing, variegation, and/or delayed flowering time that can be observed either in any combination or in isolation.

As used herein, the phrase "heterologous sequence", when used in the context of an operably linked promoter, refers to any sequence or any arrangement of a sequence that is distinct from the sequence or arrangement of the sequence with the promoter as it is found in nature. As such, an MSH1 promoter can be operably linked to a heterologous sequence that includes, but is not limited to, MSH1 sense, MSH1 antisense, combinations of MSH1 antisense and MSH1 sense, and other MSH1 sequences that are distinct from, or arranged differently than, the operably linked sequences of the MSH1 transcription unit as they are found in nature.

As used herein, the phrase "MSH1-dr phenotypes refers to phenotypes that include leaf variegation, cytoplasmic male sterility (CMS), a reduced growth-rate phenotype, delayed or non-flowering phenotype, leaf wrinkling, increased plant tillering, decreased height, decreased internode elongation, plant tillering, and/or stomatal density changes that are observed in plants subjected to suppression of organellar perturbation target genes.

As used herein, the phrase "organellar perturbation target genes" includes plastid perturbation target genes and mitochondrial perturbation target genes. Organellar target genes that can be suppressed to produce an MSH1-dr phenotype include, but not limited to, MSH1 and PPD3.

As used herein, the phrase "organellar perturbation" includes perturbation of plastid function and/or mitochondrial functions. For proteins that function in plastids and mitochondria, organellar perturbation can include perturbation of plastid function, perturbation of mitochondrial function, or perturbation of both functions. Proteins that function in both plastids and mitochondria include, but are not limited to, the MSH1 protein.

As used herein, the term "heterotic group" refers to genetically related germplasm that produce superior hybrids when crossed to genetically distinct germplasm of another heterotic group.

As used herein, the term "progeny" refers to any one of a first, second, third, or subsequent generation obtained from a parent plant or plant cell.

As used herein, the phrase "quantitative variation" or "$V_Q$" refers to phenotypic variation that is observed in individual progeny lines derived from outcrosses of plants where MSH1 expression was suppressed and that exhibit discrete variation to other plants.

As used herein the terms "microRNA" or "miRNA" refers to both a miRNA that is substantially similar to a native miRNA that occurs in a plant as well as to an artificial miRNA. In certain embodiments, a transgene can be used to produce either a miRNA that is substantially similar to a native miRNA that occurs in a plant or an artificial miRNA.

As used herein, the phrase "obtaining a nucleic acid associated with the altered chromosomal locus" refers to any method that provides for the physical separation or enrichment of the nucleic acid associated with the altered chromosomal locus from covalently linked nucleic that has not been altered. In this context, the nucleic acid does not necessarily comprise the alteration (i.e. such as methylation) but at least comprises one or more of the nucleotide base or bases that are altered. Nucleic acids associated with an altered chromosomal locus can thus be obtained by methods including, but not limited to, molecular cloning, PCR, or direct synthesis based on sequence data.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter is linked such that the resulting translation product is in frame with the translational open reading frame that encodes the protein desired. Nucleic acid sequences that can be operably linked include, but are not limited to, sequences that provide gene expression functions (i.e., gene expression elements such as promoters, 5' untranslated regions, introns, protein coding regions, 3' untranslated regions, polyadenylation sites, and/ or transcriptional terminators), sequences that provide DNA transfer and/or integration functions (i.e., site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences, homologous recombination sequences), and sequences that provide replication functions (i.e., bacterial origins of replication, autonomous replication sequences, centromeric sequences).

As used herein, the phrases "suppressing expression" of a gene refer to any genetic or environmental manipulation that provides for decreased levels of functional gene activity in a plant or plant cell relative to the levels of functional gene activity that occur in an otherwise isogenic plant or plant cell that had not been subjected to this genetic or environmental manipulation.

As used herein, the term "transgene", in the context of a chromosomal modification, refers to any DNA from a heterologous source that has been integrated into a chromosome that is stably maintained in a host cell. In this context, heterologous sources for the DNA include, but are not limited to, DNAs from an organism distinct from the host cell organism, species distinct from the host cell species, varieties of the same species that are either distinct varieties or identical varieties, DNA that has been subjected to any in vitro modification, recombinant DNA, and any combination thereof.

As used herein, the term "non-regenerable" refers to a plant part or plant cell that cannot give rise to a whole plant.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Methods for introducing heritable and epigenetic and/or genetic variation that result in plants that have useful traits exhibiting nuclear inheritance are provided herewith along with plants, plant seeds, plant parts, plant cells, and processed plant products obtainable by these methods. In certain embodiments, methods provided herewith can be used to introduce epigenetic and/or genetic variation into varietal or non-hybrid plants that result in useful traits as well as useful plants, plant parts including, but not limited to, seeds, plant cells, and processed plant products that exhibit, carry, or otherwise reflect benefits conferred by the useful traits. In other embodiments, methods provided herewith can be used to introduce epigenetic and/or genetic variation into plants that are also amenable to hybridization.

Also provided herein are grafted plants comprising a scion to which a rootstock had been grafted, wherein either the scion or the rootstock is obtained from a plant or a parent plant thereof had been subjected to perturbation of organellar function, as well as progeny plants and clonal propagates obtained from the grafted plant. Such scions or rootstocks can be also used to introduce epigenetic and/or genetic variation into varietal or non-hybrid plants that result in useful traits as well as useful plants, plant parts including, but not limited to, seeds, plant cells, and processed plant products that exhibit, carry, or otherwise reflect benefits conferred by the useful traits. In other embodiments, such rootstocks can also be used to introduce epigenetic and/or genetic variation into plants that are also amenable to hybridization.

Scions and rootstocks useful for introducing epigenetic and/or genetic variation into plants can be obtained from a variety of scion or rootstock source plants that had been subjected to organellar perturbation. In certain embodiments, the scion or rootstock source plant is a plant that had itself been subjected to organellar perturbation. In other embodiments, the scion or rootstock source plant is the progeny of a parental plant that had itself been subjected to organellar perturbation. Various methods of making scion or rootstock source plants by organellar perturbation are provided herein. Plants that can serve as scion or rootstock source plants and methods of making such plants are also disclosed in U.S. Patent Application Publication No. 20120284814, U.S. patent application Ser. No. 14/454,518 and U.S. patent application Ser. No. 14/495,498, which are all co-assigned and are each specifically incorporated herein by reference in their entireties. Methods for obtaining grafted plants and the progeny thereof by grafting rootstock subjected to plastid perturbation are also provided in co-assigned U.S. Provisional patent application Ser. No. 14/495,498, which is specifically incorporated herein by reference in its entirety.

In certain embodiments where the plant, a scion source plant, a rootstock source plant, or a parental plant thereof, had been subjected to organellar perturbation, a population of progeny plants obtained from the plant or grafted plant are screened and individual progeny plants are selected for one or more useful traits. Such populations of progeny plants can be obtained by methods including, but not limited to, selfing or outcrossing the plant or the grafted plant comprising the scion or rootstock had been subjected to organellar perturbation to obtain seed that give rise to the population. Such populations of progeny plants can also be obtained by methods including, but not limited to, growing a population of plants that are derived from independent clonal propagates obtained from the plants or the grafted plant comprising the scion or rootstock. Such selected individual progeny plants that exhibit the useful trait can then be sexually or asexually propagated to yield populations of plants that exhibit the useful trait or seed lots that exhibit or harbor the useful trait. Such sexual propagation can be accomplished by selfing or outcrossing the selected individual progeny plants that exhibit the useful trait.

In certain embodiments where the plant, the scion source plant, or the rootstock source plant is the progeny of a parental plant that had been subjected to organellar perturbation, the plant, the scion source plant, or the rootstock source plant itself can be a plant that was selected for one or more useful traits. Grafting rootstock from a plant that had been selected for a useful trait to a scion that does not exhibit the trait can impart the trait to the resultant grafted plant or to progeny thereof. Grafting a scion from a plant that had been selected for a useful trait to rootstock from a plant that does not exhibit the trait can impart the trait to the resultant grafted plant or to progeny thereof. Resultant plants, grafted plants or progeny thereof that exhibit the useful trait can then be sexually or asexually propagated to yield populations of plants that exhibit the useful trait or seed lots that exhibit or harbor the useful trait.

In plants, grafted plants or progeny thereof, perturbation of organellar function in the plants, scions, or rootstock can be continuous and ongoing or can be transient. Non-limiting and useful methods for effecting continuous and ongoing perturbation of organellar function in the plants, scions, or rootstock include suppressing expression of a organellar perturbation target gene with mutations in the endogenous gene or with a transgene that yields a product that suppresses expression of the endogenous gene. Alternatively, the perturbation of organellar function in the plants, scions, or rootstock can be transient or have occurred in a parental plant from which the plant or rootstock was obtained but not in the rootstock that was used in the graft. Non-limiting and useful methods for effecting transient suppressing of organellar function in the plants, scions, or rootstock include suppressing expression of a organellar perturbation target gene with a transgene that provides for inducible or repressible expression of a product that suppresses expression of the endogenous gene, with a transgene that can be excised, with a heterozygous transgene insert that is removed from the rootstock by segregation, or by use of a Viral Induced Gene Silencing (VIGS) vector that suppresses expression of a organellar perturbation target gene. Any of the methods described herein for restoring organellar function after perturbation can be used to generate the plants, scions, or rootstock used in certain embodiments.

Grafting can be effected by any method that provides for establishment of a vascular connection between the rootstock and the scion. Methods of grafting that can be used to effect the connection between the scion and the rootstock include, but are not limited to, apical graftage, side graftage, bark graftage, and root graftage. Such methods for effecting grafts of scions to rootstock are disclosed in "Plant Propagation: Principles and Practices; Chapter 12: Techniques of Grafting" Ed. Hartman, Kester, Davies, and Geneve, 7$^{th}$ Edition. Methods for effecting grafts of monocot plant scions to rootstocks that can be used with the scions and rootstocks provided herein are disclosed in Muzik and La Rue, The Grafting of Large Monocotyledonous Plants, Science 116, No. 3022: 589-591, 1952.

Plants, progeny thereof, scions thereof, or rootstocks thereof subjected to organellar perturbation or obtained from a parental plant that had been subjected to organellar perturbation can exhibit modifications of one or more nuclear chromosomes. In certain embodiments, such plants, progeny thereof, scions, or rootstocks can exhibit characteristic DNA methylation and/or gene transcription patterns that occur in plants subjected to suppression of an MSH1 target gene. Such characteristic DNA methylation and/or gene transcription patterns that occur in plants or seeds subjected suppression of an MSH1 target gene include, but are not limited to, those patterns disclosed in Example 2 and Example 4 of U.S. patent application Ser. No. 14/454,518, the data and disclosure of which is specifically incorporated herein by reference in its entirety. In certain embodiments, a scion or rootstock of first generation progeny of a plant subjected to suppression of a organellar perturbation target gene will exhibit CG differentially methylated regions (DMR) of various discrete chromosomal regions that include, but are not limited to, regions that encompass the MSH1 locus. In certain embodiments, a CG hypermethylated region that encompasses the MSH1 locus will be about 5 to about 8 MBp (mega base pairs) in length. In certain embodiments, rootstock of first generation progeny of a plant subjected to suppression of a organellar perturbation target gene will also exhibit changes in plant defense and stress response gene expression. In certain embodiments, a plant, progeny thereof, a scion, a rootstock grafted thereto, a rootstock, a scion grafted thereto, and/or a plant cell, a seed, a progeny plant, plant populations, seed populations, and/or processed products obtained therefrom that has been subject to suppression of a organellar perturbation target gene will exhibit pericentromeric CHG hypermethylation and CG hypermethlation of various discrete or localized chromosomal regions. Such discrete or localized hypermethylation is distinct from generalized hypermethylation across chromosomes that have been previously observed (U.S. Pat. No. 6,444,469). Such CHG hypermethylation is understood to be methylation at the sequence "CHG" where H=A, T, or C. Such CG and CHG hypermethylation can be assessed by comparing the methylation status of a sample from rootstocks, scions of plants grafted to root stocks, plants or seed that had been subjected to suppression of a organellar perturbation target gene, or a sample from progeny plants or seed derived therefrom, to a sample from control plants or seed that had not been subjected to suppression of a organellar perturbation target gene. In this and certain other contexts, such control plants include, but are not limited to, plants, grafted plants, scions thereof and rootstocks thereof that had not been subjected to organellar perturbation. In certain embodiments, such aforementioned changes in the methylation patterns exhibited by plants, progeny thereof, scions that are grafted to the rootstocks, rootstocks that are grafted to the scions, or exhibited by a plant cell, a seed, a progeny plant, plant populations, seed populations, and/or processed products obtained from the grafted plant, be used to monitor the effectiveness of the graft in transmitting desirable epigenetic changes or to identify a plant cell, a seed, a progeny plant, plant populations, seed populations, and/or processed products obtained from the plant or grafted plant.

Also provided herein are various methods for producing a plant exhibiting a useful trait that comprise crossing plants that had been subjected to perturbation of organellar function or grafted plants comprising a scion grafted to rootstock that had been subjected to perturbation of organellar function with another plant or a scion that had been subjected to perturbation of organellar function grafted to rootstock, or crossing progeny plants obtained from the grafted plant with another second plant, and selecting one or more progeny plants obtained from the cross for an improvement in the useful trait in comparison to a control plant. In certain embodiments, the second plant can also be a grafted plant comprising a scion grafted to rootstock that had been subjected to perturbation of organellar function, a scion that had been subjected to perturbation of organellar function grafted to rootstock, progeny plants obtained from a grafted plant comprising a scion grafted to rootstock that had been subjected to perturbation of organellar function, any other ungrafted plant that had been subjected to perturbation of organellar function, or any other ungrafted plant obtained from one or more parental plants that had been subjected to perturbation of organellar function. Such second plants can be plants that were selected for a useful trait and that were progeny of any plant or grafted plant that had subjected to perturbation of organellar function. Control plants used as comparators to identify progeny of the cross that exhibit an improvement in the useful trait include, but are not limited to: progeny of a cross between a plant which lacks a graft to the rootstock and a plant that is isogenic to the second plant, progeny of a self of a plant that lacks a graft to the rootstock, progeny of a self of the second plant; progeny of a cross between a plant that is isogenic to the plant source of the scion of the grafted plant and a plant that is isogenic to the second plant; and, progeny of a cross between a plant that is isogenic to the plant source of the scion of the grafted plant and that is isogenic to the plant source of a scion of the second plant when the second plant is a grafted plant. Also provided are methods where at least the first plant or the scion of the first plant is from a different heterotic group than the second plant or where at least the scion of the first plant is from the same heterotic group than the second plant.

Also provided herein are various methods for producing a plant exhibiting a useful trait that comprise selfing plants that had been subjected to perturbation of organellar function or grafted plants comprising scions or rootstocks that had been subjected to perturbation of organellar function with another plant, or selfing progeny plants obtained from the plant OR grafted plant, and selecting one or more progeny plants obtained from the self for an improvement in the useful trait in comparison to a control plant to produce a plant exhibiting a useful trait. In certain embodiments, the selfed plant is the progeny of a parental plant that had been subjected to organellar perturbation. In certain embodiments, the selfed plant is the progeny of a parental plant that had been subjected to organellar perturbation that was selected for and exhibits one or more useful traits. In certain embodiments, the selfed plant is a grafted plant where the rootstock source plant is the progeny of a parental plant that had been subjected to organellar perturbation and the rootstock source plant itself was selected for and exhibits one or more useful traits. Control plants used as comparators to identify progeny of the self that exhibit an improvement in the useful trait include, but are not limited to: progeny of a self of a plant that was not subjected to organellar perturbation, progeny of a self of a plant which lacks a graft to the rootstock, progeny of a self of a plant that has a graft to rootstock that had not been subjected to organellar perturbation, and progeny of a self of a plant that is isogenic to the plant source of the scion of the grafted plant.

In certain embodiments, useful traits provided herein can be exhibited to a greater extent in subsequent generations of plants that are obtained from any of the plants, grafted plants, parental plants, or parental plant cells that had been subjected to organellar perturbation that are provided herein. As such, a given initial plant obtained from a parent plant that was subjected to organellar perturbation can be selfed to obtain first, second, third, or later generations of progeny that exhibit a given useful trait to a greater extent in comparison to either the initial plant or in comparison to a control plant. An initial plant subjected to organellar perturbation, or an initial grafted plant comprising a scion grafted to rootstock subjected to organellar perturbation or to rootstock obtained from a parent plant that had been subjected to organellar perturbation, can be selfed to obtain first, second, third, or later generations of progeny that exhibit a given useful trait to a greater extent in comparison to either the initial plant, the initial grafted plant or in comparison to a control plant. In other embodiments, a given initial plant or initial grafted plant obtained from a parent plant that was subjected to organellar perturbation can be outcrossed to obtain F1, F2, F3, or later generations of progeny that exhibit a given useful trait to a greater extent in comparison to either the initial plant or the initial grafted plant or in comparison to a control plant. In certain embodiments, a useful trait harbored by an initial plant or an initial grafted plant is not exhibited, or is exhibited to a lesser degree extent, in the initial plant or an initial grafted plant. However, the useful trait harbored by such an initial plant or an initial grafted plant is exhibited or is exhibited to a greater extent in progeny obtained by outcrossing the initial plant or the initial grafted plant to another plant. A useful trait harbored by such an initial plant or an initial grafted plant can also be exhibited or is exhibited to a greater extent in progeny obtained by selfing the initial plant or the initial grafted plant. In certain embodiments, plants or grafted plants that are selfed or outcrossed can be inbred lines. In certain embodiments, a useful trait harbored by an inbred line is not exhibited, or is exhibited to a lesser degree extent, in the inbred line. However, the useful trait harbored by such inbred lines is exhibited or is exhibited to a greater extent in progeny obtained by outcrossing the inbred line to another plant. An initial plant or an initial grafted plant comprising a scion grafted to rootstock subjected to organellar perturbation or to rootstock obtained from a parent plant that had been subjected to organellar perturbation can be outcrossed to obtain F1, F2, F3, or later generations of progeny that exhibit a given useful trait to a greater extent in comparison to either the initial plant or the initial grafted plant or in comparison to a control plant. Outcrosses of such initial plants or grafted plants can be to isogenic plants or to genetically distinct plants. In the methods provided herein, initial or subsequent generations of progeny obtained from such selfs or crosses can thus be selected for useful traits. The methods provided herein also permit the identification of plants that harbor, but do not necessarily exhibit to a full extent, various useful traits.

In certain embodiments, methods provided herewith involve suppressing expression of plant organellar perturbation target genes, restoring expression of a functional plant organellar perturbation target gene, and selecting progeny plants that exhibit one or more useful traits. In certain embodiments, these useful traits are associated with either one or more altered chromosomal loci that have undergone a heritable and reversible epigenetic change.

In certain embodiments, methods for selectively suppressing expression of plant organellar perturbation target genes in sub-populations of cells found in plants that contain plastids referred to herein as "sensory plastids" are provided. Sensory plastids are plastids that occur in cells that exhibit preferential expression of at least the MSH1 promoter. In certain embodiments, MSH1 and other promoters active in sensory plastids can thus be operably linked to a heterologous sequence that perturbs plastid function to effect selective suppression of genes in cells containing the sensory plastids. In certain embodiments, MSH1 and other promoters active in sensory plastids can thus be operably linked to a heterologous sequence that perturbs mitochondrial function to effect selective suppression of genes in cells containing the sensory plastids. In addition to the distinguishing characteristic of expressing MSH1, such cells containing sensory plastids can also be readily identified as their plastids are only about 30-40% of the size of the chloroplasts contained within mesophyll cells. Other promoters believed to be active in sensory plastids include, but are not limited to, PPD3 gene promoters. Selective suppression of organellar perturbation target genes in cells containing sensory plastids can trigger epigenetic changes that provide useful plant traits. Suppression of plant plastid perturbation target genes including but not limited to, photosynthetic components, in specific sub-sets of plant cells that contain the sensory plastids is preferred as suppression of those genes in most other plant cell types is detrimental or lethal to the plant due to impairment of its photosynthetic or other capabilities.

Plastid perturbation target genes that can be suppressed by various methods provided herein to trigger epigenetic or other changes that provide useful traits include, but are not limited to, genes that encode components of plant plastid thylakoid membranes and the thylakoid membrane lumen. In certain embodiments, the plastid perturbation target genes are selected from the group consisting of sensor, photosystem I, photosystem II, the NAD(P)H dehydrogenase (NDH) complex of the thylakoid membrane, the Cytochrome b6f complex, and plastocyanin genes. A non-limiting and useful list of plastid pertubation targets is provided in Table 1. The plastid functions of the organellar perturbation target MSH1 and PPD3 genes can be suppressed to impart useful traits. However, embodiments where perturbation of both mitochondrial and plastid functions of the MSH1 and the PPD3 genes, perturbation of only any mitochondrial functions of the MSH1 and PPD3 genes, or perturbation of only any plastid functions of the MSH1 and PPD3 genes are used to impart the useful traits are also provided herein.

TABLE 1

Plastid Perturbation Target Genes

| Category | Gene name(s) and/or Activity | Target Genes Database Accession Numbers and/or SEQ ID NO |
|---|---|---|
| Sensor | MSH1 | SEQ ID NO: 1, 3-11. |
| Sensor | PPD3 | AT1G76450; SEQ ID NO: 16-40 |
| Photosystem I | PHOTOSYSTEM I SUBUNIT G, PSAG | PSAG AT1G55670.1 |
| Photosystem I | PHOTOSYSTEM I SUBUNIT D-2, PSAD-2 | PSAD-2 AT1G03130.1 |
| Photosystem I | PHOTOSYSTEM I SUBUNIT O, PSAO | PSAO AT1G08380 |
| Photosystem I | PHOTOSYSTEM I SUBUNIT K, PSAK | PSAK AT1G30380.1 |
| Photosystem I | PHOTOSYSTEM I SUBUNIT F, PSAF | PSAF AT1G31330.1 |
| Photosystem I | Photosystem I PsaN, reaction centre subunit N | PsaN AT1G49975.1 |
| Photosystem I | PHOTOSYSTEM I SUBUNIT H-2, PHOTOSYSTEM I SUBUNIT H2, PSAH-2, PSAH2, PSI-H | PSAH-2, PSAH2, PSI-H AT1G52230.1 |
| Photosystem I | PHOTOSYSTEM I SUBUNIT E-2, PSAE-2 | PSAE-2 AT2G20260.1 |
| Photosystem I | PHOTOSYSTEM I P SUBUNIT, PLASTID TRANSCRIPTIONALLY ACTIVE 8, PSAP, PSI-P, PTAC8, THYLAKOID MEMBRANE PHOSPHOPROTEIN OF 14 KDA, TMP14 | PSAP AT2G46820.1 |
| Photosystem I | PHOTOSYSTEM I SUBUNIT H-1, PSAH-1 | PSAH-1 AT3G16140.1 |
| Photosystem I | PHOTOSYSTEM I SUBUNIT D-1, PSAD-1 | PSAD-1 AT4G02770 |
| Photosystem I | PHOTOSYSTEM I SUBUNIT L, PSAL | PSAL AT4G12800 |
| Photosystem I | PSAN LHCA5, PHOTOSYSTEM I LIGHT HARVESTING COMPLEX GENE 5 | PSAN AT5G64040 LHCA5 AT1G45474 |
| Photosystem II | PsbY | PsbY AT1G67740 |
| Photosystem II | PsbW | PsbW AT2G30570 |
| Photosystem II | PsbW-like | PsbW-like AT4G28660 |
| Photosystem II | PsbX | PsbX AT2G06520 |
| Photosystem II | PsbR | PsbR AT1G79040 |
| Photosystem II | PsbTn | PsbTn AT3G21055 |
| Photosystem II | PsbO-1 | PsbO-1 AT5G66570 |
| Photosystem II | PsbO-2 | PsbO-2 AT3G50820 |
| Photosystem II | PsbP1 | PsbP1 AT1G06680 |
| Photosystem II | PsbP2 | PsbP2 At2g30790 |
| Photosystem II | PsbS | PsbS AT1G44575 |
| Photosystem II | PsbQ-1 | PsbQ-1, AT4G21280 |
| Photosystem II | PsbQ-2, | PsbQ-2, AT4G05180 |
| Photosystem II | PPL1 | PPL1 At3g55330 |
| Photosystem II | PSAE-1 | PSAE-1 AT4G28750 |
| Photosystem II | LPA2 | LPA2 AT5G51545 |
| Photosystem II | PsbQ-like PQL1 | PQL1 AT1G14150 |
| Photosystem II | PsbQ-like PQL2 | PQL2 AT3G01440 |
| Photosystem II | PsbQ-like PQL3 | PQL3 AT2G01918 |
| NAD(P)H dehydrogenase (NDH) Complex | PHOTOSYNTHETIC NDH SUBCOMPLEX L 1, PNSL1, PPL2, PSBP-LIKE PROTEIN 2 | PPL2 At2g39470 |
| NAD(P)H dehydrogenase (NDH) Complex | NAD(P)H DEHYDROGENASE SUBUNIT 48, NDF1, NDH-DEPENDENT CYCLIC ELECTRON FLOW 1, NDH48, PHOTOSYNTHETIC NDH SUBCOMPLEX B 1, PNSB1 | NDH48 AT1G15980 |

TABLE 1-continued

Plastid Perturbation Target Genes

| Category | Gene name(s) and/or Activity | Target Genes Database Accession Numbers and/or SEQ ID NO |
|---|---|---|
| NAD(P)H dehydrogenase (NDH) Complex | NDF6, NDH DEPENDENT FLOW 6, PHOTOSYNTHETIC NDH SUBCOMPLEX B 4, PNSB4 | NDF6 AT1G18730 |
| NAD(P)H dehydrogenase (NDH) Complex | NAD(P)H DEHYDROGENASE SUBUNIT 45, NDF2, NDH-DEPENDENT CYCLIC ELECTRON FLOW 1, NDH45, PHOTOSYNTHETIC NDH SUBCOMPLEX B 2, PNSB2 | NDH45 AT1G64770 |
| NAD(P)H dehydrogenase (NDH) Complex | NDF5, NDH-DEPENDENT CYCLIC ELECTRON FLOW 5 | NDF5 AT1G55370 |
| NAD(P)H dehydrogenase (NDH) Complex | CHLORORESPIRATORY REDUCTION 23, CRR23, NADH DEHYDROGENASE-LIKE COMPLEX L, NDHL | NDHL AT1G70760 |
| NAD(P)H dehydrogenase (NDH) Complex | NAD(P)H: PLASTOQUINONE DEHYDROGENASE COMPLEX SUBUNIT O, NADH DEHYDROGENASE-LIKE COMPLEX), NDH-O, NDHO | NDHO AT1G74880 |
| NAD(P)H dehydrogenase (NDH) Complex | PIFI, POST-ILLUMINATION CHLOROPHYLL FLUORESCENCE INCREASE | PIFI AT3G15840 |
| NAD(P)H dehydrogenase (NDH) Complex | NDF4, NDH-DEPENDENT CYCLIC ELECTRON FLOW 1, PHOTOSYNTHETIC NDH SUBCOMPLEX B 3, PNSB3 | NDF4 AT3G16250 |
| NAD(P)H dehydrogenase (NDH) Complex | NADH DEHYDROGENASE-LIKE COMPLEX M, NDH-M, NDHM, SUBUNIT NDH-M OF NAD(P)H: PLASTOQUINONE DEHYDROGENASE COMPLEX | NDHM AT4G37925 |
| NAD(P)H dehydrogenase (NDH) Complex | FK506-BINDING PROTEIN 16-2, FKBP16-2, PHOTOSYNTHETIC NDH SUBCOMPLEX L 4, PNSL4 | AT4G39710 |
| NAD(P)H dehydrogenase (NDH) Complex | CYCLOPHILIN 20-2, , CYCLOPHILIN 20-2, CYP20-2, PHOTOSYNTHETIC NDH SUBCOMPLEX L 5, PNSL5 | PNSL5 AT5G13120 |
| NAD(P)H dehydrogenase (NDH) Complex | CHLORORESPIRATORY REDUCTION L, CRRL, NADH DEHYDROGENASE-LIKE COMPLEX U, NDHU | NDHU AT5G21430 |
| NAD(P)H dehydrogenase (NDH) Complex | CHLORORESPIRATORY REDUCTION 7, CRR7 | CRR7 AT5G39210 |
| NAD(P)H dehydrogenase (NDH) Complex | NAD(P)H DEHYDROGENASE 18, NDH18, PHOTOSYNTHETIC NDH SUBCOMPLEX B 5, PNSB5 | NDH18 AT5G43750 |
| NAD(P)H dehydrogenase (NDH) Complex | NADH DEHYDROGENASE-LIKE COMPLEX N, NDHN | NDHN AT5G58260 |
| Cytochrome b6f complex | Rieske iron-sulfur protein containing a [2Fe—2S] cluster, OetC | PetC At4g03280 |
| Cytochrome b6f complex | ferredoxin: NADP- reductase [FNR1 and FNR2] | FNR1 AT5G66190 FNR2 AT1G20020 |
| plastocyanin | PETE1, PLASTOCYANIN 1 | PETE1 AT1G76100 |
| plastocyanin | PETE2, PLASTOCYANIN 2 | PETE2 AT1G20340 |
| other | PPD1, PSBP-DOMAIN PROTEIN1 | PPD1 At4g15510 |
| other | PPD2, PSBP-DOMAIN PROTEIN2 | PPD2 At2g28605 |
| other | PPD4, PSBP-DOMAIN PROTEIN4 | PPD4 At1g77090 |
| other | PPD5, PSBP DOMAIN PROTEIN 5 | PPD5 At5g11450 |

TABLE 1-continued

Plastid Perturbation Target Genes

| Category | Gene name(s) and/or Activity | Target Genes Database Accession Numbers and/or SEQ ID NO |
|---|---|---|
| other | PPD6, PSBP-DOMAIN PROTEIN 6 | PPD6 At3g56650 |
| other | PPD7, PSBP-DOMAIN PROTEIN 7 | PPD7 At3g05410 |
| MSH1 interacting proteins identified by Yeast Two Hybrid | CAD9 (CINNAMYL ALCOHOL DEHYDROGENASE 9); binding/catalytic/oxidoreductase/zinc ion binding | CAD9 AT4G39330 |
| MSH1 interacting proteins identified by Yeast Two Hybrid | KAB1 (POTASSIUM CHANNEL BETA SUBUNIT); oxidoreductase/potassium channel | KAB1 AT1G04690 |
| MSH1 interacting proteins identified by Yeast Two Hybrid | GOS12 (GOLGI SNARE 12); SNARE binding | GOS12 AT2G45200 |
| MSH1 interacting proteins identified by Yeast Two Hybrid | ELI3-1 (ELICITOR-ACTIVATED GENE 3-1); binding/catalytic/oxidoreductase/zinc ion binding (CAD7), response to bacterium, plant-type hypersensitive response | ELI3-1 AT4G37980 |
| MSH1 interacting proteins identified by Yeast Two Hybrid | STT3B (staurosporin and temperature sensitive 3-like b); oligosaccharyl transferase | STT3B AT1G34130 |
| MSH1 interacting proteins identified by Yeast Two Hybrid | tRNA synthetase beta subunit family protein, FUNCTIONS IN: phenylalanine-tRNA ligase activity, RNA binding, magnesium ion binding, nucleotide binding, ATP binding (unknown to date) | AT1G72550 |
| MSH1 interacting proteins identified by Yeast Two Hybrid | high mobility group (HMG1/2) family protein, FUNCTIONS IN: sequence-specific DNA binding transcription factor activity; LOCATED IN: nucleus, chloroplast | AT4G23800 |
| MSH1 interacting proteins identified by Yeast Two Hybrid | Protein kinase superfamily protein, FUNCTIONS IN: protein kinase activity, ATP binding; INVOLVED IN: protein amino acid phosphorylation; LOCATED IN: chloroplast | AT3G24190 |
| MSH1 interacting proteins identified by Yeast Two Hybrid | Protein kinase superfamily protein, FUNCTIONS IN: inositol or phosphatidylinositol kinase activity, phosphotransferase activity (interacts with SNARE At2G45200) | AT1G64460 |
| MSH1 interacting proteins identified by Yeast Two Hybrid | RNA-binding (RRM/RBD/RNP motifs) family protein; FUNCTIONS IN: RNA binding, nucleotide binding, nucleic acid binding; (interactomes map) | AT1G20880 |
| MSH1 interacting proteins identified by Yeast Two Hybrid | unknown protein, LOCATED IN: chloroplast | AT5G55210 |
| MSH1 interacting proteins identified by Yeast Two Hybrid | ATPase, F0/V0 complex, subunit C protein; FUNCTIONS IN: ATPase activity; INVOLVED IN: ATP synthesis coupled proton transport (vacuole) | AT4G32530 |
| MSH1 interacting proteins identified by Yeast Two Hybrid | RNA binding; FUNCTIONS IN: RNA binding; mRNA processing, RNA processing | AT3G11964 |

Useful plastid perturbation target genes from *Arabidopsis* with the accession number for the corresponding sequences in the *Arabidopsis* genome database (on the world wide web at the address "*Arabidopsis*.org") are provided in Table 1. Orthologous genes from many crop species can be obtained through the BLAST comparison of the protein sequences of the *Arabidopsis* genes above to the genomic databases (NCBI and publically available genomic databases for specific crop species), as well as from the specific names of the subunits. Specifically the genome, cDNA, or EST sequences are available for apples, beans, barley, *Brassica napus*, rice, Cassava, Coffee, Eggplant, Orange, *sorghum*, tomato, cotton, grape, lettuce, tobacco, *papaya*, pine, rye, soybean, sunflower, peach, poplar, scarlet bean, spruce, cocoa, cowpea, maize, onion, pepper, potato, radish, sugarcane, wheat, and other species at the following internet or world wide web addresses: "compbio.dfci.harvard.edu/tgi/plant.html"; "genomevolution.org/wiki/index.php/Sequenced_plant_genomes"; "ncbi.nlm.nih.gov/genomes/PLANTS/PlantList.html"; "plantgdb.org/"; "*arabidopsis*.org/portals/genAnnotation/other_genomes/"; "gramene.org/resources/"; "genomenewsnetwork.org/resources/sequenced_genomes/genome_guide_p1.shtml"; "jgi.doe.gov/programs/plants/index.jsf"; "chibba.agtec.uga.edu/duplication/"; "mips.helmholtz-muenchen.de/plant/genomes.jsp"; "science.co.il/biomedical/Plant-Genome-Databases.asp"; "jcvi.org/cms/index.php?id=16"; and "phyto5.phytozome.net/Phytozome_resources.php". The main protein complexes involved in photon capture and electron transport of photosystem II (PSII), NAD(P)H dehydrogenase (NDH), Cytochrome b6f complex, plastocyanin, photosystem I (PSI), and associated plastid proteins that represent certain plastid perturbation targets are also described in Grouneva, I., P. J. Gollan, et al. (2013) Planta 237(2): 399-412 Ifuku, K., S. Ishihara, et al. (2010). J Integr Plant Biol 52(8): 723-734.

In general, methods provided herewith for introducing epigenetic and/or genetic variation in plants simply require that organellar perturbation target gene expression be suppressed for a time sufficient to introduce the variation and/or in appropriate subsets of cells (i.e cells containing sensory plastids). As such, a wide variety of organellar perturbation target gene suppression methods can be employed to practice the methods provided herewith and the methods are not limited to a particular suppression technique.

Sequences of organellar perturbation target gene genes or fragments thereof from *Arabidopsis* and various crop plants are provided herewith. In certain embodiments, such genes may be used directly in either the homologous or a heterologous plant species to provide for suppression of the endogenous organellar perturbation target gene in either the homologous or heterologous plant species. A non-limiting demonstrative example where an MSH1 plastid perturbation target gene from one species was shown to be effective in suppressing the endogenous MSH1 gene in both a homologous and a heterologous species is provided by Sandhu et al. 2007, where a transgene that provides for an MSH1 inhibitory RNA (RNAi) with tomato MSH1 sequences was shown to inhibit the endogenous MSH1 plastid perturbation target gene genes of both tomato and tobacco. A transgene that provides for a organellar perturbation target gene inhibitory RNA (RNAi) with maize organellar perturbation target gene sequences can be used in certain embodiments to inhibit the endogenous organellar perturbation target gene genes of millet, *sorghum*, and maize. Organellar perturbation target gene genes from other plants including, but not limited to, cotton, canola, wheat, barley, flax, oat, rye, turf grass, sugarcane, alfalfa, banana, broccoli, cabbage, carrot, cassava, cauliflower, celery, citrus, a cucurbit, eucalyptus, garlic, grape, onion, lettuce, pea, peanut, pepper, potato, poplar, pine, sunflower, safflower, soybean, blackberry, blueberry, sugar beet, sweet potato, tobacco, strawberry, sugar beet, sweet potato, *Jatropha, Camelina*, and *Agave* can be obtained by a variety of techniques and used to suppress expression of either the corresponding organellar perturbation target gene in those plants or the organellar perturbation target gene in a distinct plant. Methods for obtaining organellar perturbation target genes for various plants include, but are not limited to, techniques such as: i) searching amino acid and/or nucleotide sequence databases comprising sequences from the plant species to identify the organellar perturbation target gene by sequence identity comparisons; ii) cloning the organellar perturbation target gene by either PCR from genomic sequences or RT-PCR from expressed RNA; iii) cloning the organellar perturbation target gene from a genomic or cDNA library using PCR and/or hybridization based techniques; iv) cloning the organellar perturbation target gene from an expression library where an antibody directed to the organellar perturbation target gene protein is used to identify the organellar perturbation target gene containing clone; v) cloning the organellar perturbation target gene by complementation of an organellar perturbation target gene mutant or organellar perturbation target gene deficient plant; or vi) any combination of (i), (ii), (iii), (iv), and/or (v). The DNA sequences of the target genes can be obtained from the promoter regions or transcribed regions of the target genes by PCR isolation from genomic DNA, or PCR of the cDNA for the transcribed regions, or by commercial synthesis of the DNA sequence. RNA sequences can be chemically synthesized or, more preferably, by transcription of suitable DNA templates. Recovery of the organellar perturbation target gene from the plant can be readily determined or confirmed by constructing a plant transformation vector that provides for suppression of the gene, transforming the plants with the vector, and determining if plants transformed with the vector exhibit the characteristic responses that are typically observed in various plant species when MSH1 expression is suppressed that include leaf variegation, cytoplasmic male sterility (CMS), a reduced growth-rate phenotype, and/or delayed or non-flowering phenotype. The characteristic responses of MSH1 suppression have been described previously as developmental reprogramming or "MSH1-dr1" (Xu et al. Plant Physiol. Vol. 159:711-720, 2012).

In certain embodiments, organellar perturbation target genes or fragments thereof used in the methods provided herein will have nucleotide sequences with at least 50%, 60%, 70%, 80%, 90%, 95%, 98%, 99%, or 100% nucleotide sequence identity to one or more of the organellar perturbation target genes or fragments thereof provided herein that include, but are not limited to, genes provided in Table 1 and orthologs thereof found in various crop plants. In certain embodiments, organellar perturbation target genes or fragments thereof used in the methods provided herein encode organellar perturbation target gene proteins or portions thereof will have amino acid sequences with at least 50%, 60%, 70%, 80%, 90%, 95%, 98%, 99%, or 100% amino acid sequence identity to one or more of the organellar perturbation target gene proteins provided herein that include, but are not limited to, the organellar perturbation target gene proteins encoded by genes provided in Table 1. In certain embodiments, organellar perturbation target genes or fragments thereof used in the methods provided herein will have nucleotide sequences with at least 50%, 60%, 70%, 80%, 90%, 95%, 98%, 99%, or 100% nucleotide sequence identity to one or more of the PPD3 organellar perturbation target genes fragments thereof, orthologs thereof, or homologs thereof, provided herein that include, but are not limited to, SEQ ID NO:16-40. In certain embodiments, organellar perturbation target gene genes or fragments thereof used in the methods provided herein encode organellar perturbation target gene proteins or portions thereof will have amino acid sequences with at least 50%, 60%, 70%, 80%, 90%, 95%, 98%, 99%, or 100% amino acid sequence identity to one or more of the PPD3 organellar perturbation target gene proteins or organellar perturbation target gene homologs provided herein that include, but are not limited to, the proteins encoded by SEQ ID NO:16-40. PPD3 organellar perturbation target gene genes from plants other than those provided herein can also be identified by the encoded regions with homology to the PsbP1 and PsbP2 gene domains that characterize many PPD3 genes. In certain embodiments, organellar perturbation target genes or fragments thereof used in the methods provided herein will have nucleotide sequences with at least 50%, 60%, 70%, 80%, 90%, 95%, 98%, 99%, or 100% nucleotide sequence identity to one or more of the MSH1 organellar perturbation target genes fragments thereof, orthologs thereof, or homologs thereof, provided herein that include, but are not limited to, SEQ ID NO:1, 3-11. In certain embodiments, organellar perturbation target gene genes or fragments thereof used in the methods provided herein encode organellar perturbation target gene proteins or portions thereof will have amino acid sequences with at least 50%, 60%, 70%, 80%, 90%, 95%, 98%, 99%, or 100% amino acid sequence identity to one or more of the MSH1 organellar perturbation target gene proteins or organellar perturbation target gene homologs provided herein that include, but are not limited to, the proteins encoded by SEQ ID NO:1, 3-11.

It is anticipated that organellar perturbation target gene nucleic acid fragments of 18 to 20 nucleotides, but more preferably 21 nucleotides or more, can be used to effect suppression of the endogenous organellar perturbation target gene. In certain embodiments, organellar perturbation target gene nucleic acid fragments of at least 18, 19, 20, or 21 nucleotides to about 50, 100, 200, 500, or more nucleotides can be used to effect suppression of the endogenous organellar perturbation target gene. Regions of 20, 50, 100, 500, or more nucleotides are suitable for this purpose, with lengths of 100 to 300 bases of the target gene sequences preferable, and lengths of 300 to 500 bp or more being most preferable. In certain embodiments, regions of 20, 50, or 100 to 200, 300, 500, 750, or a 1000 or more nucleotides are used to effect suppression of the organellar target gene. For use in a hairpin or inverted repeat knockdown design, a spacer region with a sequence not related to the sequence of the genome of the target plant can be used. A hairpin construct containing 15, 18, or 20 to 500 bp or more of a target gene sequence in the antisense orientation, followed by a spacer region whose sequence is not critical but can be a intron or non-intron. If the spacer is an intron, the caster bean catalase intron which is effectively spliced in both monocots and dicots (Tanaka, Mita et al. *Nucleic Acids Res* 18(23): 6767-6770, 1990), is known to those skilled in the art and is useful for the present embodiment. After the spacer the same target gene sequence in the sense orientation is present, such that the antisense and sense strands can form a double stranded RNA after transcription of the transcribed region. The target gene sequences are followed by a polyadenylation region. 3' polyadenylation regions known to those skilled in the art to function in monocots and dicot plants include but are not limited to the Nopaline Synthase (NOS) 3' region, the Octapine Synthase (OCS) 3' region, the Cauliflower Mosaic Virus 35S 3' region, the Mannopine Synthase (MAS) 3' region. Additional 3' polyadenylation regions from monocotyledonous genes such as those from rice, *sorghum*, wheat, and maize are available to those skilled in the art to provide similar polyadenylation region and function in DNA constructs in the present embodiments. In certain embodiments, a transgene designed to suppress a target gene in dicots is designed to have the following order: promoter/antisense to target gene/catalase intron/sense gene A/polyadenylation region. In embodiments where a gene is designed to suppress a target gene in monocots can have the following order: promoter/intron for monocots/antisense to target gene/catalase intron/sense gene A/polyadenylation region.

Sequences that provide for suppression of a organellar perturbation target gene can include sequences that exhibit complementarity to either strand of the promoter, 5' or 3' untranslated region, intron, coding regions, and/or any combination thereof. A target gene promoter region for gene suppression can include the transcription start site, the TATA box, and upstream regions. The promoter region for gene silencing can be about 20, 50, 80, or 100 nucleotides in length, and more preferably is about 100 to 500 nucleotides in length. The promoter region used for such suppression can be from different regions in the upstream promoter, preferably containing at least about 500 nucleotides upstream from the start of transcription, and most preferably containing at least about 500 nucleotides upstream from the start of translation of the native coding region of the native gene. This would include the UTR which may or may not be part of the promoter. A description of various recombinant DNA constructs that target promoter and/or adjoining regions of target genes are described in U.S. Pat. No. 8,293,975, which is incorporated herein by reference in its entirety.

For gene targets with closely related family members, sense, antisense or double hairpin suppression designs can include sequences from more than one family member, following the designs described above. In certain embodiments, a transgene to suppress two genes, target gene A and target gene B, is designed to have the following order: promoter/optional intron/antisense to target gene A/antisense to target gene B/spacer sequence/sense target gene B/sense gene A/polyadenylation region. In certain embodiments, this spacer sequence can be an intron. Useful embodiments include, but are not limited to, the following combinations of gene family members that can each be arranged in a single recombinant DNA construct any order that provides for hairpin formation and suppression of the gene targets:

(a) Construct 1: PsbQ-like PQL1, PsbQ-like, PsbQ-like PQL3, and any combination thereof;
(b) Construct 2: PsbO-1 and PsbO-2;
(c) Construct 3: PsbP1 and PsbP2;
(d) Construct 4: PsbQ-1 and PsbQ-2;
(e) Construct 5: FNR1 and FNR2;
(f) Construct 6: PETE1 and PETE2; and,
(g) Construct 7: PsbW and PsbW-like.

In certain embodiments, suppression of organellar perturbation target gene in a plant is effected with a transgene. Transgenes that can be used to suppress expression of organellar perturbation target gene include, but are not limited to, transgenes that produce dominant-negative mutants of a organellar perturbation target gene, a small inhibitory RNA (siRNA), a microRNA (miRNA), a co-suppressing sense RNA, and/or an anti-sense RNA that provide for inhibition of the endogenous organellar perturbation target gene. U.S. patents incorporated herein by reference in their entireties that describe suppression of endogenous plant genes by transgenes include U.S. Pat. No. 7,109,393, U.S. Pat. No. 5,231,020 and U.S. Pat. No. 5,283,184 (co-suppression methods); and U.S. Pat. No. 5,107,065 and U.S. Pat. No. 5,759,829 (antisense methods). In certain embodiments, transgenes specifically designed to produce double-stranded RNA (dsRNA) molecules with homology to the organellar perturbation target gene can be used to decrease expression of the endogenous organellar perturbation target gene. In such embodiments, the sense strand sequences of the dsRNA can be separated from the antisense sequences by a spacer sequence, preferably one that promotes the formation of a dsRNA (double-stranded RNA) molecule. Examples of such spacer sequences include, but are not limited to, those set forth in Wesley et al., Plant J., 27(6):581-90 (2001), and Hamilton et al., Plant J., 15:737-746 (1998). One useful and non-limiting vector that has been shown to provide for suppression of organellar perturbation target gene in tobacco and tomato has been described by Sandhu et al., 2007 where an intron sequence separates the sense and antisense strands of the organellar perturbation target gene sequence. The design of recombinant DNA constructs for suppression of gene expression are also described in Helliwell, C. and P. Waterhouse (2003). "Constructs and methods for high-throughput gene silencing in plants." *Methods* 30(4): 289-295.

In certain embodiments, transgenes that provide for organellar perturbation target gene suppression can comprise regulated promoters that provide for either induction or down-regulation of operably linked organellar perturbation target gene inhibitory sequences. In this context, organellar perturbation target gene inhibitory sequences can include, but are not limited to, dominant-negative mutants of organellar perturbation target gene, a small inhibitory RNA (siRNA), a microRNA (miRNA), a co-suppressing sense RNA, and/or an anti-sense RNA that provide for inhibition of the endogenous organellar perturbation target gene of a plant. Such promoters can provide for suppression of organellar perturbation target gene during controlled time periods by either providing or withholding the inducer or down regulator. Inducible promoters include, but are not limited to, a PR-1a promoter (U.S. Patent Application Publication Number 20020062502) or a GST II promoter (WO 1990/008826 A1). In other embodiments, both a transcription factor that can be induced or repressed as well as a promoter recognized by that transcription factor and operably linked to the organellar perturbation target gene inhibitory sequences are provided. Such transcription factor/promoter systems include, but are not limited to: i) RF2a acidic domain-ecdysone receptor transcription factors/cognate promoters that can be induced by methoxyfenozide, tebufenozide, and other compounds (U.S. Patent Application Publication Number 20070298499); ii) chimeric tetracycline repressor transcription factors/cognate chimeric promoters that can be repressed or de-repressed with tetracycline (Gatz, C., et al. (1992). Plant J. 2, 397-404), and the like.

In certain embodiments, a promoter that provides for selective expression of a heterologous sequence that suppresses expression of the target gene in cells containing sensory plastids is used. In certain embodiments, this promoter is an MSH1 or a PPD3 promoter. In certain embodiments, this promoter is an MSH1 or a PPD3 promoter and the operably linked heterologous sequence suppresses expression of a target gene provided in Table 1 (above). MSH1 promoters that can be used to express heterologous sequences in cells containing sensor plastids include, but are not limited to, the *Arabidopsis, sorghum*, tomato, and maize promoters provided herewith (SEQ ID NO:11, 12, 13, 14, and 41) as well as functional derivatives thereof that likewise provide for expression in cells that contain sensor plastids. In certain embodiments, deletion derivatives of the MSH1 promoters comprising about 1500 Bp, 1000 Bp, or about 750 Bp of SEQ ID NO:11, 12, 13, 14, and 41 can also be used to express heterologous sequences. PPD3 promoters that can be used to express heterologous sequences in cells containing sensor plastids include, but are not limited to, the *Arabidopsis*, rice, and tomato promoters provided herewith as SEQ ID NO:52, 53, and 54 as well as functional derivatives thereof that provide for expression in cells that contain sensor plastids. In certain embodiments, deletion derivatives of the MSH1 promoters comprising about 800 Bp, 600 Bp, or about 500 Bp of SEQ ID NO: 52, 53, and 54 can also be used to express heterologous sequences. In certain embodiments, PPD3 promoters comprising SEQ ID NO:52, 53, and 54 and an additional 200, 500, or 1000 base pairs of the endogenous 5' PPD3 promoter sequences can be used to express heterologous sequences. Additional 200, 500, or 1000 base pairs of the endogenous 5' PPD3 promoter sequences can be obtained by methods including, but not limited to, retrieval of sequences from databases provided herein and recovery of the adjoining promoter DNA by PCR amplification of genomic template sequences or by direct synthesis. In certain embodiments, recombinant DNA constructs for suppression of dicot target genes can comprise a MSH1 or PPD3 promoter from a dicotyledonous species such as *Arabidopsis*, soybeans or canola, is attached to a hairpin construct containing 300 to 500 bp or more of a target gene sequence in the antisense orientation, followed by a spacer region whose sequence is not critical but can be a intron or non-intron. The caster bean catalase intron (Tanaka, Mita et al. Nucleic Acids Res 18(23): 6767-6770, 1990), can be used as a spacer in certain embodiments. After the spacer the same target gene sequence in the sense orientation is present, such that the antisense and sense strands can form a double stranded RNA after transcription of the transcribed region. The target gene sequences are followed by a polyadenylation region. Various 3' polyadenylation regions known to function in monocots and dicot plants include but are not limited to the Nopaline Synthase (NOS) 3' region, the Octopine Synthase (OCS) 3' region, the Cauliflower Mosaic Virus 35S 3' region, the Mannopine Synthase (MAS) 3' region. In certain embodiments recombinant DNA constructs for suppression of monocot target genes can comprise MSH1 or PPD3 promoter from a monocot species such as rice, maize, *sorghum* or wheat can either be attached directly to the hairpin region or to a monocot intron before the hairpin region. Monocot introns that are beneficial to gene expression when located between the promoter and coding region are the first intron of the maize ubiquitin (described in U.S. Pat. No. 6,054,574, which is incorporated herein by reference in its entirety) and the first intron of rice actin 1 (McElroy, Zhang et al. Plant Cell 2(2): 163-171, 1990). Additional introns that are beneficial to gene expression when located between the promoter and coding region are the maize hsp70 intron (described in U.S. Pat. No. 5,859,347, which is incorporated herein by reference in its entirety), and the maize alcohol dehydrogenase 1 genes introns 2 and 6 (described in U.S. Pat. No. 6,342,660, which is incorporated herein by reference in its entirety).

In still other embodiments, transgenic plants are provided where the transgene that provides for organellar perturbation target gene suppression is flanked by sequences that provide for removal for the transgene. Such sequences include, but are not limited to, transposable element sequences that are acted on by a cognate transposase. Non-limiting examples of such systems that have been used in transgenic plants include the cre-lox and FLP-FRT systems.

In certain embodiments, organellar perturbation target gene suppression can be effected by Viral Induced Gene Silencing (VIGS) methods. In general, such methods entail insertion of a organellar perturbation target gene sequence into a cloned viral genome that can be introduced directly into a target plant or target plant cell to effect organellar perturbation target gene suppression or that can produce an infectious nucleic acid that is introduced into a target plant or target plant cell to effect organellar perturbation target gene suppression. Various methods and vectors used for suppression of other gene targets by VIGS can also be adapted for use in suppressing organellar perturbation target genes by use of appropriate organellar perturbation target gene sequences disclosed herein. Such VIGS methods and vectors that can be adapted for suppressing organellar perturbation target genes include, but are not limited to, those disclosed in U.S. Pat. Nos. 5,922,602, 6,635,805, 6,369,296, and 7,229,829 that are especially, but not exclusively, useful for performing VIGS in dicot plants. Other VIGS methods and vectors that can be adapted for suppressing organellar perturbation target genes include, but are not limited to, those disclosed in U.S. Pat. No. 6,800,748 that are especially, but not exclusively, useful for performing VIGS in monocot plants. U.S. Pat. Nos. 5,922,602, 6,635,805, 6,369,296, 6,800,748, and 7,229,829 are each incorporated herein by reference in their entireties with respect to their disclosure of VIGS vectors and methods. VIGS vectors and methods based on cloned Hordeivirus (including, but not limited to, barley stripe mosaic virus ("BSMV"), poa semilatent virus ("PSLV"), lychnis ringspot virus ("LRSV"), and anthoxanthum latent blanching virus ("ALBV")), tobacco mosaic virus (TMV), Cucumber Green Mottle Mosaic virus watermelon strain (CGMMV-W); Brome Mosaic virus (BMV), Potyvirus (including, but not limited to, Rice Necrosis virus, and Potato Virus Y (PVY)), Rice tungro bacilliform virus (RTBV) and Geminivirus genomes all can be used to suppress organellar perturbation target genes. In certain embodiments, cloned viral genomes containing a organellar perturbation target gene sequence can be operably linked to a promoter that is active in cells containing sensor organellars to effect suppression of the organellar perturbation target gene in those cells. Such promoters that can be used to express heterologous sequences in cells containing sensor organellars include MSH1 and PPD3 promoters. In certain embodiments of any of the aforementioned methods, a organellar perturbation target gene sequence is inserted into a Barley stripe mosaic virus (BSMV), a Brome Mosaic Virus (BMV), or a Rice tungro bacilliform virus (RTBV) genome to effect suppression of a organellar perturbation target gene in a monocot plant. In certain embodiments of any of the aforementioned methods, a organellar perturbation target gene sequence is inserted into a viral genome of Table 2 to effect suppression of a organellar perturbation target gene in a dicot plant.

TABLE 2

| Viral Genomes Used for VIGS in Dicot plants | |
|---|---|
| ALSV | Apple latent spherical virus |
| ACMV | African cassava mosaic virus |
| BPMV | Bean pod mottle virus |
| BCTV | Beet curly top virus |
| CymMV | *Cymbidium* mosaic virus |
| CbLCV | Cabbage leaf curl virus |
| CMV | Cucumber mosaic virus |
| CLCrV | Cotton leaf crumple virus |
| GVA | Grapevine virus A |
| PVX | Potato virus X |
| PEBV | Pea early browning virus |
| PopMV | Poplar mosaic virus |
| SHMV | Sunn - hemp mosaic virus |
| TMV | Tobacco mosaic virus |
| TRV | Tobacco rattle virus |

TABLE 2-continued

| Viral Genomes Used for VIGS in Dicot plants | |
|---|---|
| TYLCCV | Tomato yellow leaf curl China virus |
| TYMV | Turnip yellow mosaic virus |
| ToMV | Tomato mosaic virus |

Methods for identifying agents that provide for organellar perturbation are also provided herein. Such methods broadly comprise screening and selecting for agents that inhibit or interfere with binding or other productive interactions between an MSH1 protein or a fragment thereof and at least one assistant proteins or fragment thereof that interact with MSH1 and fragments thereof. Assistant proteins that interact with MSH1 include, but are not limited to proteins selected from the group consisting of PPD3, PsbA (D1), a PsbO-1, a PsbO-2, PetC, CAD9, KAB1, GOS12, ELI3-1, STT3B, a fragment thereof, and combinations thereof. In certain embodiments, inhibitors of MSH1 interactions with the assistant proteins can be identified in biological "one-hybrid" or "two-hybrid" assays based on microbial, yeast, or mammalian systems (Velasco-García R, Vargas-Martínez R. The study of protein-protein interactions in bacteria. Can J Microbiol. 2012 November; 58(11):1241-57; Rajagopala S V, et al. Studying protein complexes by the yeast two-hybrid system. Methods. 2012 December; 58(4):392-9; Lievens et al. The use of mammalian two-hybrid technologies for high-throughput drug screening. Methods. 2012 December; 58(4):335-42). A non-limiting example of a yeast two-hybrid assay that can be used to screen and select for such agents is disclosed in co-assigned U.S. patent application Ser. No. 14/454,518, which is specifically incorporated herein by reference in its entirety. In certain embodiments, the assays can comprise biochemical assays for inhibition of binding of MSH1 or fragments thereof to an assistant protein or fragment thereof. In certain embodiments, the fragment of MSH-1 comprises a peptide of at least about 10 amino acids located within Domain 2, 3, or 6 of MSH-1. Various domains of the MSH-1 protein suitable for use in the assays are described in Abdelnoor et al. Proc Natl Acad Sci USA. 2003 May 13; 100(10): 5968-5973; and in US Patent Application Publication 20060248614, which is incorporated herein by reference in its entirety. Sequences of certain domains of MSH1 are as follows:

```
Combined Domains II III IV (Residues 156 to 722
of SEQ ID NO: 2)
CILVEYAGLNPFGGLRSDSIPKAGCPIMNLRQTLDDLTRNGYSVC
IVEEVQGPTPARSRKGRFISGHAHPGSPYVYGLVGVDHDLDFPDPMPVVG
ISRSARGYCMISIPETMKAYSLDDGLTEEALVTKLRTRRCHHLFLHASLR
HNASGTCRWGEFGEGGLLWGECSSRNFEWFEGDTLSELLSRVKDVYGLDD
EVSFRNVNVPSKNRPRPLHLGTATQIGALPTEGIPCLLKVLLPSTCSGLP
SLYVRDLLLNPPAYDIALKIQETCKLMSTVTCSIPEFTCVSSAKLVKLLE
QREANYIEFCRIKNVLDDVLHMHRHAELVEILKLLMDPTWVATGLKIDFD
TFVNECHWASDTIGEMISLDENESHQNVSKCDNVPNEFFYDMESSWRGRV
KGIHIEEEITQVEKSAEALSLAVAEDFHPIISRIKATTASLGGPKGEIAY
AREHESVWFKGKRFTPSIWAGTAGEDQIKQLKPALDSKGKKVGEEWFTTP
KVEIALVRYHEASENAKARVLELLRELSVKLQTKINVLVFASMLLVISKA
LFSHACEGRRRKWVFPTLVGFS Domain VI ENDONUCLEASE (Residues 900 to 1118
SEQ ID NO: 2)
MGAENVEGQTKPTWKLTDGVCRESLAFETAKREGVPESVIQRAEALYLSV
YAKDASAEVVKPDQIITSSNNDQQIQKPVSSERSLEKDLAKAIVKICGKK
MIEPEAIECLSIGARELPPPSTVGSSCVYVMRRPDKRLYIGQTDDLEGRI
RAHRAKEGLQGSSFLYLMVQGKSMACQLETLLINQLHEQGYSLANLADGK
HRNFGTSSSLSTSDVVSIL
```

In certain embodiments, the agents that are screened are selected from the group consisting of compounds, peptides, and peptidomimetic compounds.

Organellar perturbation target gene suppression can be readily identified or monitored by molecular techniques. In certain embodiments where the endogenous organellar perturbation target gene is intact but its expression is inhibited, production or accumulation of the RNA encoding organellar perturbation target gene can be monitored. Molecular methods for monitoring organellar perturbation target gene RNA expression levels include, but are not limited to, use of semi-quantitive or quantitative reverse transcriptase polymerase chain reaction (qRT-PCR) techniques. The use of semi-quantitive PCR techniques to monitor organellar perturbation target gene suppression resulting from RNAi mediated suppression of plastid perturbation target gene has been described (Sandhu et al. 2007). Various quantitative RT-PCR procedures including, but not limited to, TaqMan™ reactions (Applied Biosystems, Foster City, Calif. US), use of SCORPION™ or Molecular Beacon™ probes, or any of the methods disclosed in Bustin, S. A. (Journal of Molecular Endocrinology (2002) 29, 23-39) can be used. It is also possible to use other RNA quantitation techniques such as Quantitative Nucleic Acid Sequence Based Amplification (Q-NASBA™) or the Invader™ technology (Third Wave Technologies, Madison, Wis.).

In certain embodiments where organellar perturbation target gene suppression is achieved by use of a mutation in the endogenous organellar perturbation target gene of a plant, the presence or absence of that mutation in the genomic DNA can be readily determined by a variety of techniques. Certain techniques can also be used that provide for identification of the mutation in a hemizygous state (i.e. where one chromosome carries the mutated msh1 gene and the other chromosome carries the wild type organellar perturbation target gene). Mutations in organellar perturbation target DNA sequences that include insertions, deletions, nucleotide substitutions, and combinations thereof can be detected by a variety of effective methods including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. For example, mutations can be detected by hybridization to allele-specific oligonucleotide (ASO) probes as disclosed in U.S. Pat. Nos. 5,468,613 and 5,217,863. U.S. Pat. No. 5,210,015 discloses detection of annealed oligonucleotides where a 5' labelled nucleotide that is not annealed is released by the 5'-3' exonuclease activity. U.S. Pat. No. 6,004,744 discloses detection of the presence or absence of mutations in DNA through a DNA primer extension reaction. U.S. Pat. No. 5,468,613 discloses allele specific oligonucleotide hybridizations where single or multiple nucleotide variations in nucleic acid sequence can be detected by a process in which the sequence containing the nucleotide variation is amplified, affixed to a support and exposed to a labeled sequence-specific oligonucleotide probe. Mutations can also be detected by probe ligation methods as disclosed in U.S. Pat. No. 5,800,944 where sequence of interest is amplified and hybridized to probes followed by ligation to detect a labeled part of the probe. U.S. Pat. Nos. 6,613,509 and 6,503,710, and references found therein provide methods for identifying mutations with mass spectroscopy. These various methods of identifying mutations are provided as examples and are not intended to be limiting as the methods of the present disclosure can be used in conjunction with any polymorphism typing method to identify the presence of absence of mutations in an organellar perturbation target gene in genomic DNA samples. Furthermore, genomic DNA samples used can include, but are not limited to, genomic DNA isolated directly from a plant, cloned genomic DNA, or amplified genomic DNA. The use of mutations in endogenous PPD3 genes is specifically provided herein.

Mutations in endogenous plant organellar perturbation target gene genes can be obtained from a variety of sources and by a variety of techniques. A homologous replacement sequence containing one or more loss of function mutations in the organellar perturbation target gene and homologous sequences at both ends of the double stranded break can provide for homologous recombination and substitution of the resident wild-type organellar perturbation target gene sequence in the chromosome with an msh1 replacement sequence with the loss of function mutation(s). Such loss of function mutations include, but are not limited to, insertions, deletions, and substitutions of sequences within an organellar perturbation target gene that result in either a complete loss of organellar perturbation target gene function or a loss of organellar perturbation target gene function sufficient to elicit alterations (i.e. heritable and reversible epigenetic changes) in other chromosomal loci or mutations in other chromosomal loci. Loss-of-function mutations in an MSH1 organellar perturbation target gene include, but are not limited to, frameshift mutations, pre-mature translational stop codon insertions, deletions of one or more functional domains that include, but are not limited to, a DNA binding (Domain I), an ATPase (Domain V) domain, and/or a carboxy-terminal GIY-YIG type endonuclease domain, and the like. Also provided herein are mutations analogous the *Arabidopsis* msh1 mutation that are engineered into endogenous plastid perturbation target gene plant gene to obtain similar effects. Methods for substituting endogenous chromosomal sequences by homologous double stranded break repair have been reported in tobacco and maize (Wright et al., Plant J. 44, 693, 2005; D'Halluin, et al., Plant Biotech. J. 6:93, 2008). A homologous replacement msh1 sequence (i.e. which provides a loss of function mutation in an organellar perturbation target gene sequence) can also be introduced into a targeted nuclease cleavage site by non-homologous end joining or a combination of non-homologous end joining and homologous recombination (reviewed in Puchta, J. Exp. Bot. 56, 1, 2005; Wright et al., Plant J. 44, 693, 2005). In certain embodiments, at least one site specific double stranded break can be introduced into the endogenous organellar perturbation target gene by a meganuclease. Genetic modification of meganucleases can provide for meganucleases that cut within a recognition sequence that exactly matches or is closely related to specific endogenous organellar perturbation target gene sequence (WO/06097853A1, WO/06097784A1, WO/04067736A2, U.S. 20070117128A1). It is thus anticipated that one can select or design a nuclease that will cut within a target organellar perturbation target gene sequence. In other embodiments, at least one site specific double stranded break can be introduced in the endogenous organellar perturbation target gene target sequence with a zinc finger nuclease. The use of engineered zinc finger nuclease to provide homologous recombination in plants has also been disclosed (WO 03/080809, WO 05/014791, WO 07014275, WO 08/021207). In still other embodiments, mutations in endogenous organellar perturbation target gene genes can be identified through use of the TILLING technology (Targeting Induced Local Lesions in Genomes) as described by Henikoff et al. where traditional chemical mutagenesis would be followed by high-throughput screening to identify plants comprising point mutations or other mutations in the endogenous organellar perturbation target gene (Henikoff et al., Plant Physiol. 2004, 135:630-636). The recovery of mutations in endogenous PPD3 genes is specifically provided herein.

Any of the recombinant DNA constructs provided herein can be introduced into the chromosomes of a host plant via methods such as *Agrobacterium*-mediated transformation, *Rhizobium*-mediated transformation, *Sinorhizobium*-mediated transformation, particle-mediated transformation, DNA transfection, DNA electroporation, or "whiskers"-mediated transformation. Aforementioned methods of introducing transgenes are well known to those skilled in the art and are described in U.S. Patent Application No. 20050289673 (*Agrobacterium*-mediated transformation of corn), U.S. Pat. No. 7,002,058 (*Agrobacterium*-mediated transformation of soybean), U.S. Pat. No. 6,365,807 (particle mediated transformation of rice), and U.S. Pat. No. 5,004,863 (*Agrobacterium*-mediated transformation of cotton), each of which are incorporated herein by reference in their entirety. Methods of using bacteria such as *Rhizobium* or *Sinorhizobium* to transform plants are described in Broothaerts, et al., Nature. 2005, 10; 433(7026):629-33. It is further understood that the recombinant DNA constructs can comprise cis-acting site-specific recombination sites recognized by site-specific recombinases, including Cre, Flp, Gin, Pin, Sre, pinD, Int-B13, and R. Methods of integrating DNA molecules at specific locations in the genomes of transgenic plants through use of site-specific recombinases can then be used (U.S. Pat. No. 7,102,055). Those skilled in the art will further appreciate that any of these gene transfer techniques can be used to introduce the recombinant DNA constructs into the chromosome of a plant cell, a plant tissue or a plant.

Methods of introducing plant minichromosomes comprising plant centromeres that provide for the maintenance of the recombinant minichromosome in a transgenic plant can also be used in practicing certain embodiments of this disclosure (U.S. Pat. No. 6,972,197 and U.S. Patent Application Publication 20120047609). In these embodiments of the present disclosure, the transgenic plants harbor the minichromosomes as extrachromosomal elements that are not integrated into the chromosomes of the host plant. It is anticipated that such mini-chromosomes may be useful in providing for variable transmission of a resident recombinant DNA construct that suppresses expression of a organellar perturbation target gene.

In certain embodiments, it is anticipated that PPD3 suppression can be effected by exposing whole plants, or reproductive structures of plants, to stress conditions that result in suppression of an endogenous PPD3 gene. Such stress conditions include, but are not limited to, high light stress, and heat stress. Useful and non-limiting high light stress conditions include continuous exposure to about 300 to about 1200 µmol photons/m2·s for about 24 to about 120 hours. Useful and non-limiting heat stress conditions include continuous exposure to temperatures of about 32° C. to about 37° C. for about 2 hours to about 24 hours. Useful and non-limiting heat, light, and other environmental stress conditions that can provide for MSH1 suppression are also disclosed for heat (Shedge et al. 2010), high light stress (Xu et al. 2011) and other environmental stress conditions (Hruz et al. 2008) and can also be adapted to effect PPD3 suppression.

Methods where organellar perturbation target gene suppression is effected in plant cells or cultured plant cells are also provided herein. In certain embodiments, organellar perturbation target gene suppression can be effected by culturing plant cells under stress conditions that result in suppression of endogenous organellar perturbation target gene. Such stress conditions include, but are not limited to, high light stress. Useful and non-limiting high light stress conditions include continuous exposure to about 300 to about 1200 µmol photons/m2·s for about 24 to about 120 hours. Useful and non-limiting heat stress conditions include continuous exposure to temperatures of about 32° C. to about 37° C. for about 2 hours to about 24 hours. Useful and non-limiting heat, light, and other environmental stress conditions also that can provide for organellar perturbation target gene suppression are also disclosed for heat (Shedge et al. 2010), high light stress (Xu et al. 2011) and other environmental stress conditions (Hruz et al. 2008). In certain embodiments, organellar perturbation target gene suppression is effected in plant cells or cultured plant cells by introducing a nucleic acid that provides for such suppression into the plant cells. Nucleic acids that can be used to provide for suppression of organellar perturbation target gene in cultured plant cells include, but are not limited to, transgenes that produce a small inhibitory RNA (siRNA), a microRNA (miRNA), a co-suppressing sense RNA, and/or an anti-sense RNA directed to the organellar perturbation target gene. Nucleic acids that can be used to provide for suppression of organellar perturbation target gene in plant cells or cultured plant cells include, but are not limited to, a small inhibitory RNA (siRNA) or a microRNA (miRNA) directed against the endogenous organellar perturbation target gene. RNA molecules that provide for inhibition of organellar perturbation target gene can be introduced by electroporation. Introduction of inhibitory RNAs to cultured plant cells to inhibit target genes can in certain embodiments be accomplished as disclosed in Vanitharani et al. (Proc Natl Acad Sci USA., 2003, 100(16):9632-6), Qi et al. (Nucleic Acids Res. 2004 Dec. 15; 32(22):e179), or J. Cheon et al. (Microbiol. Biotechnol. (2009), 19(8), 781-786). The suppression of endogenous PPD3 genes in cultured plant cells is specifically provided herein.

Methods where organellar perturbation target gene suppression is effected in vegetatively or clonally propagated plant materials are also provided herein. Such vegetatively or clonally propagated plant materials can include, but are not limited to, cuttings, cultured plant materials, and the like. In certain embodiments, recovery of such plant or clonally propagated plant materials that have been subjected to organellar perturbation can be accomplished by methods that allow for transient suppression of the organellar perturbation target gene. In certain non-limiting examples, plant or clonally propagated plant materials that have been subjected to plant organellar perturbation are recovered by placing recombinant DNA constructs that suppress a organellar perturbation target gene in vectors that provide for their excision or segregation. In certain embodiments, such excision can be facilitated by use of transposase-based systems or such segregation can be facilitated by use of mini-chromosomes. In certain embodiments, such excision or segregation can be facilitated by linking a transgene that provides for a "conditional-lethal" counter selection to the transgene that suppresses a organellar perturbation target in the recombinant DNA construct. Vegetatively or clonally propagated plant materials that have been subjected to organellar perturbation and lacking recombinant DNA constructs that suppress a organellar perturbation target gene can then be screened and/or selected for useful traits. Also provided are methods where vegetatively or clonally propagated plant materials are obtained from a plant resulting from a self or outcross or from a cultured plant cell, where either the plant or plant cell had been subjected to suppression of a organellar perturbation target gene. Such vegetatively or clonally propagated plant materials obtained from such plants resulting from a self or outcross or from a plant cell that have been subjected to organellar perturbation can also be screened and/or selected for useful traits. Also provided herein are methods where a sexually reproducing plant or plant population comprising useful traits is vegetatively or clonally propagated, and a plant or a plant population derived therefrom is then used to produce seed or a seed lot. In certain embodiments of any of the aforementioned methods, the organellar perturbation target gene can be a MSH1 or a PPD3 gene.

Organellar perturbation target gene suppression can also be readily identified or monitored by traditional methods where plant phenotypes are observed. For example, organellar perturbation target gene suppression can be identified or monitored by observing organellar effects that include leaf variegation, cytoplasmic male sterility (CMS), a reduced growth-rate phenotype, and/or delayed or non-flowering phenotype. Phenotypes indicative of MSH1 organellar perturbation target gene suppression in various plants are provided in U.S. Patent Application Publication No. US20140157452, which is incorporated herein by reference in its entirety. These phenotypes that are associated with organellar perturbation target gene suppression are referred to herein as "discrete variation" ($V_D$). Organellar perturbation target gene suppression can also produce changes in plant phenotypes including, but not limited to, male sterility, plant tillering, height, internode elongation and stomatal density (referred to herein as "MSH1-dr phenotypes") that can be used to identify or monitor organellar perturbation target gene suppression in plants. Other biochemical and molecular traits can also be used to identify or monitor organellar perturbation target gene suppression in plants. Such molecular traits can include, but are not limited to, changes in expression of genes involved in cell cycle regulation, Giberrellic acid catabolism, auxin biosynthesis, auxin receptor expression, flower and vernalization regulators (i.e. increased FLC and decreased SOC1 expression), as well as increased miR156 and decreased miR172 levels. Such biochemical traits can include, but are not limited to, up-regulation of most compounds of the TCA, NAD and carbohydrate metabolic pathways, down-regulation of amino acid biosynthesis, depletion of sucrose in certain plants, increases in sugars or sugar alcohols in certain plants, as well as increases in ascorbate, alphatocopherols, and stress-responsive flavones apigenin, and apigenin-7-o-glucoside, isovitexin, kaempferol 3-O-beta-glucoside, luteolin-7-O-glucoside, and vitexin. In certain embodiments, elevated plastochromanol-8 levels in plant stems can serve as a biochemical marker that can be used to identify or monitor organellar perturbation target gene suppression. In particular, plastochromanol-8 levels in stems of plants subjected to organellar perturbation target gene suppression can be compared to the levels in control plants that have not been subjected to such suppression to identify or monitor organellar perturbation target gene suppression. It is further contemplated that in certain embodiments, a combination of both molecular, biochemical, and traditional methods can be used to identify or monitor organellar perturbation target gene suppression in plants.

Organellar perturbation target gene suppression that results in useful epigenetic changes and useful traits can also be readily identified or monitored by assaying for characteristic DNA methylation and/or gene transcription patterns that occur in plants subject to such perturbations. In certain embodiments, characteristic DNA methylation and/or gene transcription patterns that occur in plants subject suppression of an MSH1 target gene can be monitored in a plant, a plant cell, plants, seeds, and/or processed products obtained therefrom to identify or monitor effects mediated by suppression of other target plant organellar perturbation genes. Such plant organellar perturbation genes that include, but are not limited to, genes provided herewith in the sequence listing and Table 1 are expected to give rise to the characteristic DNA methylation and/or gene transcription patterns that occur in plants subject suppression of an MSH1 target gene. Such characteristic DNA methylation and/or gene transcription patterns that occur in plants or seeds subjected suppression of an MSH1 target gene include, but are not limited to, those patterns disclosed in Examples 2 and 4 of U.S. patent application Ser. No. 14/454,518, which is specifically incorporated herein by reference in its entirety. In certain embodiments, first generation progeny of a plant subjected to suppression of a organellar perturbation target gene will exhibit CG differentially methylated regions (DMR) of various discrete chromosomal regions that include, but are not limited to, regions that encompass the MSH1 locus. In certain embodiments, a CG hypermethylated region that encompasses the MSH1 locus will be about 5 to about 8 MBp (mega base pairs) in length. In certain embodiments, first generation progeny of a plant subjected to suppression of a organellar perturbation target gene will also exhibit changes in plant defense and stress response gene expression. In certain embodiments, a plant, a plant cell, a seed, plant populations, seed populations, and/or processed products obtained therefrom that has been subject to suppression of a organellar perturbation target gene will exhibit pericentromeric CHG hypermethylation and CG hypermethlation of various discrete or localized chromosomal regions. Such discrete or localized hypermethylation is distinct from generalized hypermethylation across chromosomes that have been previously observed (U.S. Pat. No. 6,444,469). Such CHG hypermethylation is understood to be methylation at the sequence "CHG" where H=A, T, or C. Such CG and CHG hypermethylation can be assessed by comparing the methylation status of a sample from plants or seed that had been subjected to suppression of a organellar perturbation target gene, or a sample from progeny plants or seed derived therefrom, to a sample from control plants or seed that had not been subjected to suppression of a organellar perturbation target gene. A variety of methods that provide for suppression of organellar perturbation target gene in a plant followed by recovery of progeny plants where organellar perturbation target gene function is recovered are provided herein. In certain embodiments, such progeny plants can be recovered by downregulating expression of a organellar perturbation target gene-inhibiting transgene or by removing the organellar perturbation target gene-inhibiting transgene with a transposase. In certain embodiments of the methods provided herein, organellar perturbation target gene is suppressed in a target plant or plant cell and progeny plants that express organellar perturbation target gene are recovered by genetic techniques. In one useful and non-limiting embodiment, progeny plants can be obtained by selfing a plant that is heterozygous for the transgene that provides for organellar perturbation target gene segregation. Selfing of such heterozygous plants (or selfing of heterozygous plants regenerated from plant cells) provides for the transgene to segregate out of a subset of the progeny plant population. Where a organellar perturbation target gene is suppressed by use of a recessive mutation in an endogenous organellar perturbation target gene can, in yet another useful and non-limiting embodiment, be crossed to wild-type plants that had not been subjected to organellar perturbation and then selfed to obtain progeny plants that are homozygous for a functional, wild-type organellar perturbation target gene allele. In other embodiments, a organellar perturbation target gene is suppressed in a target plant or plant cell and progeny plants that express the organellar perturbation target gene are recovered by molecular genetic techniques. Non limiting and useful embodiments of such molecular genetic techniques include: i) downregulation of an organellar perturbation target gene suppressing transgene under the control of a regulated promoter by withdrawal of an inducer required for activity of that promoter or introduction of a repressor of that promoter; or, ii) exposure of the an organellar perturbation target gene suppressing transgene flanked by transposase recognition sites to the cognate transposase that provides for removal of that transgene.

Plants or rootstocks subjected to organellar perturbation, and scions grafted to such rootstocks, as well as the progeny thereof, can exhibit a variety of nuclear chromosomal DNA methylation patterns that are absent from control plants, rootstocks, or scions that were not subjected to organellar perturbation. Such methylation patterns can include, but are not limited to, CG hypermethylation, pericentromeric CHG hypermethylation, and/or additional characteristic methylation patterns observed in plants or progeny thereof that had been subjected to suppression of MSH1 gene expression. Such methylation patterns can also include, but are not limited to, changes in 5-hydroxymethylation and in particular, the occurrence of 5-hydroxymethylcytosine (5-hmC). Changes in 5-hmC can be monitored by immunoassays (Quest 5-hmC™ DNA ELISA Kit, Zymo Research Corp., Irvine, Calif., USA; or EpiSeeker™ hydroxymethylated DNA Quantification Kit, Abcam, Inc., Cambridge, Mass.). It is anticipated that plants, plant parts, processed plant products, rootstocks, and scions provided herein or produced by the methods provided herein can be identified by comparing methylation patterns in the genomic DNA of such materials to the methylation patterns of control plants, plant parts, processed plant products, rootstocks, and scions.

In certain embodiments of the methods provided herein, progeny plants derived from plants where organellar perturbation target gene expression was suppressed that exhibit one or more of male sterility, dwarfing, variegation, and/or delayed flowering time (i.e. MSH1-dr phenotypes) and express functional organellar perturbation target gene are obtained and maintained as independent breeding lines or as populations of plants. It has been found that such phenotypes appear to sort, so that it is feasible to select a cytoplasmic male sterile (CMS) plant displaying normal growth rate and no variegation, for example, or a stunted, male fertile plant that is highly variegated. We refer to this phenomenon herein as discrete variation ($V_D$). A plant that exhibits such discrete variation is a plant that exhibits one or more, but not all, MSH1-dr phenotypes that occur in that plant type when it is subject to MSH1 suppression. MSH1-dr phenotypes that occur in sorghum, millet, soybean, tobacco, and tomato include CMS, leaf variegation, dwarfed growth and reduced internode elongation, enhanced branching, altered leaf morphology, extended juvenility, and delayed flowering. In soybean, the altered leaf morphology can comprise a leaf wrinkling phenotype that resembles viral infection and dramatic delays in flowering. In sorghum, the MSH1-dr phenotypes include enhanced plant tillering, reduced height, reduced internode elongation, and changes in stomatal density. Useful and non-limiting illustrations of the discrete variation ($V_D$) phenomenon as it occurs in selfed plant populations that have lost an MSH1 organellar perturbation target gene-inhibiting transgene by segregation have been disclosed (U.S. Patent Application Publication No. US20140157452, incorporated herein by reference in its entirety). It is further contemplated that such individual lines that exhibit discrete variation ($V_D$) can be obtained by any of the aforementioned genetic techniques, molecular genetic techniques, or combinations thereof.

Individual lines or populations of plants obtained from plants where organellar perturbation target gene expression was suppressed that exhibit discrete variation ($V_D$) or that exhibit all MSH1-dr phenotypes can be crossed to other plants to obtain progeny plants that lack the phenotypes associated with discrete variation ($V_D$) (i.e. male sterility, dwarfing, variegation, and/or delayed flowering time). In certain embodiments, progeny of such outcrosses can be selfed to obtain individual progeny lines that exhibit significant phenotypic variation. Such phenotypic variation that is observed in these individual progeny lines derived from outcrosses of plants where organellar perturbation target gene expression was suppressed and that exhibit discrete variation to other plants is herein referred to as "quantitative variation" ($V_Q$). Certain individual progeny plant lines obtained from the outcrosses of plants where organellar perturbation target gene expression was suppressed to other plants can exhibit useful phenotypic variation where one or more traits are improved relative to either parental line and can be selected. Useful phenotypic variation that can be selected in such individual progeny lines includes, but is not limited to, increases in fresh and dry weight biomass relative to either parental line. An useful and non-limiting illustration of this phenomenon as it occurs in F2 progeny of outcrosses of plants that exhibit discrete variation to plants that do not exhibit discrete variation is provided in U.S. Patent Application Publication No. US20140157452, which is incorporated herein by reference in its entirety. Such selected individual lines with the useful trait can either be bred (i.e. crossed or selfed) individually or as a population. In certain embodiments, about 1% to about 45% of the population of progeny plants are selected for the useful trait and subsequently crossed the selected individual plants are crossed or selfed as a collected group of two or more selected plants to obtain populations of progeny plants that are enriched for the trait. In certain embodiments, about 1% to about 45% of the population of progeny plants are selected for the useful trait and subsequently crossed or selfed to obtain progeny plant populations that are enriched for the trait.

Individual lines or populations of plants obtained from plants where organellar perturbation target gene expression was suppressed that exhibit discrete variation ($V_D$) or that exhibit all MSH1-dr phenotypes can also be selfed to obtain progeny plants that lack the phenotypes associated with discrete variation ($V_D$) (i.e. male sterility, dwarfing, variegation, and/or delayed flowering time). Recovery of such progeny plants that lack the undesirable phenotypes can in certain embodiments be facilitated by removal of the transgene or endogenous locus that provides for organellar perturbation target gene suppression. In certain embodiments, progeny of such selfs can be used to obtain individual progeny lines or populations that exhibit significant phenotypic variation. Certain individual progeny plant lines or populations obtained from selfing plants where organellar perturbation target gene expression was suppressed can exhibit useful phenotypic variation where one or more traits are improved relative to the parental line that was not subjected to organellar perturbation target gene suppression and can be selected. Useful phenotypic variation that can be selected in such individual progeny lines includes, but is not limited to, increases in fresh and dry weight biomass relative to the parental line. Such selected individual lines with the useful trait can either be bred (i.e. crossed or selfed) individually or as a population. In certain embodiments, the selected individual plants are crossed or selfed as a collected group of two or more selected plants to obtain populations of progeny plants that are enriched for the trait. In certain embodiments, about 1% to about 45% of the population of progeny plants are selected for the useful trait and subsequently crossed or selfed to obtain progeny plant populations that are enriched for the trait.

In certain embodiments of the methods provided herein, progeny plants derived from plants where organellar perturbation target gene expression was suppressed that do not exhibit any MSH1-dr phenotypes and thus do not exhibit discrete variation ($V_D$) are obtained and maintained as independent breeding lines or as populations of plants that exhibit, contain, or harbor useful traits with nuclear inheritance. Useful traits that exhibit nuclear inheritance can thus occur in progeny plants derived from either selfs or crosses of plants that had been subjected to organellar perturbation but that did not exhibit any of the MSH1-dr phenotypes. More specifically, a plant that is subjected to perturbation of organellar target gene suppression that exhibits a wild type phenotype, a more robust growth habit, or even an improvement in a useful trait in comparison to a control plant that had not been subjected to perturbation of organellar target gene suppression can exhibit, contain, or harbor useful traits with nuclear inheritance. In certain embodiments, the useful traits that are exhibited, contained, or harbored in such plants that do not exhibit any MSH1-dr phenotypes and thus do not exhibit discrete variation ($V_D$) can be transmitted to progeny plants by selfing or outcrossing. In certain embodiments, the useful traits that are exhibited, contained, or harbored in such plants that do not exhibit any MSH1-dr phenotypes and thus do not exhibit discrete variation ($V_D$) can be transmitted to a scion from a plant that had not been subjected to organellar perturbation by using the plant that exhibits, contains, or harbors the useful trait as the rootstock in a graft to the scion. It is further contemplated that such individual lines that have the useful traits but that do not exhibit any MSH1-dr phenotypes and thus do not exhibit discrete variation ($V_D$) can be obtained by any of the aforementioned genetic techniques, molecular genetic techniques, or combinations thereof.

Individual lines or populations of plants obtained from plants where organellar perturbation target gene expression was suppressed that have the useful traits but that do not exhibit any MSH1-dr phenotypes and thus do not exhibit discrete variation ($V_D$) can be crossed to other plants to obtain progeny plants that exhibit the useful trait. In certain embodiments, the plants where organellar perturbation target gene expression was suppressed that have the useful traits but that do not exhibit any MSH1-dr phenotypes exhibit a wild type phenotype, a more robust growth habit, or even an improvement in a useful trait in comparison to a control plant that had not been subjected to perturbation of organellar target gene suppression can exhibit, contain, or harbor useful traits with nuclear inheritance. In certain embodiments, progeny of such outcrosses can be selfed to obtain individual progeny lines that exhibit significant phenotypic variation. Certain individual progeny plant lines obtained from the outcrosses of plants where organellar perturbation target gene expression was suppressed to other plants can exhibit useful phenotypic variation where one or more traits are improved relative to either parental line and can be selected. Such selected individual lines with the useful trait can either be bred (i.e. crossed or selfed) individually or as a population. Useful phenotypic variation that can be selected in such individual progeny lines includes, but is not limited to, increases in fresh and dry weight biomass relative to either parental line and/or increases in seed yield. Such selected individual lines with the useful trait can either be bred (i.e. crossed or selfed) individually or as a population. In certain embodiments, the selected individual plants are crossed or selfed as a collected group of two or more selected plants to obtain populations of progeny plants that are enriched for the trait. In certain embodiments, about 1% to about 45% of the population of progeny plants are selected for the useful trait and subsequently crossed or selfed to obtain progeny plant populations that are enriched for the trait.

Individual lines or populations of plants obtained from plants where organellar perturbation target gene expression was suppressed that have the useful traits but that do not exhibit any MSH1-dr phenotypes and thus do not exhibit discrete variation ($V_D$) that can also be selfed to obtain progeny plants that exhibit, contain, or harbor the useful traits. In certain embodiments, the plants where organellar perturbation target gene expression was suppressed that have the useful traits but that do not exhibit any MSH1-dr phenotypes exhibit a wild type phenotype, a more robust growth habit, or even an improvement in a useful trait in comparison to a control plant that had not been subjected to perturbation of organellar target gene suppression can exhibit, contain, or harbor useful traits with nuclear inheritance. Recovery of such progeny plants that lack the undesirable phenotypes can in certain embodiments be facilitated by removal of the transgene or endogenous locus that provides for organellar perturbation target gene suppression. In certain embodiments, progeny of such selfs can be used to obtain individual progeny lines or populations that exhibit significant phenotypic variation. Certain individual progeny plant lines or populations obtained from selfing plants where organellar perturbation target gene expression was suppressed can exhibit useful phenotypic variation where one or more traits are improved relative to the parental line that was not subjected to organellar perturbation target gene suppression and can be selected. Such selected individual lines with the useful trait can either be bred (i.e. crossed or selfed) individually or as a population. Useful phenotypic variation that can be selected in such individual progeny lines includes, but is not limited to, increases in fresh and dry weight biomass relative to the parental line. Such selected individual lines with the useful trait can either be bred (i.e. crossed or selfed) individually or as a population. In certain embodiments, the selected individual plants are crossed or selfed as a collected group of two or more selected plants to obtain populations of progeny plants that are enriched for the trait. In certain embodiments, about 1% to about 45% of the population of progeny plants are selected for the useful trait and subsequently crossed or selfed to obtain progeny plant populations that are enriched for the trait.

In certain embodiments, an outcross of an individual line or lines exhibiting, containing, or harboring the useful traits can be to a plant or plants that have not been subjected to organellar perturbation target gene suppression but are otherwise isogenic to the individual line or lines. In certain embodiments, a line or lines exhibiting, containing, or harboring the useful traits is obtained by suppressing organellar perturbation target gene in a given germplasm and can outcrossed to a plant having that same germplasm that was not subjected to organellar perturbation target gene suppression. In other embodiments, an outcross of an individual line or lines exhibiting, containing, or harboring the useful traits can be to a plant or plants that have not been subjected to organellar perturbation target gene suppression but are not isogenic to the individual line(s). Thus, in certain embodiments, an outcross of an individual line or lines exhibiting, containing, or harboring the useful traits can also be to a plant or plants that comprise one or more chromosomal polymorphisms that do not occur in the individual line(s), to a plant or plants derived from partially or wholly different germplasm, or to a plant or plant of a different heterotic group (in instances where such distinct heterotic groups exist). It is also recognized that such an outcross can be made in either direction. Thus, an individual line exhibiting discrete variability can be used as either a pollen donor or a pollen recipient to a plant that has not been subjected to organellar perturbation target gene suppression in such outcrosses. In certain embodiments, the progeny of the outcross are then selfed to establish individual lines that can be separately screened to identify lines with improved traits relative to parental lines. Such individual lines that exhibit the improved traits are then selected and can be propagated by further selfing. An useful and non-limiting illustration of this procedure where F2 progeny of outcrosses of plants that exhibit discrete variation to plants that do not exhibit discrete variation are obtained is provided in co-assigned U.S. Patent Application Publication No. US20140157452, which is incorporated herein by reference in its entirety. Such F2 progeny lines are screened for desired trait improvements relative to the parental plants and lines exhibiting such improvements are selected.

In certain embodiments, the methods provided herein can comprise selecting one or more progeny plants having the useful trait that exhibit nuclear inheritance. Nuclear inheritance can be established by demonstrating that the trait is pollen transmissible. Nuclear inheritance can also be established by demonstrating that the trait is associated with one or more chromosomal alterations that are present in the plants, grafted plants, or progeny thereof subjected to organellar perturbation but that are absent from control plants that had not been subjected to such organellar perturbation.

In certain embodiments, sub-populations of plants comprising the useful traits and epigenetic changes induced by suppression of the organellar perturbation target gene can be selected and bred as a population. Such populations can then be subjected to one or more additional rounds of selection for the useful traits and/or epigenetic changes to obtain subsequent sub-populations of plants exhibiting the useful trait. Any of these sub-populations can also be used to generate a seed lot. In one embodiment, organellar perturbed plants that do or do not exhibit an MSH1-dr phenotype can be selfed or outcrossed to obtain an F1 generation. A bulk selection at the F1, F2, and/or F3 generation can thus provide a population of plants exhibiting the useful trait and/or epigenetic changes or a seed lot. In certain embodiments, it is also anticipated that populations of progeny plants or progeny seed lots comprising a mixture of inbred and hybrid germplasms can be derived from populations comprising hybrid germplasm (i.e. plants arising from cross of one inbred line to a distinct inbred line). In certain embodiments, such sub-populations can comprise plants that had been subjected to organellar perturbation or grafted plants comprising a scion grafted to rootstock that had been subjected to organellar perturbation. Sub-populations of plants or grafted plants where the plant or the rootstock source plant is the progeny of a parental plant that had been subjected to organellar perturbation and that was selected for one or more useful traits can also be selected and bred as a population. Any of the aforementioned subpopulations can comprise 2 or more, 10 or more, 50 or more, 100 or more, 1000 or more, or 10,000 or more plants. Seed lots thus obtained from these methods or other methods provided herein can comprise seed wherein at least 25%, 50%, 60%, 70%, 80%, 90%, or 95% of progeny plants grown from the seed exhibit a useful trait. The selection would provide the most robust and vigorous of the population for seed lot production. Seed lots produced in this manner could be used for either breeding or sale. In certain embodiments, a seed lot comprising seed wherein at least 25%, 50%, 60%, 70%, 80%, 90%, or 95% of progeny plants grown from the seed exhibit a useful trait associated with one or more epigenetic changes, wherein the epigenetic changes are associated with CG hyper-methylation and/or CHG hyper-methylation at one or more nuclear chromosomal loci in comparison to a control plant that does not exhibit the useful trait, and wherein the seed or progeny plants grown from said seed that is epigenetically heterogenous are obtained. A seed lot obtainable by these methods can include at least 100, 500, 1000, 5000, or 10,000 seeds.

In certain embodiments, methods for producing a seed lot comprising: (i) growing a population of plants, wherein said population comprises two or more plants that had been subjected to organellar perturbation, two or more grafted plants comprising a scion and rootstock obtained from a plant that had been subjected to organellar perturbation, or two or more plants from a parental plant that had been subjected to organellar perturbation; and (ii) obtaining a seed lot from the population are provided. Populations of grafted plants where the rootstock source plant is the progeny of a parental plant that had been subjected to organellar perturbation and that was selected for one or more useful traits can also be selected and bred as a population. Any of the aforementioned populations can comprise 2 or more, 10 or more, 50 or more, 100 or more, 1000 or more, or 10,000 or more plants. Seed lots thus obtained from these methods or other methods provided herein can comprise seed wherein at least 25%, 50%, 60%, 70%, 80%, 90%, or 95% of progeny plants grown from the seed exhibit a useful trait. The selection would provide the most robust and vigorous of the population for seed lot production. Seed lots produced in this manner could be used for either breeding or sale. In certain embodiments, a seed lot comprising seed wherein at least 25%, 50%, 60%, 70%, 80%, 90%, or 95% of progeny plants grown from the seed exhibit a useful trait associated with one or more epigenetic changes, wherein the epigenetic changes are associated with CG hyper-methylation and/or CHG hyper-methylation at one or more nuclear chromosomal loci in comparison to corresponding nuclear chromosomal loci of a control plant that does not exhibit the useful trait, and wherein the seed or progeny plants grown from said seed that is epigenetically heterogenous are obtained. A seed lot obtainable by these methods can include at least 100, 500, 1000, 5000, or 10,000 seeds.

Altered chromosomal loci that can confer useful traits can also be identified and selected by performing appropriate comparative analyses of reference plants that do not exhibit the useful traits and test plants obtained from a parental plant or plant cell that had been subjected to organellar perturbation target gene suppression and obtaining either the altered loci or plants comprising the altered loci. It is anticipated that a variety of reference plants and test plants can be used in such comparisons and selections. In certain embodiments, the reference plants that do not exhibit the useful trait include, but are not limited to, any of: a) a wild-type plant;

b) a distinct subpopulation of plants within a given F2 population of plants of a given plant line (where the F2 population is any applicable plant type or variety); c) an F1 population exhibiting a wild type phenotype (where the F1 population is any applicable plant type or variety); and/or, d) a plant that is isogenic to the parent plants or parental cells of the test plants prior to suppression of organellar perturbation target gene in those parental plants or plant cells (i.e. the reference plant is isogenic to the plants or plant cells that were later subjected to organellar perturbation target gene suppression to obtain the test plants). In certain embodiments, the test plants that exhibit the useful trait include, but are not limited to, any of: a) any non-transgenic segregants that exhibit the useful trait and that were derived from parental plants or plant cells that had been subjected to transgene mediated organellar perturbation target gene suppression, b) a distinct subpopulation of plants within a given F2 population of plants of a given plant line that exhibit the useful trait (where the F2 population is any applicable plant type or variety); (c) any progeny plants obtained from the plants of (a) or (b) that exhibit the useful trait; or d) a plant or plant cell that had been subjected to organellar perturbation target gene suppression that exhibit the useful trait.

In general, an objective of these comparisons is to identify differences in the small RNA profiles and/or methylation of certain chromosomal DNA loci between test plants that exhibit the useful traits and reference plants that do not exhibit the useful traits. Altered loci thus identified can then be isolated or selected in plants to obtain plants exhibiting the useful traits.

In certain embodiments, altered chromosomal loci can be identified by identifying small RNAs that are up or down regulated in the test plants (in comparison to reference plants). This method is based in part on identification of altered chromosomal loci where small interfering RNAs direct the methylation of specific gene targets by RNA-directed DNA methylation (RdDM). The RNA-directed DNA methylation (RdDM) process has been described (Chinnusamy V et al. Sci China Ser C-Life Sci. (2009) 52(4): 331-343). Any applicable technology platform can be used to compare small RNAs in the test and reference plants, including, but not limited to, microarray-based methods (Franco-Zorilla et al. Plant J. 2009 59(5):840-50), deep sequencing based methods (Wang et al. The Plant Cell 21:1053-1069 (2009)), and the like.

In certain embodiments, altered chromosomal loci can be identified by identifying histone proteins associated with a locus and that are methylated or acylated in the test plants (in comparison to reference plants). The analysis of chromosomal loci associated with methylated or acylated histones can be accomplished by enriching and sequencing those loci using antibodies that recognize methylated or acylated histones. Identification of chromosomal regions associated with methylation or acetylation of specific lysine residues of histone H3 by using antibodies specific for H3K4me3, H3K9ac, H3K27me3, and H3K36me3 has been described (Li et al., Plant Cell 20:259-276, 2008; Wang et al. The Plant Cell 21:1053-1069 (2009).

In certain embodiments, altered chromosomal loci can be identified by identifying chromosomal regions (genomic DNA) that has an altered methylation status in the test plants (in comparison to reference plants). An altered methylation status can comprise either the presence or absence of methylation in one or more chromosomal loci of a test plant comparison to a reference plant. Any applicable technology platform can be used to compare the methylation status of chromosomal loci in the test and reference plants. Applicable technologies for identifying chromosomal loci with changes in their methylation status include, but not limited to, methods based on immunoprecipitation of DNA with antibodies that recognize 5-methylcytidine, methods based on use of methylation dependent restriction endonucleases and PCR such as McrBC-PCR methods (Rabinowicz, et al. Genome Res. 13: 2658-2664 2003; Li et al., Plant Cell 20:259-276, 2008), sequencing of bisulfite-converted DNA (Frommer et al. Proc. Natl. Acad. Sci. U.S.A. 89 (5): 1827-31; Tost et al. BioTechniques 35 (1): 152-156, 2003), methylation-specific PCR analysis of bisulfite treated DNA (Herman et al. Proc. Natl. Acad. Sci. U.S.A. 93 (18): 9821-6, 1996), deep sequencing based methods (Wang et al. The Plant Cell 21:1053-1069 (2009)), methylation sensitive single nucleotide primer extension (MsSnuPE; Gonzalgo and Jones Nucleic Acids Res. 25 (12): 2529-2531, 1997), fluorescence correlation spectroscopy (Umezu et al. Anal Biochem. 415(2):145-50, 2011), single molecule real time sequencing methods (Flusberg et al. Nature Methods 7, 461-465), high resolution melting analysis (Wojdacz and Dobrovic (2007) Nucleic Acids Res. 35 (6): e41), and the like.

Methods for introducing various chromosomal modifications that can confer a useful trait into a plant, as well as the plants, plant parts, and products of those plant parts are also provided herein. Chromosomal alterations and/or chromosomal mutations induced by suppression of organellar perturbation target gene can be identified as described herein. Once identified, chromosomal modifications including, but not limited to, chromosomal alterations, chromosomal mutations, or transgenes that provide for the same genetic effect as the chromosomal alterations and/or chromosomal mutations induced by suppression of organellar perturbation target gene can be introduced into host plants to obtain plants that exhibit the desired trait. In this context, the "same genetic effect" means that the introduced chromosomal modification provides for an increase and/or a reduction in expression of one or more endogenous plant genes that is similar to that observed in a plant that has been subjected to organellar perturbation target gene suppression and exhibits the useful trait. In certain embodiments where an endogenous gene is methylated in a plant subjected to organellar perturbation target gene suppression and exhibits both reduced expression of that gene and a useful trait, chromosomal modifications in other plants that also result in reduced expression of that gene and the useful trait are provided. In certain embodiments where an endogenous gene is methylated in a plant subjected to organellar perturbation target gene suppression and exhibits both increased expression of that gene and a useful trait, chromosomal modifications in other plants that also result in increased expression of that gene and the useful trait are provided. In certain embodiments where an endogenous gene is demethylated in a plant subjected to organellar perturbation target gene suppression and exhibits both increased expression of that gene and a useful trait, chromosomal modifications in other plants that also result in increased expression of that gene and that useful trait are provided. In certain embodiments where an endogenous gene is demethylated in a plant subjected to organellar perturbation target gene suppression and exhibits both decreased expression of that gene and a useful trait, chromosomal modifications in other plants that also result in decreased expression of that gene and that useful trait are provided.

In certain embodiments, the chromosomal modification that is introduced is a chromosomal alteration. Chromosomal alterations including, but not limited to, a difference in a methylation state can be introduced by crossing a plant comprising the chromosomal alteration to a plant that lacks the chromosomal alteration and selecting for the presence of the alteration in F1, F2, or any subsequent generation progeny plants of the cross. In still other embodiments, the chromosomal alterations in specific target genes can be introduced by expression of a siRNA or hairpin RNA targeted to that gene by RNA directed DNA methylation (Chinnusamy V et al. Sci China Ser C-Life Sci. (2009) 52(4): 331-343; Cigan et al. Plant J 43 929-940, 2005; Heilersig et al. (2006) Mol Genet Genomics 275 437-449; Miki and Shimamoto, Plant Journal 56(4):539-49; Okano et al. Plant Journal 53(1):65-77, 2008).

In certain embodiments, the chromosomal modification is a chromosomal mutation. Chromosomal mutations that provide for reductions or increases in expression of an endogenous gene of a chromosomal locus can include, but are not limited to, insertions, deletions, and/or substitutions of nucleotide sequences in a gene. Chromosomal mutations can result in decreased expression of a gene by a variety of mechanisms that include, but are not limited to, introduction of missense codons, frame-shift mutations, premature translational stop codons, promoter deletions, mutations that disrupt mRNA processing, and the like. Chromosomal mutations that result in increased expression of a gene include, but are not limited to, promoter substitutions, removal of negative regulatory elements from the gene, and the like. Chromosomal mutations can be introduced into specific loci of a plant by any applicable method. Applicable methods for introducing chromosomal mutations in endogenous plant chromosomal loci include, but are not limited to, homologous double stranded break repair (Wright et al., Plant J. 44, 693, 2005; D'Halluin, et al., Plant Biotech. J. 6:93, 2008), non-homologous end joining or a combination of non-homologous end joining and homologous recombination (reviewed in Puchta, J. Exp. Bot. 56, 1, 2005; Wright et al., Plant J. 44, 693, 2005), meganuclease-induced, site specific double stranded break repair (WO/06097853A1, WO/06097784A1, WO/04067736A2, U.S. 20070117128A1), and zinc finger nuclease mediated homologous recombination (WO 03/080809, WO 05/014791, WO 07014275, WO 08/021207). In still other embodiments, desired mutations in endogenous plant chromosomal loci can be identified through use of the TILLING technology (Targeting Induced Local Lesions in Genomes) as described (Henikoff et al., Plant Physiol. 2004, 135:630-636).

In other embodiments, chromosomal modifications that provide for the desired genetic effect can comprise a transgene. Transgenes that can result in decreased expression of an gene by a variety of mechanisms that include, but are not limited to, dominant-negative mutants, a small inhibitory RNA (siRNA), a microRNA (miRNA), a co-suppressing sense RNA, and/or an anti-sense RNA and the like. U.S. patents incorporated herein by reference in their entireties that describe suppression of endogenous plant genes by transgenes include U.S. Pat. No. 7,109,393, U.S. Pat. No. 5,231,020 and U.S. Pat. No. 5,283,184 (co-suppression methods); and U.S. Pat. No. 5,107,065 and U.S. Pat. No. 5,759,829 (antisense methods). In certain embodiments, transgenes specifically designed to produce double-stranded RNA (dsRNA) molecules with homology to the endogenous gene of a chromosomal locus can be used to decrease expression of that endogenous gene. In such embodiments, the sense strand sequences of the dsRNA can be separated from the antisense sequences by a spacer sequence, preferably one that promotes the formation of a dsRNA (double-stranded RNA) molecule. Examples of such spacer sequences include, but are not limited to, those set forth in Wesley et al., Plant J., 27(6):581-90 (2001), and Hamilton et al., Plant J., 15:737-746 (1998). Vectors for inhibiting endogenous plant genes with transgene-mediated expression of hairpin RNAs are disclosed in U.S. Patent Application Publication Nos. 20050164394, 20050160490, and 20040231016, each of which is incorporated herein by reference in their entirety.

Transgenes that result in increased expression of a gene of a chromosomal locus include, but are not limited to, a recombinant gene fused to heterologous promoters that are stronger than the native promoter, a recombinant gene comprising elements such as heterologous introns, 5' untranslated regions, 3' untranslated regions that provide for increased expression, and combinations thereof. Such promoter, intron, 5' untranslated, 3' untranslated regions, and any necessary polyadenylation regions can be operably linked to the DNA of interest in recombinant DNA molecules that comprise parts of transgenes useful for making chromosomal modifications as provided herein.

Promoters useful for expression of transgenes include, but are not limited to, enhanced or duplicate versions of the viral CaMV35S and FMV35S promoters (U.S. Pat. No. 5,378,619, incorporated herein by reference in its entirety), the cauliflower mosaic virus (CaMV) 19S promoters, the rice Act1 promoter and the Figwort Mosaic Virus (FMV) 35S promoter (U.S. Pat. No. 5,463,175; incorporated herein by reference in its entirety). Introns useful for transgene expression include, but are not limited to, the maize hsp70 intron (U.S. Pat. No. 5,424,412; incorporated herein by reference in its entirety), the rice Act1 intron (McElroy et al., 1990, The Plant Cell, Vol. 2, 163-171), the CAT-1 intron (Cazzonnelli and Velten, Plant Molecular Biology Reporter 21: 271-280, September 2003), the pKANNIBAL intron (Wesley et al., Plant J. 2001 27(6):581-90; Collier et al., 2005, Plant J 43: 449-457), the PIV2 intron (Mankin et al. (1997) Plant Mol. Biol. Rep. 15(2): 186-196) and the "Super Ubiquitin" intron (U.S. Pat. No. 6,596,925, incorporated herein by reference in its entirety; Collier et al., 2005, Plant J 43: 449-457). Polyadenylation sequences include, but are not limited to, and Agrobacterium tumor-inducing (Ti) plasmid nopaline synthase (NOS) gene and the pea ssRUBISCO E9 gene polyadenylation sequences.

Plant lines and plant populations obtained by the methods provided herein can be screened and selected for a variety of useful traits by using a wide variety of techniques. In particular embodiments provided herein, individual progeny plant lines or populations of plants obtained from the selfs or outcrosses of plants where organellar perturbation target gene expression was suppressed to other plants are screened and selected for the desired useful traits.

In certain embodiments, the screened and selected trait is improved plant yield. In certain embodiments, such yield improvements are improvements in the yield of a plant line relative to one or more parental line(s) under non-stress conditions. Non-stress conditions comprise conditions where water, temperature, nutrients, minerals, and light fall within typical ranges for cultivation of the plant species. Such typical ranges for cultivation comprise amounts or values of water, temperature, nutrients, minerals, and/or light that are neither insufficient nor excessive. In certain embodiments, such yield improvements are improvements in the yield of a plant line relative to parental line(s) under abiotic stress conditions. Such abiotic stress conditions include, but are not limited to, conditions where water, temperature, nutrients, minerals, and/or light that are either insufficient or excessive. Abiotic stress conditions would thus include, but are not limited to, drought stress, osmotic stress, nitrogen stress, phosphorous stress, mineral stress, heat stress, cold stress, and/or light stress. In this context, mineral stress includes, but is not limited to, stress due to insufficient or excessive potassium, calcium, magnesium, iron, manganese, copper, zinc, boron, aluminum, or silicon. In this context, mineral stress includes, but is not limited to, stress due to excessive amounts of heavy metals including, but not limited to, cadmium, copper, nickel, zinc, lead, and chromium.

Improvements in yield in plant lines obtained by the methods provided herein can be identified by direct measurements of wet or dry biomass including, but not limited to, grain, lint, leaves, stems, or seed. Improvements in yield can also be assessed by measuring yield related traits that include, but are not limited to, 100 seed weight, a harvest index, and seed weight. In certain embodiments, such yield improvements are improvements in the yield of a plant line relative to one or more parental line(s) and can be readily determined by growing plant lines obtained by the methods provided herein in parallel with the parental plants. In certain embodiments, field trials to determine differences in yield whereby plots of test and control plants are replicated, randomized, and controlled for variation can be employed (Giesbrecht F G and Gumpertz M L. 2004. Planning, Construction, and Statistical Analysis of Comparative Experiments. Wiley. New York; Mead, R. 1997. Design of plant breeding trials. In Statistical Methods for Plant Variety Evaluation. eds. Kempton and Fox. Chapman and Hall. London.). Methods for spacing of the test plants (i.e. plants obtained with the methods of this disclosure) with check plants (parental or other controls) to obtain yield data suitable for comparisons are provided in references that include, but are not limited to, any of Cullis, B. et al. J. Agric. Biol. Env. Stat.11:381-393; and Besag, J. and Kempton, R A. 1986. Biometrics 42: 231-251.).

In certain embodiments, the screened and selected trait is improved resistance to biotic plant stress relative to the parental lines. Biotic plant stress includes, but is not limited to, stress imposed by plant fungal pathogens, plant bacterial pathogens, plant viral pathogens, insects, nematodes, and herbivores. In certain embodiments, screening and selection of plant lines that exhibit resistance to fungal pathogens including, but not limited to, an *Alternaria* sp., an *Ascochyta* sp., a *Botrytis* sp.; a *Cercospora* sp., a *Colletotrichum* sp., a *Diaporthe* sp., a *Diplodia* sp., an *Erysiphe* sp., a *Fusarium* sp., *Gaeumanomyces* sp., *Helminthosporium* sp., *Macrophomina* sp., a *Nectria* sp., a *Peronospora* sp., a *Phakopsora* sp., *Phialophora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Scerotium* sp., a *Sclerotinia* sp., a *Septoria* sp., a *Thielaviopsis* sp., an *Uncinula* sp, a *Venturia* sp., and a *Verticillium* sp. is provided. In certain embodiments, screening and selection of plant lines that exhibit resistance to bacterial pathogens including, but not limited to, an *Erwinia* sp., a *Pseudomonas* sp., and a *Xanthamonas* sp. is provided. In certain embodiments, screening and selection of plant lines that exhibit resistance to insects including, but not limited to, aphids and other piercing/sucking insects such as *Lygus* sp., lepidoteran insects such as *Armigera* sp., *Helicoverpa* sp., *Heliothis* sp., and *Pseudoplusia* sp., and coleopteran insects such as *Diabroticus* sp. is provided. In certain embodiments, screening and selection of plant lines that exhibit resistance to nematodes including, but not limited to, *Meloidogyne* sp., *Heterodera* sp., *Belonolaimus* sp., *Ditylenchus* sp., *Globodera* sp., *Naccobbus* sp., and *Xiphinema* sp. is provided.

Other useful traits that can be obtained by the methods provided herein include various seed quality traits including, but not limited to, improvements in either the compositions or amounts of oil, protein, or starch in the seed. Still other useful traits that can be obtained by methods provided herein include, but are not limited to, increased biomass, non-flowering, male sterility, digestability, seed filling period, maturity (either earlier or later as desired), reduced lodging, and plant height (either increased or decreased as desired). Still other useful traits that can be obtained by methods provided herein include, but are not limited to, delayed leaf senescence, increased flower number, improved architecture for high density planting, improved photosynthesis, increased root mass, increased cell number, improved seedling vigor, improved seedling size, increased rate of cell division, improved metabolic efficiency, and increased meristem size.

In addition to any of the aforementioned traits, particularly useful traits for *sorghum* that can be obtained by the methods provided herein also include, but are not limited to: i) agronomic traits (flowering time, days to flower, days to flower-post rainy, days to flower-rainy; ii) fungal disease resistance (*sorghum* downy mildew resistance—glasshouse, *sorghum* downy mildew resistance-field, *sorghum* grain mold, *sorghum* leaf blight resistance, *sorghum* rust resistance; iii) grain related trait: (Grain dry weight, grain number, grain number per square meter, Grain weight over panicle. seed color, seed luster, seed size); iv) growth and development stage related traits (basal tillers number, days to harvest, days to maturity, nodal tillering, plant height, plant height-postrainy); v) infloresence anatomy and morphology trait (threshability); vi) Insect damage resistance (*sorghum* shoot fly resistance-post-rainy, *sorghum* shoot fly resistance-rainy, *sorghum* stem borer resistance); vii) leaf related traits (leaf color, leaf midrib color, leaf vein color, flag leaf weight, leaf weight, rest of leaves weight); viii) mineral and ion content related traits (shoot potassium content, shoot sodium content); ix) panicle related traits (number of panicles, panicle compactness and shape, panicle exertion, panicle harvest index, panicle length, panicle weight, panicle weight without grain, panicle width); x) phytochemical compound content (plant pigmentation); xii) spikelet anatomy and morphology traits (glume color, glume covering); xiii) stem related trait (stem over leaf weight, stem weight); and xiv) miscellaneous traits (stover related traits, metabolised energy, nitrogen digestibility, organic matter digestibility, stover dry weight).

EXAMPLES

The following examples are included to demonstrate certain embodiments of the present disclosure. It should be appreciated by those of skill in the art that the techniques disclosed in the examples which follow represent techniques determined by the inventors to function well in the practice of the present disclosure. However, those of skill in the art should, in light of the present disclosure, appreciate that many changes can be made in the specific embodiments which are disclosed and still obtain a like or similar result without departing from the spirit and scope of the present disclosure.

Example 1. Implementing Selection of MSH1-Induced Non-Genetic Variation in Sorghum Bicolor as a Model for Epigenetic Breeding Here we investigate the implications of MSH1 modulation in a crop species. We found that MSH1-mediated phenotypic variation in *Sorghum bicolor* is heritable, responsive to selection, and potentially valuable for crop breeding. We observed phenotypic variation for grain yield, plant height, flowering time, panicle architecture, and above-ground biomass. Focusing on grain yield and plant height, we selected these traits for three cycles with progress each cycle. Based on amenability of this system to implementation in a range of crops, and the scope of phenotypic variation that is derived, our results suggest that MSH1 suppression provides a novel model for epigenetic breeding in crops.

Here we investigate the consequences of incorporating the MSH1-dr condition to plant selection, using *sorghum* as a model. We show that crossing with a transgene-null MSH1-dr line produces an unexpected range of phenotypic variation that is both heritable and responsive to selection. This variation appears to be stable over at least four generations. We also show evidence of epi-type x environment interactions. Finally, we demonstrate gains in grain yield over only two generations of selection, suggesting that this non-genetic variation may prove valuable for agricultural production as a novel crop breeding strategy.

Plant Materials and Growth Conditions.

*Sorghum* MSH1-dr plants used in these experiments were derived as described in Xu et al (2012). Six $T_3$ individuals displaying the MSH1-dr phenotype but null for the MSH1-RNAi transgene were used as females in crosses to wild-type inbred Tx430 to derive $F_1$ seed. Another three $T_3$ individuals were used as males in the reciprocal crosses to Tx430. The number of $F_1$ plants derived from each cross ranged from 5 to 19 individuals. Parents and $F_1$ progeny were grown under greenhouse conditions on a 14 hr/10 hr day-night cycle with 28° C./22° C. day-night temperatures. Self-pollinated seed of $F_1$ plants was harvested individually to generate corresponding $F_2$ families.

Field Experiments and Phenotyping.

Plants were thinned to a final density of 15 plants/m². The 2011 $F_2$, $F_3$, and $F_4$ combined field experiment comprised seven blocks of 28 entries each (28×7 alpha lattice design), with two replicates grown under fertilized soil conditions. In total, the 2011 field experiment comprised 48 $F_2$ entries, 77 $F_3$ entries, and 39 $F_4$, with additional wild-type Tx430 rows as a control.

For estimating grain yield, threshed panicles from three plants were pooled and converted to grams/m², with 2-3 such measurements taken per row. The histogram figure for yield variation used individual panicle grain yield (prior to pooling). For flowering time, plant height, and rachis length, measurements were taken on individual plants. For each dry biomass measurement, three fully dried plants were pooled together then converted to grams/plant.

The 2012 multi-location experiment included Lincoln, Nebr. (40° 51' N, 96° 35' W) and Mead, N E (41° 9' N, 96° 24' W) sites, which received 178 mm and 158 mm of precipitation over the growing season, respectively. Within each location, lines were grown in two-row plots arranged in a randomized complete block design with two replications. All sites were fertilized identically according to standard growing practices. For this experiment, grain yield was estimated by taking threshed panicles from a meter-length area of each row and converting to grams/m².

Statistical Analysis.

For evaluations in a single environment, mean phenotypic values and standard errors for each line were estimated using the linear mixed model $y_{ijk} = \mu + \alpha_i + r_k + (b/r)_{jk} + \varepsilon_{ijk}$ where $y_{ijk}$ is the trait response, $\mu$ is the population mean, $\alpha_i$ is the effect of line i, $r_k$ is the effect of replicate k, $(b/r)_{jk}$ is the effect of block j nested within replicate k, and $\varepsilon_{ijk}$ is the residual error. For evaluations over multiple environments, mean phenotypic values and standard errors for each line were estimated using the linear mixed model $y_{ijkm} = \mu + \alpha_i + e_m + (r/e)_{km} + (b/r/e)_{jkm} + (\alpha e)_{im} + \varepsilon_{ijkm}$ where $y_{ijkm}$ is the trait response, $\mu$ is the population mean, $\alpha_i$ is the effect of line i, $e_m$ is the effect of environment m, $(r/e)_{km}$ is the effect of replicate nested within environment, $(b/r/e)_{jkm}$ is the effect of block j nested within replicate k of environment m, $(\alpha e)_{im}$ is the interaction between line i and environment m, and $\varepsilon_{ijkm}$ is the residual. Line, environment, and line x environment effects were treated as fixed while block and replicate effects were treated as random. Models were fit by restricted maximum likelihood using the R package "nlme" (Pinheiro et al. 2013). Residuals were graphically examined for anomalies. When deemed appropriate, Box-cox transformations were performed. In some cases, heteroscedasticity was modeled by specifying separate variance estimates stratified by generation/type (e.g. epi-$F_2$, wild-type Tx430, etc.) or broad height class (short, tall, mixed). $F_4$ mean comparisons excluded lines exhibiting mixed heights or lines with inadequate data for one or more traits of interest. Contrasts for differences in trait means between lines were performed using the R package "multcomp" (Hothorn et al. 2008).

PCR Assay for RNAi Transgene and SSR Marker Analysis.

PCR assay for MSH1-RNAi transgene presence in *sorghum* materials used primers RNAi-F 5'GTGTACTCATCTGGATCTGTATTG-3' (SEQ ID NO:55) and RNAi-R 5'GGTTGAGGAGCCTGAATCTCTGAAC3' (SEQ ID NO:56) Positive and negative controls were included from a confirmed transgenic line and wildtype Tx430, respectively.

SSR marker analysis used SSR primers that were developed and mapped previously (Schloss et al. 2002; Li et al. 2009). Fragments were assayed by capillary electrophoresis on an Advanced Analytical Fragment Analyzer™ (Advanced Analytical Technologies, Inc. Ames, Iowa) using the dsDNA Reagent kit, 35-1,500 bp 500S that separates DNA in the size range of 35-1,500 bp. Of 136 primers that were tested, 43 produced unambiguous polymorphisms between Tx430 and the sweet *sorghum* control line 'Wray' and were used for testing the epi-lines.

*Sorghum* SNP Survey.

Leaf tissue sample was collected from plants grown under controlled greenhouse conditions three weeks after germination. Genomic DNA was extracted from freeze-dried leaf tissue and processed following manufacturer's recommendations prior to Infinium™ beadchip hybridization (Illumina, San Diego, Calif.). The genotyping of five MSH1-epiF$_4$ lines and wild type Tx430 was carried out at the Monsanto Applied Genotyping Labs (Chesterfield, Mo.). The platform used was an exclusive custom-designed *Sorghum bicolor* Infinium™ high-density beadchip containing 1,885 internally validated SNP markers.

For the six samples, 107 of the 1,885 SNP markers, ca 5.68%, provided invalid data due to one of the following: low marker signal intensity, marker failed data QC, or unscorable allele calls. The remaining 1,778 SNP markers were used for the analysis. These 1,778 SNP markers are distributed across all 10 *sorghum* chromosomes with genome coverage approximating 90%. The number of heterozygotes (#Het) and percentage of heterozygotes (% Het) were calculated based on the 1778 SNP markers.

Results

MSH1-Altered Lines and Reciprocal Crosses.

Previously, we described MSH1-RNAi lines displaying numerous physiological changes, a condition of developmental reprogramming that was termed MSH1-dr (Xu et al. 2012). Segregation of the MSH1-RNAi transgene gave rise to some MSH1+/+ individuals that retained the characteristic msh1 phenotype despite having normal MSH1 transcript levels (Xu et al. 2012). These plants maintain the altered MSH1-dr growth phenotype through multiple (at least nine, to date) generations of self-pollination.

To investigate the mechanism of inheritance, we performed reciprocal crosses in sorghum of MSH1-dr individuals to their wild-type counterpart. FIG. 1 illustrates the transgene and crossing process used in this study, with all sorghum materials generated from the inbred line Tx430 (Miller 1984). When crossed to the wild-type inbred Tx430 line, the transgene-null MSH1-dr individuals produced progeny that were restored to normal phenotype (FIG. 1a). The derived $F_1$ progeny no longer showed the dwarfed, tillering, and late flowering phenotype; instead, many of the plants grew taller and produced more seed than the wild-type. This was repeatedly observed in $F_1$ populations derived from nine separate crosses, three of which used an MSH1-dr plant as the pollen donor (Xu et al. 2012).

Lack of the MSH1-dr phenotype in the $F_1$ generation from either direct or reciprocal crosses argues against the observed phenotypes being inherited via cytoplasmic organellar genomes. Analogously generated crosses in Arabidopsis with msh1 point or T-DNA insertion mutations also display enhanced vigor, and whole-genome bisulfite sequencing of those materials revealed significant changes in pericentromeric CHH methylation and in CG methylation of particular genomic regions (Xu et al. 2013). In other species, including tomato, soybean and tobacco, heritable MSH1-dr phenotypes also persist despite restored MSH1 expression following RNAi silencing (Xu et al. 2012 and unpublished), and crosses in those species to their respective wild-type counterparts similarly produce progeny with enhanced growth phenotypes (unpublished). Taken together, the evidence suggests that the MSH1-dr and $F_1$ observations involve a conserved, programmed epigenetic pathway, and we therefore designated the $F_1$ progeny as MSH1-epi$F_1$.

MSH1-epi$F_2$ Populations Show Enhanced Variation.

Self-pollination of the MSH1-epi$F_1$ plants produced an $F_2$ population (MSH1-epi$F_2$) variable in plant phenotype (FIG. 1b, c, d, f, FIG. 2, Table 3), with a minority exhibiting the MSH1-dr phenotype (FIG. 1e). Notably increased variation in the $F_2$ was detected for grain yield and plant height (FIG. 2, Table S1). Although we did not detect a very significant increase in variance for flowering time or panicle length in the epi-$F_2$, by the $F_4$ we were able to detect lines different from wild-type Tx430 for those traits (FIG. 5), indicating modest but heritable variation for flowering time and panicle length.

TABLE 3

Sorghum epi-lines families showed overall increased variation compared to wild-type Tx430.

| Trait | Population | Population Size | Mean within-row variance | F-value | Brown-Forsythe test p-value |
|---|---|---|---|---|---|
| Grain Yield (grams/m²) | Tx430 | 55 | 38.02 | — | — |
| | epiF2 | 318 | 64.41 | 9.6194 | <0.01 |

TABLE 3-continued

Sorghum epi-lines families showed overall increased variation compared to wild-type Tx430.

| Trait | Population | Population Size | Mean within-row variance | F-value | Brown-Forsythe test p-value |
|---|---|---|---|---|---|
| | epiF3 | 348 | 87.04 | 19.582 | <0.001 |
| | epiF4 | 235 | 45.75 | 6.9213 | <0.01 |
| Plant Height (cm) | Tx430 | 192 | 38.03 | — | — |
| | epiF2 | 1493 | 789.94 | 301.04 | <0.001 |
| | epiF3 | 1587 | 668.49 | 306.61 | <0.001 |
| | epiF4 | 947 | 356.42 | 79.396 | <0.001 |
| Flowering Time (DAS) | Tx430 | 134 | 1.04 | — | — |
| | epiF2 | 908 | 1.15 | 0.2843 | >0.1 |
| | epiF3 | 635 | 0.86 | 16.819 | <0.001 |
| | epiF4 | 524 | 0.76 | 3.0162 | <0.1 |
| Rachis Length (cm) | Tx430 | 288 | 3.31 | — | — |
| | epiF2 | 1980 | 4.20 | 0.1348 | >0.1 |
| | epiF3 | 2412 | 4.75 | 3.3373 | >0.1 |
| | epiF4 | 1404 | 3.86 | 0.328 | >0.1 |
| Dry Biomass (grams/plant) | Tx430 | 23 | 86.48 | — | — |
| | epiF2 | 163 | 183.05 | 17.137 | <0.001 |
| | epiF3 | 188 | 199.31 | 18.313 | <0.001 |
| | epiF4 | 116 | 174.46 | 7.2468 | <0.01 |

Data for Table 3 were acquired from a 2011 field experiment. Brown-Forsythe tests for homogeneous variances were performed between epi-line generation and wild-type (e.g. all epiF2 vs Tx430, all epiF3 vs Tx430).

A small proportion of greenhouse-grown MSH1-epi$F_3$ families also showed the MSH1-dr phenotype, with an overall frequency of ca. 8% (Table 4). By the $F_4$ generation, we estimate that the overall frequency drops to below 2%. Although the progeny from these sporadic MSH1-dr types in advanced generations have not been thoroughly investigated, some families appear more likely than others to produce this phenotype. When MSH1-dr frequencies were compared between parental and progeny generations, each derived from a single individual, the phenotype was only observed in progeny generations whose parental generation had some incidence of the phenotype (Table 5). Currently, we cannot rule out that the overall rarity of the MSH1-dr phenotype by the $F_4$ generation may be the consequence of inadvertent selection rather than a natural tendency to gradually stabilize away from the phenotype.

TABLE 4

Frequency of MSH1-dr phenotype (8.4%) in epi-F3 families derived from sorghum MSH1-dr x Tx430, and grown in the greenhouse.

| F3 family | Sample size | Mean plant height (cm) | # Individuals with wild-type height or higher | # Individuals with dwarf height |
|---|---|---|---|---|
| 1 | 10 | 160 | 10 | 0 |
| 2 | 9 | 208 | 9 | 0 |
| 3 | 10 | 167 | 10 | 0 |
| 4 | 10 | 189 | 10 | 0 |
| 5 | 8 | 186 | 7 | 1 |
| 6 | 10 | 114 | 10 | 0 |
| 7 | 9 | 203 | 9 | 0 |
| 8 | 7 | 102 | 6 | 1 |
| 9 | 2 | 107 | 2 | 0 |
| 10 | 9 | 116 | 9 | 0 |
| 11 | 4 | 89 | 3 | 1 |
| 12 | 6 | 118 | 6 | 0 |
| 13 | 10 | 187 | 10 | 0 |
| 14 | 8 | 150 | 6 | 2 |
| 15 | 7 | 81 | 3 | 4 |
| 16 | 10 | 143 | 7 | 3 |

TABLE 4-continued

Frequency of MSH1-dr phenotype (8.4%) in epi-F3 families derived from *sorghum* MSH1-dr x Tx430, and grown in the greenhouse.

| F3 family | Sample size | Mean plant height (cm) | # Individuals with wild-type height or higher | # Individuals with dwarf height |
|---|---|---|---|---|
| 17 | 5 | 122 | 5 | 0 |
| 18 | 10 | 137 | 9 | 1 |
| 19 | 10 | 98 | 10 | 0 |
| Total | 19 | 154 | — | 141 | 13 |

TABLE 5

From each of ten epi-lines, a single individual that did not display the MSH1-dr phenotype was grown along with its parental generation. Parental and progeny generation frequencies were then counted with N ≥ 105 in each generation.

| | Frequency of MSH1-dr phenotype | | | |
|---|---|---|---|---|
| Line | Parental Frequency | % | Progeny Frequency | % |
| Msh1 . . . #11 x Tx430 #2-6-10-8 | 0/118 | 0% | 0/114 | 0% |
| Msh1 . . . #11 x Tx430 #2-6-3-23 | 0/116 | 0% | 0/119 | 0% |
| Msh1 . . . #15 x Tx430 #7-1-1-5 | 0/118 | 0% | 0/117 | 0% |
| Msh1 . . . #15 x Tx430 #7-1-3-1 | 3/105 | 2.86% | 2/122 | 1.64% |
| Msh1 . . . #15 x Tx430 #7-1-9-10 | 0/115 | 0% | 0/111 | 0% |
| Msh1 . . . #22 x Tx430 #4-3-1-3 | 9/119 | 7.56% | 1/112 | 0.89% |
| Msh1 . . . #22 x Tx430 #4-4-10-28 | 0/126 | 0% | 0/125 | 0% |
| Msh1 . . . #24 x Tx430 #13-8-6 | 0/118 | 0% | 0/128 | 0% |
| Msh1 . . . #24 x Tx430 #19-11-7 | 5/116 | 4.31% | 7/122 | 5.74% |
| Msh1 . . . #28 x Tx430 #13-3-1 | 0/119 | 0% | 0/120 | 0% |

Figure 6:
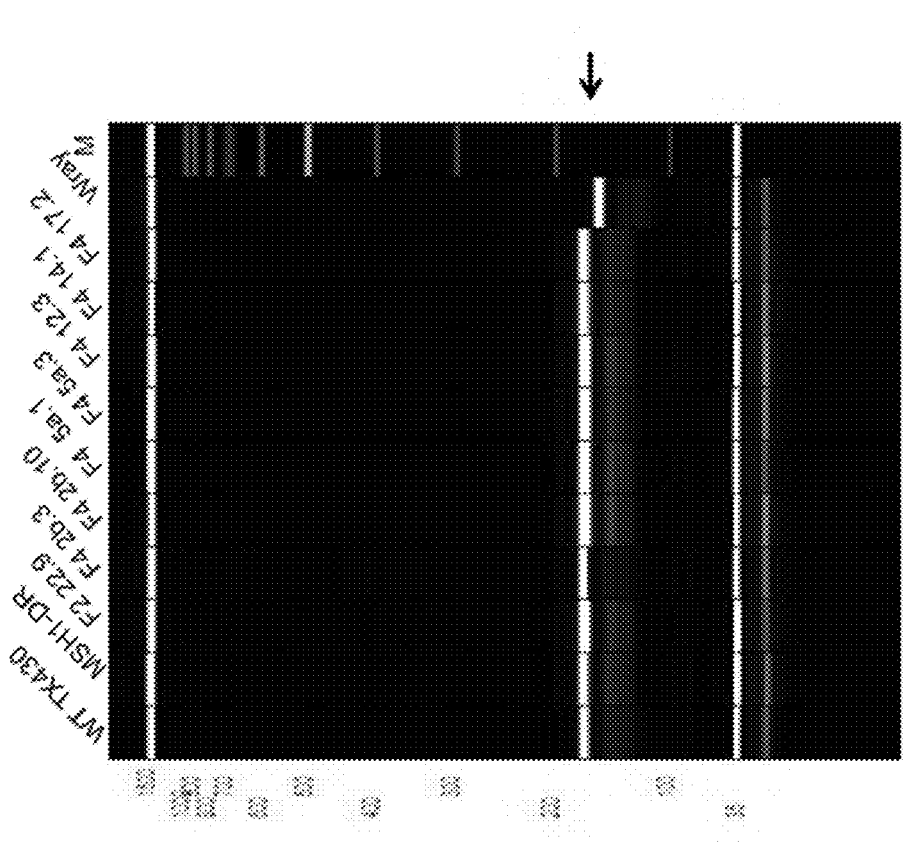
FIG. 6 illustrates sample SSR marker analysis. *Sorghum* genomic DNAs were prepared from wildtype Tx430, Tx430 MSH1-DR line (transgene-null, displaying the dwarfed, tillered, delayed flowering phenotype), one epi-F2 and seven epi-F4 lines selected for phenotypic diversity. Sweet *sorghum* line 'Wray' was included as a control. The SSR marker shown is generated with SAM16073 primers. Arrow shows detected DNA polymorphism. M designates marker lane, with fragment sizes (bp) shown at left. The 1500 and 35 bp fragments are internal markers used to calibrate each lane.
Figure 7:
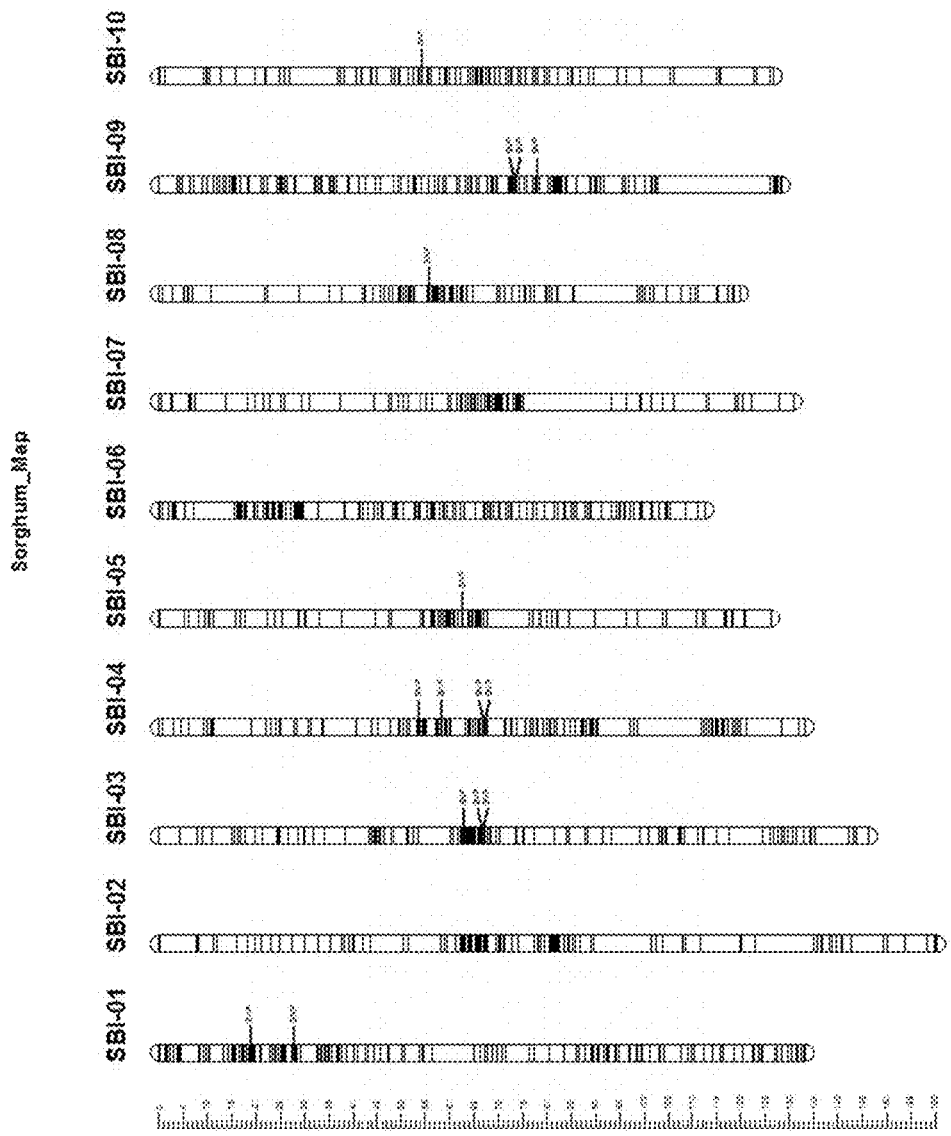
FIG. 7 illustrates a *sorghum* genetic map with markers displaying heterozygous genotype.

To ensure that the observed variation was not the consequence of inadvertent seed contamination or outcrossing, SSR markers were used to test a number of derived lines, which produced no evidence of polymorphism (FIG. 6; Table 6). This analysis was extended with 1778 SNP markers that, when assayed across five different MSH1-epiF2 individuals and the wildtype Tx430, detected less than 0.8% variation (Tables 7, 8; FIG. 7). In *Arabidopsis*, the msh1 mutant genome was DNA sequenced, with genome alignment and de novo assembly producing no evidence of unexplained genome rearrangement or unusual mutation frequency (Xu et al. 2013). These data, together with reproducibility of the phenomenon, argue against the developmental reprogramming phenotype as a consequence of genome hypermutability.

TABLE 6

SSR marker polymorphism data for 43 markers. Markers were scored as + or − relative the pattern of Tx430 wildtype. SSR markers were selected based on their polymorphic behavior in comparisons of Tx430 and 'Wray'. Assays included a transgene-null Tx-430 line displaying the developmental reprogramming phenotype (DR), one epi-F2, two epi-F3 and seven epi-F4 lines.

| SSR Marker | Tx430 | Tx430-DR | Wray | F2-22.9 | F3-53 | F3-68 | F4-22.9 | F4-2b.3 | F4-2b.10 | F4-5a.3 | F4-12.3 | F4-14.1 | F4-17.2 |
|---|---|---|---|---|---|---|---|---|---|---|---|---|---|
| XCUP 1 | − | − | + | − | − | − | − | − | − | − | − | − | − |
| XCUP 5 | − | − | + | − | − | − | − | − | − | − | − | − | − |
| XCUP 26 | − | − | + | − | − | − | − | − | − | − | − | − | − |
| XCUP 28 | − | − | + | − | − | − | − | − | − | − | − | − | − |
| XCUP 32 | − | − | + | − | − | − | − | − | − | − | − | − | − |
| XCUP 48 | − | − | + | − | − | − | − | − | − | − | − | − | − |
| XCUP 50 | − | − | + | − | − | − | − | − | − | − | − | − | − |
| XCUP 61 | − | − | + | − | − | − | − | − | − | − | − | − | − |
| XCUP 69 | − | − | + | − | − | − | − | − | − | − | − | − | − |
| SAM 03605 | − | − | + | − | − | − | − | − | − | − | − | − | − |
| SAM 06337 | − | − | + | − | − | − | − | − | − | − | − | − | − |
| SAM 16073 | − | − | + | − | − | − | − | − | − | − | − | − | − |
| SAM 19028 | − | − | + | − | − | − | − | − | − | − | − | − | − |
| SAM 18581 | − | − | + | − | − | − | − | − | − | − | − | − | − |
| SAM 21112 | − | − | + | − | − | − | − | − | − | − | − | − | − |
| SAM 01312 | − | − | + | − | − | − | − | − | − | − | − | − | − |
| SAM 51414 | − | − | + | − | NA | NA | − | − | − | − | − | − | − |
| SAM 56359 | − | − | + | − | NA | NA | − | − | − | − | − | − | − |
| SAM 55010 | − | − | + | − | NA | NA | − | − | − | − | − | − | − |
| SAM 56942 | − | − | + | − | NA | NA | − | − | − | − | − | − | − |
| SAM 62005 | − | − | + | − | NA | NA | − | − | − | − | − | − | − |
| SAM 62186b | − | − | + | − | NA | NA | − | − | − | − | − | − | − |
| SAM 59974 | − | − | + | − | NA | NA | − | − | − | − | − | − | − |
| SAM 61376 | − | − | + | − | NA | NA | − | − | − | − | − | − | − |
| SAM 65125 | − | − | + | − | NA | NA | − | − | − | − | − | − | − |
| SAM 66160 | − | − | + | − | NA | NA | − | − | − | − | − | − | − |
| SAM 26858a | − | − | + | − | − | − | − | − | − | − | − | − | − |

TABLE 6-continued

SSR marker polymorphism data for 43 markers. Markers were scored as + or − relative the pattern of Tx430 wildtype. SSR markers were selected based on their polymorphic behavior in comparisons of Tx430 and 'Wray'. Assays included a transgene-null Tx-430 line displaying the developmental reprogramming phenotype (DR), one epi-F2, two epi-F3 and seven epi-F4 lines.

| SSR Marker | Tx430 | Tx430-DR | Wray | F2-22.9 | F3-53 | F3-68 | F4-22.9 | F4-2b.3 | F4-2b.10 | F4-5a.3 | F4-12.3 | F4-14.1 | F4-17.2 |
|---|---|---|---|---|---|---|---|---|---|---|---|---|---|
| SAM 27170 | − | − | + | − | − | − | − | − | − | − | − | − | − |
| SAM 33545 | − | − | + | − | NA | NA | − | − | − | − | − | − | − |
| SAM 36890 | − | − | + | − | NA | NA | − | − | − | − | − | − | − |
| SAM 47801 | − | − | + | − | NA | NA | − | − | − | − | − | − | − |
| SAM 48589 | − | − | + | − | NA | NA | − | − | − | − | − | − | − |
| SAM 48870 | − | − | + | − | NA | NA | − | − | − | − | − | − | − |
| SAM 49411b | − | − | + | − | NA | NA | − | − | − | − | − | − | − |
| SAM 64056 | − | − | + | − | NA | NA | − | − | − | − | − | − | − |
| SAM 62693 | − | − | + | − | NA | NA | − | − | − | − | − | − | − |
| SAM 67633 | − | − | + | − | NA | NA | − | − | − | − | − | − | − |
| SAM 63126c | − | − | + | − | NA | NA | − | − | − | − | − | − | − |
| SAM 64809 | − | − | + | − | NA | NA | − | − | − | − | − | − | − |
| SAM 01952 | − | − | + | − | NA | NA | − | − | − | − | — | − | − |
| SAM 40439 | − | − | + | − | NA | NA | − | − | − | − | − | − | − |
| SAM 42610 | − | − | + | − | NA | NA | − | − | − | − | − | − | − |
| SAM 39963 | − | − | + | − | NA | NA | − | − | − | − | − | − | − |

TABLE 7

SNP marker analysis: Summary of Het %

| Pedigree | Total #markers | #Het | % Het |
|---|---|---|---|
| (Msh1epi11/Tx430): 0002.0006.0010. | 1778 | 13 | 0.73% |
| (Msh1epi15/Tx430): 0007.0001.0001. | 1778 | 13 | 0.73% |
| (Msh1epi15/Tx430): 0008.0001.0002. | 1778 | 13 | 0.73% |
| (Msh1epi22/Tx430): 0004.0004.0010. | 1776 | 14 | 0.79% |
| (Msh1epi24/Tx430): 0019.0004. | 1774 | 13 | 0.73% |
| RTx430WT | 1773 | 14 | 0.79% |

TABLE 8

SNP marker analysis: A list of all the markers with heterozygous genotype.

| Marker | Chr | Genetic Distance (cM) | Physical Distance (bp) | a1 | a2 | (MSH1epi 11/Tx430): 0002.0006. 0010. | (MSH1epi 15/Tx430): 0007.0 001.0001. | (MSH1epi 15/Tx430): 0008.0 001.0002. | (MSH1epi 22/Tx430): 0004.0004. 0010. | (MSHh1epi 24/Tx430): 0019.0004. | RTx430WT |
|---|---|---|---|---|---|---|---|---|---|---|---|
| SNP1 | 1 | 18.8 | 19772012 | C | G | CG | CG | CG | CG | CG | CG |
| SNP2 | 1 | 27.7 | 31762071 | A | G | AG | AG | AG | AG | AG | AG |
| SNP3 | 3 | 62.9 | 33270511 | C | T | CT | CT | CT | CT | CT | CT |
| SNP4 | 3 | 66.6 | 42615046 | C | G | GG | GG | GG | CG | GG | GG |
| SNP5 | 3 | 66.9 | 35965148 | A | G | AG | AG | AG | AG | AG | AG |
| SNP6 | 4 | 53.6 | 13022975 | C | T | CT | CT | CT | CT | CT | CT |
| SNP7 | 4 | 58.4 | 23297070 | A | G | AG | AG | AG | AG | AG | AG |
| SNP8 | 4 | 66.9 | 41492135 | C | T | CT | CT | CT | CT | CT | CT |
| SNP9 | 4 | 67.3 | 42325806 | C | T | CT | CT | CT | CT | CT | CT |
| SNP10 | 5 | 62.6 | 16905084 | A | G | AG | AG | AG | AG | AG | AG |
| SNP11 | 8 | 55.7 | 12142806 | C | G | CC | CC | CC | CC | CC | CG |
| SNP12 | 9 | 73.1 | 43494421 | C | T | CT | CT | CT | CT | CT | CT |
| SNP13 | 9 | 73.6 | 43961814 | C | T | CT | CT | CT | CT | CT | CT |
| SNP14 | 9 | 77.8 | 46574813 | A | G | AG | AG | AG | AG | AG | AG |
| SNP15 | 10 | 54.2 | 10653756 | G | T | GT | GT | GT | GT | GT | GT |

In Table 8, markers with heterozygous genotypes are ordered by chromosome and genetic distance. The remainder (not shown) had homozygous genotypes. Marker genotypes of the six lines are similar but for the two markers highlighted in yellow. The markers showing a heterozygous genotype represent the true heterozygous genotype, not heterogeneity at the markers since only a single plant was sampled for DNA.

Significant Increases in Trait Values Persist for Multiple Generations.

Figure 5:
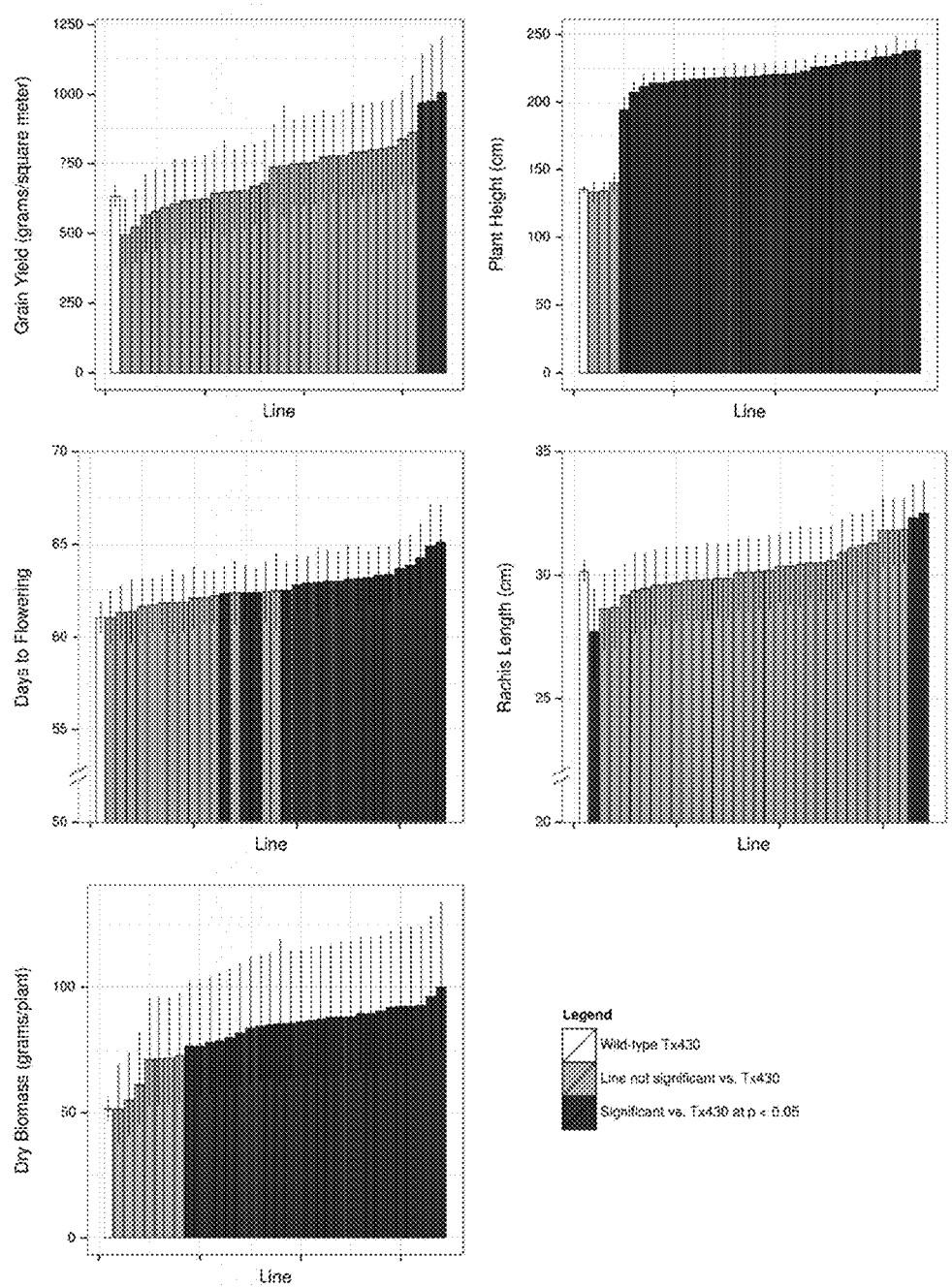
FIG. 5 illustrates that the MSH1-$F_4$ generation shows significant trait differences in multiple lines (ordered by increasing mean value) compared to wild-type Tx430. Means and 95% confidence intervals (error bars) were estimated by mixed model analysis. Only lines with stable within-row height and data for all five traits were used for mean comparison here. Type I error was conservatively controlled by Bonferroni adjustment (m=165, total number of comparisons including all traits).
Figure 8:
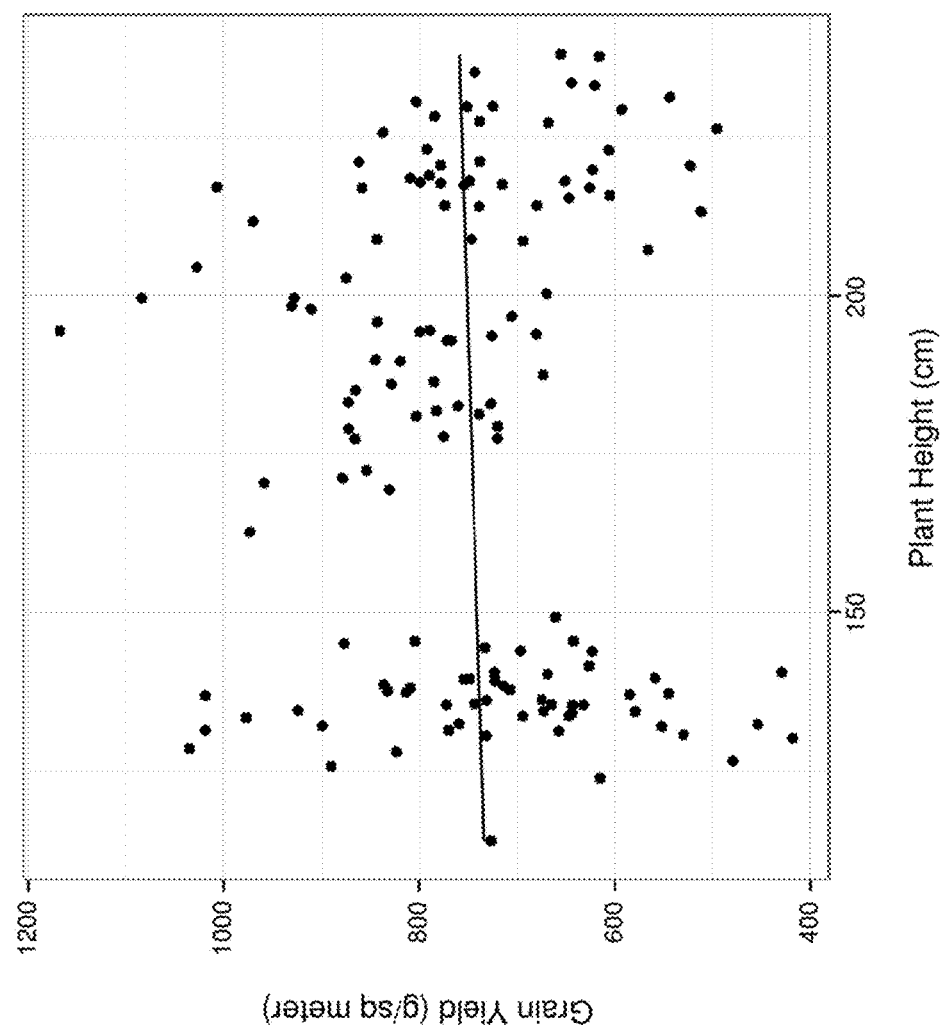
FIG. 8 illustrates that no correlation was found between plant height and grain yield (Spearman's rho=0.02, p=0.83). Each point represents a line mean.

From the MSH1-epiF$_2$ families, individuals were self-pollinated and selected for grain yield and plant height to the F$_3$ and F$_4$ generations. F$_4$ lines, along with F$_3$ and F$_2$ lines from remnant seed, were evaluated together in the same 2011 field experiment. Despite weak selection intensity (33% and 38% of phenotyped plants were propagated to F$_3$ and F$_4$, respectively), derived F$_3$ and F$_4$ lines showed significant differences in grain yield and plant height, as well as differences in dry biomass and panicle length (FIGS. 3, 5, Table 9). Differences were detectable even when F3 and F4 lines were analyzed separately or when a model term for generation was included, indicating that the variation did not simply come from maternal effects. While some traits appeared to be correlated, such as flowering time and grain yield, no correlation was detected between plant height and grain yield, indicating that height was not pleiotropically affecting grain yield (FIG. 8).

TABLE 9

Data for each trait listed below were fit to a linear mixed model (see methods), with results indicating differences between lines.

| Population | Response variable of model | df | Sample size | F-statistic of Line effect | p-value of Line effect |
|---|---|---|---|---|---|
| All lines | Grain Yield (g/m$^2$) [a] | 160 | 956 | 4.985 | <0.001 |
| | Plant height (cm) [b] | 167 | 3537 | 159.6 | <0.001 |
| | Flowering time (DAS) [a, b] | 136 | 1874 | 6.13 | <0.001 |
| | Rachis Length (cm) [a, b] | 165 | 3495 | 5.06 | <0.001 |
| | Dry Biomass (g/plant) [a] | 167 | 490 | 5.1 | <0.001 |

[a] Box-cox transformed for model fit.
[b] Separate variances estimated by generation or height strata.

Line was treated as a fixed effect while block and replicate were treated as random effects. Separately analyzing lines by generation or general height class, or adding a model term for generation and height class, did not affect conclusions. The models were used to estimate trait means and confidence intervals (FIGS. 3B, 5).

Figure 2A:
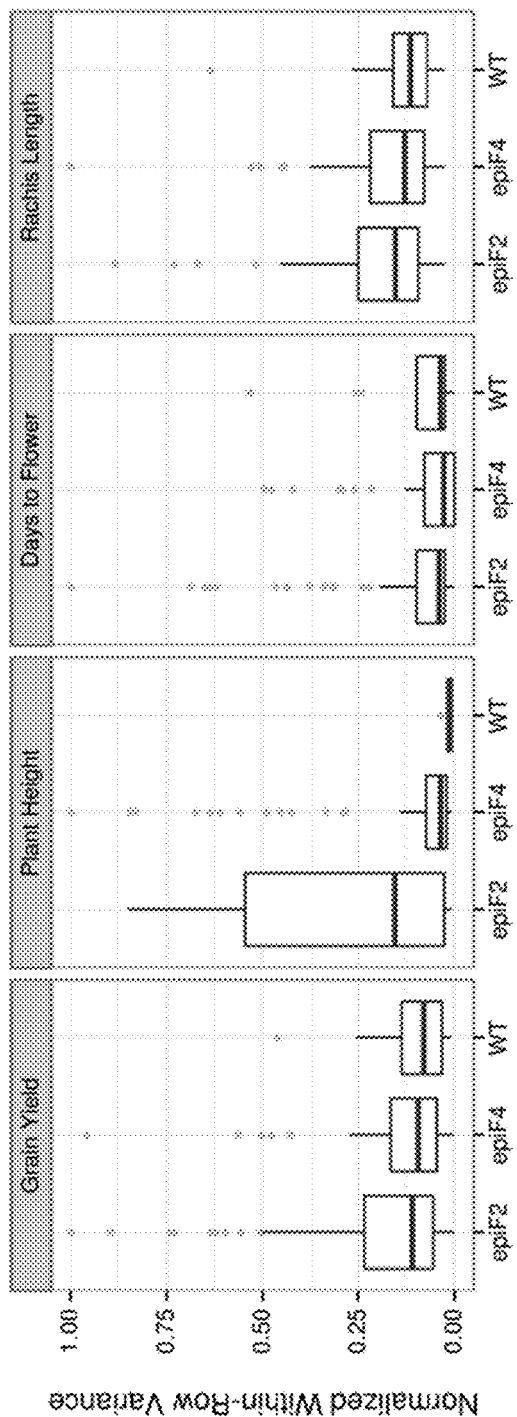
FIG. 2A, B illustrate the enhanced phenotypic variation in *sorghum* MSH1-epiF2 lines. A, Boxplots of within-row field variance for several traits, with values normalized as a proportion of the maximum observed row variance for that trait. Differences in variances between the epi-F2 and wild-type populations were significant for plant height (Brown-Forsythe test, $p<0.001$) and grain yield ($p<0.01$). Method of harvesting biomass precluded within-row variance assessment. B, Example of the distribution of values for grain yield when measured per panicle, and plant height in an epi-F2 family (epi-F2 individuals derived from same parental cross) compared to wild-type.
Figure 2B:
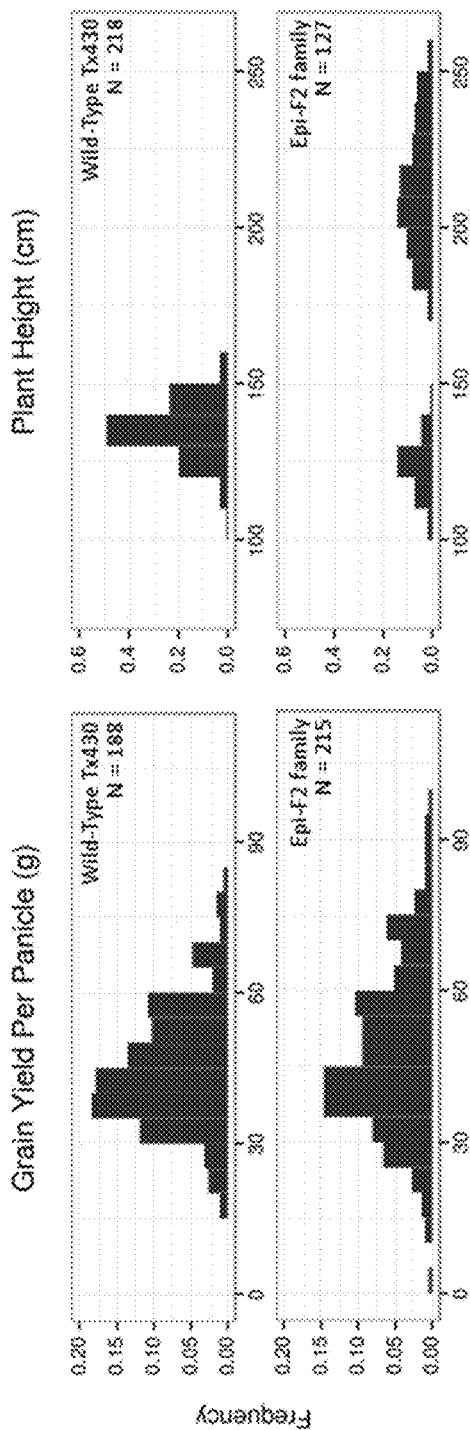

Although the $F_3$ generation showed higher variance for some traits compared to the $F_2$ generation, for all measured traits the $F_4$ generation showed lower variance compared to the $F_2$ generation (FIG. 2A). Furthermore, in contrast to the $F_2$ generation, we did not find significant heterogeneity for variance in grain yield among wild-type, $F_3$ and $F_4$ lines (p>0.1, Brown-Forsythe test; p<0.01 in $F_2$ with wild-type).

Figure 3A:
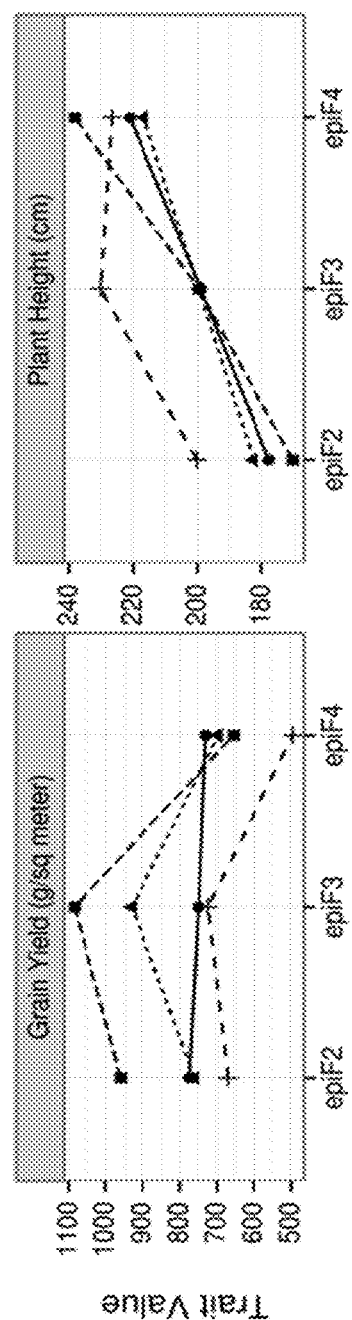
FIG. 3A, B illustrate the phenotypic variation in *sorghum* MSH1-epiF2, F3 and F4 lines. A. Selection had varying results, with response for yield into the F3 generation, but not into the F4 generation. For each lineage, the mean generation performance is represented as a point. B. Boxplots of epiF2, F3, and F4 line means for various traits, giving a population-wide view of epi-line performance. Dashed lines indicate the 95% confidence interval for wild-type TX430 mean.
Figure 3B:
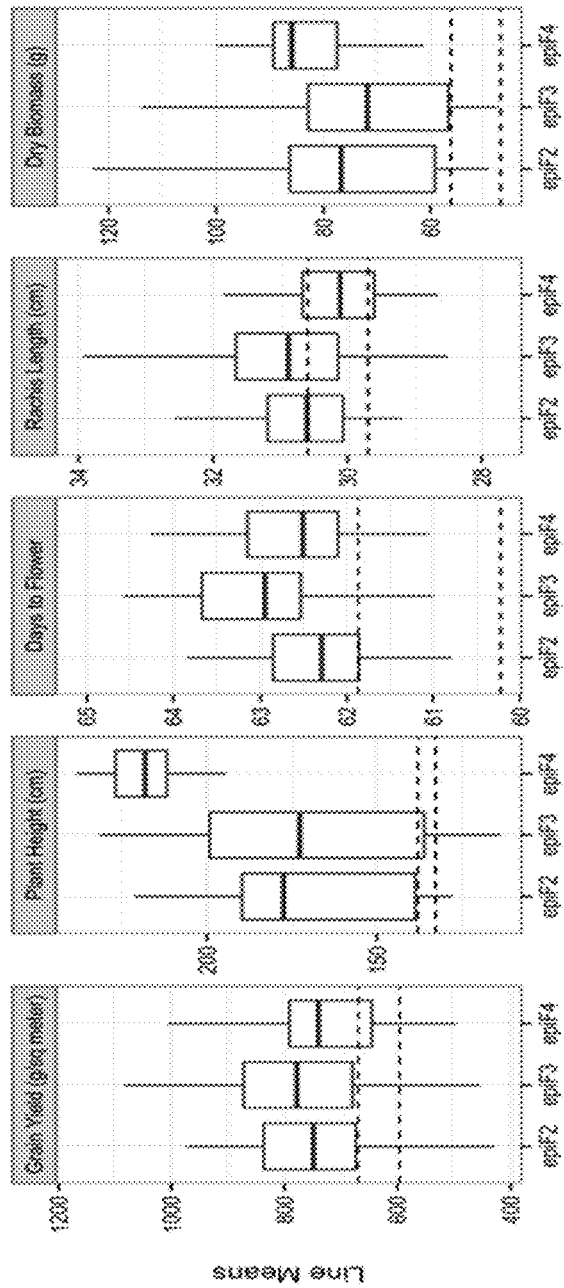

Analysis of direct lineages from $F_2$ to $F_4$ showed high response to selection for plant height but variable response for grain yield; however, in the most extreme examples, we observed gains of up to 87% over wild-type for above-ground dry biomass and 61% for grain yield (FIG. 3A). Overall, gains in the $F_4$ were more modest compared to the $F_3$, implying progress may taper off by $F_4$ in self-pollinated lineages. Indeed, there is evidence that the epi-$F_3$ generation may be the most vigorous. As a population, it appears to have slightly higher overall grain yield than the epi-F2 or epi-F4. Nevertheless, the population mean for grain yield in the epi-F4 remains higher than that of wild-type Tx430 (FIG. 3B).

Line x Environment Interactions Suggest an Epigenetic Component to GxE.

Figure 4:
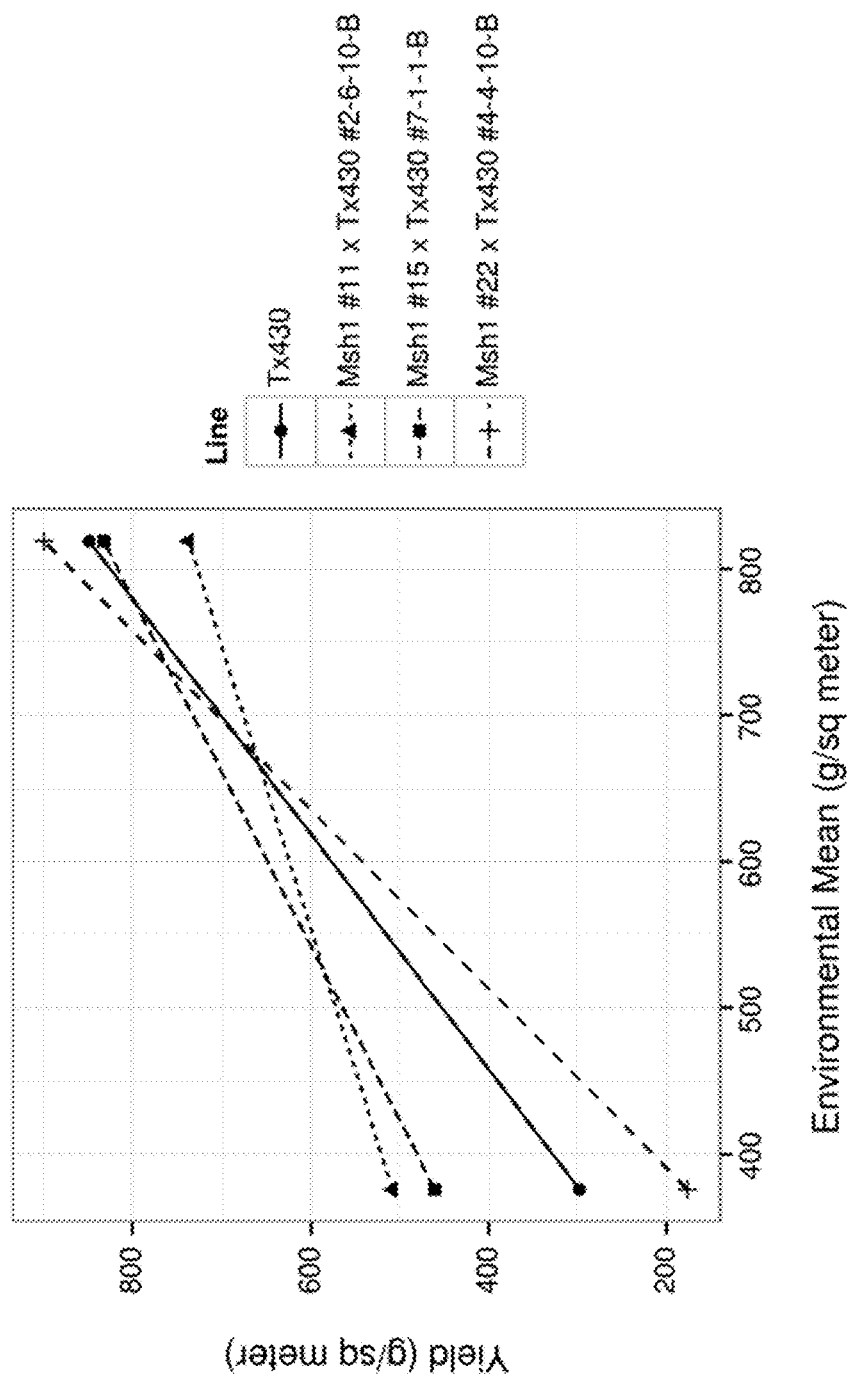
FIG. 4 illustrates the epi-type x environment interactions. Joint regression (with Wright modification) indicates differential response between lines to location.
Figure 9B:
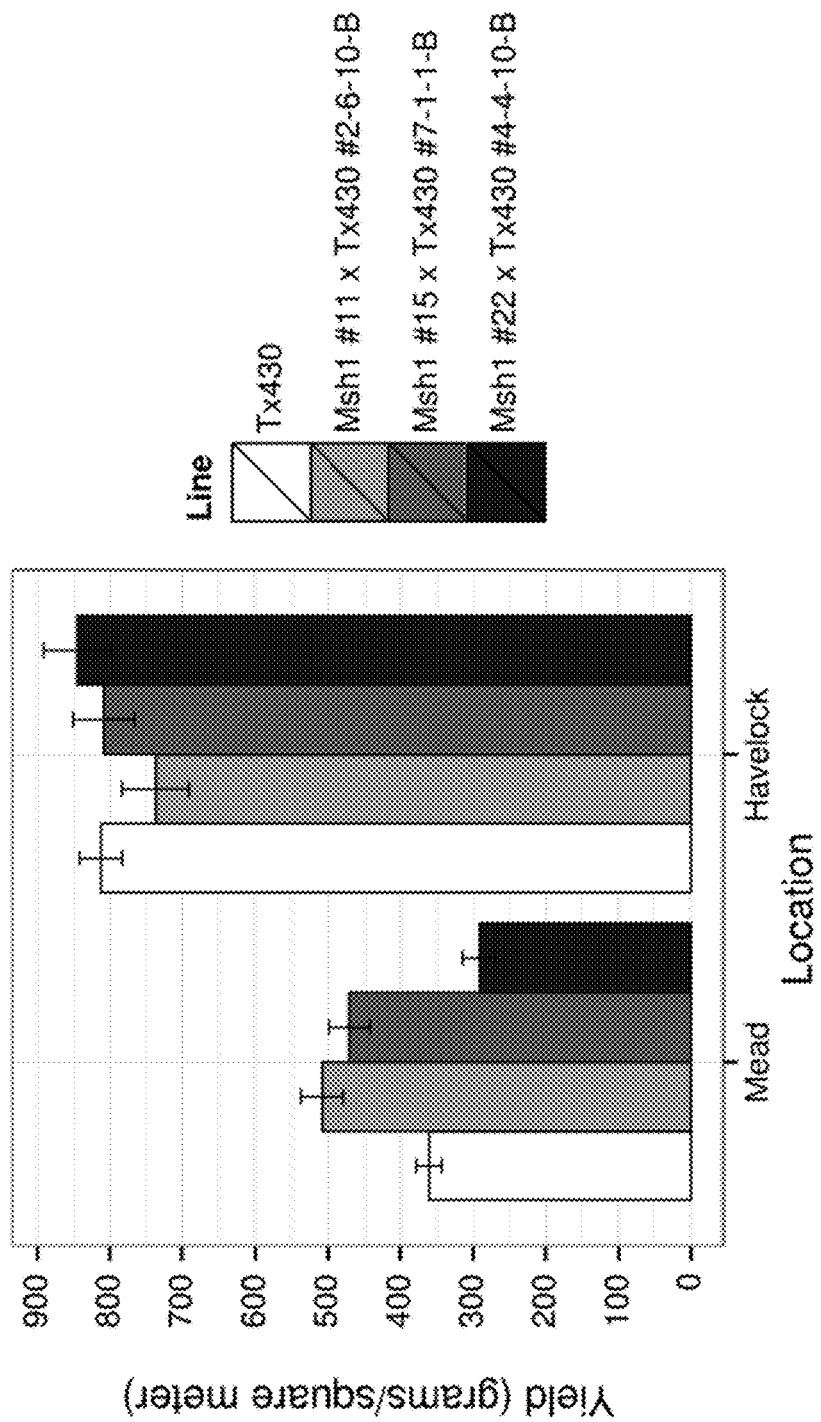
FIG. 9A, B illustrate that Epi-line x environment effects were detected from a multiple location experiment. A) Analysis for significant effects using a mixed model indicates that line, location, and line x location are all significant. Sample size N=121. B) Although three epi-F4 lines were similar to wild-type Tx430 in grain yield when grown in one location (Havelock), significant differences emerged when grown another location with a more challenging environment (Mead). Data were collected from a field trial in 2012.

We evaluated the yield performance of three MSH1-epiF$_5$ families alongside wild-type Tx430 at two different locations. The two locations displayed a large difference in environmental means. Surprisingly, the lines showed little between-line difference at the site of the earlier experiments; however, they showed large differences at the second site, which was more drought-stressed, demonstrating a line x environment effect (FIGS. 4, 9A,B). Results at the first site also suggest that, depending on conditions, epigenetic variation in these materials could begin to dissipate at around the $F_5$ generation. The outcomes of these experiments indicate that plant materials with little to no genetic variation have the potential to exhibit substantial variation in response to environmental influence, which may reflect epigenetic x environmental interactions.

The substantial range of *sorghum* phenotypic variation observed in this study appears to be non-genetic, and is induced by crossing to a MSH1-dr line, altered through MSH1 suppression in a previous generation. The MSH1-dr lines used in this study were maintained as transgene-nulls seven generations following segregation of the transgene, suggesting that the epigenetic properties of the MSH1-dr line are stable through multiple rounds of self-pollination (Xu et al. 2012). We do not presume that all of the variation observed is non-genetic; the observed bimodal distribution for plant height could support an alternative hypothesis of markedly enhanced reversion frequency for the dwarfing gene, dw3, in line Tx430 (Multani et al. 2003). If this is the case, the unusually high reversion rate may be the consequence of increased local recombination, one side-effect of cytosine methylation pattern redistribution (Colomé-Tatché et al. 2012; Migicovsky and Kovalchuk 2013). We are investigating this possibility presently. Nevertheless, we see additional height variation within short and tall plants, indicating variation beyond a single-locus.

The range of phenotypic variation observed is surprising. While we were not able to take measurements of all parameters for this initial study, the $F_3$ and the $F_4$ generations showed highly significant increases in above-ground biomass and grain yield over Tx430 wild type. One interpretation of these increases would be that dw3 reversion could cause pleiotropic changes in plant architecture. However, the greater range of plant height, panicle architecture and yield variation observed in this study appears to exclude that possibility (Brown et al. 2008).

The observation of epi-type x environment interaction in test plots suggests that at least some portion of the genotype x environment interaction that is commonly observed in varietal studies may be non-genetic, which is supported by other recent studies (Zhang et al. 2013). The MSH1 system may be useful in understanding this type of environmental influence and selecting for enhanced stability of crop performance.

To date, relatively few plant systems have permitted resolution of epigenetic variation as it influences plant phenotype. In *Arabidopsis*, mutation of genes that comprise the DNA methylation machinery, followed by crossing to wild-type for development of recombinant inbred lines, has provided valuable information on the phenotypic consequences of epigenomic perturbation, as well as heritability and stability of epigenetic changes (Johannes et al. 2009; Reinders et al. 2009). It has been suggested that doubled haploids, subjected to recursive selection for mitochondrial behavior, can produce epigenetic variation that may be amenable to selection (Hauben et al. 2009). Somaclonal variation derived from plant tissue culture has also been associated with epigenetic changes (Stroud et al. 2013).

MSH1-dr transgene null lines developed on elite inbred genetic backgrounds would permit direct incorporation of the MSH1-enhanced growth phenomenon to hybrid production. However, studies to date have not observed the greatest gain in growth to occur in the derived $F_1$ populations, suggesting that the effects we observe in this system may be distinct from heterosis. It is possible that self- or open-pollination breeding will prove more effective at capturing maximal growth gain derived from MSH1 manipulation. The transgene-null MSH1-dr line crossed to its wild-type counterpart produces maximum variation in the epiF$_2$ population, at which point selection appears to be most effective. Large-scale seed increase in $F_3$ and $F_4$ generations permits rapid capture of the growth enhancement as variation tapers off. Extrapolation of this approach from *sorghum* data in this study would predict at least 25% overall enhancement of yield. In our experience with this system, variation observed in the epi-$F_2$ population tends to produce above-wildtype performance more often than below (FIG. 3B, FIG. 8). Consequently, development of MSH1-dr in an elite line followed by selection in the epi-$F_2$, appears to result in, by the epiF$_4$, a population that is uniform genetically, variable epigenetically, and significantly enhanced in growth vigor and productivity.

The progress, response to selection, and final phenotypic outcomes observed in this study were of sufficient magnitude to suggest that untapped epigenetic potential may reside within crops. Whether crop enhancement using MSH1 manipulation will produce crop vulnerabilities not yet considered is under investigation. However, the performance of these plant materials under low rainfall conditions suggests that this methodology holds significant promise.

LITERATURE CITED

Abdelnoor R V, Yule R, Elo A, Christensen A C, Meyer-Gauen G, et al. 2003 Substoichiometric shifting in the plant mitochondrial genome is influenced by a gene homologous to MutS. Proc. Natl. Acad. Sci. USA 100: 5968-5973.

Brown, P J, Rooney W L, Franks C, Kresovich S. 2008. Efficient mapping of plant height quantitative trait loci in a sorghum association population with introgressed dwarfing genes. Genetics 180: 629-637.

Cheptou P O, Donohue K. 2013 Epigenetics as a new avenue for the role of inbreeding depression in evolutionary ecology. Heredity (Edinb). 110:205-6.

Colomé-Tatché M, Cortijo S, Wardenaar R, Morgado L, Lahouze B, et al. 2012. Features of the Arabidopsis recombination landscape resulting from the combined loss of sequence variation and DNA methylation. Proc Natl Acad Sci USA. 109:16240-5.

Cowling, W. 2013. Sustainable plant breeding. Plant Breeding 132:1-9.

Dooner H K, Weil D F 2007. Give-and-take: interactions between DNA transposons and their host plant genomes. Curr Opin Genet Dev 17:486-492.

Gressel, J. 2008 Genetic Glass Ceilings: Transgenics for Crop Biodiversity. John Hopkins Univ. Press Groszmann M, Greaves I K, Albert N, Fujimoto R, Helliwell C A, Dennis E S, Peacock W J. 2011 Epigenetics in plants-vernalisation and hybrid vigour. Biochim Biophys Acta. 1809:427-37.

Hauben M, Haesendonckx B, Standaert E, Van Der Kelen K, Azmi A, Akpo H, Van Breusegem F, Guisez Y, Bots M, Lambert B, Laga B, De Block M. 2009. Energy use efficiency is characterized by an epigenetic component that can be directed through artificial selection to increase yield. Proc Natl Acad Sci USA. 106:20109-14.

Heo J B, Sung 5.2011 Encoding memory of winter by noncoding RNAs. Epigenetics. 6:544-7 Hothorn T, Bretz F, and Westfal P. 2008. Simultaneous Inference in General Parametric Models. Biometrical Journal 50: 346-363.

Johannes F, Porcher E, Teixeira F K, Saliba-Colombani V, Simon M, et al. 2009. Assessing the impact of transgenerational epigenetic variation on complex traits. PLoS Genet. 5(6):e1000530.

Li, M. Yuyama, N., Le Luo, Mariko Hirata, Cai, H. 2009. In silico mapping of 1758 new SSR markers developed from public genomic sequences for sorghum. Mol. Breed. 24: 41-47.

Lu, P. et al. 2012 Analysis of Arabidopsis genome-wide variations before and after meiosis and meiotic recombination by resequencing Landsberg erecta and all four products of a single meiosis. Genome Res. 22: 508-518.

Meaburn E L, Schalkwyk L C, Mill J. 2010. Allele-specific methylation in the human genome: implications for genetic studies of complex disease. Epigenetics. 5:578-82.

Migicovsky Z, Kovalchuk I. 2013. Changes to DNA methylation and homologous recombination frequency in the progeny of stressed plants. Biochem Cell Biol. 91:1-5

Miller F R 1984. Registration of RTx430 sorghum parental line. Crop Sci. 24:1224.

Multani D S, Briggs S P, Chamberlin M A, Blakeslee J J, Murphy A S, Johal G S. 2003. Loss of an MDR transporter in compact stalks of maize br2 and sorghum dw3 mutants. Science 302:81-4

Pinheiro J, Bates D, DebRoy S, Sarkar D and the R Development Core Team. 2013. Nlme: Linear and Nonlinear Mixed Effects Models. R package version 3.1-109.

Reinders J, Wulff B B, Mirouze M, Marí-Ordóñez A, Dapp M, et al. 2009. Compromised stability of DNA methylation and transposon immobilization in mosaic Arabidopsis epigenomes. Genes Dev. 23:939-50.

Schloss, S. J. et al. 2002. Characterization of RFLP probe sequence for gene discovery and SSR development in Sorghum bicolor (L.) Moench. Theor. Appl. Genet 105, 912-920.

Schmitz R J, Amasino R M. (2007) Vernalization: a model for investigating epigenetics and eukaryotic gene regulation in plants. Biochim Biophys Acta. 1769:269-75.

Shedge V, Davila J, Arrieta-Montiel M P, Mohammed S, Mackenzie S A 2010. Extensive rearrangement of the Arabidopsis mitochondrial genome elicits cellular conditions for thermotolerance. Plant Physiol. 152:1960-1970.

Shivaprasad P V, Dunn R M, Santos B A, Bassett A, Baulcombe D C. 2012 Extraordinary transgressive phenotypes of hybrid tomato are influenced by epigenetics and small silencing RNAs. EMBO J.31:257-66.

Smith A M, Hansey C N, Kaeppler S M 2012. TCUP: A novel hAT transposon active in maize tissue culture. Front Plant Sci 3:6.

Stokes, T. L., Kunkel, B. N. & Richards, E. J 2002. Epigenetic variation in Arabidopsis disease resistance. Genes Dev 16:171-182.

Stroud H, Ding B, Simon S A, Feng S, Bellizzi M, Pellegrini M, Wang G L, Meyers B C, Jacobsen S E. 2013. Plants regenerated from tissue culture contain stable epigenome changes in rice. Elife 2:e00354. doi: 10.7554/eLife.00354.

Tsaftaris, A. S., Polidoros, A. N., Kapazoglou, A., Tani, E. and Kovačević, N. M. 2008 Epigenetics and Plant Breeding, in Plant Breeding Reviews, Volume 30 (ed J. Janick), John Wiley & Sons, Inc., Hoboken, N J, USA. doi: 10.1002/97804703801 30.ch2

Xu Y Z, Arrieta-Montiel M P, Virdi K, De Paula W B M, Widhalm J R, et al. 2011. MSH1 is a nucleoid protein that alters mitochondrial and plastid properties and plant response to high light. Plant Cell 239:3428-41

Xu, Y-Z, Santamaria, R., Virdi K S, Arrieta-Montiel M P, Razvi F, et al. 2012. The chloroplast triggers developmental reprogramming when MUTS HOMOLOG1 is suppressed in plants. Plant Physiol. 159:710-20.

Xu Y-Z, Laurie J D, Wang D, Virdi K S, Feng S, Yu J, Wamboldt Y, Chen M, Riethoven J J M, Arrieta-Montiel M P, Kundariya H, Mackenzie S A. 2013. MSH1 mutation alters the epigenome to produce heritable changes in plant growth. Submitted.

Zhang Y Y, Fischer M, Colot V, Bossdorf O. 2013. Epigenetic variation creates potential for evolution of plant phenotypic plasticity. New Phytol. 197:314-22.

Figure 10A:
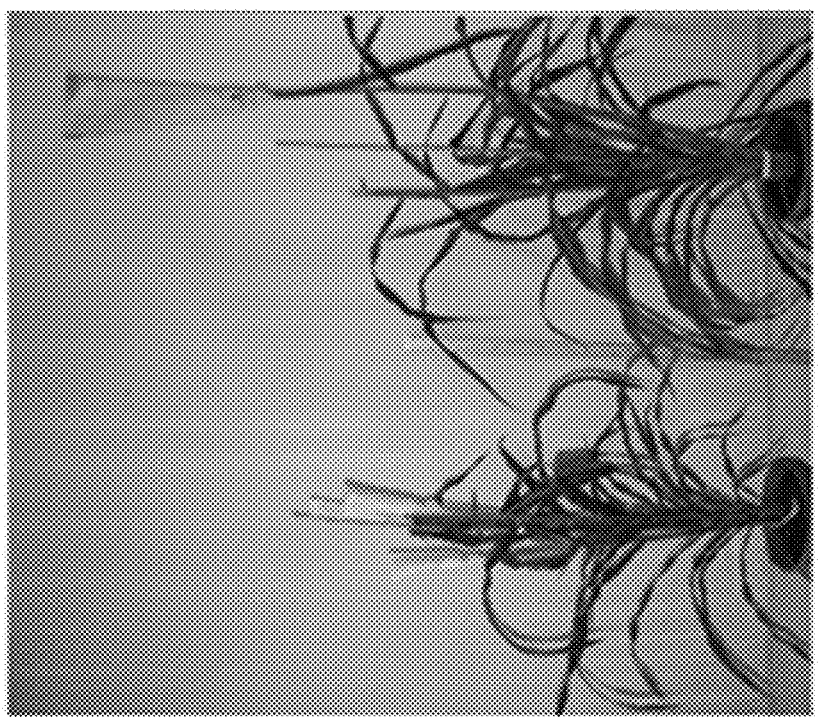
FIG. 10A, B. Evidence of growth variation in millet Tift23BDE following suppression of MSH1 in a T0 plant and recovery of MSH1 function in T3 progeny. (A) Wildtype control plant (left) and transgene-null T3 plant with bagged panicles (right; obtained from selfed progeny of a selfed MSH1-suppressed T0 plant). (B) Sample panicle from wild-type Tift23BDE control line that had not been subjected to MSH1 suppression. (C) Sample panicle from the robust, transgene-null T3 millet line showing markedly larger size.
Figure 10B:
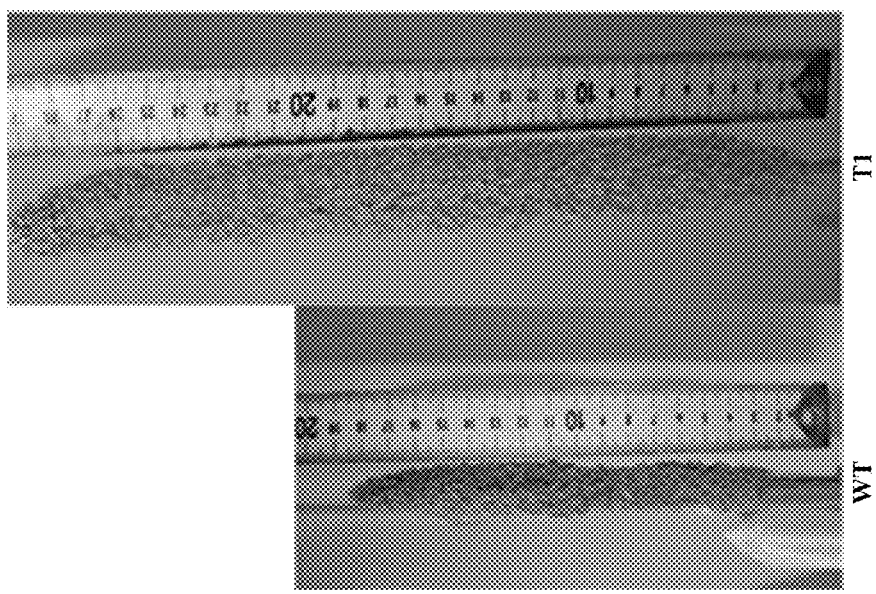
Figure 12A:
FIG. 12 A, B, C, D. Robust growth in a transgene-null line of Rutgers tomato obtained by selfing progeny of a selfed T0 tomato plant subjected to MSH1 suppression with a transgene. (A) Rutgers (left) is wild-type control. Transgene-plus T5 generation self containing MSH1 suppressing transgene is designated "T17-12-15-4-9-4 (+ transgene)" (second from left). Transgene-null T5 generation robust self is designated "T17-12-15-4-6-3 (− transgene)" (third from left). The epiF2 line (far right) was derived by crossing a dwarf msh1-dr type x Rutgers wildtype to generate an F2 population. (B) Single plant fruit production from Rutgers and the transgene negative T6 generation robust inbred T17-12-15-4-6-1-6. (C) Graph of fruit production in T5 generation progeny from the robust selection of T5 generation progeny of T17-12-15-4-6. (D) Graph of total yield from Rutgers versus the T6 generation robust selection of selfed progeny.
Figure 12B:
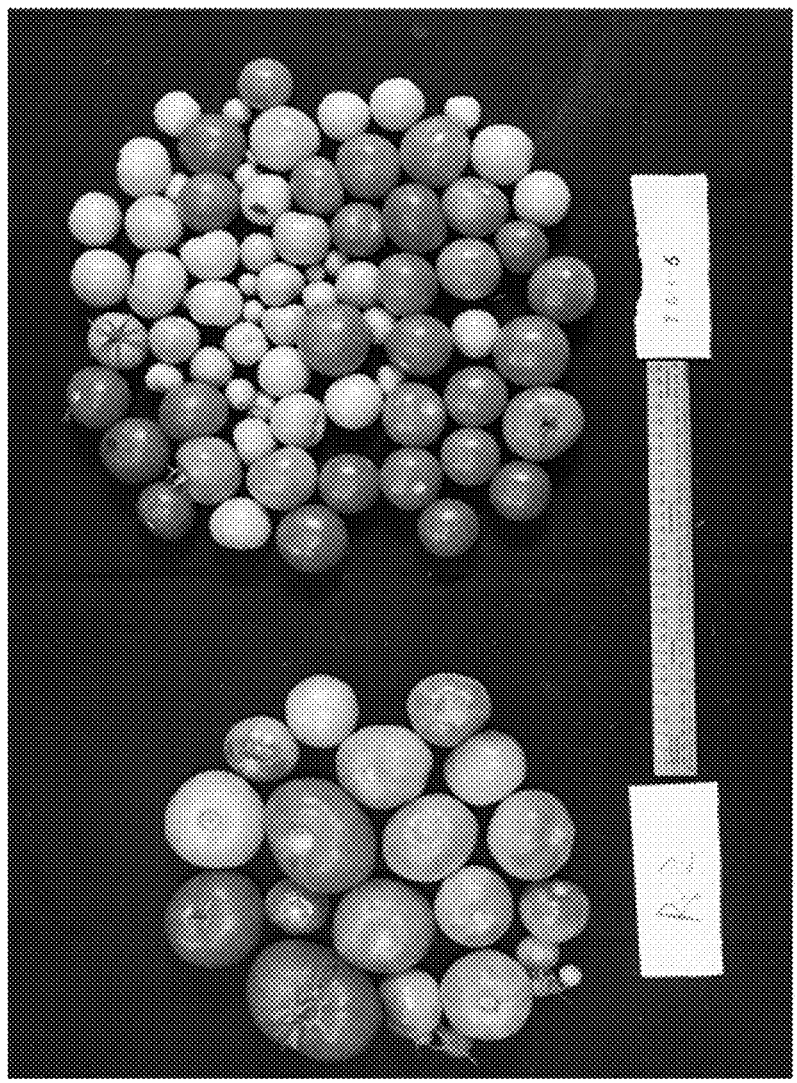
Figure 12C:
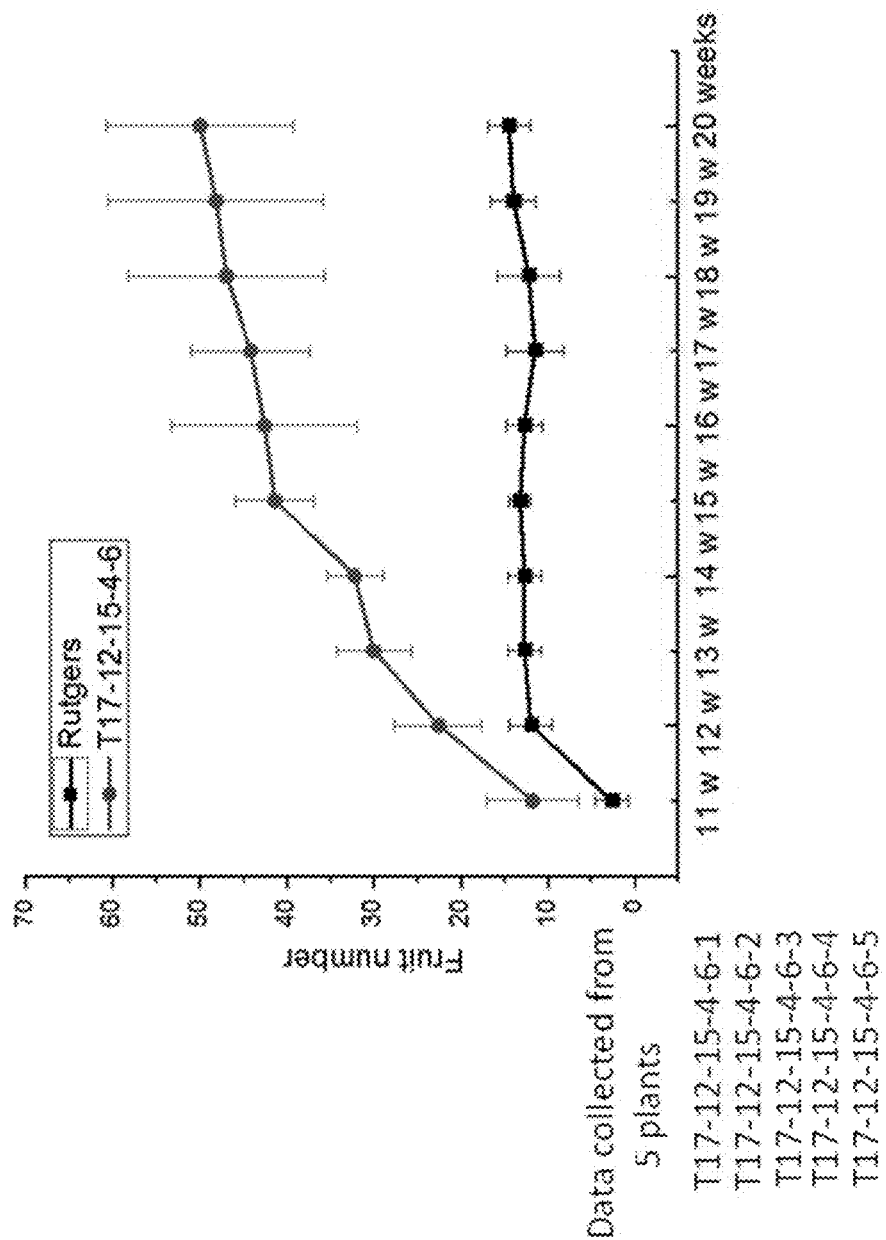
Figure 12D:
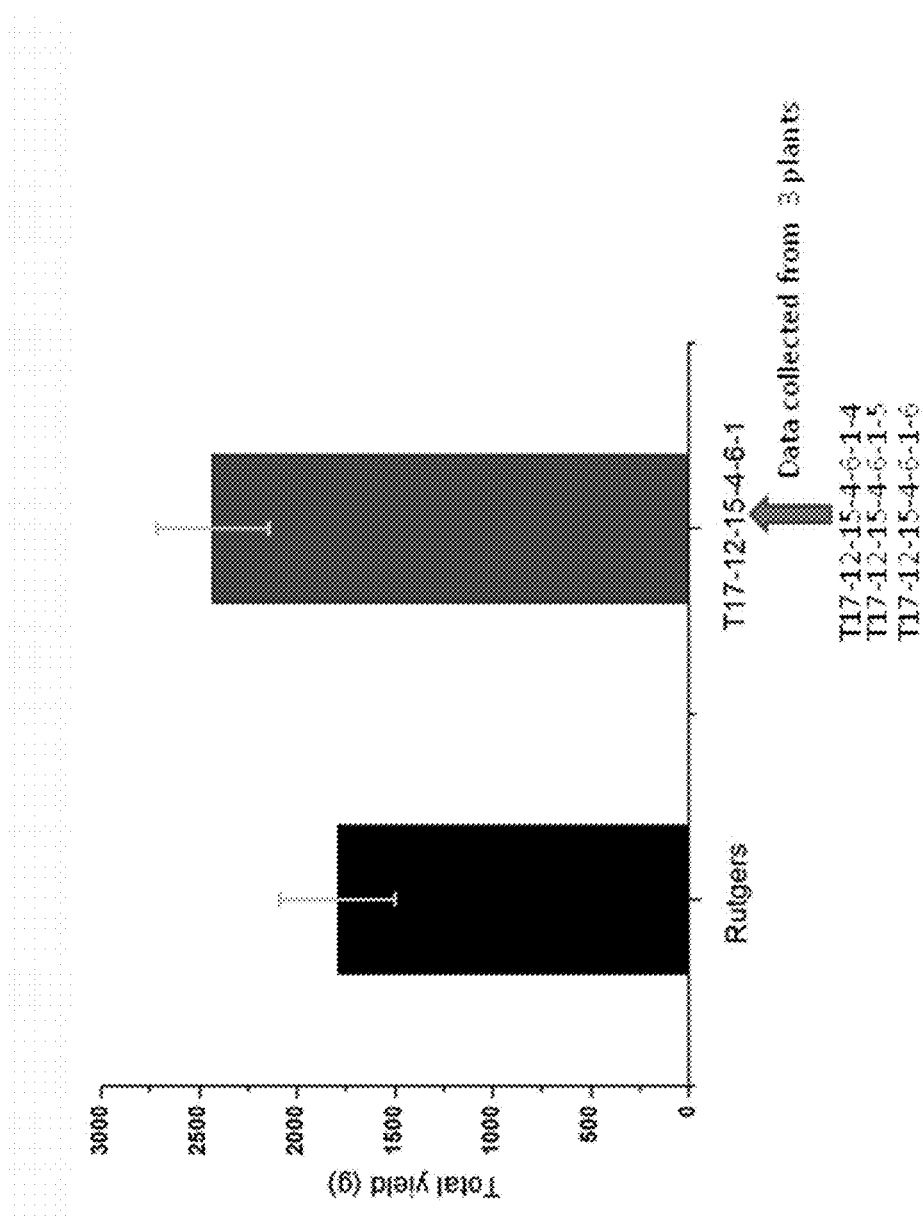

Example 2. Use of Msh1-Perturbed Plants that do not Exhibit an MSH1-Dr Phenotype to Obtain Progeny Plants with Useful Traits Transformation of tomato and millet with a transgene that provides for RNAi suppression of the MSH-1 gene of the MSH1 gene results in suppression of MSH1 expression (as described in US Patent Application Publication No. 20120284814, which is incorporated herein by reference in its entirety) and the emergence of variant plant phenotypes. Progeny obtained by selfing the progeny of selfed T0 transformants with MSH1 suppression were grown, and displayed segregation for the MSH1 suppressing transgene and a wide range of variant phenotypes. Selection and self-pollination of the dwarf types produced predominantly dwarf types. However, selection and self-pollination of the larger or normal growth types produced progeny displaying a wide range of phenotypes. This is illustrated in FIGS. 10A and 10B for millet, where a robust plant progeny line lacking the transgene was obtained from a subsequent generation of selfed progeny of a selfed MSH1 suppressed transgenic parent. In tomato, it has been possible to identify a robust transgene-null T5 and T6 line that was obtained by selfing five (T5) or six (T6) generations of progeny from selfed T0 plants that had been subjected to MSH1 suppression (FIG. 12A). This robust tomato line obtained by selfing progeny of a selfed MSH1 suppressed transgenic parent out-performed the wildtype plants in plant growth rate and fruit number (FIG. 12B, C, D. To date, tomato has been shown to breed true for this enhanced growth capacity for two additional generations. Data comparing the robust inbred tomato plant lines obtained by selfing progeny of a selfed MSH1 suppressed transgenic parent (i.e. progeny from selfs of line T17-12-15-4-6; shown in boldface) are provided in the following Tables.

TABLE 10

Height Data.

| Height data (cm) | 6 weeks | 8 weeks | 10 weeks | 12 weeks | 14 weeks |
|---|---|---|---|---|---|
| Rutgers-1 | 28.6 | 53.6 | 103.6 | 131.2 | 151.2 |
| Rutgers-3 | 26.2 | 58.9 | 119.4 | 141.8 | 158.8 |
| Rutgers-4 | 26.4 | 63.8 | 120.6 | 154.2 | 169.4 |
| Rutgers-5 | 25.8 | 61.0 | 101.9 | 134.8 | 147.4 |
| AVG | 26.8 | 59.3 | 111.4 | 140.5 | 156.7 |
| SD | 1.3 | 4.3 | 10.0 | 10.1 | 9.7 |
| (T X R 7)-1 F2 | 39.2 | 64.5 | 102.5 | 113.9 | 125.5 |
| (TXR7)-2 F2 | 40.2 | 88.5 | 112.5 | 118.3 | 141.4 |
| (TXR7)-3 F2 | 44.8 | 80.5 | 107.8 | 120.4 | 145.7 |
| (TXR7)-4 F2 | 38.2 | 82.5 | 124.9 | 156.2 | 174.6 |
| (TXR7)-5 F2 | 39.0 | 72.8 | 108.2 | 115.4 |  |
| AVG | 40.3 | 77.8 | 111.2 | 124.8 | 146.8 |
| SD | 2.6 | 9.3 | 8.5 | 17.7 | 20.5 |
| (TXR8)-1 F2 | 41.4 | 83.1 | 117.2 | 135.2 | 136.9 |
| (TXR8)-2 F2 | 37.5 | 86.4 | 127.5 | 146.4 | 161.8 |
| (TXR8)-3 F2 | 39.5 | 77.4 | 116.8 | 128.7 | 141.8 |
| (TXR8)-4 F2 | 34.4 | 78.9 | 127.2 | 157.3 | 183.6 |
| (TXR8)-5 F2 | 44.7 | 85.4 | 115.4 | 123.7 | 138.6 |
| AVG | 39.5 | 82.2 | 120.8 | 138.3 | 152.5 |
| SD | 3.9 | 4.0 | 6.0 | 13.6 | 20.0 |
| (TXR3)-1 F2 | 21.0 | 65.2 | 99.2 | 133.4 | 139.5 |
| (TXR3)-2 F2 | 36.1 | 64.5 | 107.9 | 123.8 | 135.2 |
| (TXR3)-3 F2 | 33.8 | 68.6 | 104.5 | 118.8 | 134.3 |
| (TXR3)-4 F2 | 38.2 | 76.6 | 112.6 | 142.3 | 162.1 |
| AVG | 32.3 | 68.7 | 106.1 | 129.6 | 142.8 |
| SD | 7.7 | 5.5 | 5.6 | 10.4 | 13.1 |
| (TXR5)-1 F2 | 41.5 | 80.4 | 108.8 | 127.2 | 131.4 |
| (TXR5)-2 F2 | 30.1 | 69.8 | 104.5 | 145.9 | 165.8 |
| (TXR5)-3 F2 | 56.2 | 105.6 | 128.8 | 146.8 | 150.3 |
| (TXR5)-4 F2 | 39.6 | 76.8 | 110.5 | 139.4 | 155.2 |
| (TXR5)-5 F2 | 36.2 | 76.8 | 102.1 | 122.0 | 140.6 |
| AVG | 40.7 | 81.9 | 110.9 | 136.3 | 148.7 |
| SD | 9.7 | 13.8 | 10.5 | 11.2 | 13.2 |
| (T17-12-15-4-6)-1 | 39.5 | 69.8 | 131.5 | 174.2 | 204.8 |
| (T17-12-15-4-6)-2 | 16.2 | 55.8 | 121.6 | 179.6 | 222.2 |
| (T17-12-15-4-6)-3 | 35.2 | 79.6 | 138.5 | 188.8 | 194.2 |
| (T17-12-15-4-6)-4 | 27.2 | 62.8 | 119.7 | 168.5 | 205.2 |
| (T17-12-15-4-6)-5 | 29.8 | 75.4 | 134.2 | 181.9 | 180.2 |
| AVG | 29.6 | 68.7 | 129.1 | 178.6 | 201.3 |
| SD | 8.9 | 9.6 | 8.1 | 7.7 | 15.5 |
| (T17-12-15-4-8)-1 | 18.6 | 40.5 | 63.2 | 98.4 | 116.8 |
| (T17-12-15-4-8)-2 | 12.5 | 21.5 | 40.8 | 61.4 | 77.1 |
| (T17-12-15-4-8)-3 | 6.5 | 8.7 | 24.2 | 44.9 | 48.2 |
| (T17-12-15-4-8)-4 | 16.2 | 22.6 | 40.9 | 65.5 | 96.5 |
| (T17-12-15-4-8)-5 | 12.0 | 23.3 | 43.6 | 63.5 | 89.6 |
| AVG | 13.2 | 23.3 | 42.5 | 66.7 | 85.6 |
| SD | 4.6 | 11.3 | 13.9 | 19.5 | 25.4 |
| (T17-12-15-4-9)-1 | 12.8 | 28.6 | 58.5 | 85.4 | 94.2 |
| (T17-12-15-4-9)-2 | 9.8 | 19.8 | 40.5 | 60.8 | 68.8 |
| (T17-12-15-4-9)-4 | 13.2 | 23.8 | 42.8 | 65.2 | 87.5 |
| (T17-12-15-4-9)-5 | 10.5 | 20.7 | 35.8 | 58.4 | 70.8 |
| AVG | 11.6 | 23.2 | 44.4 | 67.5 | 80.3 |
| SD | 1.7 | 4.0 | 9.8 | 12.3 | 12.5 |
| (T17-12-15-4-14)-1 | 33.2 | 63.8 | 104.5 | 129.8 | 148.8 |
| (T17-12-15-4-14)-2 | 22.2 | 58.3 | 92.8 | 117.4 | 145.9 |
| (T17-12-15-4-14)-3 | 27.2 | 57.2 | 76.8 | 109.8 | 141.6 |
| (T17-12-15-4-14)-4 | 26.8 | 60.5 | 90.1 | 129.6 | 163.9 |
| (T17-12-15-4-14)-5 | 28.2 | 57.8 | 92.5 | 116.8 | 149.8 |
| AVG | 27.5 | 59.5 | 91.3 | 120.7 | 150.0 |
| SD | 3.9 | 2.7 | 9.9 | 8.8 | 8.4 |

Data for robust line in bold.

TABLE 11

Total Fruit Number

| Total fruit number | 12 weeks | 14 weeks | 16 weeks | 18 weeks | 20 weeks |
|---|---|---|---|---|---|
| Rutgers-1 | 9.0 | 10.0 | 10.0 | 7.0 | 12.0 |
| Rutgers-3 | 12.0 | 13.0 | 13.0 | 13.0 | 13.0 |
| Rutgers-4 | 12.0 | 14.0 | 15.0 | 15.0 | 16.0 |
| Rutgers-5 | 15.0 | 14.0 | 13.0 | 14.0 | 17.0 |
| AVG | 12.0 | 12.8 | 12.8 | 12.3 | 14.5 |
| SD | 2.4 | 1.9 | 2.1 | 3.6 | 2.4 |
| (TXR7)-1 F2 | 18.0 | 27.0 | 28.0 | 26.0 | 36.0 |
| (TXR7)-2 F2 | 12.0 | 17.0 | 29.0 | 26.0 | 27.0 |
| (TXR7)-3 F2 | 17.0 | 24.0 | 30.0 | 30.0 | 35.0 |
| (TXR7)-4 F2 | 16.0 | 20.0 | 23.0 | 26.0 | 34.0 |
| AVG | 15.8 | 22.0 | 27.5 | 27.0 | 33.0 |
| SD | 2.6 | 4.4 | 3.1 | 2.0 | 4.1 |
| (TXR8)-1 F2 | 19.0 | 26.0 | 38.0 | 26.0 | 32.0 |
| (TXR8)-2 F2 | 15.0 | 29.0 | 31.0 | 33.0 | 38.0 |
| (TXR8)-3 F2 | 16.0 | 21.0 | 27.0 | 28.0 | 32.0 |
| (TXR8)-4 F2 | 13.0 | 16.0 | 23.0 | 19.0 | 24.0 |
| (TXR8)-5 F2 | 15.0 | 24.0 | 20.0 | 30.0 | 34.0 |
| AVG | 14.8 | 22.5 | 25.3 | 27.5 | 32.0 |
| SD | 1.3 | 5.4 | 4.8 | 6.0 | 5.9 |
| (TXR3)-1 F2 | 11.0 | 14.0 | 15.0 | 24.0 | 25.0 |
| (TXR3)-2 F2 | 17.0 | 23.0 | 30.0 | 32.0 | 32.0 |
| (TXR3)-3 F2 | 8.0 | 20.0 | 22.0 | 31.0 | 32.0 |
| (TXR3)-4 F2 | 10.0 | 17.0 | 17.0 | 17.0 | 20.0 |
| AVG | 11.5 | 18.5 | 21.0 | 26.0 | 27.3 |
| SD | 3.4 | 3.4 | 5.8 | 6.0 | 5.1 |
| (TXR5)-1 F2 | 16.0 | 21.0 | 22.0 | 24.0 | 28.0 |
| (TXR5)-2 F2 | 14.0 | 20.0 | 23.0 | 30.0 | 31.0 |
| (TXR5)-3 F2 | 18.0 | 31.0 | 32.0 | 31.0 | 38.0 |
| (TXR5)-4 F2 | 13.0 | 23.0 | 26.0 | 29.0 | 39.0 |
| (TXR5)-5 F2 | 14.0 | 17.0 | 19.0 | 17.0 | 26.0 |
| AVG | 15.0 | 22.4 | 24.4 | 26.2 | 32.4 |
| SD | 2.0 | 5.3 | 4.9 | 5.8 | 5.9 |
| (T17-12-15-4-6)-1 | 26.0 | 37.0 | 51.0 | 59.0 | 64.0 |

TABLE 11-continued

Total Fruit Number

| Total fruit number | 12 weeks | 14 weeks | 16 weeks | 18 weeks | 20 weeks |
|---|---|---|---|---|---|
| (T17-12-15-4-6)-2 | 14.0 | 28.0 | 24.0 | 29.0 | 34.0 |
| (T17-12-15-4-6)-3 | 26.0 | 33.0 | 46.0 | 45.0 | 49.0 |
| (T17-12-15-4-6)-4 | 24.0 | 32.0 | 47.0 | 51.0 | 51.0 |
| (T17-12-15-4-6)-5 | 23.0 | 31.0 | 45.0 | 51.0 | 52.0 |
| AVG | 22.6 | 32.2 | 42.6 | 47.0 | 50.0 |
| SD | 5.0 | 3.3 | 10.6 | 11.2 | 10.7 |
| (T17-12-15-4-8)-1 | 3.0 | 4.0 | 5.0 | 6.0 | 6.0 |
| (T17-12-15-4-8)-2 | 0.0 | 0.0 | 0.0 | 0.0 | 0.0 |
| (T17-12-15-4-8)-3 | 0.0 | 0.0 | 0.0 | 0.0 | 0.0 |
| (T17-12-15-4-8)-4 | 0.0 | 0.0 | 0.0 | 0.0 | 0.0 |
| (T17-12-15-4-8)-5 | 0.0 | 0.0 | 0.0 | 0.0 | 0.0 |
| AVG | 0.6 | 0.8 | 1.0 | 1.2 | 1.2 |
| SD | 1.3 | 1.8 | 2.2 | 2.7 | 2.7 |
| (T17-12-15-4-9)-1 | 2.0 | 7.0 | 7.0 | 8.0 | 7.0 |
| (T17-12-15-4-9)-2 | 0.0 | 0.0 | 0.0 | 0.0 | 0.0 |
| (T17-12-15-4-9)-4 | 0.0 | 0.0 | 0.0 | 0.0 | 0.0 |
| (T17-12-15-4-9)-5 | 0.0 | 0.0 | 0.0 | 0.0 | 0.0 |
| AVG | 0.5 | 1.8 | 1.8 | 2.0 | 1.8 |
| SD | 1.0 | 3.5 | 3.5 | 4.0 | 3.5 |
| (T17-12-15-4-14)-1 | 8.0 | 10.0 | 17.0 | 17.0 | 20.0 |
| (T17-12-15-4-14)-2 | 8.0 | 10.0 | 10.0 | 22.0 | 25.0 |
| (T17-12-15-4-14)-3 | 8.0 | 8.0 | 14.0 | 27.0 | 17.0 |
| (T17-12-15-4-14)-4 | 5.0 | 10.0 | 14.0 | 24.0 | 25.0 |
| (T17-12-15-4-14)-5 | 5.0 | 8.0 | 11.0 | 14.0 | 20.0 |
| AVG | 6.8 | 9.2 | 13.2 | 20.8 | 21.4 |
| SD | 1.6 | 1.1 | 2.8 | 5.3 | 3.5 |

Data for robust line in bold.

TABLE 12

Red Fruit Number

| red fruit number | 14 weeks | 15 weeks | 16 weeks | 17 weeks | 18 weeks | 19 weeks | 20 weeks |
|---|---|---|---|---|---|---|---|
| Rutgers-1 | 0.0 | 2.0 | 5.0 | 5.0 | 5.0 | 7.0 | 7.0 |
| Rutgers-3 | 0.0 | 0.0 | 1.0 | 5.0 | 13.0 | 13.0 | 13.0 |
| Rutgers-4 | 1.0 | 2.0 | 4.0 | 5.0 | 12.0 | 15.0 | 15.0 |
| Rutgers-5 | 1.0 | 3.0 | 3.0 | 3.0 | 7.0 | 10.0 | 11.0 |
| AVG | 0.5 | 1.8 | 3.3 | 4.5 | 9.3 | 11.3 | 11.5 |
| SD | 0.6 | 1.3 | 1.7 | 1.0 | 3.9 | 3.5 | 3.4 |
| (T X R 7)-1 F2 | 4.0 | 9.0 | 14.0 | 16.0 | 20.0 | 22.0 | 24.0 |
| (TXR7)-2 F2 | 2.0 | 5.0 | 7.0 | 7.0 | 9.0 | 9.0 | 11.0 |
| (TXR7)-3 F2 | 5.0 | 10.0 | 15.0 | 16.0 | 19.0 | 24.0 | 24.0 |
| (TXR7)-4 F2 | 0.0 | 4.0 | 7.0 | 16.0 | 15.0 | 16.0 | 24.0 |
| (TXR7)-5 F2 | | | | | | | |
| AVG | 2.8 | 7.0 | 10.8 | 13.8 | 15.8 | 17.8 | 20.8 |
| SD | 2.2 | 2.9 | 4.3 | 4.5 | 5.0 | 6.8 | 6.5 |
| (TXR8)-1 F2 | 3.0 | 16.0 | 16.0 | 6.0 | 10.0 | 12.0 | 20.0 |
| (TXR8)-2 F2 | 3.0 | 7.0 | 12.0 | 15.0 | 16.0 | 21.0 | 30.0 |
| (TXR8)-3 F2 | 1.0 | 4.0 | 5.0 | 17.0 | 17.0 | 20.0 | 25.0 |
| (TXR8)-4 F2 | 1.0 | 2.0 | 6.0 | 12.0 | 11.0 | 13.0 | 16.0 |
| (TXR8)-5 F2 | 3.0 | 7.0 | 9.0 | 16.0 | 22.0 | 25.0 | 27.0 |
| AVG | 2.0 | 5.0 | 8.0 | 15.0 | 16.5 | 19.8 | 24.5 |
| SD | 1.2 | 2.4 | 3.2 | 2.2 | 4.5 | 5.0 | 6.0 |
| (TXR3)-1 F2 | 0.0 | 3.0 | 7.0 | 14.0 | 17.0 | 18.0 | 19.0 |
| (TXR3)-2 F2 | 1.0 | 13.0 | 15.0 | 17.0 | 20.0 | 24.0 | 29.0 |
| (TXR3)-3 F2 | 1.0 | 7.0 | 8.0 | 10.0 | 18.0 | 24.0 | 26.0 |
| (TXR3)-4 F2 | 1.0 | 6.0 | 7.0 | 12.0 | 12.0 | 14.0 | 16.0 |
| AVG | 0.8 | 7.3 | 9.3 | 13.3 | 16.8 | 20.0 | 22.5 |
| SD | 0.4 | 3.6 | 3.3 | 2.6 | 2.9 | 4.2 | 5.2 |
| (TXR5)-1 F2 | 0.0 | 6.0 | 12.0 | 17.0 | 20.0 | 20.0 | 21.0 |
| (TXR5)-2 F2 | 1.0 | 5.0 | 6.0 | 14.0 | 16.0 | 17.0 | 19.0 |
| (TXR5)-3 F2 | 4.0 | 15.0 | 15.0 | 12.0 | 15.0 | 20.0 | 24.0 |
| (TXR5)-4 F2 | 1.0 | 6.0 | 9.0 | 12.0 | 15.0 | 20.0 | 24.0 |
| (TXR5)-5 F2 | 1.0 | 6.0 | 7.0 | 10.0 | 12.0 | 13.0 | 15.0 |
| AVG | 1.4 | 7.6 | 9.8 | 13.0 | 16.0 | 18.0 | 20.6 |
| SD | 1.5 | 4.2 | 3.7 | 2.6 | 2.9 | 3.1 | 3.8 |
| (T17-12-15-4-6)-1 | 2.0 | 13.0 | 17.0 | 19.0 | 27.0 | 35.0 | 40.0 |
| (T17-12-15-4-6)-2 | 0.0 | 3.0 | 5.0 | 8.0 | 18.0 | 23.0 | 26.0 |
| (T17-12-15-4-6)-3 | 3.0 | 5.0 | 6.0 | 12.0 | 20.0 | 24.0 | 36.0 |
| (T17-12-15-4-6)-4 | 2.0 | 7.0 | 14.0 | 15.0 | 27.0 | 28.0 | 39.0 |
| (T17-12-15-4-6)-5 | 1.0 | 6.0 | 16.0 | 19.0 | 25.0 | 31.0 | 34.0 |
| AVG | 1.6 | 6.8 | 11.6 | 14.6 | 23.4 | 28.2 | 35.0 |

TABLE 12-continued

Red Fruit Number

| red fruit number | 14 weeks | 15 weeks | 16 weeks | 17 weeks | 18 weeks | 19 weeks | 20 weeks |
|---|---|---|---|---|---|---|---|
| SD | 1.1 | 3.8 | 5.7 | 4.7 | 4.2 | 5.0 | 5.6 |
| (T17-12-15-4-8)-1 | 0.0 | 0.0 | 1.0 | 1.0 | 5.0 | 5.0 | 5.0 |
| (T17-12-15-4-8)-2 | 0.0 | 0.0 | 0.0 | 0.0 | 0.0 | 0.0 | 0.0 |
| (T17-12-15-4-8)-3 | 0.0 | 0.0 | 0.0 | 0.0 | 0.0 | 0.0 | 0.0 |
| (T17-12-15-4-8)-4 | 0.0 | 0.0 | 0.0 | 0.0 | 0.0 | 0.0 | 0.0 |
| (T17-12-15-4-8)-5 | 0.0 | 0.0 | 0.0 | 0.0 | 0.0 | 0.0 | 0.0 |
| AVG | 0.0 | 0.0 | 0.2 | 0.2 | 1.0 | 1.0 | 1.0 |
| SD | 0.0 | 0.0 | 0.4 | 0.4 | 2.2 | 2.2 | 2.2 |
| (T17-12-15-4-9)-1 | 0.0 | 0.0 | 0.0 | 2.0 | 1.0 | 6.0 | 6.0 |
| (T17-12-15-4-9)-2 | 0.0 | 0.0 | 0.0 | 0.0 | 0.0 | 0.0 | 0.0 |
| (T17-12-15-4-9)-4 | 0.0 | 0.0 | 0.0 | 0.0 | 0.0 | 0.0 | 0.0 |
| (T17-12-15-4-9)-5 | 0.0 | 0.0 | 0.0 | 0.0 | 0.0 | 0.0 | 0.0 |
| AVG | 0.0 | 0.0 | 0.0 | 0.5 | 0.3 | 1.5 | 1.5 |
| SD | 0.0 | 0.0 | 0.0 | 1.0 | 0.5 | 3.0 | 3.0 |
| (T17-12-15-4-14)-1 | 0.0 | 2.0 | 3.0 | 7.0 | 10.0 | 11.0 | 15.0 |
| (T17-12-15-4-14)-2 | 0.0 | 1.0 | 2.0 | 8.0 | 11.0 | 11.0 | 10.0 |
| (T17-12-15-4-14)-3 | 0.0 | 0.0 | 1.0 | 7.0 | 7.0 | 8.0 | 11.0 |
| (T17-12-15-4-14)-4 | 0.0 | 0.0 | 2.0 | 6.0 | 9.0 | 10.0 | 12.0 |
| (T17-12-15-4-14)-5 | 0.0 | 2.0 | 5.0 | 2.0 | 4.0 | 4.0 | 6.0 |
| AVG | 0.0 | 1.0 | 2.6 | 6.0 | 8.2 | 8.8 | 10.8 |
| SD | 0.0 | 1.0 | 1.5 | 2.3 | 2.8 | 2.9 | 3.3 |

Data for robust line in bold.

TABLE 13

Inflorescence Number

| Inflorescence Number | 8 weeks | 10 weeks | 12 weeks | 14 weeks | 16 weeks |
|---|---|---|---|---|---|
| Rutgers-1 | 1.0 | 2.0 | 3.0 | 10.0 | 9.0 | 8.0 |
| Rutgers-3 | 1.0 | 2.0 | 3.0 | 9.0 | 7.0 | 10.0 |
| Rutgers-4 | 1.0 | 2.0 | 8.0 | 12.0 | 11.0 | 15.0 |
| Rutgers-5 | 1.0 | 2.0 | 7.0 | 10.0 | 6.0 | 10.0 |
| AVG | 1.0 | 2.0 | 5.3 | 10.3 | 8.3 | 10.8 |
| SD | 0.0 | 0.0 | 2.6 | 1.3 | 2.2 | 3.0 |
| (T17-12-5-11 X Rutgers 7)-1 F2 | 3.0 | 6.0 | 16.0 | 19.0 | 21.0 | 19.0 |
| (T17-12-5-11 X Rutgers 7)-2 F2 | 2.0 | 4.0 | 13.0 | 20.0 | 17.0 | 22.0 |
| (T17-12-5-11 X Rutgers 7)-3 F2 | 4.0 | 6.0 | 16.0 | 20.0 | 20.0 | 21.0 |
| (T17-12-5-11 X Rutgers 7)-4 F2 | 2.0 | 3.0 | 14.0 | 21.0 | 20.0 | 27.0 |
| (T17-12-5-11 X Rutgers 7)-5 F2 | 2.0 | 4.0 | 13.0 | 19.0 | | |
| AVG | 2.6 | 4.6 | 14.4 | 19.8 | 19.5 | 22.3 |
| SD | 0.9 | 1.3 | 1.5 | 0.8 | 1.7 | 3.4 |
| (T17-12-5-11 X Rutgers 8)-1 F2 | 2.0 | 4.0 | 16.0 | 18.0 | 20.0 | 23.0 |
| (T17-12-5-11 X Rutgers 8)-2 F2 | 2.0 | 3.0 | 14.0 | 22.0 | 28.0 | 24.0 |
| (T17-12-5-11 X Rutgers 8)-3 F2 | 2.0 | 4.0 | 13.0 | 17.0 | 16.0 | 16.0 |
| (T17-12-5-11 X Rutgers 8)-4 F2 | 1.0 | 3.0 | 12.0 | 17.0 | 21.0 | 19.0 |
| (T17-12-5-11 X Rutgers 8)-5 F2 | 2.0 | 4.0 | 13.0 | 21.0 | 18.0 | 22.0 |
| AVG | 1.8 | 3.6 | 13.6 | 19.0 | 20.6 | 20.8 |
| SD | 0.4 | 0.5 | 1.5 | 2.3 | 4.6 | 3.3 |
| (T17-12-5-11 X Rutgers 3)-1 F2 | 1.0 | 1.0 | 7.0 | 13.0 | 15.0 | 15.0 |
| (T17-12-5-11 X Rutgers 3)-2 F2 | 2.0 | 4.0 | 15.0 | 16.0 | 17.0 | 19.0 |
| (T17-12-5-11 X Rutgers 3)-3 F2 | 2.0 | 3.0 | 10.0 | 20.0 | 21.0 | 21.0 |
| (T17-12-5-11 X Rutgers 3)-4 F2 | 2.0 | 4.0 | 17.0 | 22.0 | 21.0 | 23.0 |
| AVG | 1.8 | 3.0 | 12.3 | 17.8 | 18.5 | 19.5 |
| SD | 0.5 | 1.4 | 4.6 | 4.0 | 3.0 | 3.4 |
| (T17-12-5-11 X Rutgers 5)-1 F2 | 2.0 | 3.0 | 16.0 | 20.0 | 18.0 | 21.0 |

TABLE 13-continued

| Inflorescence Number | 8 weeks | 10 weeks | 12 weeks | 14 weeks | 16 weeks |
|---|---|---|---|---|---|
| (T17-12-5-11 X Rutgers 5)-2 F2 | 2.0 | 4.0 | 12.0 | 20.0 | 25.0 | 27.0 |
| (T17-12-5-11 X Rutgers 5)-3 F2 | 2.0 | 6.0 | 16.0 | 20.0 | 16.0 | 17.0 |
| (T17-12-5-11 X Rutgers 5)-4 F2 | 2.0 | 5.0 | 15.0 | 17.0 | 24.0 | 29.0 |
| (T17-12-5-11 X Rutgers 5)-5 F2 | 2.0 | 3.0 | 16.0 | 21.0 | 18.0 | 22.0 |
| AVG | 2.0 | 4.2 | 15.0 | 19.6 | 20.2 | 23.2 |
| SD | 0.0 | 1.3 | 1.7 | 1.5 | 4.0 | 4.8 |
| (T17-12-15-4-6)-1 | 2.0 | 4.0 | 10.0 | 14.0 | 17.0 | 24.0 |
| (T17-12-15-4-6)-2 | 1.0 | 1.0 | 4.0 | 11.0 | 15.0 | 29.0 |
| (T17-12-15-4-6)-3 | 1.0 | 2.0 | 5.0 | 16.0 | 14.0 | 20.0 |
| (T17-12-15-4-6)-4 | 1.0 | 2.0 | 8.0 | 16.0 | 16.0 | 20.0 |
| (T17-12-15-4-6)-5 | 1.0 | 4.0 | 8.0 | 14.0 | 12.0 | 18.0 |
| AVG | 1.2 | 2.6 | 7.0 | 14.2 | 14.8 | 22.2 |
| SD | 0.4 | 1.3 | 2.4 | 2.0 | 1.9 | 4.4 |
| (T17-12-15-4-8)-1 | 0.0 | 0.0 | 4.0 | 10.0 | 21.0 | 24.0 |
| (T17-12-15-4-8)-2 | 0.0 | 0.0 | 1.0 | 2.0 | 7.0 | 10.0 |
| (T17-12-15-4-8)-3 | 0.0 | 0.0 | 0.0 | 0.0 | 0.0 | 0.0 |
| (T17-12-15-4-8)-4 | 0.0 | 0.0 | 0.0 | 0.0 | 4.0 | 8.0 |
| (T17-12-15-4-8)-5 | 0.0 | 0.0 | 2.0 | 7.0 | 8.0 | 6.0 |
| AVG | 0.0 | 0.0 | 1.4 | 3.8 | 8.0 | 9.6 |
| SD | 0.0 | 0.0 | 1.7 | 4.5 | 7.9 | 8.9 |
| (T17-12-15-4-9)-1 | 0.0 | 0.0 | 3.0 | 10.0 | 13.0 | 17.0 |
| (T17-12-15-4-9)-2 | 0.0 | 0.0 | 1.0 | 2.0 | 2.0 | 0.0 |
| (T17-12-15-4-9)-4 | 0.0 | 0.0 | 2.0 | 9.0 | 10.0 | 14.0 |
| (T17-12-15-4-9)-5 | 0.0 | 0.0 | 1.0 | 3.0 | 6.0 | 1.0 |
| AVG | 0.0 | 0.0 | 1.8 | 6.0 | 7.8 | 8.0 |
| SD | 0.0 | 0.0 | 2.7 | 10.1 | 12.5 | 16.8 |
| (T17-12-15-4-14)-1 | 1.0 | 2.0 | 11.0 | 21.0 | 25.0 | 30.0 |
| (T17-12-15-4-14)-2 | 1.0 | 1.0 | 9.0 | 13.0 | 18.0 | 16.0 |
| (T17-12-15-4-14)-3 | 1.0 | 2.0 | 9.0 | 15.0 | 18.0 | 17.0 |
| (T17-12-15-4-14)-4 | 1.0 | 2.0 | 7.0 | 13.0 | 20.0 | 25.0 |
| (T17-12-15-4-14)-5 | 1.0 | 2.0 | 7.0 | 12.0 | 12.0 | 18.0 |
| AVG | 1.0 | 1.8 | 8.6 | 14.8 | 18.6 | 21.2 |
| SD | 0.0 | 0.4 | 1.7 | 3.6 | 4.7 | 6.1 |

Data for robust line in bold.

A similar range of plant phenotypes arise in *Arabidopsis* msh1 T-DNA insertion mutants that are selfed. In brief, an *Arabidopsis* strain that was heterozygous for an T-DNA insertional mutation in the endogenous Msh1 gene and obtained from the *Arabidopsis* Stock Center (*Arabidopsis* Biological Resource Center, Columbus, Ohio, USA) was selfed to obtain msh1 plants homozygous for this T-DNA insertion that lack a functional MSH1 gene. These homozygous msh1 null plants are subsequently selfed to obtain subsequent generations of msh1 null plants that exhibit phenotypic variability that includes certain useful traits. Useful traits observed in the selfed msh1 lines include increased above-ground biomass and drought tolerance (FIG. 11A, B, C, D).

At low frequency, it is feasible in all of these cases to identify robust variants that out-perform wildtype in above-ground biomass (*Arabidopsis*), fruit number (tomato) or panicle size (millet) by selecting for robust progeny of plants subjected to MSH1 suppression. For tomato and millet, this result was obtained by selfing and did not entail outcrossing. This is in contrast to previously reported results described in U.S. patent application Ser. No. 13/155,505 where variants that out-perform isogenic wildtype were obtained by outcrossing plants subjected to MSH1 suppression and selecting for progeny that exhibited one or more MSH1-dr phenotypes (CMS, leaf variegation, dwarfed growth and reduced internode elongation, enhanced branching, altered leaf morphology, extended juvenility, and delayed flowering).

Example 3. Summary Tables of Nucleic Acid Sequences and SEQ ID NO

TABLE 14

Nucleotide Sequences provided in the Sequence Listing

| Internet Accession Information | SEQ ID NO | Comments |
|---|---|---|
| The *Arabidopsis* Information Resource (TAIR) 1009043787 on the internet (world wide web) at arabidopsis.org | 1 | *Arabidopsis* MSH1 Full length cDNA (DNA sequence) |
| The *Arabidopsis* Information Resource (TAIR) 1009118392 on the internet (world wide web) at arabidopsis.org | 2 | *Arabidopsis* MSH1 Protein (amino acid sequence) |
| NCBI AY856369 on the world wide web at ncbi.nlm.nih.gov/nuccore | 3 | Soybean MSH1 >gi\|61696668\|gb\|AY856369.1\| *Glycine max* DNA mismatch repair protein (MSH1) complete cds; (DNA sequence) |
| NCBI Accession AY856370 on the world wide web at ncbi.nlm.nih.gov/nuccore | 4 | *Zea mays* MSH1 gi\|61696670\|gb\|AY856370.1\| *Zea mays* DNA mismatch repair protein (MSH1), complete cds; (DNA sequence) |
| NCBI Accession AY866434.1 on the world wide web at ncbi.nlm.nih.gov/nuccore | 5 | Tomato MSH1 >gi\|61696672\|gb\|AY866434.1\| *Lycopersicon esculentum* DNA mismatch repair protein (MSH1), partial cds; (DNA sequence) |

TABLE 14-continued

Nucleotide Sequences provided in the Sequence Listing

| Internet Accession Information | SEQ ID NO | Comments |
|---|---|---|
| NCBI XM002448093.1 on the world wide web at ncbi.nlm.nih.gov/nuccore | 6 | *Sorghum* MSH1 >gi\|242076403: 1-3180 *Sorghum bicolor* hypothetical protein; (DNA sequence) |
| Os04g42784.1 Rice Genome Annotation Project - MSU Rice Genome Annotation (Osa1) Release 6.1 Internet address rice.plantbiology.msu.edu/index.shtml | 7 | Rice (*Oryza sativa*) MSH1 coding sequence (DNA sequence) |
| *Brachypodium* Bradi5g15120.1 On the world wide web at gramene.org/Brachypodium_distachyon/ Gene/Summary? db = core; g = BRADI5G15120; r = 5: 18500245-18518223; t = BRADI5G15120.1 | 8 | *Brachypodium* MSH1 coding region (DNA sequence) |
| GSVIVT01027931001 On the world wide web at genoscope.cns.fr/spip/Vitis-vinifera-e.html | 9 | *Vitis Vinifera* MSH1 cDNA (DNA sequence) |
| Cucsa.255860.1 On the internet (world wide web) at phytozome.net/ | 10 | Cucumber (*Cucumis sativa*) MSH1 coding sequence; (DNA sequence) |
| GenBank Accession ES831813.1 on the world wide web at ncbi.nlm.nih.gov/nucest | 11 | Cotton (*Gossypium hirsutum*) MSH1 partial cDNA sequence (EST); (DNA sequence) |
| Oryza_sativa_msh1_2000up >Rice-LOC_Os04g42784 | 12 | Oryza_sativa_msh1_Promoter and 5' UTR |
| Solanum_lycopersicum_2000up >Tomato-Solyc09g090870.2 | 13 | Solanum_lycopersicum msh1 promoter and 5' UTR |
| Sorghum_bicolor_MSH1_2000up_Phytozome>Sb06g021950 | 14 | *Sorghum bicolor* msh1 promoter and 5' UTR |
| Arabidopsis-Col0-MSH1 | 15 | Arabidopsis-Col0-MSH1 promoter and 5' UTR |
| >gi\|145337631\|ref\|NM_106295.3\| *Arabidopsis thaliana* photosystem II reaction center PsbP family protein cDNA, complete cds | 16 | *Arabidopsis* PPD3 coding region |
| >gi\|297839518\|ref\|XM_002887595.1\| *Arabidopsis lyrata* subsp. *lyrata* hypothetical protein, cDNA | 17 | *Arabidopsis* PPD3 coding region |
| >gi\|449522158\|ref\|XM_004168047.1\| PREDICTED: *Cucumis sativus* psbP domain-containing protein 3, chloroplastic-like (LOC101211525), cDNA | 18 | *Cucumis sativus* PPD3 coding region |
| >gi\|255539323\|ref\|XM_002510681.1\| *Ricinus communis* conserved hypothetical protein cDNA | 19 | *Ricinus communis* PPD3 coding region |
| >gi\|359491869\|ref\|XM_002273296.2\| PREDICTED: *Vitis vinifera* psbP domain-containing protein 3, chloroplastic-like (LOC100263326), cDNA | 20 | *Vitis vinifera* PPD3 coding region |
| >gi\|357467178\|ref\|XM_003603826.1\| *Medicago truncatula* PsbP domain-containing protein (MTR_3g116110) cDNA, complete cds | 21 | *Medicago truncatula* PPD3 coding region |
| >gi\|224083365\|ref\|XM_002306962.1\| *Populus trichocarpa* predicted protein, cDNA | 22 | *Populus trichocarpa* PPD3 coding region |
| >gi\|388521576\|gb\|BT149056.1\| *Lotus japonicus* clone JCVI-FLLj-8L12 unknown cDNA | 23 | *Lotus japonicus* PPD3 coding region |
| gi\|470131466\|ref\|XM_004301567.1\| PREDICTED: *Fragaria vesca* subsp. *vesca* psbP domain-containing protein 3, chloroplastic-like (LOC101302662), mRNA | 24 | *Fragaria vesca* PPD3 coding region |
| >gi\|356517169\|ref\|XM_003527214.1\| PREDICTED: *Glycine max* psbP domain-containing protein 3, chloroplastic-like (LOC100805637), mRNA | 25 | *Glycine max* PPD3 coding region |
| *Solanum lycopersicum* psbP domain-containing protein 3, chloroplastic-like (LOC101247415), mRNA | 26 | *Solanum lycopersicum* PPD3 coding region |

TABLE 14-continued

Nucleotide Sequences provided in the Sequence Listing

| Internet Accession Information | SEQ ID NO | Comments |
|---|---|---|
| >gi\|502130964\|ref\|XM_004500773.1\| PREDICTED: *Cicer arietinum* psbP domain-containing protein 3, chloroplastic-like (LOC101499898), transcript variant X2, mRNA | 27 | *Cicer arietinum* PPD3 coding region |
| >gi\|241989846\|dbj\|AK330387.1\| *Triticum aestivum* cDNA, clone: SET4_F09, cultivar: Chinese Spring | 28 | *Triticum aestivum* PPD3 coding region |
| >gi\|115477245\|ref\|NM_001068754.1\| *Oryza sativa Japonica* Group Os08g0512500 (Os08g0512500) mRNA, complete cds | 29 | *Oryza sativa* PPD3 coding region |
| >gi\|357141873\|ref\|XM_003572329.1\| PREDICTED: *Brachypodium distachyon* psbP domain-containing protein 3, chloroplastic-like (LOC100840022), mRNA | 30 | *Brachypodium distachyon* PPD3 coding region |
| >gi\|242383886\|emb\|FP097685.1\| *Phyllostachys edulis* cDNA clone: bphylf043n24, full insert sequence | 31 | *Phyllostachys edulis* PPD3 coding region |
| >gi\|326512571\|dbj\|AK368438.1\| *Hordeum vulgare* subsp. *vulgare* mRNA for predicted protein, partial cds, clone: NIASHv2073K06 | 32 | *Hordeum vulgare* PPD3 coding region |
| >gi\|195613363\|gb\|EU956394.1\| *Zea mays* clone 1562032 thylakoid lumen protein mRNA, complete cds | 33 | *Zea mays* PPD3 coding region |
| >gi\|242082240\|ref\|XM_002445844.1\| *Sorghum bicolor* hypothetical protein, mRNA | 34 | *Sorghum bicolor* PPD3 coding region |
| >gi\|514797822\|ref\|XM_004973837.1\| PREDICTED: *Setaria italica* psbP domain-containing protein 3, chloroplastic-like (LOC101754517), mRNA | 35 | *Setaria italica* PPD3 coding region |
| >gi\|270145042\|gb\|BT111994.1\|*Picea glauca* clone GQ03308_J01 mRNA sequence | 36 | *Picea glauca* PPD3 coding region |
| >gi\|215274040\|gb\|EU935214.1\| *Arachis diogoi* clone AF1U3 unknown mRNA | 37 | *Arachis diogoi* PPD3 coding region |
| >gi\|168003548\|ref\|XM_001754423.1\| *Physcomitrella patens* subsp. *patens* predicted protein (PHYPADRAFT_175716) mRNA, complete cds | 38 | *Physcomitrella patens* PPD3 coding region |
| >gi\|302809907\|ref\|XM_002986600.1\| *Selaginella moellendorffii* hypothetical protein, mRNA | 39 | *Selaginella moellendorffii* PPD3 coding region |
| >gi\|330318510\|gb\|HM003344.1\| *Camellia sinensis* clone U10BcDNA 3162 | 40 | *Camellia sinensis* PPD3 coding region |
| Zea_mays_2000up_phytozome >GRMZM2G360873 | 41 | *Zea mays* MSH1 promoter and 5' UTR |
| AT5G67120RING-F | 42 | primer |
| AT5G67120RING-R | 43 | primer |
| AT1G20690SWI-F | 44 | primer |
| AT1G20690SWI-R | 45 | primer |
| AT3g271501stMir2-F | 46 | primer |
| AT3g271501stMir2-R | 47 | primer |
| AT3g271502ndMir2-F | 48 | primer |
| AT3g271502ndMir2-R | 49 | primer |
| RNAi-F | 50 | primer |
| RNAi-R | 51 | primer |
| upstream_1 kb\| photosystem II reaction center PsbP family protein mRNA | 52 | *Arabidopsis thaliana* PPD3 promoter |
| upstream_1 kb\|*Oryza sativa Japonica* Group Os08g0512500 (Os08g0512500) mRNA | 53 | *Oryza sativa* PPD3 promoter |
| upstream_1 kb\|PREDICTED: *Solanum lycopersicum* psbP domain-containing protein 3, chloroplastic-like | 54 | *Solanum lycopersicum* PPD3 promoter |

Sequence Listing is provided herewith as a computer readable form (CRF) named "46589_126309_SEQ_LST-.txt" and is incorporated herein by reference in its entirety. This sequence listing contains SEQ ID NO:1-56 that are referred to herein.

The embodiments were chosen and described in order to best explain the principles of the present disclosure and its practical application to thereby enable others skilled in the art to best utilize the present disclosure in various embodiments and with various modifications as are suited to the particular use contemplated.

As various modifications could be made in the constructions and methods herein described and illustrated without departing from the scope of the present disclosure, it is intended that all matter contained in the foregoing description or shown in the accompanying drawings shall be interpreted as illustrative rather than limiting. Thus, the breadth and scope of the present disclosure should not be limited by any of the above-described embodiments, but should be defined only in accordance with the following claims appended hereto and their equivalents.

What is claimed is:

1. A method for producing a plant having a useful trait that exhibits nuclear inheritance comprising the steps of:
   (a) crossing one or more first plant(s) to one or more second plant(s), or selfing a first plant(s), wherein at least said first plant(s) or a parent plant thereof is or had been subjected to perturbation of organellar function by genetic suppression of an endogenous MSH1 gene with: (i) a transgene, a Viral-Induced Gene Silencing (VIGS) vector, or nucleic acid, wherein said transgene, VIGS vector, or nucleic acid produces or comprises a nucleic acid of at least 18 nucleotides in length that is identical or complementary to the endogenous MSH1 gene; or (ii) a loss of function mutation in the endogenous MSH1 gene; and wherein the first plant or a parent plant thereof does not exhibit any MSH1-dr phenotypes;
   (b) screening a population of progeny plants obtained from the cross or self of step (a) for the useful trait, wherein the useful trait is at least one of an increase in biomass or an increase in yield relative to a control plant; and,
   (c) selecting one or more progeny plants having the useful trait that exhibits nuclear inheritance and having recovered organellar function, thereby producing a plant exhibiting the useful trait of at least one of an increase in biomass or an increase in yield relative to a control plant, and wherein the useful trait exhibits nuclear inheritance.

2. The method of claim 1, wherein organellar function has been recovered in any of: (i) the first plant in step (a); (ii) at least a portion of the population of progeny plants of step (b); or (iii) one or more of the selected progeny plants in step (c).

3. The method of claim 1, wherein the first plant(s) of step (a) exhibit a wild type phenotype or an increase in biomass or an increase in yield relative to a control plant in comparison to a control plant.

4. The method of claim 1, further comprising the step of producing seed or a progeny plant from the progeny plant selected in step (c), wherein the produced seed or produced progeny plant carry the useful trait, and wherein the useful trait exhibits nuclear inheritance.

5. The method of claim 1, wherein the plant is a corn, soybean, cotton, canola, wheat, rice, tomato, tobacco, millet, potato, sugarbeet, cassava, alfalfa, barley, oat, sugarcane, sunflower, strawberry, or *sorghum* plant.

6. The method of claim 1, wherein the plant is a tomato or *sorghum* plant.

7. The method of claim 1, further comprising the step of producing a seed lot from the one or more progeny plants selected in step (c) or from one or more progeny plants obtained therefrom.

* * * * *